US005858989A

United States Patent [19]
Babiuk et al.

[11] Patent Number: 5,858,989
[45] Date of Patent: Jan. 12, 1999

[54] VACCINES COMPRISING NUCLEOTIDE SEQUENCES ENCODING BOVINE HERPESVIRUS TYPE 1 G1, G111 AND GIV

[75] Inventors: Lorne Babiuk; Sylvia van der Hurk; Tim Zamb, all of Saskatoon, Canada; David Fitzpatrick, Subiaco, Australia

[73] Assignee: University of Saskatchewan, Saskatchewan, Canada

[21] Appl. No.: 682,847

[22] Filed: Jul. 10, 1996

Related U.S. Application Data

[60] Division of Ser. No. 921,849, Jul. 29, 1992, Pat. No. 5,585,264, which is a continuation-in-part of Ser. No. 805, 524, Dec. 11, 1991, abandoned, which is a continuation-in-part of Ser. No. 219,939, Jul. 15, 1988, Pat. No. 5,151,267.

[51] Int. Cl.$^6$ ........................ A61K 48/00; A61K 39/245; C12N 15/38; C07K 14/03

[52] U.S. Cl. ..................... 514/44; 424/185.1; 424/229.1; 435/69.3; 530/350; 530/395; 536/23.72

[58] Field of Search ...................... 536/23.72; 424/185.1, 424/229.1; 514/44; 530/350, 395; 435/69.3

[56] References Cited

U.S. PATENT DOCUMENTS

| | | | |
|---|---|---|---|
| 4,335,105 | 6/1982 | Gough | 530/395 |
| 4,341,784 | 7/1982 | Kaplan et al. | 530/395 |
| 4,642,333 | 2/1987 | Person | 424/89 |
| 4,661,349 | 4/1987 | Kino et al. | 424/89 |
| 4,680,176 | 7/1987 | Beins et al. | 424/89 |
| 4,709,011 | 11/1987 | Cohen et al. | 424/89 |
| 4,724,146 | 2/1988 | Kino et al. | 424/89 |
| 5,151,267 | 9/1992 | Babiuk et al. . | |
| 5,585,264 | 12/1996 | Babiuk et al. | 435/240.2 |

FOREIGN PATENT DOCUMENTS

| | | | |
|---|---|---|---|
| 0362531 | 4/1990 | European Pat. Off. | 530/395 |
| 1340418 | 3/1923 | United Kingdom | 424/89 |
| WO 88/02634 | 4/1988 | WIPO . | |
| 8802634 | 4/1989 | WIPO | 424/89 |

OTHER PUBLICATIONS

Manickan, E. et al., Crit. Rev. Immunol. 17:139–154, "DNA Vaccines —a modern gimmick or a boon to vaccinology?", 1997.
Wolff et al.., Science 247:1465, 1990.
Robinson et al., Vaccine 11:975–, 1990.
Ulmer et al., Science 254:1745–, 1993.
Babiuk et al. (1975) Infect. Immun. 12:958–963.
Misra et al. (1981) J. Virol. 40:367–378.
van Drunen Littel–van den Hurk et al. (1984) Virology 135:466–479.
van Drunen Littel–van den Hurk et al. (1985) Virology 144:216–227.
Collins et al. (1984) J. Virol. 52:403–409.
Okazaki et al. (1986) Virology 150:260–264.
van Drunen Littel–van den Hurk et al. (1985) Virology 144:204–215.
van Drunen Littel–van den Hurk et al. (1986) J. Clin. Microbiol. 23:274–282.
Okazaki et al. (1987) Arch. Virol. 92:17–26.
Mayfield et al. (1983) J. Virol. 47:259–264.
Pachl et al. (1987) J. Virol. 61:315–325.
Babiuk et al. (1987) Virology 159:57–66.
Lupton et al. (1980) Am. J. Vet. Res. 41:383–390.
Cox et al., "Bovine herpesvirus 1: immune responses in mice and cattle injected with plasmid DNA" *J. Virology* (1993) 67:5664–5667.
Hammerschmidt et al., "Common epitopes of glycoprotein B map within the major DNA–binding proteins of bovine herpesvirus type 2 (BHV–2) and herpes simplex virus type 1 (HVS–1)" *Virology* (1988) 165:408–418.

Lawrence et al., "Map location of the gene for a 130, 000–dalton glycoprotein of bovine herpesvirus 1" *J. Virol.* (1986) 60:405–414.

Liang et al., "An in vivo study of a glycoprotein gill–negative bovine herpesvirus 1 (BHV–1) mutant expressing B–galactosidase: evaluation of the role of gill in virus infectivity and its use as a vector for mucosal immunization" *Virology* (1992) 189:629–639.

Misra et al., "Sequence of a bovine herpesvirus type–1 glycoprotein gene that is homologous to the herpes simplex gene for glycoprotein gβ" *Virology* (1988) 166:542–549.
van Drunen Littel–van den hurk et al., "Synthesis and processing of bovine herpesvirus 1 glycoproteins" *J. Virology* (1986) 59:401–410.
van Drunen Littel–van den Hurk et al., "Epitope specificity of the protective immune response induced by individual bovine herpesvirus–1 glycoproteins" *Vaccine* (1990) 8:358–368.

Leary et al., "Recombinant herpesviral proteins produced by cell–free translation provide a novel approach for the mapping of T lymphocyte epitopes" *J. Immunol.* (1990) 145:718–723. (Medline accession No. 07401317).

Leary et al., "Constitutively expressing cell lines that secrete a truncated bovine herpes virus–1 glycoprotein (gpl) stimulates T–lymphocyte responsiveness" *Immunology* (1992) 76:3673–3672.

Palmer et al., "Bovine natural killer–like cell responses against cell lines expressing recombinant bovine herpesvirus type 1 glycoproteins" *J. Innumol.* (1990) 145:1009–1014.

Babiuk et al., "Protection of cattle from bovine herpesvirus type 1 (BHV–1) infection by immunization with individual viral glycoproteins" *Virol.* (1987) 159:57–66.

Collins et al., "Neutralizing determinants defined by monoclonal antibodies on polypeptides specified by bovine herpesvirus 1" *J. Virol.* (1984) 52:403–409.

Fitzpatrick et al., "Expression of bovine herpesvirus 1 glycoproteins gl and glll in transfected murine cells" *J. Virol.* (1988) 62:4239:4248.

(List continued on next page.)

*Primary Examiner*—Thomas M. Cunningham
*Attorney, Agent, or Firm*—Morrison & Foerster, LLP

[57] ABSTRACT

Recombinant subunit vaccines against bovine herpesvirus type 1 (BHV-1) are provided, as well as methods of vaccination and methods of recombinantly producing the subunit antigens or nucleotide sequences employed in the vaccines.

12 Claims, 50 Drawing Sheets

OTHER PUBLICATIONS

Fitzpatrick et al., "Mapping of 10 epitopes on bovine herpesvirus type, glycoproteins gI and gIII" *Virol.* (1990) 176:145–157.

Gerber et al., "Local and systemic cellular and antibody immune responses of cattle to infectious bovine rhinotracheitis virus vaccines administered intranasally or intramuscularly" *Am. J. Vet. Res.* (1978) 39:753–760.

Hughes et al., "Functional and topographical analyses of epitopes on bovine herpesvirus type 1 glycoprotein IV" *Arch. Virol.* (1988) 103:47–60.

Jericho et al., "The effect of dose, route and virulence of bovine herpesvirus 1 vaccine on experimental respiratory disease in cattle" *Can. J. Com. Med.* (1983) 47:133–139.

Mayfield et al., "Cloning and cleavage site mapping of DNA from bovine herpesvirus 1 (Cooper Strain)" *J. Virol.* (1983) 47:259–264.

Misra et al., "Proteins specified by bovine herpesvirus 1(Infectious Bovine Rhinotracheitis Virus)" *J. Virol.* (1981) 40:367–378.

Okazaki et al., "Mechanisms of neutralization by monoclonal antibodies to different antigenic sites on the bovine herpesvirus type 1 glycoproteins" *Virology* (1986) 150:260–264.

Pachl et al., "Expression of cell–associated and secreted forms of herpes simplex virus Type 1 glycoprotein gB in mammalian cells" *J. Virol.* (1987) 61:315–325.

Pastoret et al., "Reactivation of temperature–sensitive and non–temperature sensitive infectious bovine rhinotracheitis vaccine virus with dexamethasone" *Infect. Immun.* (1980) 29:483–488.

Tikoo et al., "Molecular cloning, sequencing, and expression of functional bovine herpesvirus 1 glycoprotein gIV in transfected bovine cells" *J. Virol.* (1990) 64:5132–5142.

van Drunen Littel–van den Hurk et al., "Interactions of monoclonal antibodies and bovine herpesvirus type 1 (BHV–1) glycoproteins: characterization of their biochemical and immunological properties" *Virology* (1984) 135:466–479.

van Drunen Littel–van den Hurk et al., "Antigenic and immunogenic characteristics of bovine herpesvirus type–1 glycoproteins GVP 3/9 and GVP 6/11a/16, urified by immunoadsorbent chromatography" *Virology* (1985) 144:204–215.

van Drunen Littel–van den Hurk et al., "Topographical analysis of bovine herpesvirus type–1 glycoproteins: use of monoclonal antibodies to identify and characterize functional epitopes" *Virology* (1985) 144:216–227.

van Drunen Littel–van den Hurk et al., "Polypeptide specificity of the antibody response after primary and recurrent infection with bovine herpesvirus 1" *J. Clin. Microbiol.* (1986) 23:274–282.

van Drunen Littel–van den Hurk et al., "Synthesis, cellular location, and immunogenicity of bovine herpesvirus 1 glycoproteins gI and gIII expressed by recombinant vaccinia virus" *J. Virol.* (1989) 63:2159–2168.

van Drunen Littel–van den Hurk et al., "Expression of bovine herpesvirus 1 glycoprotein gIV by recombinant baculovirus and analysis of its immunogenic properties" *J. Virol.* (1991) 65:263–271.

```
BHV-1 gI: Sequence Range: 1 to 3382
GTCGACCCGG CAACGTGGCC CGCGTTGACG CACCAGTTCT TCGACCTAGT TAACGGGCCG CTCTTTGACG      70
GCAGCGCGCA CAACTTCGCG CAGCCGCCAA ACACCGCGCT GTACTTTAGC GTGGAAAACG TGGGCCTGCT     140
CCCGCACCTC AAGGAGGAGC TGGCCGCGTT TATGCTGGCG GCCGCGGGGG GCGGGTGGGC GGTAAGCGAC     210
TTCCAGCAGT TTTTTGCTT CGCATCCGCG CGGGCGCGGG GCGTCACCGC CGGGCAGCGG CTCGCCTGGC      280
AATATATCCG CGAGCTCGTT CTGGCCCGCG CCGTCTTTGC GTCCGTCTTC CACTGCGGAC GCGTCCCGCT     350
GCTGCGTGCG GACCGAACGG CGCCGGGCCC CGCCGGGCGG GACGGGCCCC CAGTCGTGTC CCAGCGGGCGT CTACCTGACC     420
TACGAGGAGT C ATG GCC GCT CGC GGC GGT GCT GAA CGC GGC GCC GGC GGA GAC GGT      479
            Met Ala Ala Arg Gly Gly Ala Glu Arg Ala Ala Gly Ala Gly Asp Gly
              1               5                  10                  15

CGG CGA GGA CAG CGT CGT CAT CTA CGA CCG GGA CGT GTT CTC GCT GCT CTA CGC GGT     536
Arg Arg Gly Gln Arg Arg His Leu Arg Pro Gly Arg Val Leu Ala Ala Leu Arg Gly
            20                  25                  30                  35

CCT GCA GCG CCT GGC GGC GCC GGG CGC CAT GCC GCT GCC GCT GCC CTG CTA CTG TGG     593
Pro Ala Ala Pro Gly Gly Ala Gly Arg His Ala Ala Ala Ala Ala Leu Leu Leu Trp
            40                  45                  50

GCG ACG TGG GCC CTG CTG CTG GCG GCG GCG GCG GCG GCG CCG GCG ACA ACG CCC         650
Ala Thr Trp Ala Leu Leu Leu Ala Ala Ala Ala Ala Ala Pro Ala Thr Thr Pro
            55                  60                  65                  70

CCG GCG GCC CCC CCG CCC GAA GAG GCC GGC GCC CCC GCC AGC CCC GCG AGC CCC         707
Pro Ala Ala Pro Pro Pro Glu Glu Ala Gly Ala Pro Ala Ser Pro Ala Ser Pro
            75                  80                  85                  90

CCC GGC GAC CCC GAC GGC GAC GAC GCC GAC CCC AGC ACA GAC GTG CGC GCC             764
Pro Gly Asp Pro Asp Gly Asp Asp Ala Ala Ser Pro Asn Ser Thr Asp Val Arg Ala
            95                 100                 105                 110
```

```
GCG CTC CGG CTC GCG CAG GCC GGG GAA AAC TCG CGC TTC GTG TGC CCG CCG      821
Ala Leu Arg Leu Ala Gln Ala Gly Glu Asn Ser Arg Phe Val Cys Pro Pro
115                     120                     125                 130

CCC TCG GGC ACG GTC GTC CTC CGG CGG CCC TGC GAG TAC CCT TAC GGG          878
Pro Ser Gly Thr Val Val Leu Arg Arg Pro Cys Glu Tyr Pro Tyr Gly
        135                     140                     145

CTC GGG CGG AAC TAC TAC GAG GGC ATC ATC GGC GAG AAC ATC CCG              935
Leu Gly Arg Asn Tyr Tyr Glu Gly Ile Ile Gly Glu Asn Ile Ala Pro
150                     155                     160                 165

TAC ACG TTC AAG GCC TAC ATT TAC AAA TAC AAG GTG ATC GTG ACG CCG          992
Tyr Thr Phe Lys Ala Tyr Ile Tyr Lys Tyr Lys Val Ile Val Thr Ala
        170                     175                     180

GGA AGC ACG ACG GCC ATT ACA AAC CAG ATC GTG ACC ACG ACT TGG GCG         1049
Gly Ser Thr Thr Ala Ile Thr Asn Gln Ile Val Thr Thr Thr Trp Ala
190                     195                     200                 205

GGC GAG ATC ACG GAC CTG GTG GAC TAC CGG CTT TCG AAA GCC GGC ATG         1106
Gly Glu Ile Thr Asp Leu Val Asp Tyr Arg Leu Ser Lys Ala Gly Met
        210                     215                     220

CTG CGC AGC CGG GCG GTG GTG GAC TTT GAC GAC CCC TGG GAG GAC GCC         1163
Leu Arg Ser Arg Ala Val Val Asp Phe Asp Asp Pro Trp Glu Asp Ala
230                     235                     240

CCG AAG CCT GCG AGC CCC GGG CTG GTG CCC CAC TGG ACG ACG GAC             1220
Pro Lys Pro Ala Ser Pro Gly Val Gly Pro His Trp Thr Thr Asp
245                     250                     255                 260

GAT GTG TAC ACG GCG TCG GCG CGC CTC TAC ACC GGC GTG AAC                 1277
Asp Val Tyr Thr Ala Leu Gly Ser Ala Arg Tyr Leu Tyr Thr Gly Val Asn
265                     270                     275                 280
```

```
TGC ATC GTG GAA GAA GTG GAG GCG CGC TCG TAC GTG TAC CCG TAC GAC TCG TTC GCG CTC    1334
Cys Ile Val Glu Glu Val Glu Ala Arg Ser Tyr Val Tyr Pro Tyr Asp Ser Phe Ala Leu
            285             290             295             300

TCG ACC GGG GAC ATT ATC TAC ATG TCG CCC TTT TAC CCG TAC GGG CTG CGC GCG CAC        1391
Ser Thr Gly Asp Ile Ile Tyr Met Ser Pro Phe Tyr Pro Tyr Gly Leu Arg Ala His
                    305             310             315             320

CGC GAG CAC ACC AGC TAC TCG CCG TCG CGA GAG TTC CAG CAG CAG CAC GAG GGC GGG AAG    1448
Arg Glu His Thr Ser Tyr Ser Pro Ser Arg Glu Phe Gln Gln Gln His Glu Gly Gly Lys
                325             330             335

CGC GAG ATG GCC ACG GGC CGG CGC TCG AAG GAG CCG GTC CGG AAC GGG TAC TAC TAC        1505
Arg Glu Met Ala Thr Gly Arg Arg Ser Lys Glu Pro Val Arg Asn Gly Tyr Tyr Tyr
340                 345             350             355

ACA CAG CAC GTG ACG GCC GTA CTC GTG GAC CCG GTG TTT GTG GTC CCC AAA GGG TGC TCG    1562
Thr Gln His Val Thr Ala Val Leu Val Asp Pro Val Phe Val Val Pro Lys Gly Cys Ser
                                    365             370             375

CTG GCC AAG TGG CGC GAG GCG GAC TGG CGA ATG CTG GAC GAG GAC GAG GGG AAC TTC        1619
Leu Ala Lys Trp Arg Glu Ala Asp Trp Arg Met Leu Asp Glu Asp Glu Gly Asn Phe
                380             385             390             395

CGC TTC ACG GCC GCC CTC TCG AGC GAC TGG ACC TTT GTG GAG AGC CAC ACC TTC GCG        1676
Arg Phe Thr Ala Ala Leu Ser Ser Asp Trp Thr Phe Val Glu Ser His Thr Phe Ala
                    400             405             410             415

TTG CAG AAT GTG CCG AGC GAC TGC TGT GTG ATC GAA GAG GCC GCC GCG GTC GAG            1733
Leu Gln Asn Val Pro Ser Asp Cys Cys Val Ile Glu Glu Ala Ala Ala Val Glu
            420             425             430

CGC GTC TAC CGC GAG CGC TAC AAC GGC ACG ACG CAC GTG CTG TCG GGC AGC TTG ACG        1790
Arg Val Tyr Arg Glu Arg Tyr Asn Gly Thr Thr His Val Leu Ser Gly Ser Leu Glu Thr
435             440             445             450
```

FIGURE 5C

```
TAC CTG GCG CGC GGC GGC TTT GTC GCC TTC CGG CCG ATG CTC AGC AAC GAG CTG     1847
Tyr Leu Ala Arg Gly Gly Phe Val Ala Phe Arg Pro Met Leu Ser Asn Glu Leu
455             460             465             470

GCC AAG CTG TAC CTG CAG GAG CTG GCC AAC GGC ACG CTC GAG GGG CTG TTC         1904
Ala Lys Leu Tyr Leu Gln Glu Leu Ala Asn Gly Thr Leu Glu Gly Leu Phe
    475             480             485             490

GCC GCC GCC CCC AAG CCG TTT GCC CGG CGC CCG ATG GCG GCG CCG TCT GCG         1961
Ala Ala Ala Pro Lys Pro Phe Ala Arg Arg Pro Met Ala Ala Pro Ser Ala
495             500             505             510

CCC GGC GGG CCC AAC GCG GCG CCC CCG CGC CGC GAC GCG GCC GGG GGG CGG         2018
Pro Gly Gly Pro Asn Ala Ala Pro Pro Arg Arg Asp Ala Ala Gly Gly Arg
515             520             525

GTG ACT GTG AGC TCG GAG GCG TTT GCC CTG CAG TTC CAG GGG GGA CAC ATC         2075
Val Thr Val Ser Ser Glu Ala Phe Ala Leu Gln Phe Gln Gly Gly His Ile
530             535             540             545

CAG GAC GTG AAC ACC ATG TTC GCC CTG CTG AGC TGC TGG TCC CCC AGC CTG CAG     2132
Gln Asp Val Asn Thr Met Phe Ala Leu Leu Ser Cys Trp Ser Pro Ser Leu Gln
550             555             560             565

AAC AAG GAG CTG TGG CGC GCT AAG CTC ATG GGG GAC GCC GCG ATG GCC GCC         2189
Asn Lys Glu Leu Trp Arg Ala Lys Leu Met Gly Asp Ala Ala Met Ala Ala
570             575             580             585

AGC GCT GCG CGC GAG GAC CGC CGC CGC CGC ATG TTG GGG GAC GCC GTG GCC GCC     2246
Ser Ala Ala Arg Glu Asp Arg Arg Arg Arg Met Leu Gly Asp Ala Val Ala Ala
590             595             600             605

ACG TAC TGC CAC GAG GGG CTG GAG GGG CGC GTG TTC ATC TCG ATG CGC GCG         2303
Thr Tyr Cys His Glu Gly Leu Glu Gly Arg Val Phe Ile Ser Met Arg Ala
610             615             620
```

FIGURE 5D

```
CCC GGC GTT TGC TAC AGC CGC CCG GTC TCC TTT GCC TTC GGC AAC GAG AGC              2360
Pro Gly Val Cys Tyr Ser Arg Pro Val Ser Phe Ala Phe Gly Asn Glu Ser
625             630             635             640

GAG CCG GTG GAG CCC TGC ACC GCC CAG CTC GGG CAG CTC CCG CCG GAG CTC              2417
Glu Pro Val Glu Pro Cys Thr Ala Gln Leu Gly Gln Leu Pro Pro Glu Leu
    645             650             655             660

GTG GAG AAC GCC ACC TGC CAA AAC CAC CGG TAC TTT CGC TTT GGC GCA GAG CTC          2474
Val Glu Asn Ala Thr Cys Gln Asn His Arg Tyr Phe Arg Phe Gly Ala Glu Leu
    665             670             675             680

TAC TAC AAC GCC TAC GCG CTA AAG CGG CGC TAC TAC CCG CCG TAC GAC GTG              2531
Tyr Tyr Asn Ala Tyr Ala Leu Lys Arg Arg Tyr Tyr Pro Pro Tyr Asp Val
                685             690             695             700

AGC ACC TTT GTG GAC CTA AAC CTC CCG CCG ACG GTT CTG GAG GCG CGA ATC             2588
Ser Thr Phe Val Asp Leu Asn Leu Pro Pro Thr Val Leu Glu Ala Arg Ile
        705             710             715             720

GAA GTG TAC ACG CGC AAC CAG CGC ATC CGC GAC ACG GGT TAC ACG TAC AGC GAG ATA     2645
Glu Val Tyr Thr Arg Asn Gln Arg Ile Arg Asp Thr Gly Tyr Thr Tyr Ser Glu Ile
            725             730             735

CAG CGC CGC AAC CAG CTG CAC CTG CTG GAG CTC CTC CGC GTC GTG GTC AAG            2702
Gln Arg Arg Asn Gln Leu His Leu Leu Glu Leu Leu Arg Val Val Val Lys
740             745             750             755

ACG GAC GGC AAT ATG GCC ATC GAC ATG CGA GGG CTC TTC TTC TTT CAG CTG GGC          2759
Thr Asp Gly Asn Met Ala Ile Asp Met Arg Gly Leu Phe Phe Phe Gln Leu Gly
    760             765             770             775

GCC GTC GGG CAG CAG GCG GCG ACG GTG GTG CTG GCG ATT GGT GCC GCC GCT CTC TCG    2816
Ala Val Gly Gln Gln Ala Ala Thr Val Val Leu Ala Ile Gly Ala Ala Ala Leu Ser
        780             785             790             795
```

FIGURE 5E

| | | | | | | | | | | | | | | | | | | | |
|---|---|---|---|---|---|---|---|---|---|---|---|---|---|---|---|---|---|---|---|
| ACC | GTG | TCG | GGC | ATC | GCC | TCG | TTT | ATT | GCG | AAC | CCG | TTC | GGC | GCG | CTG | GCC | ACG | GGG | 2873 |
| Thr | Val | Ser | Gly | Ile | Ala | Ser | Phe | Ile | Ala | Asn | Pro | Phe | Gly | Ala | Leu | Ala | Thr | Gly | |
| | | | | 800 | | | | | 805 | | | | | 810 | | | | | |
| CTG | CTG | CTC | GCC | GGG | CTG | GTG | GCC | TTC | CTG | GCG | GCT | TTC | CTG | TAC | ATT | TCC | CGC | | 2930 |
| Leu | Leu | Leu | Ala | Gly | Leu | Val | Ala | Phe | Leu | Ala | Ala | Phe | Leu | Tyr | Ile | Ser | Arg | | |
| 815 | | | | 820 | | | | | 825 | | | | | 830 | | | | | |
| CTC | CGC | AGC | AAC | CCC | ATG | AAG | GCG | CTG | TAC | CCG | ATC | ACC | ACG | CGC | GCG | CTC | AAG | GAC | 2987 |
| Leu | Arg | Ser | Asn | Pro | Met | Lys | Ala | Leu | Tyr | Pro | Ile | Thr | Thr | Arg | Ala | Leu | Lys | Asp | |
| 835 | | | | | 840 | | | | 845 | | | | | 850 | | | | | |
| GAC | GCC | CGG | GGC | GCA | ACC | GCC | CCG | GCC | CTG | GAG | GAA | GAG | GGC | TTT | GAC | GCG | GCC | AAA | 3044 |
| Asp | Ala | Arg | Gly | Ala | Thr | Ala | Pro | Ala | Leu | Glu | Glu | Glu | Gly | Phe | Asp | Ala | Ala | Lys | |
| | 855 | | | | | 860 | | | | 865 | | | | | 870 | | | | |
| CTG | GAG | CAG | GCC | CGC | GAG | ATG | ATC | AAG | TAT | ATG | TCG | CTC | GTG | TCA | GCG | GTC | GAG | CGG | 3101 |
| Leu | Glu | Gln | Ala | Arg | Glu | Met | Ile | Lys | Tyr | Met | Ser | Leu | Val | Ser | Ala | Val | Glu | Arg | |
| | | 875 | | | | | 880 | | | | 885 | | | | | 890 | | | |
| CAA | GAG | CAC | AAG | GCG | AAA | AAG | AGC | AAC | AAG | GGC | CCG | GGC | CTG | CTG | GCG | ACC | CGG | CTG | 3158 |
| Gln | Glu | His | Lys | Ala | Lys | Lys | Ser | Asn | Lys | Gly | Pro | Gly | Leu | Leu | Ala | Thr | Arg | Leu | |
| | | | | 895 | | | | | 900 | | | | | 905 | | | | | |
| ACG | CAG | GAG | CTT | CGG | CGG | CGA | CCG | GAG | TAC | CAG | CTT | CCG | ATG | GCC | | | | | 3215 |
| Thr | Gln | Glu | Leu | Arg | Arg | Arg | Pro | Glu | Tyr | Gln | Leu | Pro | Met | Ala | | | | | |
| 910 | | | | 915 | | | | | 920 | | | | | 925 | | | | | |
| GAC | GTC | GGG | GCA | TGAGGCCTAT GTATGGGCAG TTCGGGTGCC AATAATAAAT TTTGCGCGAA | | | | | | | | | | | | | | | 3280 |
| Asp | Val | Gly | Gly | Ala | | | | | | | | | | | | | | | |
| | | 930 | | | | | | | | | | | | | | | | | |

TCTTATTTAA GTGCACACCG TGTTATTTGC GGCTGTTTGT TTTTCCTGGA GGCGGGACGC TGCGCGCGAG 3350

CTCGGCCGGA TTAGGGTTCG GCGCCACCCG GG 3382

FIGURE 5F

```
BHV-1 gIII:Sequence Range: 1 to 1829
CGCGCCTGCA GCCGCGCGTG TGCTCAATCC CGGACCACGA AAGCACAAAA CGGACGCCCT TAAAAATGTA   70

GCCCGCGCCG CGGTCGCGGC CATCTTGGAT CCACCCGCGC GCACGACCGC CGAGAGACCG CCAGCCCGAG  140

ACCTCGCCGC GCGTCCGCC ATG GGC CCG CTG GGG CGA GCG TGG CTG ATC GCA GCT ATT TTC  201
                     Met Gly Pro Leu Gly Arg Ala Trp Leu Ile Ala Ala Ile Phe
                      1               5                  10

GCC TGG GCG CTC CTG TCT GCC CGG CGG GGG CTC GCC GAG GAG GCG GAA GCC TCG CCC  258
Ala Trp Ala Leu Leu Ser Ala Arg Arg Gly Leu Ala Glu Glu Ala Glu Ala Ser Pro
 15                  20                  25                  30

TCG CCT CCG CCC TCC CCG TGC CCA ACC GAG ACG GAA AGC TCC GCT GGG ACC ACC GGC  315
Ser Pro Pro Pro Ser Pro Cys Pro Thr Glu Thr Glu Ser Ser Ala Gly Thr Thr Gly
     35                  40                  45                  50

GCA ACG CCC CCC ACG CCC AAC AGC CCC GAC GCT ACG CCA GAG GAC AGC ACG CCC GGT  372
Ala Thr Pro Pro Thr Pro Asn Ser Pro Asp Ala Thr Pro Glu Asp Ser Thr Pro Gly
         55                  60                  65                  70

GCT ACT ACG CCC GTG GGG ACG CCG GAG CCG CCG TCC GTG TCC GAG CAC GAC CCG CCC  429
Ala Thr Thr Pro Val Gly Thr Pro Glu Pro Pro Ser Val Ser Glu His Asp Pro Pro
             75                  80                  85                  90
```

FIGURE 6A

```
GTT ACC AAC AGC ACG CCG CCC GCC CCG CCC GAG GAC GGG CGA CCC GGC GGC GCT    486
Val Thr Asn Ser Thr Pro Pro Ala Pro Pro Glu Asp Gly Arg Pro Gly Gly Ala
         95                 100                105

GGC AAC GCG AGC CGC GAT GGG CGA CCT AGC GGC GGG CGG CCT CGC CCG CCG CGG    543
Gly Asn Ala Ser Arg Asp Gly Arg Pro Ser Gly Gly Arg Pro Arg Pro Pro Arg
        110                 115                120                125

CCG AGC AAA GCC CCG AAG GAG CGC AAG TGG ATG CTC TGC GAG CGC GAG GCC GTG    600
Pro Ser Lys Ala Pro Lys Glu Arg Lys Trp Met Leu Cys Glu Arg Glu Ala Val
        130                 135                140                145

GCC GCC TCG TAC GCC CTG TAC GTG CAC TGC GGC GTG GCC GAC AAC GCC ACT        657
Ala Ala Ser Tyr Ala Leu Tyr Val His Cys Gly Val Ala Asp Asn Ala Thr
        150                 155                160            165

GGC GGT GCC CGC CTG GAG CTC TGG TTT CAG CGC GTG GGC AGG TTC CGC ACG CGC    714
Gly Gly Ala Arg Leu Glu Leu Trp Phe Gln Arg Val Gly Arg Phe Arg Thr Arg
        170                 175                180                185

GGC GAC GAG GCC GTG GCG CGC AAC CCC TTT CCG CGG GCC CCG GTG CTG CTG TTC    771
Gly Asp Asp Glu Val Ala Arg Asn Pro Phe Pro Arg Ala Pro Val Leu Leu Phe
        190                 195                200
```

FIGURE 6B

```
GTA GCC CAG AAC GGC TCG ATC GCG TAC CGT AGC GCG GAG CTG GGC GAC AAC TAT ATT    828
Val Ala Gln Asn Gly Ser Ile Ala Tyr Arg Ser Ala Glu Leu Gly Asp Asn Tyr Ile
205                 210                 215                 220

TTC CCT TCG CCC GCC GAC CCC CGC AAC TTG CCC CTG ACC GTG CGC TCC CTG ACG GCC    885
Phe Pro Ser Pro Ala Asp Pro Arg Asn Leu Pro Leu Thr Val Arg Ser Leu Thr Ala
        225                 230                 235                 240

GCC ACC GAG GGC GTG TAC ACT TGG CGC GAC ATG GGC ACC AAG TCA CAG CGC AAG        942
Ala Thr Glu Gly Val Tyr Thr Trp Arg Asp Met Gly Thr Lys Ser Gln Arg Lys
            245                 250                 255                 260

GTC GTG ACC GTC ACG CAC CGC GCG CCC GCT GTT TCC GTC GAA CCC CAG CCA GCG        999
Val Val Thr Val Thr His Arg Ala Pro Ala Val Ser Val Glu Pro Gln Pro Ala
                265                 270                 275                 280

CTA GAA GGC GGC GCC GGC TAC GCG GTG TGC CGC GCC GCC GAG TAC TAC CCG CCG CGC   1056
Leu Glu Gly Gly Ala Gly Tyr Ala Val Cys Arg Ala Ala Glu Tyr Tyr Pro Pro Arg
                    285                 290                 295

TCC ACG CGC CTG CAC TGG TTC CGC AAC GGC TAC CCC GTG GAG GCT CGG CAC GCG CGC   1113
Ser Thr Arg Leu His Trp Phe Arg Asn Gly Tyr Pro Val Glu Ala Arg His Ala Arg
300                 305                 310                 315
```

FIGURE 6C

```
GAC GTC TTT ACG GTC GAC GAC TCC GGG CTC TTT TCG CGC ACG TCC GTC CTT ACG CTC    1170
Asp Val Phe Thr Val Asp Asp Ser Gly Leu Phe Ser Arg Thr Ser Val Leu Thr Leu
320                     325                 330                 335

GAG GAC GCG ACG CCA ACC GCC CAC CCG AAC CTG CGC GAC TGC GAC GTC TCC TGG TTC    1227
Glu Asp Ala Thr Pro Thr Ala His Pro Asn Leu Arg Cys Asp Val Ser Trp Phe
        340                 345                 350                 355

CAG AGC GCT AAC ATG GAG CGC CGC TTT TAC GCT GGC ACG CCG GCC GTT TAC CGC        1284
Gln Ser Ala Asn Met Glu Arg Arg Phe Tyr Ala Ala Gly Thr Pro Ala Val Tyr Arg
            360                 365                 370                 375

CCG CCC GAG CTG CGC TAC TTC GAG GGC GGC GGG GGC GTC TGC GAG GCG CGC TGC        1341
Pro Pro Glu Leu Arg Val Tyr Phe Glu Gly Gly Gly Val Cys Glu Ala Arg Cys
        380                 385                 390

GTC CCC GAG GGG CGC GTC TCC CTG CGC TGG ACG GTG CGC GAC GGC ATC GCC CCG TCG    1398
Val Pro Glu Gly Arg Val Ser Leu Arg Trp Thr Val Arg Asp Gly Ile Ala Pro Ser
395                 400                 405                 410

CGC ACT GAG CAG ACC GGC GTC TGC GCC GAG CGG CCC GGG CTG GTA AAC CTG CGC GGC    1455
Arg Thr Glu Gln Thr Gly Val Cys Ala Glu Arg Pro Gly Leu Val Asn Leu Arg Gly
415                 420                 425                 430
```

FIGURE 6D

```
GTG CGC CTG CTT TCT ACA ACC GAC TAC ACC GCC ACT GGC    1512
Val Arg Leu Leu Ser Thr Thr Asp Tyr Thr Ala Thr Gly
435                 440                 445         450

TAC CCG GCA CCG CTG CCC GAG TTC TCC GCG ACC TAC GAC GCC TCG CCC GGC    1569
Tyr Pro Ala Pro Leu Pro Glu Phe Ser Ala Thr Tyr Asp Ala Ser Pro Gly
        455                 460                 465                 470

CTA ATC GGA AGC CCC GTC CTC GTC AGC GTC GCC TGC GGT CTC GGC GCC    1626
Leu Ile Gly Ser Pro Val Leu Val Ser Val Ala Cys Gly Leu Gly Ala
        475                 480                 485

GTG GGG CTC CTG CTG GTG GCG GCC TCG TGC CTG CGG AAG CGC GTA ATC CAA    1683
Val Gly Leu Leu Leu Val Ala Ala Ser Cys Leu Arg Arg Lys Ala Arg Val Ile Gln
490                 495                 500                 505

CCC GGT CTT ACT CGC GCT CGC GCC CTC GGC TCC GCG CCC TAGAGACCG GCACGGCCTG    1742
Pro Gly Leu Thr Arg Ala Arg Ala Leu Gly Ser Ala Pro
510                 515                 520

GAGGCGCTGG CGGCTGCCGG TGCCGCTCAC ACCGGCGCC ACAACCGCGA CGTGTGGCGG CGCTTTTCCC    1812

GCGTCTGCGA GGCCGGC    1829
```

FIGURE 6E

```
BHV-1 gIV:Sequence Range: 1 to 1405
GGGCCGCAGC CCCGGCTGGG TATATATCCC CGACGGGCGA CTAGAGATAC ACTCGCCCCG CGCGGCTGCT     70

GCGAGCGGGC GAAC ATG CAA GGG CCG ACA TTG GCC GTG CTG GGC GCG CTG CTC GCC GTT     129
                Met Gln Gly Pro Thr Leu Ala Val Leu Gly Ala Leu Leu Ala Val
                 1               5                  10                  15

GCG GTG AGC TTG CCT ACA CCC GCG CCG CGG GTG ACG GTA TAC GTC GAC CCG CCG GCG     186
Ala Val Ser Leu Pro Thr Pro Ala Pro Arg Val Thr Val Tyr Val Asp Pro Pro Ala
                 20                  25                  30

TAC CCG ATG CCG CGA TAC AAC TAC ACT GAA CGC TGG CAC ACT ACC GGG CCC ATA CCG     243
Tyr Pro Met Pro Arg Tyr Asn Tyr Thr Glu Arg Trp His Thr Thr Gly Pro Ile Pro
 35                  40                  45                  50

TCG CCC TTC GCA GAC GGC CGC GAG CAG CCC GTC GAG GTG CGC TAC GCG ACG AGC GCG     300
Ser Pro Phe Ala Asp Gly Arg Glu Gln Pro Val Glu Val Arg Tyr Ala Thr Ser Ala
     55                  60                  65                  70

GCG GCG TGC GAC ATG CTG GCG CTG ATC GCA GAC CCG CAG GTG GGG CGC ACG CTG TGG     357
Ala Ala Cys Asp Met Leu Ala Leu Ile Ala Asp Pro Gln Val Gly Arg Thr Leu Trp
         75                  80                  85                  90
```

FIGURE 7A

```
GAA GCG GTA CGC CGG CAC GCG CGC TAC AAC GCC ACG GTC ATA TGG TAC AAG ATC    414
Glu Ala Val Arg Arg His Ala Arg Tyr Asn Ala Thr Val Ile Trp Tyr Lys Ile
             95              100             105             110

GAG AGC GGG TGC GCC CGG CCG CTG TAC TAC ATG GAG TAC ACC GAG TGC GAG CCC AGG    471
Glu Ser Gly Cys Ala Arg Pro Leu Tyr Tyr Met Glu Tyr Thr Glu Cys Glu Pro Arg
             115             120             125

AAG CAC TTT GGG TAC TGC CGC TAC CGC ACA CCC CCG TTT TGG GAC AGC TTC CTG GCG    528
Lys His Phe Gly Tyr Cys Arg Tyr Arg Thr Pro Pro Phe Trp Asp Ser Phe Leu Ala
130              135             140             145

GGC TTC GCC TAC CCC ACG GAC GAG CTG GGA CTG ATT ATG GCG GCG CCC GCG CGG    585
Gly Phe Ala Tyr Pro Thr Asp Glu Leu Gly Leu Ile Met Ala Ala Pro Ala Arg
        150             155             160             165

CTC GTC GAG GGC CAG TAC CGA CGC GCG CTG TAC ATC GAC GGC ACG GTC GCC TAT ACA    642
Leu Val Glu Gly Gln Tyr Arg Arg Ala Leu Tyr Ile Asp Gly Thr Val Ala Tyr Thr
        170             175             180             185

GAT TTC ATG GTT TCG CTG CCG GCC GGG GAC TGC TGG TTC TCG AAA CTC GGC GCG GCT    699
Asp Phe Met Val Ser Leu Pro Ala Gly Asp Cys Trp Phe Ser Lys Leu Gly Ala Ala
        190             195             200             205
```

FIGURE 7B

```
CGC GGG TAC ACC TTT GGC GCG TGC TTC CCG GCC CGG GAT TAC GAG CAA AAG AAG GTT      756
Arg Gly Tyr Thr Phe Gly Ala Cys Phe Pro Ala Arg Asp Tyr Glu Gln Lys Lys Val
            210                     215                     220

CTG CGC CTG ACG TAT CTC ACG CAG TAC TAC CCG CAG GAG GCA CAC AAG GCC ATA GTC      813
Leu Arg Leu Thr Tyr Leu Thr Gln Tyr Tyr Pro Gln Glu Ala His Lys Ala Ile Val
225                     230                     235                     240

GAC TAC TGG TTC ATG CGC CAC GGG GGC GTC GTT CCG TAT TTT GAG GAG TCG AAG          870
Asp Tyr Trp Phe Met Arg His Gly Gly Val Val Pro Tyr Phe Glu Glu Ser Lys
            245                     250                     255         260

GGC TAC GAG CCG CCG CCT GCC GCC GAT GGG GGT TCC CCC GCG CCA CCC GGC GAC GAC      927
Gly Tyr Glu Pro Pro Pro Ala Ala Asp Gly Gly Ser Pro Ala Pro Pro Gly Asp Asp
265                     270                     275                     280

GAG GCC CGC GAG GAT GAA GGG GAG ACC GAG GAC GGG GCA GCC GGG CGG GAG GGC AAC      984
Glu Ala Arg Glu Asp Glu Gly Glu Thr Glu Asp Gly Ala Ala Gly Arg Glu Gly Asn
            285                     290                     295         300

GGC GGC CCC CCA GGA CCC GAA GGC GAC GGG GAG AGT CAG ACC CCC GAA GCC AAC GGA      1041
Gly Gly Pro Pro Gly Pro Glu Gly Asp Gly Glu Ser Gln Thr Pro Glu Ala Asn Gly
305                     310                     315
```

FIGURE 7C

```
GGC GCC GAG GGC GAG CCG AAA CCC GGC CCC AGC CCC GAC GCC GAC CGC CCC GAA GGC      1098
Gly Ala Glu Gly Glu Pro Lys Pro Gly Pro Ser Pro Asp Ala Asp Arg Pro Glu Gly
320                 325                 330                 335

TGG CCG AGC CTC GAA GCC ATC ACG CAC CCC CCG GCC CCC GCT ACG CCC GCG GCC          1155
Trp Pro Ser Leu Glu Ala Ile Thr His Pro Pro Ala Pro Ala Thr Pro Ala Ala
340                 345                 350                 355

CCC GAC GCC GTG CCG GTC AGC GTC GGG ATC GGC ATT GCG GCT GCG GCG ATC GCG TGC      1212
Pro Asp Ala Val Pro Val Ser Val Gly Ile Gly Ile Ala Ala Ala Ala Ile Ala Cys
360                 365                 370                 375

GTG GCC GCC GCC GCC GCC GGC GCG TAC TTC GTC TAT ACG CGC CGG CGC GGT GCG GGT      1269
Val Ala Ala Ala Ala Ala Gly Ala Tyr Phe Val Tyr Thr Arg Arg Arg Gly Ala Gly
380                 385                 390                 395

CCG CTG CCC AGA AAG CCA AAA AAG CTG CCG GCC TTT GGC AAC TAC AGC GCG            1326
Pro Leu Pro Arg Lys Pro Lys Lys Leu Pro Ala Phe Gly Asn Val Asn Tyr Ser Ala
400                 405                 410

CTG CCC GGG TGAGCGGGCCT AGGCCCTCCC CCGACCGCCC CCTTTGCTCC TAGCCCCGGC TCCTGCCGAG   1395
Leu Pro Gly
415

CCGCGCGGGG                                                                       1405
```

FIGURE 7D

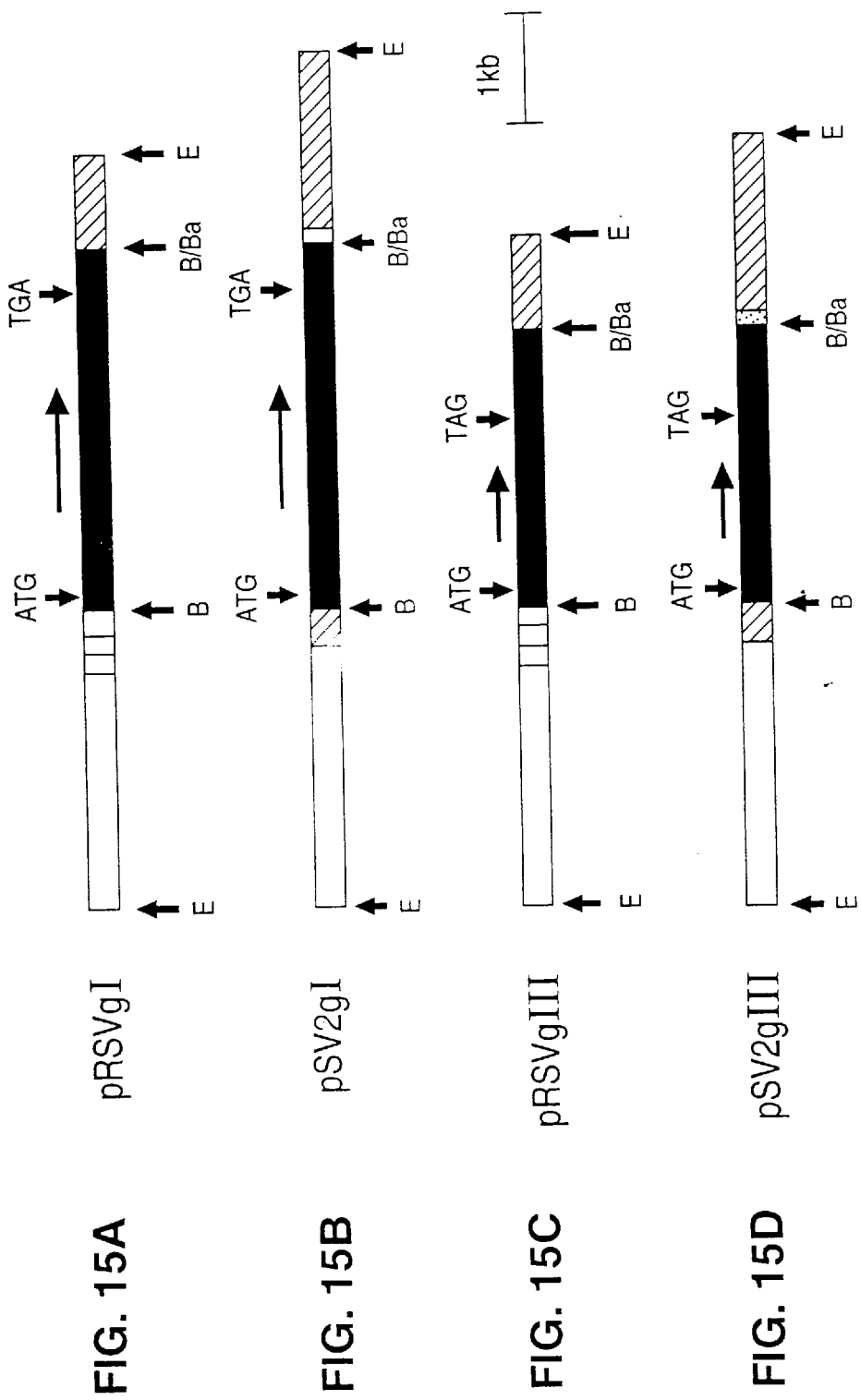
FIG. 15A  pRSVgI
FIG. 15B  pSV2gI
FIG. 15C  pRSVgIII
FIG. 15D  pSV2gIII

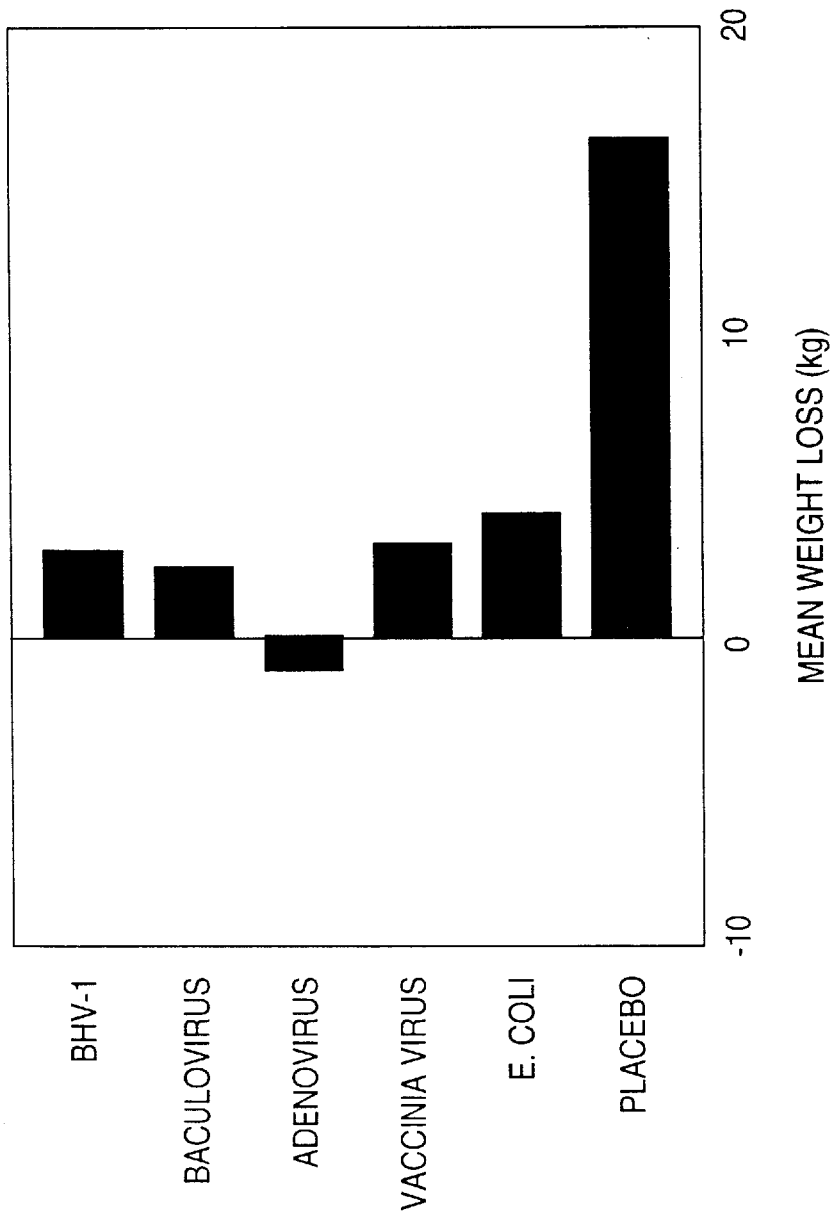

```
MAARGGAERA  AGAGDGRRGQ  RRHLRPGRVL  AALRGPAAPG   40
AGGARAAHAA  ALLWATWALL  LAAPAAGRPA  TTPPAPPPEE   80
                              RPA  TTPPAPPPEE
                       Signal ↑
AASPAPPASP  SPPGPDGDDA  ASPDNSTDVR  AALRLAQAAG  120
AASPAP
ENSRFFVCPP  PSGATVVRLA  PARPCPEYGL  GRNYTEGIGV  160
IYKENIAPYT  FKAYIYYKNV  IVTTTWAGST  YAAITNQYTD  200
RVPVGMGEIT  DLVDKKWRCL  SKAEYLRSGR  KVVAFDRDDD  240
PWEAPLKPAR  LSAPGVRGWH  TTDDVYTALG  SAGLYRTGTS  280
VNCIVEEVEA  RSVYPYDSFA  LSTGDIIYMS  PFYGLREGAH  320
REHTSYSPER  FQQIEGYYKR  DMATGRRLKE  PVSRNFLRTQ  360
HVTVAWDWVP  KRKNVCSLAK  WREADEMLRD  ESRGNFRFTA  400
RSLSATFVSD  SHTFALQNVP  LSDCVIEEAE  AAVERVYRER  440
YNGTHVLSGS  LETYLARGGF  VVAFRPMLSN  ELAKLYLQEL  480
ARSNGTLEGL  FAAAAPKPGP  RRARRAAPSA  PGGPGAANGP  520
                              ↑AAPSA  PGGPGAA
                         gIb        gIc
                          ←          →
AGDGDAGGRV  TTVSSAEFAA  LQFTYDHIQD  HVNTMFSRLA  560
TSWCLLQNKE  RALWAEAAKL  NPSAAASAAL  DRRAAARMLG  600
DAMAVTYCHE  LGEGRVFIEN  SMRAPGGVCY  SRPPVSFAFG  640
NESEPVEGQL  GEDNELLPGR  ELVEPCTANH  KRYFRFGADY  680
VYYENYAYVR  RVPLAELEVI  STFVDLNLTV  LEDREFLPLE  720
VYTRAELADT  GLLDYSEIQR  RNQLHELRFY  DIDRVVKTDG  760
NMAIMRGLAN  FFQGLGAVGQ  AVGTVVLGAA  GAALSTVSGI  800
ASFIANPFGA  LATGLLVLAG  LVAAFLAYRY  ISRLRSNPMK  840
ALYPITTRAL  KDDARGATAP  GEEEEEFDAA  KLEQAREMIK  880
YMSLVSAVER  QEHKAKKSNK  GGPLLATRLT  QLALRRRAPP  920
EYQQLPMADV  GGA                                 933
```

FIGURE 30

VACCINES COMPRISING NUCLEOTIDE SEQUENCES ENCODING BOVINE HERPESVIRUS TYPE 1 G1, G1ll AND GlV

CROSS REFERENCE TO RELATED APPLICATION

This application is a Divisional of application Ser. No. 07/921,1992, now U.S. Pat. No. 5,585,265, which is a continuation-in-part of U.S. patent application Ser. No. 07/805,524, filed Dec. 11, 1991, now abadoned which is a continuation-in-part of U.S. patent application Ser. No. 07/219,939, filed Jul. 15, 1988, now U.S. Pat. No. 5,151,267 both of which are incorporated herein by reference in its entirety and from which priority is claimed pursuant to 35 USC §120.

TECHNICAL FIELD

The present invention relates generally to the prevention of disease in cattle. More particularly, the instant invention is directed to the recombinant production of bovine herpesvirus type 1 antigens for use in subunit vaccines to protect cattle against bovine herpesvirus type 1 infection.

BACKGROUND

Bovine herpesvirus type 1 (BHV-1) is an economically significant pathogen of cattle. BHV-1, which is also known as infectious bovine rhinotracheitis virus, causes severe respiratory infections, conjunctivitis, vulvovaginitis, abortions, encephalitis, and generalized systemic infections. If an animal recovers from a primary infection, the virus remains in the host in a latent state. Reactivation of the virus can be provoked by certain endogenous or exogenous physical modifications in the animal, or experimentally by treatment of the animal with glucocorticoids like dexamethasone.

In an effort to control BHV-1 infections, killed virus and attenuated live-virus vaccines have been developed. While these vaccines appear to induce some level of protection in cattle, the level of immunity is well below that necessary to afford complete or near-complete protection. For example, the vaccines do not always prevent the establishment of a latent infection by a virulent field strain of BHV-1. Furthermore, the safety of the live-virus vaccines has been questioned. It has been shown recently that two live BHV-1 vaccine strains can be reactivated by the use of dexamethasone, indicating that at Least some BHV-1 vaccines can themselves establish a latent infection. See, e.g., Gerber et al. (1978) Am. J. Vet. Res. 39:753–760; Jericho et al. (1983) Can. J. Com. Med. 47:133–139; Pastoret et al. (1980) Infect. Immun. 29:483–488. Subunit vaccines, i.e. vaccines including select proteins separated from the whole virus, afford a method for overcoming the problems inherent in the use of live and attenuated virus vaccines.

Several polypeptides of BHV-1 have now been studied. Misra et al. (1981) J. Virol. 40:367–378, reports on the partial characterization of a number of BHV-1 polypeptides and their immunoprecipitation with antiserum. van Drunen Littel-van den Hurk et al. (1984) Virology 135:466–479 and van Drunen Littel-van den Hurk et al. (1985) Virology 144:216–227 are directed to monoclonal antibodies developed against BHV-1 glycoproteins, and the ability of the monoclonal antibodies to neutralize virus and participate in antibody-dependent complement-mediated lysis in vitro. See also Collins et al. (1984) J. Viriol. 52:403–409; Okazaki et al. (1986) Virology 150:260–264. van Drunen Littel-van den Hurk et al. (1985) Virology 144:204–215 is directed to the purification of BHV-1 glycoproteins by immunoadsorbent chromatography and the production of antiserum in rabbits. van Drunen Littel-van den Hurk et al. (1986) J. Clin. Microbiol. 23:274–282 is directed to in vitro immunoreactivity of purified BHV-1 glycoproteins and bovine antiserum. Okazaki et al. (1987) Arch. Virol. 92:17–26 pertains to in vitro studies of the reactivities of monoclonal antibodies against BHV-1 glycoproteins with infected cells. Babiuk et al. (1987) Virology 159:57–66 relates to the purification of gI, gIII and gIV from virus infected cell lysates. This reference also discloses that gI of BHV-1 corresponds to gB of herpes simplex virus (HSV); gIII corresponds to gC; and gIV corresponds to gD. Purified gI, gIII and gIV have been shown to induce high levels of neutralizing antibody in cattle and participate in antibody dependent cell cytotoxicity of BHV-1 cells. The purified glycoproteins were also shown to protect cattle from disease. Babiuk et al. (1987) Virology 159:57–66. van Drunen Littel-van den Hurk et al. (1990) Vaccine 8:358–368 confirmed the protectivity of gI, gIII and gIV and studied the epitope specificity of the immune response to the glycoprotein vaccines. Hughes et al. (1988) Arch. Virol. 103:47–60 identified three neutralizing antigenic domains on gIV.

None of the above art, however, discloses the recombinant production of BHV-1 glycoproteins for use in recombinant vaccines. Mayfield et al. (1983) J. Virol. 47:259–264 discloses the cloning of a BHV-1 strain and a restriction map. Fitzpatrick et al. (1989) Virology 173:46–57, describe the nucleotide sequence of gIII. Pachl et al. (1987) J. Virol. 61:315–325 describe the recombinant expression of a glycoprotein from the human pathogen HSV-1. There was no demonstration, however, that the recombinant polypeptide from the human virus was, in fact, protective in a human host. See also PCT Pub. No. WO88/02634; U.S. Pat. Nos. 4,661,349; 4,642,333.

Fitzpatrick et al. (1988) J. Virol. 62:4239–4248 describe the expression of gI and gIII in murine LMTK- cells. The transfected cells were shown to stimulate the production of neutralizing antibodies in mice. Fitzpatrick et al. (1990) describe the expression of deleted, truncated and hybrid forms of gI and gIII in murine LMTK-cells and epitope mapping of the same. Tikoo et al. (1990) J. Virol. 64:5132–5142 disclose the mapping, cloning and sequencing of BHV-1 gIV, as well as the expression of gIV in bovine cells. van Drunen Littel-van den Hurk et al. (1989) J. Virol. 63:2159–2168 disclose the expression of gI and gIII in a vaccinia virus vector. The recombinant vectors elicited a neutralizing antibody response in cattle immunized with the same. van Drunen Littel-van den Hurk et al. (January 1991) J. Virol. 65:263–271 describe the expression of gIV by recombinant baculovirus. This disclosure was based in part on the present invention. Cattle immunized with recombinant gIV raised neutralizing antibodies thereto.

DISCLOSURE OF THE INVENTION

It has been discovered that recombinant subunit vaccines, based on selected BHV-1 glycoproteins, will protect cattle from disease. These vaccines are particularly useful in protecting cattle from the shipping fever complex syndrome which often includes infection by BHV-1. Surprising, these subunit vaccines are substantially more protective than prior art killed virus and attenuated live-virus vaccines. The recombinant subunit vaccines do not suppress the immunological response to other components often found in multivalent shipping fever vaccines. Further, the recombinant subunit vaccines of the present invention also eliminate the risk of infection from the live-virus vaccines. It has also been discovered that recombinant BHV-1 polypeptides maintain the proper epitopes necessary to protect immunized animals from disease. Both nonglycosylated polypeptides, and polypeptides glycosylated by heterologous host organisms, effectively elicit antibodies that neutralize virus infectivity and induce complement-mediated cell lysis. Based on these discoveries, the present invention can take several embodiments.

In one embodiment, the present invention is directed to a vaccine composition comprising a pharmaceutically acceptable vehicle and at least one recombinant subunit antigen. The recombinant subunit antigen comprises one or more neutralizing epitopes of a bovine herpesvirus type 1 (BHV-1) glycoprotein. The glycoprotein selected from the group consisting of BHV-1 gI, BHV-1 gIII and BHV-1 gIV.

In other embodiments, the subject invention is directed to nucleotide sequences encoding proteins substantially homologous and functionally equivalent to BHV-1 gI, BHV-1 gIII, BHV-1 gIV, or immunogenic fragments thereof.

In yet other embodiments the subject invention is directed to DNA constructs comprising an expression cassette comprised of:

(a) a DNA coding sequence for a polypeptide containing at least one neutralizing epitope of a BHV-1 glycoprotein. The glycoprotein is selected from the group consisting of gI, gIII and gIV; and (b) control sequences that are operably linked to the coding sequence whereby the coding sequence can be transcribed and translated in a host cell, and at least one of the control sequences is heterologous to the coding sequence.

In another embodiment, the present invention is directed to host cells stably transformed by the above DNA constructs.

In still another embodiment, the subject invention is directed to methods of producing recombinant polypeptides comprising:

(a) providing a population of the above host cells; and (b) growing the population of cells under conditions whereby the polypeptide encoded by the expression cassette is expressed.

In another embodiment, the instant invention is directed to methods of treating or preventing BHV-1 infection in a bovine host comprising administering to the bovine host a therapeutically effective amount of a vaccine compositions described above.

A particular recombinant BHV-1 gI has a molecular weight of about 116 kDa and is partially cleaved to 63 kDa (gIb) and 52 kDa (gIc) subunits.

These and other embodiments of the present invention will readily be apparent to those of skill in the art from the following disclosure.

BRIEF DESCRIPTION OF THE FIGURES

FIG. 5 shows the nucleotide sequence (SEQ ID NO:1) and deduced amino acid sequence (SEQ ID NO:2) from a viral clone of the gI gene. This gene encodes the gIa/gIb/gIc complex. The gIa precursor is cleaved into two peptides, gIb and gIc, which are linked by disulfide bonds to produce mature gIa. The gIb peptide is 438 amino acids long and encoded at the N-terminus of the gI gene. The gIc peptide is 428 amino acids long and encoded at the C-terminus of the gI gene. Right-angle arrows show the start of the gIb and gIc peptides, and putative transmembrane sequences are underlined. See Example II.B.1.

FIG. 6 is the nucleotide sequence (SEQ ID NO:3) and deduced amino acid sequence (SEQ ID NO:4) from a viral clone of gIII. The gene encodes a 521 amino acid peptide. Putative transmembrane sequences are underlined. See Example II.B.1.

FIG. 7 is the nucleotide sequence (SEQ ID NO:5) and deduced amino acid sequence (SEQ ID NO:6) from a viral clone of gIV. The gene encodes a peptide 417 amino acids long. The right-angle arrow marks the position of the mature gIV sequence. Putative transmembrane sequences are underlined.

FIG. 15 shows the restriction maps for various SV40 expression vectors. 15A shows the restriction map for pRS-VgI; 15B for pSV2gI; 15C for pRSVgIII; and 15D for pSV2gIII. The origins of the DNA sequences are represented as follows: pBR322 (open boxes), Rous sarcoma virus (vertically hatched boxes), SV40 virus (diagonally hatched boxes), BHV-1 (solid boxes) and Tn5 (stippled boxes). The start and stop codons of gI and gIII are arrowed in the direction of transcription from the Rous sarcoma and SV40 virus promoters. Restriction endonuclease cleavage sites are indicated by letters: E=EcoRI, B=BglII, B/Ba=BglII-BamHI sites destroyed by ligation. See Example III.

FIG. 16 shows the immune response of calves to partially purified recombinant gIV in Emulsigen PLUS or Avridine, affinity-purified authentic gIV in Avridine, commercially available killed BHV-1 vaccine, and placebo containing AcNPV-infected SF9 cells. The bars in the graph show the data for the various immunogens left to right as follows: recombinant gIV from schematically, at the top of the figure, with signal sequence , transmembrane anchor sequence , cysteine residues (S) and potential N-linked glycosylation sites (↑). Deleted or truncated forms of gIV are shown below the diagram of intact gIV with the deleted regions indicated by solid line (). The name given to each mutant protein is indicated on the right.

Figure 34A:
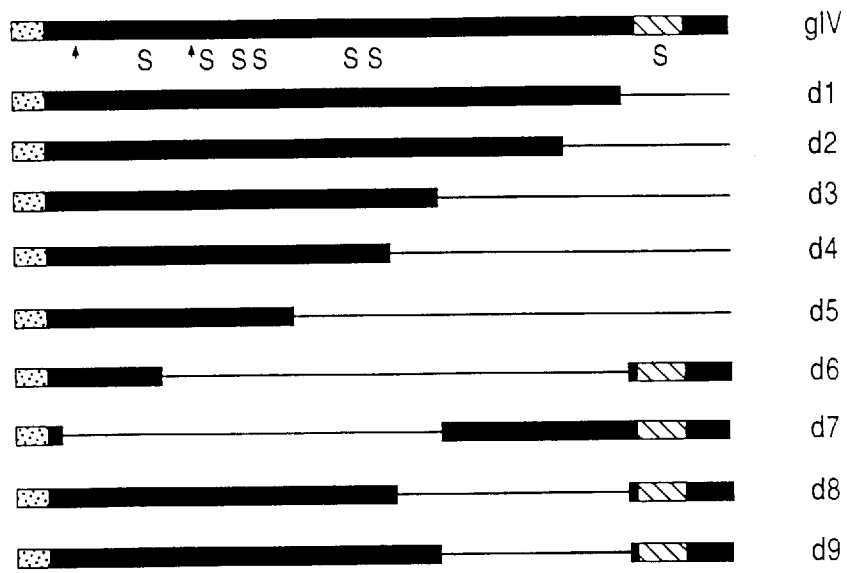
Figure 34B:
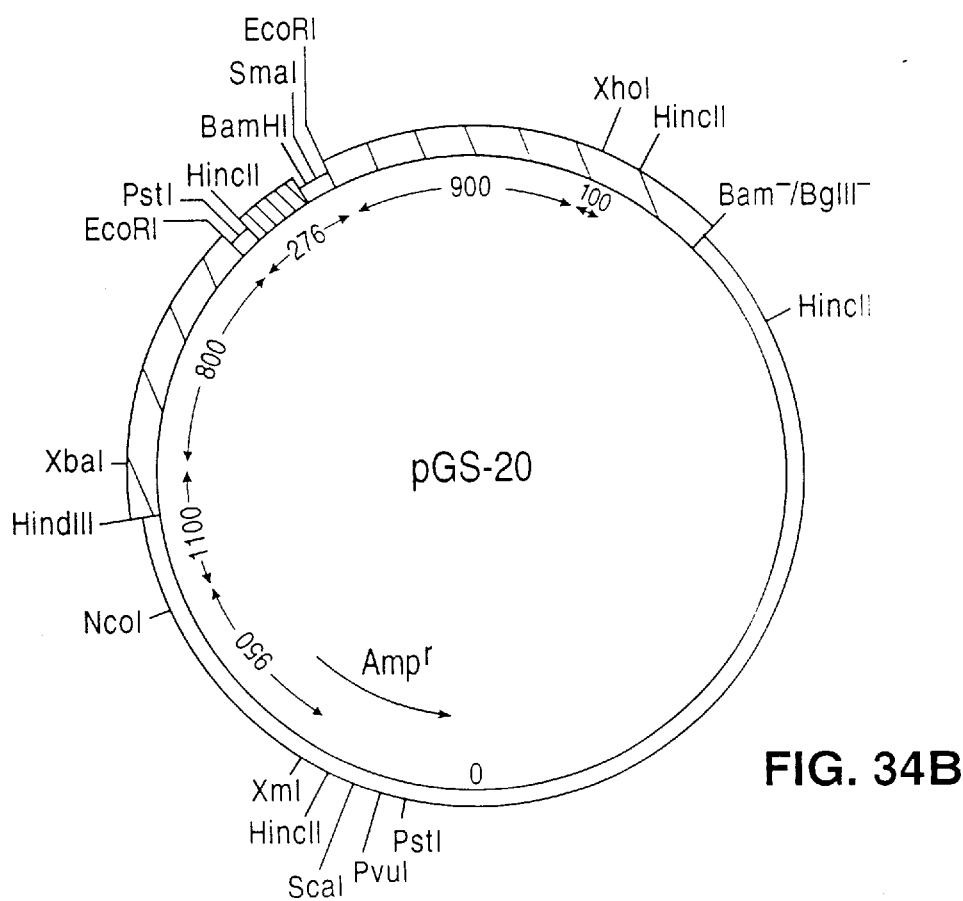

FIG. 34(b). Diagram of vaccinia virus transfer plasmid pGS20. The origin of DNA sequences included in the plasmid are as follows: pBR322 ; vaccinia virus P7.5 promoter ; viccinia virus thymidine kinase gene . Two unique cloning sites SmaI and BamHI are also depicted.

Figure 35:
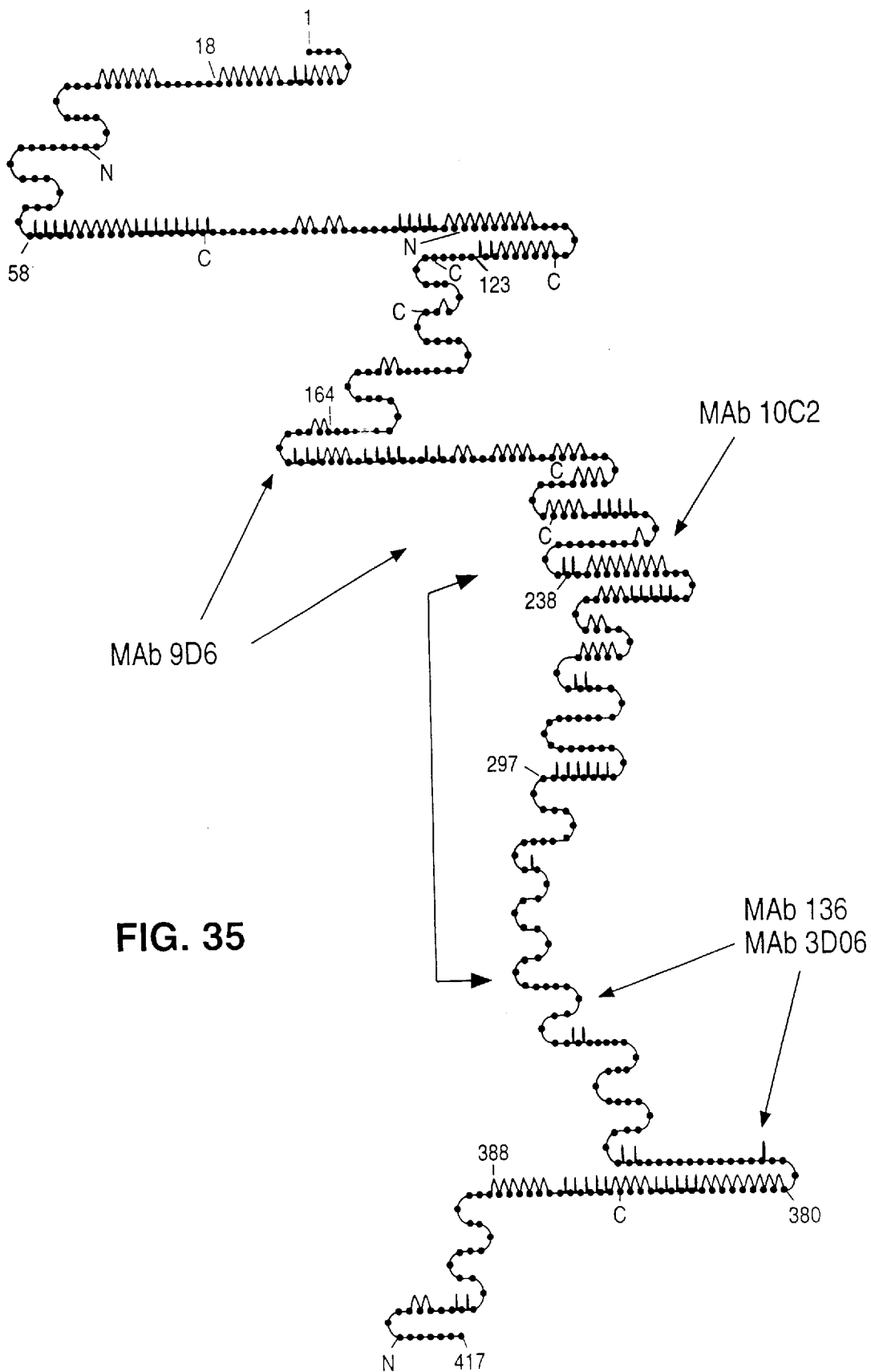

FIG. 35. Predicted secondary structure of BHV-1 gIV. The deduced amino acid sequence of gIV was analysed for alpha-helix, beta sheet, and beta turn probabilities using a version of algorithm of Chou and Fasman. Segments of alpha-helix, are looped, segments of beta sheets are zig-zagged, and beta turns are indicated as bends. Cysteine residues (C) and potential N-linked glycosylation sites (N) are indicated. The approximate location of the mapped epitopes is indicated by arrows whereas the region of the gIV required for proper processing and transport marked by bracket.

DETAILED DESCRIPTION

The practice of the present invention will employ, unless otherwise indicated, conventional virology, microbiology, molecular biology and recombinant DNA techniques within the skill of the art. Such techniques are explained fully in the literature. See, e.g., Sambrook, et al., *Molecular Cloning: A Laboratory Manual* (2nd Edition, 1989); Maniatis et al., *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984).

All patents, patent applications and publications cited herein, whether supra or infra, are hereby incorporated by reference in their entirety.

A. Definitions

The following terminology will be used in ac- cordance with the definitions set out below in describing the present invention.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A polyadenylation signal and transcription termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but now always, contain "TATA" boxes and "CAT" boxes. Procaryotic promoters contain Shine-Dalgarno sequences in addition to the −10 and −35 consensus sequences.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" or "under the control of" control sequences in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

A "clone" is a population of cells derived from a single cell or common ancestor by mitosis. A "cell line" is a clone of a primary cell that is capable of stable growth in vitro for many generations.

Two DNA or polypeptide sequences are "substantially homologous" when at least about 85% (preferably at least about 90%, and most preferably at least about 95%) of the nucleotides or amino acids match over a defined length of the molecule. DNA sequences that are substantially homologous can be identified in a Southern hybridization experiment under, for example, stringent conditions, as defined for that particular system. Defining appropriate hybridization conditions is within the skill of the art. See, e.g., Maniatis et al., supra; *DNA Cloning*, vols I & II, supra; *Nucleic Acid Hybridization*, supra.

The term "functionally equivalent" intends that the amino acid sequence of the subject protein is one that will elicit an immunological response, as defined below, equivalent to the specified BHV-1 immunogenic polypeptide.

A "heterologous" region of a DNA construct is an identifiable segment of DNA within or attached to another DNA molecule that is not found in association with the other molecule in nature. Thus, when the heterologous region encodes a viral gene, the gene will usually be flanked by DNA that does not flank the viral gene in the genome of the source virus or virus-infected cells. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

A composition containing molecule A is "substantially free of" molecule B when at least about 75% by weight of the total of A+B in the composition is molecule A. Preferably, molecule A comprises at least about 90% by weight of the total of A+B in the composition, more preferably at least about 99% by weight.

"Bovine host" refers to cattle of any breed for which it may be desirable to immunize against BHV-1 infection, whether or not the bovine host is already infected or latently infected by BHV-1. A bovine host can be of any age. Thus, the term encompasses calves as well as adult cattle.

The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like. A "glycoprotein" is a glycosylated polypeptide.

"Native" proteins or polypeptides refer to proteins or polypeptides recovered from BHV-1 virus or BHV-1-infected cells. Thus, the term "native BHV-1 polypeptide" would include naturally occurring BHV-1 proteins and fragments thereof. "Non-native" polypeptides refer to polypeptides that have been produced by recombinant DNA methods or by direct synthesis. "Recombinant" polypeptide!s refer to polypeptides produced by recombinant DNA techniques; i.e., produced from cells transformed by an exogenous DNA construct encoding the desired polypeptide.

An "antigen" refers to a molecule containing one or more epitopes that will stimulate a host's immune system to make a humoral and/or cellular antigen-specific response. The term is also used interchangeably with "immunogen."

By "subunit antigen" is meant an antigen entity separate and discrete from a whole virus (live or killed). Thus, an antigen contained in a cell free extract would constitute a "subunit antigen" as would a substantially purified antigen.

A "hapten" is a molecule containing one or more epitopes that does not stimulate a host's immune system to make a humoral or cellular response unless linked to a carrier.

The term "epitope" refers to the site on an antigen or hapten to which a specific antibody molecule binds. The term is also used interchangeably with "antigenic determinant" or "antigenic determinant site."

An "immunological response" to a composition or vaccine is the development in the host of a cellular and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

The terms "immunogenic polylpeptide" and "immunogenic amino acid sequence" refer to a polypeptide or amino acid sequence, respectively, which elicit antibodies that neutralize viral infectivity, and/or mediate antibody-complement or antibody dependent cell cytotoxicity to provide protection of an immunized host. An "immunogenic polypeptide" as used herein, includes the full length (or near full length) sequence of the desired BHV-1 glycoprotein or an immunogenic fragment thereof. By "immunogenic fragment" is meant a fragment of a polypeptide which includes one or more epitopes and thus elicits antibodies that neutralize viral infectivity, and/or mediates antibody-complement or antibody dependent cell cytotoxicity to provide protection of an immunized host. Such fragments will usually be at least about 5 amino acids in length, and preferably at least about 10 to 15 amino acids in length. There is no critical upper limit to the length of the fragment, which could comprise nearly the full length of the protein sequence, or even a fusion protein comprising fragments of two or more of the BHV-1 subunit antigens.

The term "treatment" as used herein refers to either (i) the prevention of infection or reinfection (prophylaxis), or (ii) the reduction or elimination of symptoms of BHV-1 (therapy).

B. General Methods

Bovine herpesvirus type 1, or BHV-1, is a well-known and well-characterized virus, of which many strains are known. See, e.g., Gibbs et al. (1977) Vet. Bull. (London) 47:317–343. BHV-1, also known as infectious bovine rhinotracheitis virus, is similar in structure to other herpesviruses, and possesses a linear double-stranded DNA genome of approximately 140 kilobase pairs. BHV-1 can remain latent in infected animals, probably in trigeminal or sacral ganglia, and, as discussed above, can be reactivated with relative ease.

The BHV-1 genome specifies more than 25 structural polypeptides, of which about 11 are believed to be glycosylated. Of particular interest to the present invention are the glycoproteins gI (previously referred to as GVP 6/11a/16, which comprises gIb and gIc), gIII (previously referred to as GVP 9 or its dimer, GVP 3), and gIV (previously referred to as GVP 11b). Glycoprotein gI is a complex of three glycoproteins with apparent molecular weights of approximately 130 k (gIa), 74 k (gIb), and 55 k (gIc). gIa is the precursor of gIb and gIc. Glycoprotein gIII has an apparent molecular weight of about 91 k and also occurs as a dimer with an approximate apparent molecular weight of 180 k. Glycoprotein gIV has an apparent molecular weight of approximately 71 k, and also occurs as an approximate 140 k dimer.

The BHV-1 gene for gI maps between 0.422 and 0.443 genome equivalents (FIG. 4) in the HindIII A fragment described by Mayfield et al. (1983), supra. The gIII gene maps between 0.120 and 0.131 genome equivalents (FIG. 4) in the HindIII I fragment. Id. The gIV gene maps between 0.892 and 0.902 genome equivalents in the HindIII K fragment. The nucleotide sequences of the gI, gIII, and gIV genes are shown in FIGS. 5, 6, and 7, respectively.

A key aspect of the present invention is the provision of a recombinant subunit antigen useful in the production of BHV-1 vaccines. The subunit antigens of the present invention are polypeptides from at least one of the BHV-1 glycoproteins gI, gIII, or gIV. In general, the polypeptide subunit antigens will usually be at least about 5 amino acids in length in order to encode an epitope, and preferably at least about 10–15 amino acids in length. There is no critical upper limit to the length of the subunit antigen, which could comprise the entire viral glycoprotein sequence, or even a fusion protein comprising the sequences of two or more of the viral glycoproteins.

The subunit antigens of the present invention are recombinant polypeptides. These recombinant subunits can take the form of partial glycoprotein sequences, full-length viral protein sequences, or even fusion proteins (e.g., with an appropriate leader for the recombinant host, or with another subunit antigen sequence for BHV-1 or another pathogen). The subunit antigen, even though carrying epitopes derived from glycoproteins, does not require glycosylation.

While it is preferred to use subunit glycoproteins containing the full-length (or near full-length) sequence of the selected BHV-1 glycoprotein, shorter sequences encoding one or more epitopes can also be employed. The truncated sequence need only encode a "polypeptide neutralizing epitope"; i.e., an epitope which elicits antibodies that neutralize virus infectivity, and/or mediates antibody-complement or antibody dependent cell cytotoxicity to provide protection of an immunized host. See, e.g., Babiuk et al. (1975) Infect. Immun. 12:958–963; BabLuk et al. (1987), supra. Particularly preferred epitopes for screening the subunit antigens will be those epitopes that are exposed on the cell membrane of infected host cells, as well as those epitopes encompassing the attachment site on intact virions. Such epitopes can be defined by monoclonal antibody analysis. See, e.g., van Drunen Littel-van den Hurk et al. (1985) Virology 144:216–227; Okazaki et al. (1987), supra.

In the vaccines of the present invention, it will sometimes be preferable to have more than one polypeptide neutralizing epitope in the subunit antigen(s). Furthermore, it may also be desirable to include polypeptide neutralizing epitopes from more than one glycoprotein in the subunit antigen(s). In its simplest form, this can be achieved by employing a polypeptide encoding the complete sequence of a glycoprotein (usually encompassing more than one neutralizing epitope), or by employing a combination of polypeptides encoding the sequences of two or all three of the viral glycoproteins. In a preferred embodiment employing native BHV-1 proteins, the subunit antigens would comprise, for example, gIV, a combination of gIV and gI (gIV/gI), a combination of gIV and gIII (gIV/gIII), or a combination of gI and gIII (gI/gIII), or a combination of all three glycoproteins (gI/gIII/gIV). When employing synthetic or recombinant polypeptides, the subunit antigen can be a single polypeptide encoding several neutralizing epitopes from just one of the viral glycoproteins, or several neutralizing epitopes from more than one of the viral glycoproteins (e.g., a fusion protein). Synthetic and recombinant subunit antigens can also comprise two or more discrete polypeptides encoding different neutralizing epitopes.

The subunit antigens of the present invention, particularly when they comprise short oligopeptides, may be conjugated to a vaccine carrier. Such carriers are well known in the art, such as bovine serum albumin (BSA), human serum albumin (HSA) and keyhole limpet hemocyanin (KLH). A particularly preferred carrier protein, rotavirus VP6, is disclosed in U.S. Pat. No. 5,071,651, the disclosure of which is hereby incorporated by reference it its entirety. The BHV-1 neutralizing epitopes of the present invention may also be incorporated within particle-forming viral polypeptides as a fusion protein, as described in U.S. Pat. No. 4,722,840 and EPO Pub. No. 174,759. Alternatively, the BHV-1 subunit antigens of the present invention can be incorporated into a foreign virus (e.g., vaccinia or adenovirus) as is known in the art and described more fully below in the examples.

The subunit antigen(s) are formulated into a vaccine composition comprising a pharmaceutically acceptable vehicle and, optionally, an adjuvant. Such formulations are well within the skill of the art. In general, the formulations will be particularly adapted for intramuscular injection, since intravenous injection is usually not practical for large-scale application to domestic animals. Alternatively, the vaccines are given orally or intranasally, and the subunits formulated with a suitable oral carrier. It may be preferred to administer the vaccines of the present invention orally to raise mucosal immunity, as well as intramuscularly for systemic immunity. A pharmaceutically acceptable vehicle, suitable for parenteral injection, is usually nontoxic and nontherapeutic. Examples of such vehicles are water, saline, Ringer's solution, dextrose solution, and Hank's solution. Nonaqueous vehicles, such as fixed oils, sesame oil, ethyl oleate, or triglycerides may also be used. Parenteral vehicles may also take the form of suspensions containing viscosity enhancing agents, such as sodium carboxymethylcellulose, sorbitol, or dextran. The vehicle will also usually contain minor amounts of additives, such as substances that enhance isotonicity and chemical stability. Examples of buffers include phosphate buffer, bicarbonate buffer and tris buffer, while examples of preservatives include thimerosal, m- or o-cresol, formalin and benzyl alcohol. Standard formulations will either be liquid injectables or solids which can be taken up in a suitable liquid ;as a suspension or solution for injection. Thus, in a nonliquid formulation, the vehicle may comprise dextrose, human serum albumin, preservatives, etc., to which sterile water or saline could be added prior to administration.

Various adjuvants are known in the art which can also be employed in the vaccine formulations of the present invention; e.g., Freund's adjuvant, Avridine, aluminum salts [Al $(OH)_3$, $AlPO_4$, $Al_2(SO_4)_8$], $Ca_3(PO_4)_2$, saponin, DDA, Pluronics, oil-in-water emulsions (containing, e.g., Avridine, dextran sulphate, Emulsigen PLUS or vitamin E) and water-in-oil emulsions (containing, e.g., polysorbate 80). The selection of the appropriate adjuvant and its concentration in the vaccine composition is within the skill of the art.

Many protocols for administering the vaccine composition of the present invention to animals are within the skill of the art. The preferred route of administration is parenteral, particularly intramuscular. The concentration of the subunit antigen(s) in the vaccine composition is selected so that an effective dose is presented in the bovine host to elicit antibodies to the polypeptide neutralizing epitopes. Within wide limits, the dosage is not believed to be critical. Typically, the vaccine composition is administered in a manner which will deliver between about 1 to about 1,000 μg of the subunit antigen in a convenient volume of vehicle (e.g., about 1–10 ml). Preferably, the dosage in a single immunization will deliver from about 1 to about 500 μg of subunit antigen, more preferably about 5–10 μg to about 100–200 μg (e.g., 10–100 μg). It may also be preferred, although optional, to administer a second, booster immunization to the animal several weeks to several months after the initial immunization. To insure sustained high levels of protection against disease, it may be helpful to readminister a booster immunization to the animals on a periodic basis.

The subunit antigen can be produced from protein recovered from virus or virus-infected cells, or cells expressing the recombinant glycoproteins. For example, purified virus or virus-infected cells can be disrupted or lysed and subjected to immunoadsorbent chromatography to purify gI, gIII or gIV. See, e.g., van Drunen Littel-van den Hurk et al. (1985) Virology 144:204–215. The production of monoclonal antibodies is within the skill of the art. See, e.g., van Drunen Littel-van den Hurk et al. (1984), supra; Okazaki et al. (1987), supra. Briefly, a mammal, such as a mouse, is immunized with either purified virus or the purified viral glycoprotein of interest (e.g., SDS-PAGE purified) and antibody-producing B lymphocytes recovered. Typically, these B lymphocytes are then fused with a continuous cell line to produce an immortal antibody-producing cell line; i.e., a hybridoma, trioma, etc. Immortal, antibody-producing cell lines can also be created by techniques other than fusion, such as direct transformation of B-lymphocytes with oncogenic DNA, or transfection with Epstein-Barr virus. See, e.g., M. Schreier et al. (1980) Hybridoma Techniques; Hammerling et al. (1981) Monoclonal Antibodies and T-Cell Hybridomas; Kennett et al. (1980) Monoclonal Antibodies; see also U.S. Pat. Nos. 4,341,761; 4,399,121; 4,427,783; 4,444,887; 4,451,570; 4,466,917; 4,472,500; 4,491,632; 4,493,890. Native BHV-1 proteins which are immunopurified can be used in their entirety as subunit antigens, or fragments of the entire proteins containing the neutralizing epitopes can be employed as subunit antigens.

Non-native BHV-1 polypeptides can be produced by a number of methods. For example, oligopeptides containing neutralizing epitopes can be prepared synthetically by known techniques. See, e.g., U.S. Pat. No. 4,735,896. It is preferred, however, to prepare the non-native polypeptide subunit antigens by recombinant DNA methods.

Recombinant polypeptide subunit antigens are produced according to the present invention by constructing an expression cassette and transforming a host cell therewith to provide a cell line or culture capable of expressing the subunit antigen which is encoded within the expression cassette. The first step in constructing the expression cassette is to obtain a coding sequence for the glycoprotein or glycoprotein epitopes of interest. Coding sequences for gI, gIII and gIV are shown in FIGS. 5, 6 and 7. Thus, coding sequences can either be prepared directly by synthetic methods based on the disclosed sequence (or equivalent sequences encoding the same amino acids), or by using the disclosed sequence to design oligonucleotide probes to clone coding sequence using known techniques. See, e.g., Mayfield et al. (1983), supra. The coding sequence can be comprised entirely of BHV-1 glycoprotein-encoding sequences, or such glycoprotein sequences can be fused to other sequences (e.g., leader sequences) so that a fusion protein is encoded. See, e.g., U.S. Pat. Nos. 4,431,739; 4,425,437; 4,338,397. Synthetic coding sequences will also allow for the convenient construction of coding sequences which express BHV-1 glycoprotein analogs or “muteins”. Alternatively, coding sequences for muteins can be prepared by site-directed mutagenesis of native BHV-1 nucleotide sequences. The techniques of site-directed mutagenesis are known in the art.

Once an appropriate coding sequence for the subunit antigen has been prepared or isolated, it can be cloned into any suitable vector or replicon. Numerous cloning vectors or replicons are known to those of skill in the art, and the selection of an appropriate cloning vector is a matter of choice. Examples of recombinant DNA vectors for cloning and host cells which can be transformed include various bacteriophage lambda vectors (*E. coli*), pBR322 (*E. coli*), pACYC171 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillis subtilis*), pBD9 (*Bacillis*), pIJ61 (*Streptomyces*), pUC6 (*Streptomyces*), actinophage dC31 (*Streptomyces*), YIp5 (*Saccharomyces*), YCp19 (*Saccharomyces*), 2-micron plasmid (*Saccharomyces*), and bovine papilloma virus (mammalian cells). See, generally, *DNA Cloning*, vols I & II, .supra; Maniatis et al., supra; Perbal, supra.

To complete construction of expression cassettes, the coding sequence as described above for the subunit antigens is then operably linked to control sequences (e.g., a promoter, etc.), so that the DNA sequence encoding the subunit antigen is transcribed into messenger RNA in the host cell transformed by the expression cassette. It is within the skill of the art to operably link the subunit antigen coding sequence to appropriate control sequences in order to bring about transcription and translation. In general, the coding sequence will be downstream from the promoter sequence and any expression regulatory regions, such as enhancers or operator sequence. If the subunit antigen coding sequence is linked to a heterologous coding sequence or start codon, then it is important to place the subunit antigen coding sequence in reading frame with the latter. If the intended expression host is procaryotic, then it will also be necessary to include a ribosome binding site among the upstream control sequences. Downstream operably linked control sequences will usually comprise a transcription termination sequence, and a polyadenylation signal (for mammalian expression hosts).

When the intended expression host is a procaryotic or yeast cell, the promoter and other control sequences will necessarily be heterologous to the subunit antigen coding sequence. If the selected expression host cell is a mammalian cell, the control sequences can be homologous BHV-1 sequences, or preferably heterologous mammalian control sequences. The expression cassette can be constructed, for example, as a discrete molecular entity flanked by convenient restriction sites, or it can be constructed by inserting the coding sequence into a previously constructed expression vector with an appropriate insertion site.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Publication Nos. GB2,121,054; GB2,008,123; GB2,007,675; and European Publication No. 103,395. The preferred procaryotic expression vectors are those for *E. coli*. Other preferred expression vectors are those for use in eucaryotic systems. Yeast expression vectors are also known in the art. See, e.g., U.S. Pat. Nos. 4,446,235; 4,443,539; 4,430,428; see also European Publication Nos. 103,409; 100,561; 96,491.

One of the preferred expression hosts of the present invention are mammalian cells. Various cell lines and expression vectors are known in the art. Examples of appropriate mammalian expression hosts include kidney cell lines (e.g., CV-1 monkey kidney cell lines), fibroblast cell lines (e.g., human, murine or chicken embryo fibroblast cell lines), Chinese hamster ovary (CHO) cells, HeLa cells, mouse NIH/3T3 and/or $LMTK^-$ cells. It is also known to express heterologous proteins in myeloma cell lines employing immunoglobulin promoters. See, e.g, Banerjee et al. (1983) Cell 33:729–740; U.S. Pat. No. 4,663,281. The selection of a mammalian cell line is not critical, and is within the skill of the art. Various mammalian expression vectors employing viral promoters (e.g., SV40 early region promoter, Rous sarcoma virus, LTR promoter, etc.) are also well known in the art. See, e.g., Pachl et al. (1987), supra; Gorman et al. (1982) Proc. Natl. Acad. Sci. USA 79:6777–6781; Southern et al. (1982) J. Mol. App. Genet. 1:327–341; PCT Publication No. WO87/02062. Preferred eucaryotic expression vectors are those employing the vaccinia virus, the SV40 virus, or the Rous sarcoma virus, which are also well known in the art. See, e.g., Mackett et al. (1984) J. Virol. 49:857; DNA Cloning, vol. II, pp. 191–211, supra; PCT Publication No. WO86/07593; Chakrabarty et al. (1985) Mol. Cell. Biol. 5:3403.

Another preferred embodiment of the present invention is the expression of recombinant BHV-1 polypeptides in insect cells using viral vectors, such as baculovirus. For example, high levels of expression have been achieved with vectors based on Autographa californica nuclear polyhedrosis virus (AcNPV) in Spodoptera frugiperda cells. See, e.g., Smith et al. (1983) J. Virol. 46:584–593; U.S. patent application Ser. No. 07/092,120, supra; Canadian Pat. App. Serial No. 545,803, supra.

Generally, a host cell which has been stably transformed by an expression cassette for the subunit antigen is selected to produce the recombinant polypeptide. A stably transformed host is one wherein the expression cassette has integrated into the host cell's chromosome. In the case of bacteria or yeast expression hosts, it may be preferred to select expression hosts which maintain the cassette on a non-integrating episomal element, such as a plasmid. The subunit antigen is produced by growing host cells transformed by the expression cassette under conditions which cause the expression of biologically active subunit antigen polypeptide. The appropriate conditions to bring about expression are well known in the art, and will depend primarily on the expression system and host selected. The subunit antigen polypeptide may be isolated from the host cells and purified. If the expression system secretes the subunit antigen, then the polypeptide can be purified directly from the growth media. If subunit antigen is not secreted, however, it may be necessary to disrupt the host cells and purify the subunit antigen polypeptide from the cellular lysate. Various purification techniques, such as HPLC and immunoaffinity chromatography, are known, and the selection of the appropriate purification and recovery method is within the skill of the art.

The major glycoprotein complex gI of bovine herpesvirus-1 was expressed at high levels (35 $\mu$g per $10^6$ cells) in insect cells using a recombinant baculovirus. The recombinant gI had an apparent molecular weight of 116 kDa and was partially cleaved to yield 63 kDa (gIb) and 52 kDa (gIc) subunits. This processing step was significantly less efficient in insect cells than the analogous step in mammalian cells, even though the cleavage sites of authentic and recombinant gI were shown to be identical. The oligosaccharide linkages were mostly endoglycosidase H sensitive, in contrast to those of authentic gI, which has mostly endoglycosidase H resistant linkages and an apparent molecular weight of 130/74/55 kDa. Despite the reduced cleavage and processing efficiency, the recombinant glycoprotein was transported and expressed on the surface of infected insect cells. These surface molecules were biologically active as demonstrated by their ability to induce cell-cell fusion. Fusion was inhibited by three monoclonal antibodies specific for antigenic domains I and IV on gI. Domain I maps to the extracellular region of the carboxy terminal fragment gIc and domain IV to the very amino terminus of the gIb fragment, indicating that domains mapping in two distinct regions of gI function in cell fusion. Monoclonal antibodies specific for eight different epitopes recognized recombinant gI, indicating that the antigenic characteristics of the recombinant and authentic glycoproteins are similar. In addition, the recombinant gI was as immunogenic as the authentic gI, resulting in the induction of gI-specific antibodies in cattle.

It is known that BHV-1 can be immunosuppressive. This could interfere with the effectiveness of other bacterial or viral vaccines administered concurrently with, or within a few days of BHV-1 vaccine. However, it has been discovered that vaccination with BHV-1 gIV does not have an immunosuppressive effect on other bacterial or viral vaccines. Any bovine bacterial or viral infection reducing or preventing vaccine can be the second vaccine. Such materials are well known in the art and include but are not limited to vaccines against *Pasteurella haemolytica, Haemophilus somnus*, parainfluenza virus, coronavirus, rotavirus, adenovirus, bovine respiratory syncytial virus, bovine diarrhea virus and the like. Thus, a wide variety of co-infections can be co-treated.

Accordingly, the invention also includes a method for co-treating or preventing a BHV-1 infection and a second infection in a bovine host which comprises administering to the bovine host a therapeutically effective amount of (1) a vaccine composition of BHV-gIV and (2) a vaccine against the second infection and compositions which comprise (1) and (2).

An alternative route of administration involves gene therapy or nucleic acid immunization. Thus, nucleotide sequences (and accompanying regulatory elements) encoding the subject proteins can be administered directly to a subject for in vivo translation thereof. Alternatively, gene transfer can be accomplished by transfecting the subject's cells or tissues ex vivo and reintroducing the transformed material into the host. DNA can be directly introduced into the host organism, i.e., by injection (see, International Publication No. WO90/11092; and Wolff et al., *Science* (1990) 247:1465–1468). Liposome-mediated gene transfer can also be accomplished using known methods. See e.g., Hazinski et al., *Am. J. Respir. Cell Mol. Biol.* (1991) 4:206–209; Brigham et al., *Am. J. Med. Sci.* (1989) 298:278–281; Canonico et al., *Clin. Res.* (1991) 39:219A; and Nabel et al., *Science* (1990) 249:1285–1288. Targeting agents, such as antibodies directed against surface antigens expressed on specific cell types, can be covalently conjugated to the liposomal surface so that the nucleic acid can be delivered to specific tissues and cells susceptible to BHV-1 infection.

Diagnostic Assays for BHV-1 Antibodies

The recombinant antigens of BHV-1 gI, gIII and/or gIV can be used as substrate reagents in immunoassays to identify antibodies to BHV-1 gI, gIII and/or gIV in a sample, e.g., blood, from a bovine host as one means of determining if the bovine host is infected with BHV-1 and to determine the concentration of the antibodies in the sample. The immunoassays in which the recombinant antigens of BHV-1 gI, gIII and/or gIV can be used include, but are not limited to, radioimmunoassay, competition immunoprecipitation, enzyme-linked immunoadsorbent assay, immunofluorescence assay and the like. Detection is convenient, rapid, sensitive and specific. The recombinant antigens of BHV-1 gI, gIII and/or gIV are used in assay compositions in a concentration sufficient to form a detectable complex with the antibodies. The BHV-1 antigens can be mixed with or attached to a suitable matrix (support) or carrier, such as a latex particle or plastic microtiter plate or the like. They can also be conjugated with an enzyme, dye, radio-labelled or the like, depending upon what immunological method is used. The details of conducting various types of immunoassays is well known in the art and also described in Tyssen, P., "Laboratory Techniques in Biochemistry and Molecular Biology, Practice and Theory of Enzyme Immunoassays" (Ed. R. H. Burton and P. H. van Knippenberg, the disclosures of which are incorporated by reference. Accordingly, the invention includes a method for determining the presence or absence of or concentration of antibodies for BHV-1 in a sample by employing an immunoassay, the immunoassay characterized by using recombinant antigenic BHV-1 gI, gIII and/or gIV reactive with BHV-1 antibodies as a reagent in the immunoassay, whereby a complex of the BHV-1 antibodies and the recombinant antigenic BHV-1 gI, gIII and/or gIV is formed, and determining the presence or absence of or concentration of the complex formed as indicative of the presence or absence of or concentration of the antibodies.

Described below are examples of the present invention which are provided only for illustrative purposes. The examples are not intended to limit the scope of the present invention in any way, as numerous embodiments within the scope of the claims will be apparent to those of ordinary skill in the art in light of the present disclosure. Those of ordinary skill in the art are presumed to be familiar with (or to have ready access to) the references cited in the application, and the disclosures thereof are incorporated by reference herein.

C. Experimental

EXAMPLES

I

This example demonstrates the protection of cattle immunized with subunit vaccines made from purified BHV-1 glycoproteins.

I.A. Materials and Methods

I.A.1. Virus and Bacteria

Strains P-2 and 108 of BHV-1 were propagated in Georgia bovine kidney cells as described previously. Babiuk et al. (1975) Infect. Immun. 12:958–963. For virus challenge of animals strain 108 was used, whereas for glycoprotein isolation the Cooper strain was used.

A culture of *Pasteurella haemolytica* (biotype A, serotype 1) was prepared as described previously. Bielefeldt Ohmann et al. (1985) J. Infect. Dis. 151:937–947. In each case, the bacterial challenge was in the log phase of growth and had a titer of 1 to $2\times10^9$ CFU/ml.

I.A.2. Monoclonal Antibodies and Immunoadsorbent Purification

Monoclonal antibodies against gI, gIII, and gIV were produced as described previously. van Drunen Littel-van den Hurk et al. (1984), supra. Clones 1E11-1F6, 1D6-G11 and 1G6-2D9 which recognize gI, gIII, and gIV, respectively, were selected to prepare immunoadsorbent columns.

Purification of IgG fractions of monoclonal antibodies was carried out using protein A-Sepharose CL-4B (Pharmacia Montreal, Quebec). L'Italien in *Method of Protein Microcharacterization*, pp. 279–314 (J. E. Shively ed. 1986). Monoclonal IgG was eluted from the protein A-Sepharose column with 50 mM triethylamine and was dialyzed thoroughly against 0.1 M HEPES, pH 7.5 (coupling buffer: CB). The purified IgG was linked to activated Affigel-10 (Bio-Rad Laboratories, Mississauga, Ontario) at 5 mg protein/ml gel, according to the manufacturer's instructions.

Glycoproteins gI, gIII, and gIV were purified from virus-infected cell lysate as previously described. van Drunen Littel-van den Hurk et al. (1985) Virology 144:216–227. Twenty-four hours postirifection, at a m.o.i. of 1, cultures were harvested and centrifuged at 1000 rpm to obtain infected cell pellets. Cells were resuspended in 1% Nonidet-P40 (NP-40) and 1% sodium deoxycholate (DOC) in 0.10 M Tris-hydrochloride, 0.15 M NaCl, (pH 7.5) and used as starting material for purification.

Immunoadsorbent columns with specificities for gI, gIII, and gIV, respectively, were prepared. After passage of the sample over the column in sample application buffer, the column was exchanged with 1 vol of fresh sample application buffer prior to washing with 2 vol of wash buffer [100 mM Tris, 500 mM NaCl, 1% NP-40 (pH 7.5)]. The wash buffer was displaced from the column with 2 vol of water prior to elution of the specifically bound antigen with 50 mM triethylamine. The eluted fractions were monitored by removing 5–50 µl collected fraction and performing a non-quantitative Bradford assay. Those fractions that contained protein were then directly concentrated for further analysis. The column was reequilibrated in sample application buffer for reuse or stored in sample application buffer plus 0.02% thimerosal. Columns prepared, used, and stored in this way have retained significant activity for almost a year.

I.A.3. Immunization and Pathogen Challenge

Purified glycoproteins were formulated with Avridine (N,N-dioctadecyl-N,N-bis) (2-hydroxylethylpropanediamine) as follows: 150 mg of Avridine was dissolved in 1 ml of absolute EtOH and then combined with 90 µl Tween 80 by thorough mixing. Next, 4.7 ml of Intralipid were combined with Avridine/EtOH and thoroughly mixed by vortexing. 4.0 mls of biological buffer, e.g. Hanks' buffered salt solution or PBS were added to the solution to complete the adjuvant preparation. The vaccine was prepared by mixing equal volumes of antigen and adjuvant solutions such that each animal received a dose of 100 µg of glycoprotein+15 mg of Avridine in a 2 ml volume.

Groups of five animals each were immunized intramuscularly with the above preparations. Twenty-one days later animals were boosted and then challenged 3 weeks after booster immunization. Control unvaccinated calves were immunized with Avridine (adjuvant alone). A further control group was immunized with a commercial killed virus vaccine (Triangle 3, Fort Dodge Laboratories, Iowa) as recommended by the manufacturer. Blood samples were taken from animals at 10-day intervals for assessment of antibody responses.

Following immunization, animals were transported into an isolation pen and examined clinically, and rectal temperatures were recorded and blood samples were collected for various immunological assays to establish baseline immunological activity. The calves were then individually exposed to an aerosol of BHV-1, followed 4 days later with *P. haemolytica*. In each case, the aerosol was generated by a DeVilbiss Nebulizer, Model 65 (DeVilbiss, Barry, Ontario, Canada). Treatment was for 4 min in the case of the virus and 5 min with *P. haemolytica* as described previously. Bielefeldt Ohmann et al. (1985), supra.

I.A.4. SDS-PAGE. Western Blot, ELISA and ADCC

Sodium dodecyl sulfate (SDS)-polyacrylamide gel electrophoresis (PAGE) was carried out in 7.5% discontinuous slab gels under reducing conditions, as described previously. van Drunen Litlel-van den Hurk et al. (1984), supra; Laemmli (1970) Nature (London) 227:680–685.

The Western blotting technique was performed as described previously. van Drunen Littel-van den Hurk et al. (1984), supra. After electrophoresis, virus lysates were electrophoretically transferred to nitrocellulose sheets. Subsequently, the instructions for use of the Bio-Rad (Mississaugo, Ontario) immunoblot assay kit were followed.

In order to determine the antibody responses of cattle immunized with purified glycoproteins, the ELISA was performed essentially as described previously. van Drunen Littel-van den Hurk et al. (1984), supra. However, affinity-purified, peroxidase-conjugated rabbit anti-bovine IgG (Zymed) at a dilution of 1:3000 was used as the detecting antibody.

The neutralization titers of the bovine sera were determined as described previously. Babiuk et al. (1975), supra. To determine complement-enhanced neutralization, guinea pig serum (1:40 final dilution) was added to the virus-antibody mixture. The titers were expressed as the reciprocal of the highest dilution of antibody which caused a 50% reduction of plaques relative to the virus control.

ADCC assays were performed in microtiter plates as described previously. Babiuk et al. (1975), supra. The ratio of effector cells (polymorphonuclear cells) to target cells (BHV-1-infected, $^{51}$Cr-labeled GBK cells) was 50:1. Controls consisted of BHV-l-infected GBK target cells plus anti-BHV-1 serum or targets with polymorphonuclear cells in the absence of antibody.

I.A.6. Clinical Evaluation and Necropsy

The clinical evaluations were performed at the same time each day by two independent investigators who were uninformed about the specific treatments of the individual animals. The parameters evaluated included depression, appetite, fever, conjunctivitis, rhinitis, mouth-breathing, tracheitis, and pneumonia. In each case a score of 0 was assigned to healthy animals. Clinical scores of 1–4 were assigned to sick animals for each individual parameter as follows: 4, severe; 3, marked; 2, moderate; 1, mild. Total clinical scores for each animal are the sums of scores for each parameter.

Postmortem examinations were done on animals that died or were euthanized during the experiments. The nasal passages, larynx, trachea, and lungs were examined and photographed. Viral and bacterial lesions were recorded. The extent of pneumonia was assessed by a numerical method developed by Thomson et al. (1975) Canad. J. Comp. Med. 39:194–207. The pneumonic lesions in each lung lobe (except for the accessory lobe) were graded from 0 to 5 according to the amount of tissue involved. Total scores for seven lung lobes ranged from 0 to a theoretical maximum of 35 if the entire lung was affected.

I.A.7. Leukocyte Function

To study post-BHV-l-challenge leukocyte function, venous blood was collected into syringes containing citrate dextrose. The blood was centrifuged at 1000 g for 20 min, the buffy coat was collected, and the peripheral blood mononuclear leukocytes (PBL) were further purified on Ficoll-Hypaque as described previously. Bielefeldt Ohmann et al. (1985), supra. The polymorphonuclear neutrophils (PMN) were isolated from the original pellet by lysis of the erythrocytes as described previously. The viability of both PBLs and PMNs was greater than 99% as determined by trypan blue exclusion.

(i) Functional Analysis of PBL. Lectin-driven lymphocyte proliferation was assayed as described previously. Id. Briefly, 1×10$^5$ PBL were added into quadruplicate wells of a flat-bottomed microtiter plate (Nunc, Roskilde DK) in a final volume of 200 µl of RPMI 1640 plus 5% fetal bovine serum, 50 mM HEPES, and 25 mg gentamycin (all media components are from Grand Island Biological Co., Grand Island, N.Y.). Lectins, phytohemagglutinin (PHA), and concanavalin A (Con A, Calbiochem, La Jolla, Calif.) were added to the cultures. The cultures were incubated for 72 hr and labeled with [methyl-$^3$H]thymidine (H$^3$-Tdr) (Amersham Co., Oakville, Ontario) during the last 16–18 hr of incubation. The amount of radioactivity incorporated by PBLs was quantitated by liquid scintillation counting.

(ii) Functional Analysis of PMNs. Chemotaxis of PMNs was measured using microchemotaxis chambers. Gee et al. (1983) Proc. Natl. Acad. Sci. USA 80:7215–7218. Briefly, 25 µl of the chemoattractant was added to the bottom wells of the chemotaxis chamber, whereas the top chamber wells contained 45 µl of PMNs. The chemotaxis chambers were incubated for 2 hr in a humidified $Co_2$ atmosphere at 37° C. After incubation, the membranes were removed and nonmigrating cells were scraped from the upper surface. Membranes were fixed, stained with Giemsa, and examined microscopically for the presence of migrating cells. Cell counts are presented as the mean counts of three representative high-power microscope fields.

Luminol-enhanced chemiluminescence was measured by the method of Abramson et al. (1982). Briefly, 2×10$^7$ cells were added to vials containing 5 ml of Hank's balanced salt solution, 400 µl of opsonized zymosan, and 20 µl of luminol. Immediately upon addition of the cells, the reaction was followed over time using a Packard Picolite 6500 Luminometer (United Technologies Packard, Downers Grove, Ill.). Results are plotted as CPM/10$^7$ cells at the peak of the response which occurs at 45 min.

Superoxide anion generation and release were measured by the superoxide dismutase (SOD) inhibitable reduction of ferracytochrome C as described previously. Johnson et al. (1978) J. Exp. Med. 148:115–127. All samples were assayed in duplicate and in suspension in a final volume of 1 ml. The samples were incubated for 45 min at 37° C. The reaction was terminated by transferring 1 ml aliquots to an ice bath followed by centrifugation. The cytochrome c reduction was monitored on a spectrophotometer at 550 nm. The OD value was then converted to nm $O_2$/cell.

I.B. Results

I.B.1. Immune Responses to Purified Glycoproteins

Figure 1:
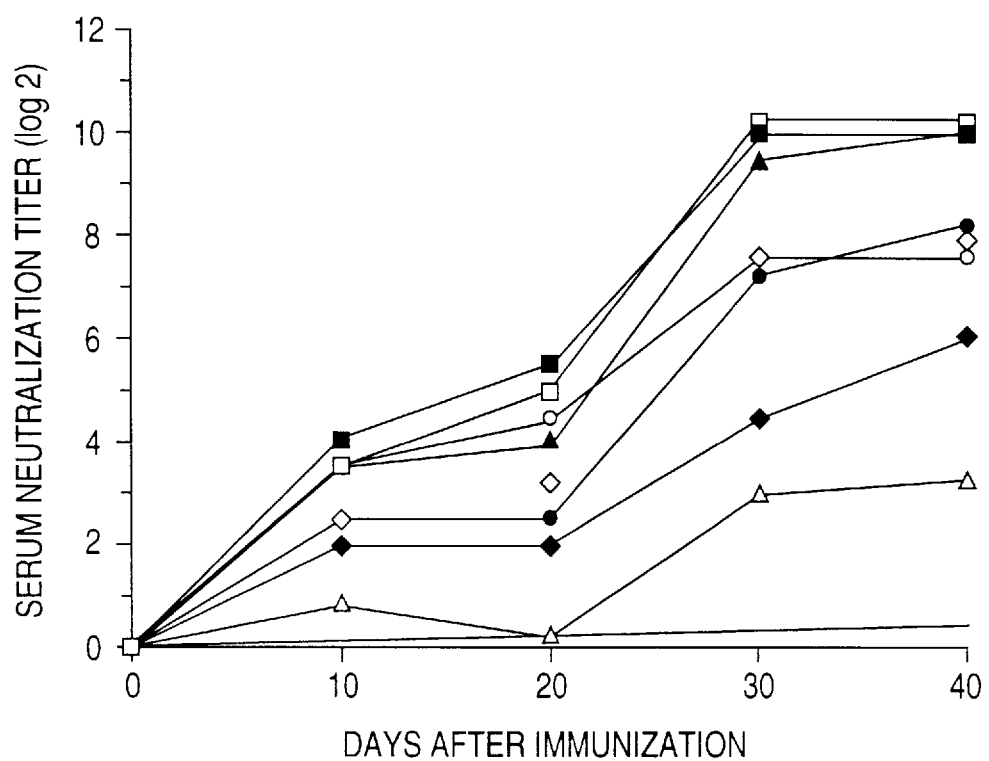
FIG. 1 shows the serum neutralizing antibody responses of animals immunized with BHV-1 glycoproteins. Animals were immunized with various glycoproteins and boosted three weeks later. Titers were determined by a 50% end point using 100 PFU of BHV-1 virus. The various glycoproteins are indicated as follows: gI (solid diamond) gIII (solid circle), gIV (solid square), gI/gIII (open diamond), gI/gIV (open square), gIII/gIV (solid triangle), gI/gIII/gIV (open circle), commercial killed vaccine (open triangle), and placebo (−). See Example I.B.1.

As explained above, the purified native BHV-1 glycoproteins were tested for their ability to induce protective immune responses in cattle. FIG. 1 indicates that within 10 days of immunization, all of the individual glycoproteins or combinations thereof induced detectable serum neutralizing titers. Following a booster immunization 21 days later, there was a further increase in the level of serum neutralizing antibodies induced by the glycoproteins. Highest responses were present in those animals immunized with gIV. In contrast, animals immunized with a commercial killed BHV-1 vaccine produced marginal antibody titers within 10 days of immunization. This antibody level decreased to preimmunization levels by 20 days after immunization. Following a second immunization with the commercial vaccine, antibody titers were boosted to approximately the level observed 10 days postimmunization with the purified glycoprotein. In no case did the placebo-vaccinated animals develop any immune responses.

To measure the specificity c)f the immune response, the serum from each animal was tested by an ELISA using individual glycoproteins as the antigens. Animals immunized with gI only reacted in the ELISA when gI antigen was used to coat the plate. In contrast, those animals that were immunized with gIII only reacted with gIII coated plates. Similarly, animals immunized with gIV only recognized gIV. These results also indicate, similar to FIG. 1, that the animals immunized with gIV had higher titers than did animals immunized with the other glycoproteins. To confirm that the animals only reacted with the specific glycoproteins with which they were immunized, Western blot analysis was performed using the sera from the individual animals. Animals immunized with gI, gIII, or gIV reacted only with their respective glycoproteins in immunoblot assays. These results further indicate that the animals were not accidentally exposed to a field strain of BHV-l during the immunization period.

Figure 2:
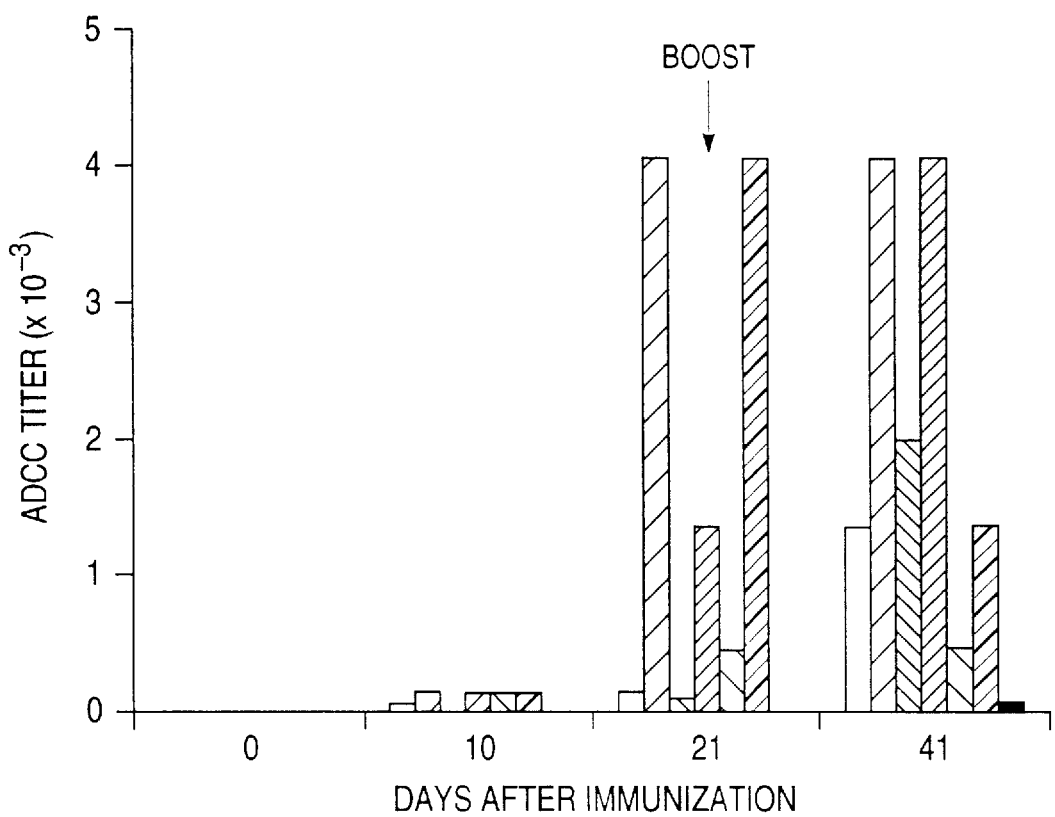
FIG. 2 shows the ADCC titers of sera obtained from calves immunized with BHV-1 glycoproteins or a commercial vaccine. The bars in the graph show the data for the various immunogens left to right as follows: gIII (open), gIV (cross-hatched), gI/gIII (small dots), gI/gIV (diagonal lines), gIII/gIV (large dots), gI/gIII/gIV (waves), and a commercial vaccine (solid) See Example I.B.1.

Since the sera from animals immunized with glycoproteins were specific for the individual glycoproteins used for immunization and could neutralize virus infectivity in vitro, attempts were made to determine whether any one of the individual glycoproteins could induce antibody capable of participating in ADCC. The results of FIG. 2 indicate that ADCC titers, although higher than SN titers, do parallel the serum neutralizing titers. Thus, animals immunized with gIV had higher ADCC titers than did animals immunized with the other glycoproteins, those immunized with gI being marginal in killing. Again, animals immunized with the commercial killed BHV-1 vaccine exhibited a marginal response.

I.B.2. Protection Studies

Figure 3:
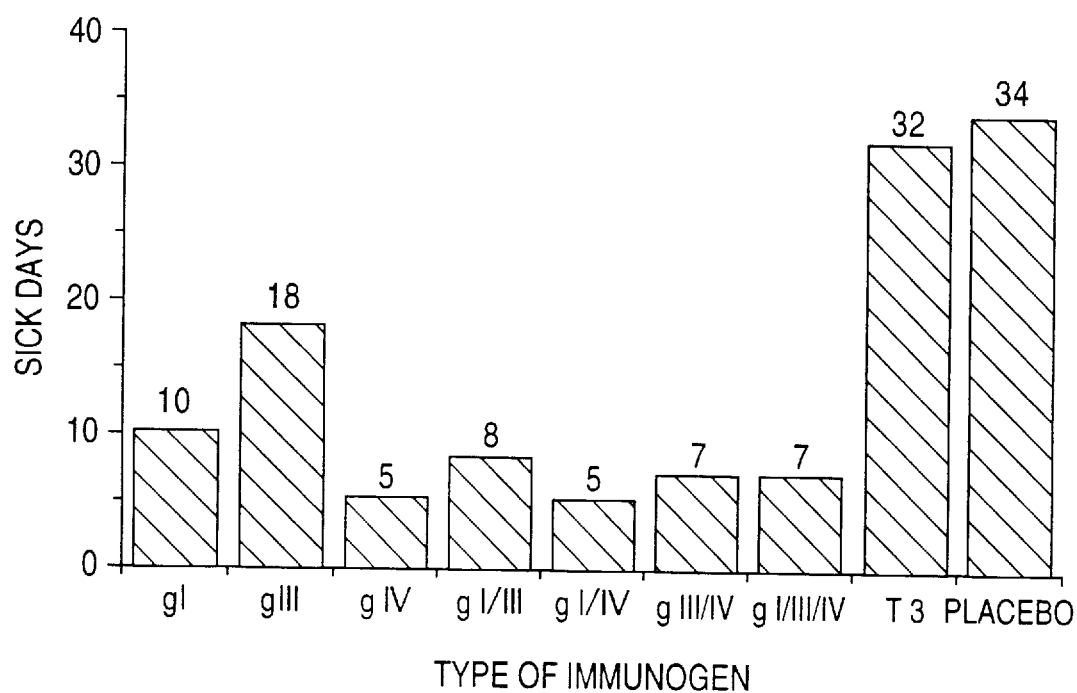
FIG. 3 shows the effect of immunization with BHV-1 glycoproteins on clinical response of calves to BHV-1/*P. Haemolytica* challenge. T3 represents a commercial vaccine. Numbers above the bars indicate the total number of sick days (a clinical score of ten or more on any specific observation) animals in each group exhibited over a ten-day observation period. See Example I.B.2.

Prior to challenge with BHV-1 and *P. haemolytica*, all animals were healthy and had a normal rectal temperature. However, within 48 hr post-BHV-1 infection, animals started exhibiting a rise in temperature. Temperature responses continued to increase until they reached peak levels 4–7 days post-BHV-1 infection. In each case, animals within the groups immunized with the glycoproteins exhibited much lower temperature responses than did the placebo or animals immunized with the commercial whole virus vaccine. In addition to temperature responses, a variety of other parameters of respiratory distress were assessed. A clinical score of 10 or greater was set to indicate severe respiratory disease, which under field conditions would result in isolation of the animal and treatment to prevent pneumonia and subsequent death. FIG. 3 indicates the total number of sick days (clinical score greater than 10) for the five animals within each individual treatment group. Animals immunized with individual glycoproteins or combinations thereof exhibited fewer days of morbidity than did the whole virus- or placebo-immunized animals. All glycoprotein groups were significantly different from placebo groups. No significant difference was present between placebo and animals immunized with the commercial vaccine.

Since the individual glycoproteins provided relatively good protection against severe respiratory disease, attempts were made to determine whether intramuscular immunization with individual glycoproteins had any effect on the extent of virus shedding from the nasal passages. All five of the placebo treated animals shed virus for the entire observation period, beginning from Day 2 to Day 10 post-BHV-1 challenge. In contrast, animals immunized with the glycoproteins shed virus for a significantly fewer number of days (P<0.005 Fisher exact test). Once again, animals immunized with the commercial vaccine shed virus for more days than did animals immunized with individual glycoproteins (not significantly different from controls).

In the present model, mortality rates of nonimmunized animals generally ranges from 40 to 80%. The mortality rate of placebo immunized animals in this particular experiment was 60%, whereas it was 40% in those immunized with the commercial vaccine. However, none of the animals immunized with the individual or glycoprotein combinations died. In an attempt to confirm that immunization with glycoproteins did induce protection and reduced lung involvement, the lungs of the animals were collected and assessed for the extent of pneumonia. The data demonstrate that the reason for the reduced morbidity of glycoprotein-immunized animals was that there was minimal infection of the lower respiratory tract. No specific glycoprotein group had more severe lung lesions or greater weight loss than the others indicating equal protection by all glycoproteins.

I.B.3. Leukocyte Functions

BHV-1 causes a significant reduction in leukocyte functions between 4 and 8 days postinfection. This immunosuppression is directly correlated to the extent of virus replication and is responsible for the secondary bacterial colonization which results in severe pneumonia. To determine the effect of immunization with various glycoproteins on macrophage functions, peripheral blood macrophages were assayed for their chemotactic response to a chemotactic agent (activated bovine serum as a putative source of C5a). Although macrophage chemotaxis was reduced in all animals, the animals immunized with the various glycoproteins had a lower degree of suppression at 5 days post-BHV-1 infection and rapidly returned to normal by 10 days postinfection. In contrast, immunosuppression was more dramatic and remained for a longer period of time in the placebo-treated animals and those immunized with the commercial vaccine. A similar pattern was observed in the case of PMNs. It is interesting to note that although there were no significant differences between the placebo and animals immunized with the commercial vaccine, these animals were actually more suppressed than was the placebo group, indicating that the vaccine does not induce significant protection from immunosuppression by BHV-1. This suggests that the level of antibody and cell-mediated immunity generated by the commercial vaccine is below protective levels. This is supported by the observation that lymphocyte blastogenesis was also suppressed in the commercial vaccine and placebo-immunized animals, whereas those immunized with any individual or combination of glycoproteins were not.

A further indication of neutrophil function was determined by measuring the ability of PMNs to produce superoxide. The PMNs from glycoprotein immunized animals produced similar levels of superoxide throughout the observation period. In contrast, the placebo group or animals immunized with a commercial vaccine had a significant reduction in their ability to produce superoxide. This reduction was a gradual decline such that by Day 10 their superoxide production capabilities were reduced to less than 30% of preinfection levels. A further indication of neutrophil function was demonstrated in a chemiluminescence assay. In this assay, instead of measuring one oxygen radical, the assay measures the ability of neutrophils to produce a number of toxic oxygen species. In this case, the glycoprotein-immunized animals did not demonstrate any significant increase in chemiluminescence for 5 days after BHV-1 infection. By 7 days post-BHV-1 infection there was an increase in chemiluminescence which began dropping by 10 days postinfection. In contrast, the placebo-treated animals and those immunized with the commercial vaccine began to have elevated chemiluminescence responses 5 days post-BHV-1 infection. These levels were extremely elevated by 7 days postinfection and began to decline by 10 days postinfection.

II

This example demonstrates the production of non-native BHV-1 subunit antigens in recombinant vaccinia virus vectors.

II.A. Methods

II.A.1. Cells and Viruses

Strain P8-2 of BHV-1 was propagated in Georgia bovine kidney (GBK) cells and quantitated by plaguing in microtiter plates with an antibody overlay as described previously. Rouse et al. (1974) J. Immunol. 113:1391–1398. Vaccinia virus (VAC) (WR strain) and recombinant vaccinia virus was propagated in BSC-1 or BSC-40 cells. Madin Darby bovine kidney (MDBK) cells, BSC-1 and –40 cells, bovine fibroblasts (BFB), bovine tracheal cells (BTB) and human thymidine kinase-negative ($TK^-$) 143 cells were grown as monolayers in Eagle minimal essential medium (MEM) (Grand Island Biological Co., Grand Island, N.Y.), supplemented with 10% fetal bovine serum (FBS) (Grand Island Biological Co.).

II.A.2. Preparation of DNA

All DNA used for ligations and transfections was CsCl gradient purified and set to concentrations of 1 $\mu g/\mu l$ in 10 mM Tris [pH 7.5], 1 mM EDTA. Maniatis et al. (1984), supra.

II.A.3. Transfection and Isolation of Recombinant Viruses

Recombinant vaccinia viruses were selected by marker rescue as previously described. Wier et al. (1982) Proc. Natl. Acad. Sci. USA 79:1210–1214. Approximately $3 \times 10^6$ BSC-40 cells (thymidine kinase-positive -TK$^+$) were infected with wild-type vaccinia virus (WR strain) at a multiplicity of infection (MOI) of 0.03 PFU per cell. At 4 h postinfection approximately 15 $\mu g$ of CaCl$_2$-precipitated (125 mM) linearized plasmid DNA (i.e., pgB vax, FIG. 8; or pgC vax, FIG. 10) was added to the infected BSC-40 cells. After 4 days of incubation at 37° C., viruses were harvested from cell supernatants following two cycles of freezing and thawing. Several dilutions of sonicated virus supernatants were plated on TK$^-$143 cells and then overlaid with 1% agarose in growth medium containing 5-bromo-2' deoxyuridine (25 $\mu g/ml$) to select for TK$^-$ virus. After three days individual TK$^-$ plaques were removed and virus from these plaques was plated on BSC-40 cells. Putative recombinant viruses were repurified by plaguing on BSC-40 cells. Individual plaques were amplified by growth on BSC-40 cells and virus supernatants were tested for the presence of gI and gIII proteins by ELISA using polyclonal rabbit antisera specific for either gI or gIII.

II.A.4. Preparation of Radiolabeled Cell Lysates

BSC-1, MDBK, BFB or BTB cells were infected with BHV-1, VAC, VAC-I or VAC-III at an MOI of 10. After adsorption of the virus for 1 h, the monolayers were overlaid with either methionine-free or glucose-free MEM (Grand Island Biological Co.) containing 2% FBS (Grand Island Biological Co.) and further incubated at 37° C. Where applicable, antibody was added, immediately after virus adsorption. Six hours after infection, 50 $\mu$Ci of L-[$^{35}$S] methionine or 50 uCi of [$^3$H] glucosamine (Amersham, Oakville, Ont.) per ml was added to the cultures. At 24 h postinfection, the cells were harvested and washed with phosphate-buffered saline (PBS: 0.01 M NaH$_2$PO$_4$/ Na$_2$HPO$_4$, 0.15 M NaCl, pH 7.4). In time course experiments, BHV-1-, VAC-, VAC-I- or VAC-III-infected BSC-1 cells were labeled with L-[$^{35}$S] methionine immediately after virus adsorption and harvested at various times after infection. To increase the incorporation of isotopically labeled methionine, the cells were grown in methionine-free MEM for 6 h before infection. In pulse-chase experiments the cells were overlaid with methionine-free MEM after virus adsorption. At 6 or 12 h postinfection, the cells were pulse-labeled for 15 min with 200 $\mu$Ci of L-[$^{35}$S] methionine in Hanks balanced salt solution (HBSS) (Grand Island Biological Co.). The cells were either harvested immediately or the label was first chased for 2 h by washing and incubating the cells in MEM containing 100 $\mu g$ of cycloheximide per ml. To prepare lysates, the cells were suspended in modified RIPA buffer (0.02 M Tris-hydrochloride [pH 8.0], 0.15 M NaCl, 1% sodium deoxycholate, 1% Nonidet P-40), left on ice for 15 min and sonicated for 15 s at a setting of 100 on a sonifier cell disrupter (Model 1510 Braunsonic Braun, Melsunger, A.G., Germany). The suspensions were clarified by centrifugation at 20,000 rpm for 15 min in a 30° A100 rotor at room temperature (Airfuge, Beckman Instruments, Inc., Fullerton, Calif.). The supernatants were used immediately for immunoprecipitation as described in Example I.

II.A.5. SDS-PAGE and ELISA

Sodium dodecylsulfate-polyacrylamide gel electrophoresis (SDS-PAGE) was performed in 7.5% polyacrylamide discontinuous gels as described in Example I. Electrophoresis was carried out under reducing conditions. Samples containing $^{35}$S were analyzed by autoradiography of the gels on 3M X-ray film (Picker, Saskatoon, Sask.). Gels containing $^3$H were impregnated with Amplify (Amersham), dried and analyzed by fluorography at −70° C. The molecular weights of the polypeptides were estimated from the molecular weight markers (BioRad, Mississauga, Ontario) that were electrophoresed in parallel with the samples.

In order to identify recombinant vaccinia virus, expressing gI or gIII, an indirect ELISA was performed essentially as described in Example I. Microtiter plates were coated with cell extracts prepared from recombinant TK$^-$ virus-infected BSC-40 cells and reacted with gI- or gIII-specific rabbit sera. Affinity-purified, horse-radish peroxidase (HRPO)-conjugated goat anti-rabbit IgG (Boehringer-Monheim, Dorval, Quebec) was used at a dilution of 1:2000 for detection.

A sandwich ELISA was used to compare the yield of glycoproteins gI and gIII from recombinant-infected cells to that from BHV-1-infected cells. Microtiter plates were coated with a mixture of monoclonal IgG as the captive antibody and then incubated with lysates from recombinant- or BHV-1-infected cells. A mixture of HRPO-conjugated monoclonal antibodies with a different epitope specificity was used for detection.

II.A.6. Cell Surface Immunofluoresence

BSC-1 cells were infected with BHV-1, VAC, VAC-I or VAC-III at an MOI of 10. After 20 h at 37° C., the cells were removed by mild trypsinization and $1 \times 10^6$ cells were resuspended in 250 $\mu l$ of 1:20 diluted rabbit antiserum, specific for gI or gIII. After reaction for 45 min on ice, the cells were washed three times in HBSS and incubated with a 1:10 dilution of fluorescein-isothiocyanate-conjugated goat anti-rabbit IgG antiserum (Cappel Laboratories, West Chester, Pa.). After further reaction for 45 min on ice, the cells were washed three times in HBSS and finally resuspended in 10% glycerol-PBS, mounted on glass slides and observed with the aid of a fluorescence microscope.

II.B. Recombinant Production of gI and gIII in a Vaccinia Vector

II.B.1. Construction of Vaccinia Virus Insertion Plasmids

Figure 4:
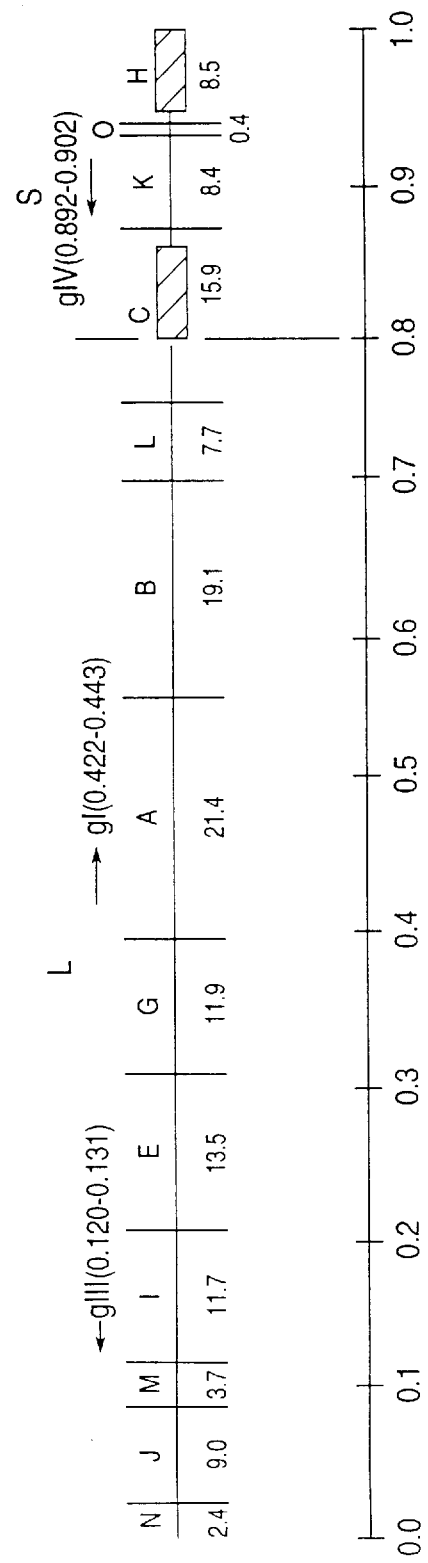
FIG. 4 shows the genomic location of BHV-1's major glycoprotein genes. The position and direction of transcription for the gIII, gI and gIV genes are shown by the arrows above the genomic map. HindIII sites are marked by vertical lines, and the size in kilobase pairs is shown below the genomic map. The scale below the map measures genomic equivalents. Numbers next to gene designations show their position in genomic equivalents. See Example II.B.1.
Figure 8:
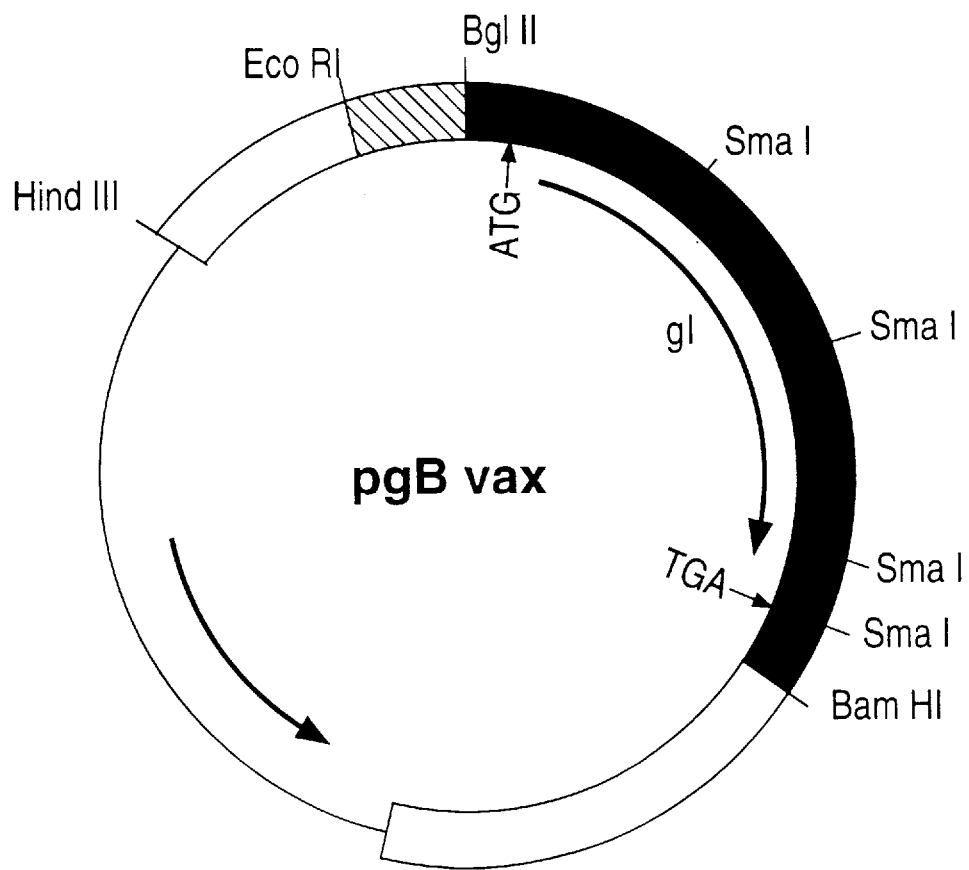
FIG. 8 shows the vaccinia transfer vector pgB vax.

The gI gene maps between 0.422 and 0.443 genome equivalents (FIGS. 4 and 5), which is within the BHV-1 HindIII A fragment described by Mayfield et al. (1983), supra. A KpnI plus AccI partial digestion of the HindIII A fragment produces a 3255 base pair (bp) subfragment which contains the entire gI gene coding sequence. DNA sequence analyses placed an AccI site 20 bp 5' to the ATG start codon, while the KpnI site is 420 bp 3' to the TGA stop codon. This fragment was inserte!d into a synthetic DNA polylinker present between the EcoRI and SalI sites of PBR328 (i.e., ppo126, not shown) to produce pgB complete. To this end, the AccI asymmetric end of the 3255 bp fragment was first blunted with Klenow enzyme and the gI fragment was then ligated to the HpaI plus KpnI sites of ppol26 to give pgB complete. HpaI and KpnI sites are within the polylinker of ppo126 and are flanked respectively by a BglII and a BamHI site. The gI gene was then transferred from pgB complete as a 3260 bp BglII+BamHI fragment to the BamHI site of the vaccinia virus insertion vector pGS20 to generate pgB vax (FIG. 8; plasmid pGS20 with gI gene). Moss et al. in *Gene Amplification and Analysis*, Vol. 3, pp. 201–213 (Papas et al. eds. 1983).

Figure 9:
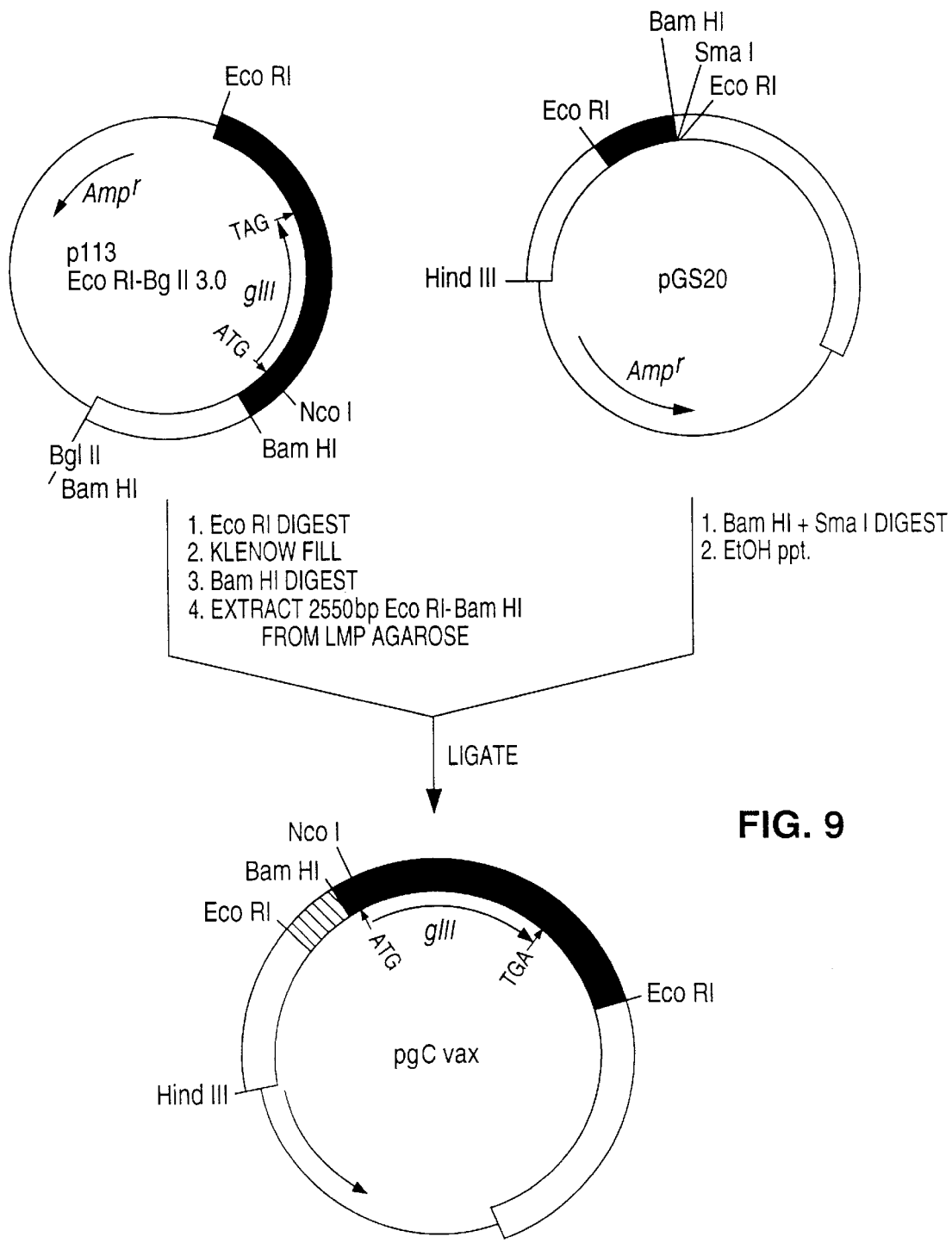
FIG. 9 shows the construction of recombinant plasmid pgC vax. See Example II.
Figure 10:
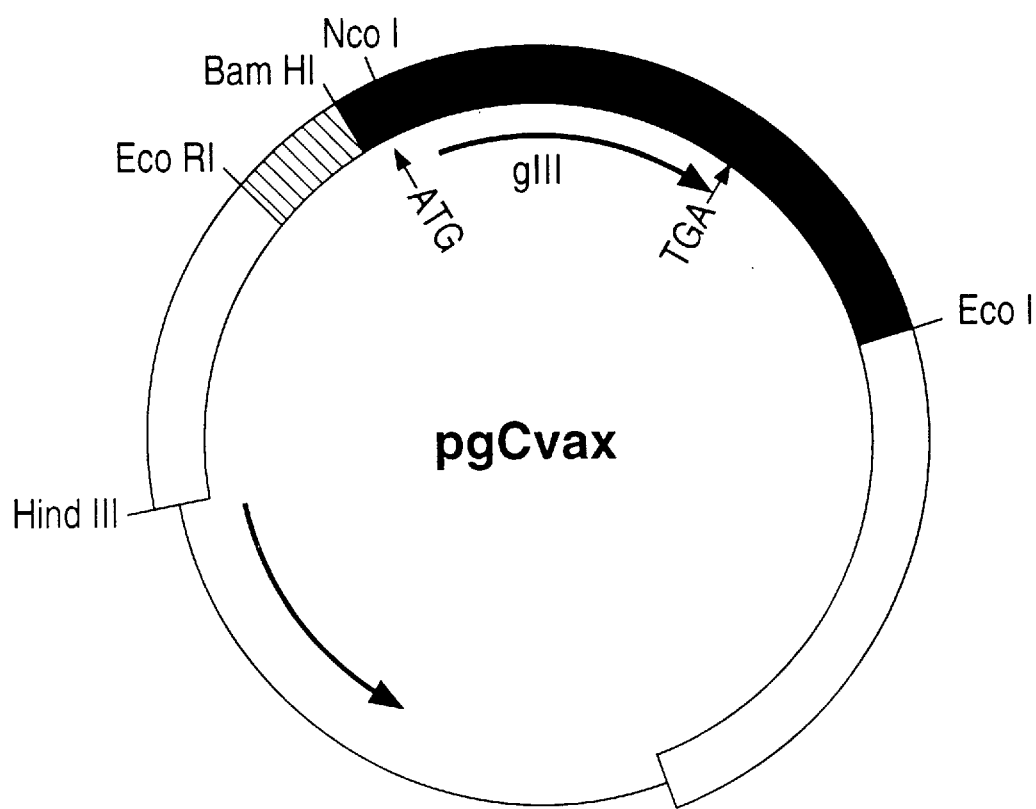
FIG. 10 depicts the vaccinina transfer vector pgC vax.

The BHV-1 gIII gene maps between 0.120 and 0.131 genome equivalents (FIGS. 4 and 6) which lay within the BHV-1 HindIII I fragment. Mayfield et al. (1983), supra. The entire gene is contained within a 3090 bp BglII+EcoRI subfragment of HindIII I which was cloned into the EcoRI plus BamHI sites. of ppo126 to yield p113R1 Bgl 3.0 (FIG. 9). The gIII gene was transferred to the BamHI plus SmaI sites of pGS20 as a 2550 bp EcoRI+BamHI subfragment of p113R1 Bgl 3.0 to generate pgC vax (FIG. 10; plasmid pGS20 with gIII gene). The BamHI site of the gIII gene subfragment is 50 bp upstream from the ATG start codon while the EcoRI site which was blunted with Klenow enzyme prior to ligation is 920 bp downstream from the TAG stop codon.

II.B.2. Construction of Recombinant Vaccinia Virus

The two plasmids pgB vax and pgC vax were then used to transfect BSC-40 cells infected with wild-type vaccinia virus (WR strain). Homologous recombination between vaccinia TK sequences in the plasmid and virus genome resulted in the insertion of the gI or gIII gene into vaccinia virus. Recombinant vaccinia viruses putatively expressing BHV-1 gI or gIII were selected as TK− plaques produced on TK− 143 cells in the presence of 5-bromodeoxyuridine, following recovery of recombinant virus from the initial BSC-40 cell infection. Recombinant vaccinia virus actually expressing BHV-1 gI or gIII was identified by screening TK− virus in an ELISA. Infected cell extracts from recombinant TK− virus were immobilized on microtiter plates and reacted with serial dilutions of gI- or gIII-specific rabbit sera. ELISA-positive infected cell extracts were used for further studies.

II.B.3. Analysis of Recombinant Virus DNA

To insure proper gene insertion, putative recombinant virus DNA was isolated, digested with restriction endonucleases known to cut within the BHV-1 gene inserts, run on agarose gels and transferred to nitrocellulose by the methods of Southern (1975) J. Mol. Biol. 98:503. Southern transfers were then probed with $^{32}$P-labeled nick-translated gI and gIII gene fragments. The order and size of the fragments generated from the recombinant viruses were consistent with those predicted by the DNA sequence analyses of the gI and gIII genes.

II.B.4. Analysis of Glycoproteins Made in Recombinant-Infected Cells

To examine the protein products translated in vitro from the BHV-1-specific transcripts, BSC-1 cells were infected with BHV-1, WR vaccinia virus (VAC), vaccinia recombinant VAC-I or vaccinia recombinant VAC-III and labeled with L-[$^{35}$S] methionine. The radiolabeled proteins were immunoprecipitated with gI-specific monoclonal antibody 1E11 or gIII-specific monoclonal antibody 1D6, and analyzed by SDS-PAGE under reducing conditions.

Monoclonal antibody 1E11 precipitated three major glycoproteins from BSC-1 cells infected with recombinant VAC-I, but did not react with any proteins from mock-, VAC-, or VAC-III-infected cells. These glycoprotein species comigrated exactly with authentic BHV-1 glycoproteins pgIa (117K), gIb (74K) and gIc (55K). BHV-1 glycoprotein gIa, the uncleaved counterpart of gIb and gIc, was not found in recombinant VAC-I-infected cells, indicating a difference in the efficiency of processing. Glycoproteins gIa and gIb, which have apparent molecular weights of respectively 130K and 74K in MDBK or GBK cells, appeared to have slightly lower molecular weights of 127K and 71K in BSC-1 cells. Similarly, monoclonal antibody 1D6 precipitated a unique glycoprotein from BSC-1 cells infected with recombinant VAC-III, which comigrated with authentic BHV-1 glycoprotein gIII. This antibody did not react with any proteins from mock-, VAC- or VAC-I-infected cells. Although this glycoprotein has an apparent molecular weight of 91K in MDBK and GBK cells, it appeared to have a molecular weight of 85K in BSC-1 cells. The observed shifts in apparent molecular weights were probably due to a difference in the extent of glycosylation.

Several other cell lines, both permissive and nonpermissive for vaccinia replication, were tested for the production of BHV-1 glycoproteins after infection by VAC I or VAC III. BFB and BTB cells, permissive for vaccinia replication, both produced the same species of BHV-1 glycoprotein, when infected with recombinant VAC-I or VAC-III. In addition to gIII, its precursor, pgIII (69K) was detected in BHV-1-infected BFB and BTB cells, indicating that in these cells recombinant-produced gIII is processed at a faster rate than its authentic counterpart. However, in MDBK cells, which are nonpermissive for vaccinia growth, no expression of the glycoproteins was observed.

These data demonstrate that the two recombinant vaccinia viruses produce BHV-1 glycoproteins gI and gIII and their electrophoretic mobility suggests that they are fully glycosylated. In support of this conclusion, BSC-1 cells were infected with BHV-1, VAC-I, or VAC-III, labeled with [$^3$H] glucosamine and analyzed by immunoprecipitation followed by SDS-PAGE. This experiment confirmed that recombinant and authentic glycoproteins gI and gIII were glycosylated in a similar, if not identical, manner.

II.B.5. Quantitation of Glycoproteins Produced in Recombinant-Infected Cells

In order to quantitate the amounts of recombinant glycoprotein produced in different cell lines, a sandwich ELISA was performed. Cell lysates were prepared from cells infected with BHV-1, VAC-I or VAC-III and assayed with respect to production of glycoproteins gI and gIII. Table 1 shows that MDBK is the cell line of choice for producing large quantities of BHV-1 glycoproteins, followed by BTB, BFB and BSC-1 respectively. In contrast, BSC-1 is the better cell line for VAC-I and VAC-III, followed by BFB and BTB. MDBK cells infected with VAC-I or VAC-III did not produce any glycoproteins, which is in accordance with the nonpermissiveness of this cell line for vaccinia replication. A comparison of the best producing cell lines for each virus, i.e., MDBK for BHV-1 and BSC-1 for VAC-I and VAC-III, showed that authentic gI and gIII were produced in approximately a 6-fold excess over recombinant gI and gIII.

Since the highest quantities of recombinant gI and gIII, as well as sufficient amounts of authentic gI and gIII, were produced in BSC-1 cells, these cells were used for all subsequent experiments.

TABLE 1

| | ELISA Titer[a] in Cell Line | | | | | | | |
|---|---|---|---|---|---|---|---|---|
| | BSC-1 | | MDBK | | BFB | | BTB | |
| Virus | gI | gIII | gI | gIII | gI | gIII | gI | gIII |
| None | 16 | 16 | 4 | 16 | 16 | 16 | 4 | 4 |
| BHV-1 | 102 | 42 | 2000 | 1200 | 170 | 25 | 256 | 48 |
| VAC | 4 | 4 | 4 | 16 | 4 | 4 | <4 | 4 |
| VAC-I | 320 | 4 | 16 | 16 | 200 | 4 | 85 | 4 |
| VAC-III | <4 | 190 | 4 | 16 | 4 | 30 | <4 | 25 |

[a]ELISA titers were expressed as the reciprocal of the highest dilution that still gave a reading of at least 0.1.

II.B.6. Posttranslational Modifications of BHV-1 Glycoproteins

Two lines of evidence suggest that the authentic and recombinant glycoproteins gI and gIII are glycosylated to the same extent. First, they comigrated in one-dimensional polyacrylamide gels and secondly, they incorporated [$^3$H]

glucosamine in an identical fashion. To support these observations, two additional experiments were performed.

The effect of tunicamycin, a drug which inhibits N-linked glycosylation, on the processing of gI and gIII was investigated. In the presence of 1 μg of tunicamycin per ml, the nonglycosylated precursor form of gI, pI (105K) was synthesized in BSC-1 cells infected with either VAC-I or BHV-1 and immunoprecipitated by monoclonal antibody 1E11. Since the nonglycosylated precursor forms comigrated, this suggests that the polypeptide backbones of authentic and recombinant gI are identical. Consequently, the fact that the glycosylated products of VAC-I and BHV-1 also comigrated, provides further support for similar or identical glycosylation.

In the presence of 0.1 or 1.0 μg/ml of tunicamycin, a polypeptide of 77K was detected in BSC-1 cells, infected with either VAC-III or BHV-1 and immunoprecipitated with monoclonal antibody 1D6. Since gIII contains O-linked carbohydrates, this species does not correspond to the nonglycosylated precursor, but to a partially glycosylated product, containing only O-linked carbohydrates. These species comigrated in VAC-III- and BHV-1-infected BSC-1 cells, suggesting that the N-linked and O-linked glycosylated processes are similar if not identical for both products.

The order and time course of synthesis of gI and gIII was investigated in a second series of experiments. BSC-1 cells were infected with BHV-1, VAC-I or VAC-III, labeled with L-[$^{35}$S] methionine immediately after virus adsorption and harvested at 2 h intervals after infection. Cell lysates were prepared and precipitated with monoclonal antibody 1E11 or 1D6. These experiments demonstrated that both recombinant and authentic gI were synthesized as early as 2 h postinfection. Recombinant gIII was also detected at 2 h after infection, but authentic gIII was not present until 8 h postinfection.

II.B.7. Cell Surface Expression of B-1 Glycoproteins

Expression of glycoproteins gI and gIII on the cell surface was examined by indirect immunofluorescence of recombinant- or BHV-1-infected live BSC-1 cells. At 20 h postinfection, the cells were incubated with either gI- or gIII-specific rabbit serum. The recombinant-derived glycoproteins had a patchy appearance over the entire cell surface, which was similar to the pattern observed for BHV-1-infected cells. The fluorescence caused by recombinant gIII was stronger than that of recombinant gI.

II.C. Recombinant Production of gIV in a Vaccinia Vector

II.C.1. Construction of the pVVSL-1 Insertion Vector

Figure 11:
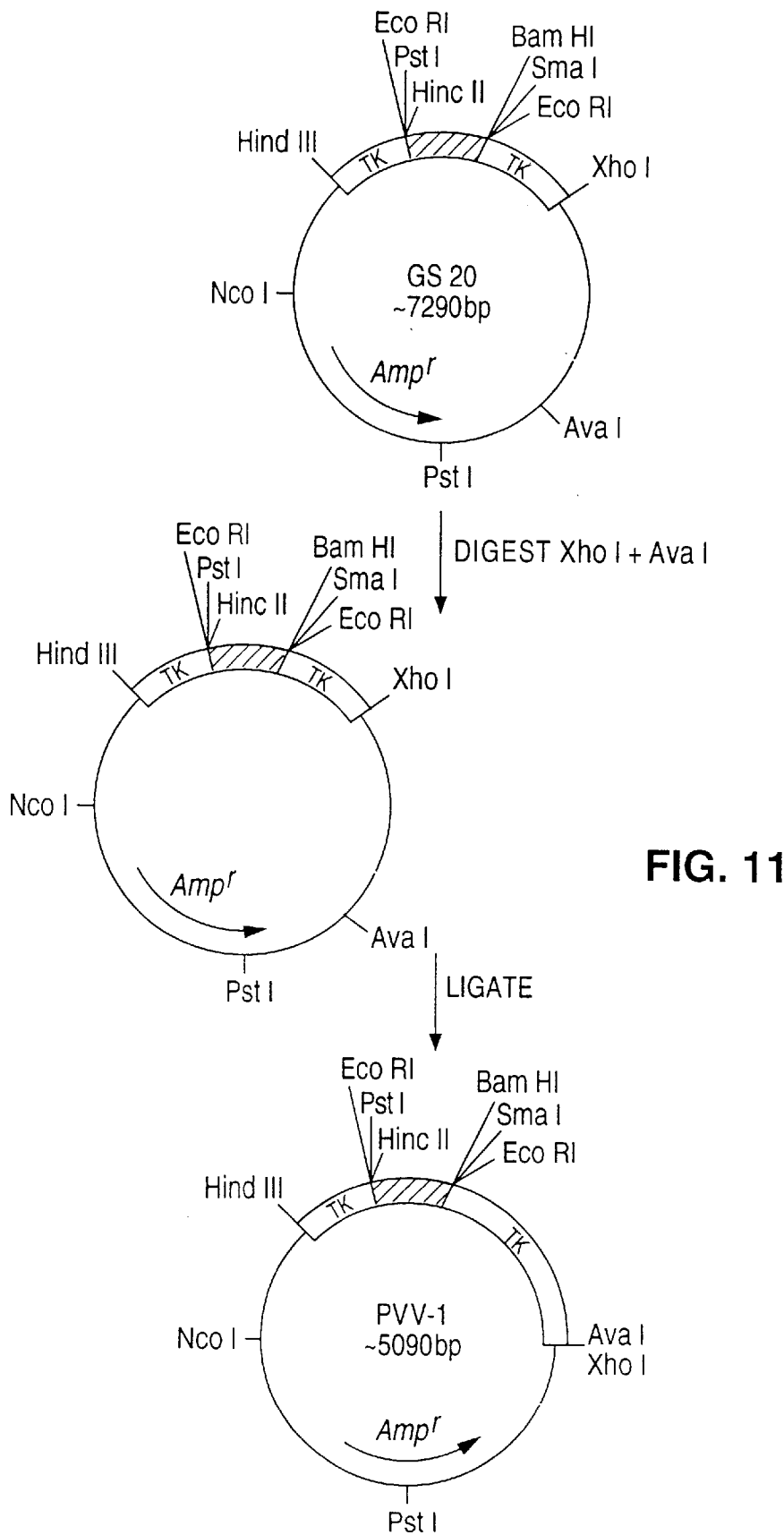
FIG. 11 shows the construction of the vaccinia expression vector pVV-1.
Figure 12:
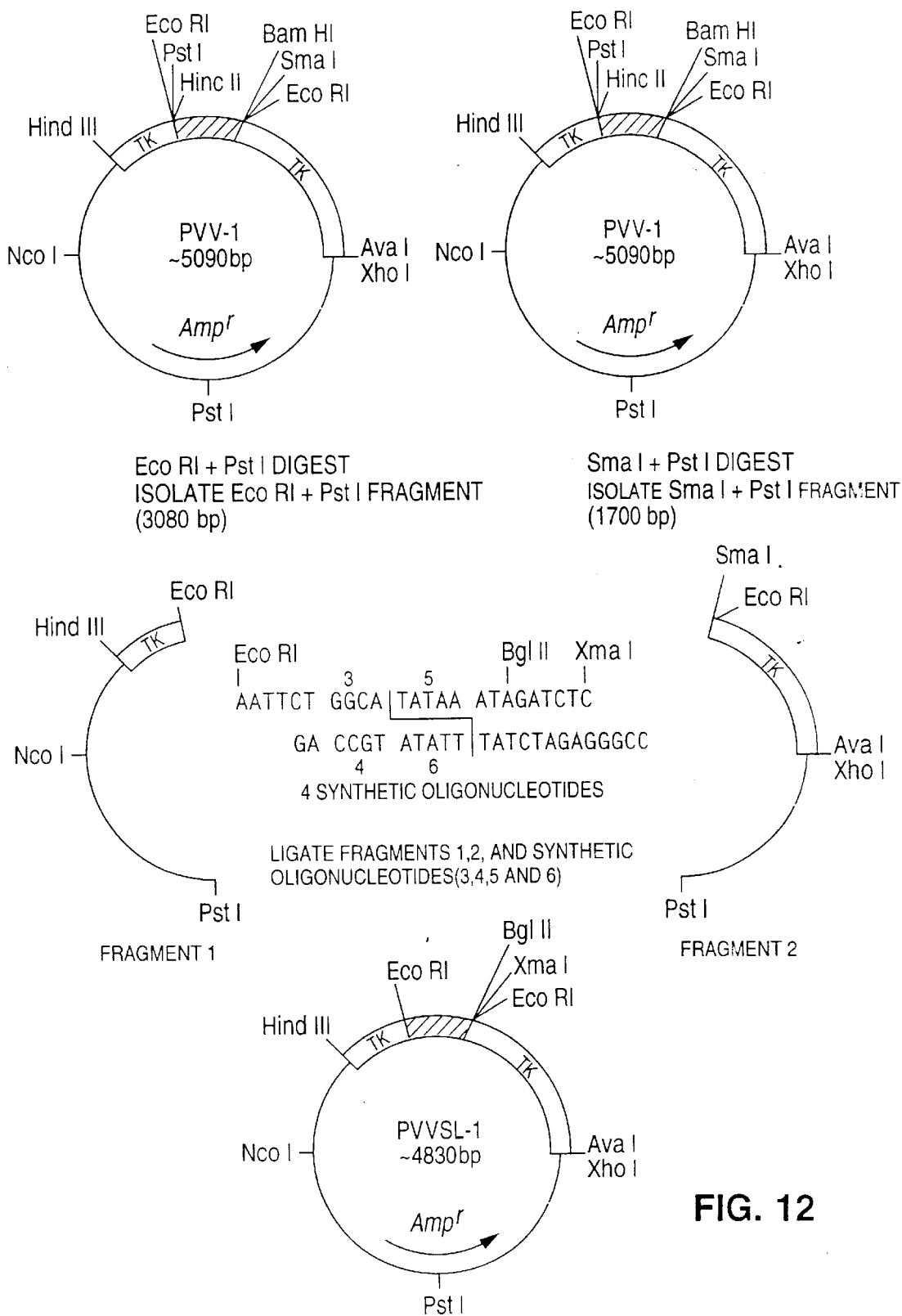
FIG. 12 depicts the construction of the vaccinia expression vector pVVSL-1.

The pVVSL-1 insertion vector was constructed as depicted in FIGS. 11 and 12. Specifically, the pVV-1 expression vector was derived from the pGS-20 plasmid (FIG. 9; van Drunen Littel-van den Hurk et al. (1989) J. Virol. 63:2159–2168). pGS-20 was digested with XhoI and AvaI and then ligated. This process resulted in the deletion of a 2,200 bp fragment and the production of pVV-1 (FIG. 11).

pVVSL-1 was then constructed from elements of pVV-1 and a series of four synthetic oligonucleotides representing an adenine rich region, a spacer and a consensus sequence from the vaccinia virus late gene promoter. (This consensus sequence, TAAAT, was based on a sequence described by Davison and Moss (1989) J. Mol. Biol. 210:771–784.) A 3,080 bp EcoRI-PstI fragment and a 1,700 bp SmaI-PstI fragment were isolated from restriction enzyme digests of pVV-1. The fragments were then ligated together with the four oligonucleotides to form pVVSL-1. The pWSL-1 has two unique cloning sites; BglII or BglII+SmaI (FIG. 12).

II.C.2. Insertion of the Full-Length BHV-1 gIV Gene into PVVSL-1

The procedures for gene insertion and recombinant vaccinia virus recovery were the same as that described for pGS-20. (See, van Drunen Littel-van den Hurk et al. (1989) J. Virol. 63:2159–2168.)

Figure 13:
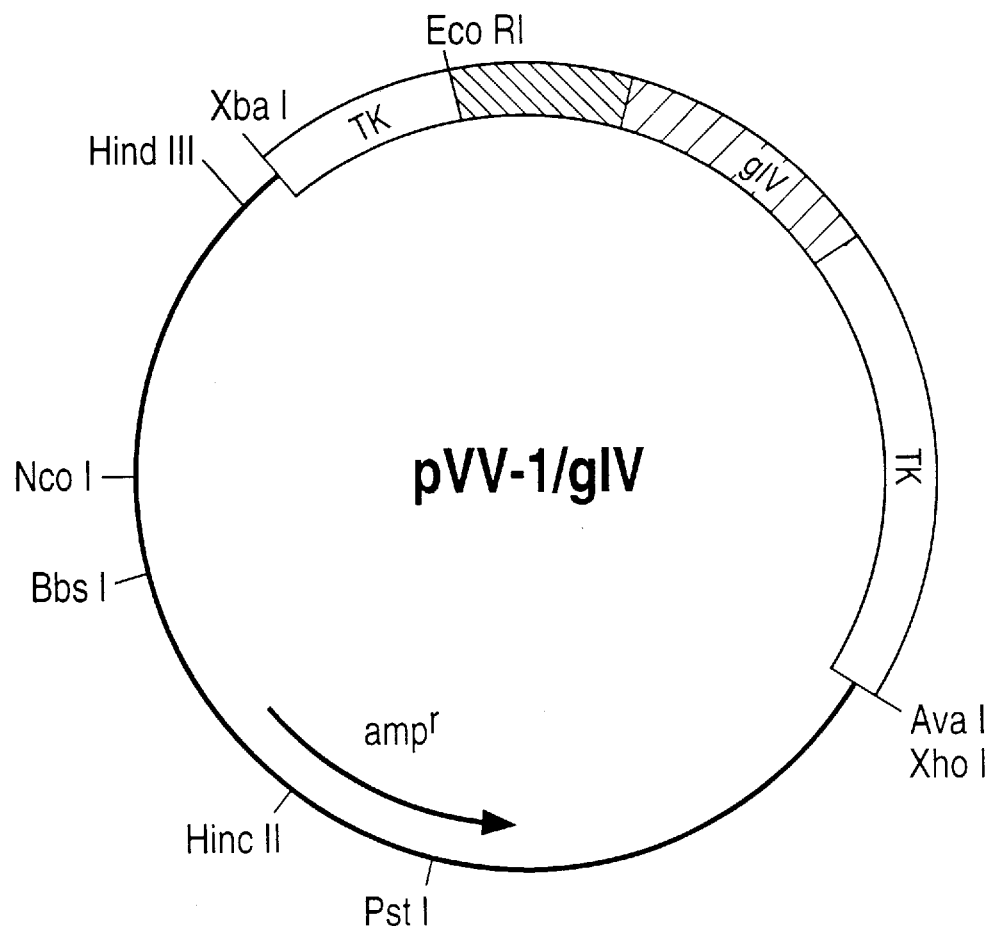
FIG. 13 depicts the vaccinia expression vector pVV-1/gIV with the full length gIV gene cloned into the BglII cloning site of pVVSL-1.

The BHV-1 gIV sequence shown in FIG. 7 was digested with MaeI restriction endonuclease. The resulting MaeI sites at sequence positions 42 and 1344 were converted to BglII sites using commercially obtained oligonucleotide linkers (Pharmacia). The resulting BglII adapted BHV-1 gIV gene was then cloned into the BglII cloning site of pVVSL-1 to yield the expression vector pVV-1/gIV (FIG. 13).

II.C.3. Insertion of a Truncated BHV-1 QIV Gene into pVVSL-1

The gene for BHV-1 gIV was modified to incorporate a stop codon in the reading frame immediately preceding the putative membrane spanning region of the mature protein (FIG. 7). The modification of the gene results in the early termination of translation and the secretion of the truncated protein. This system eliminates the requirement for extensive downstream processing that is associated with the production of antigens that are associated with membranes, and causes an up to tenfold increase in product yield.

Figure 14:
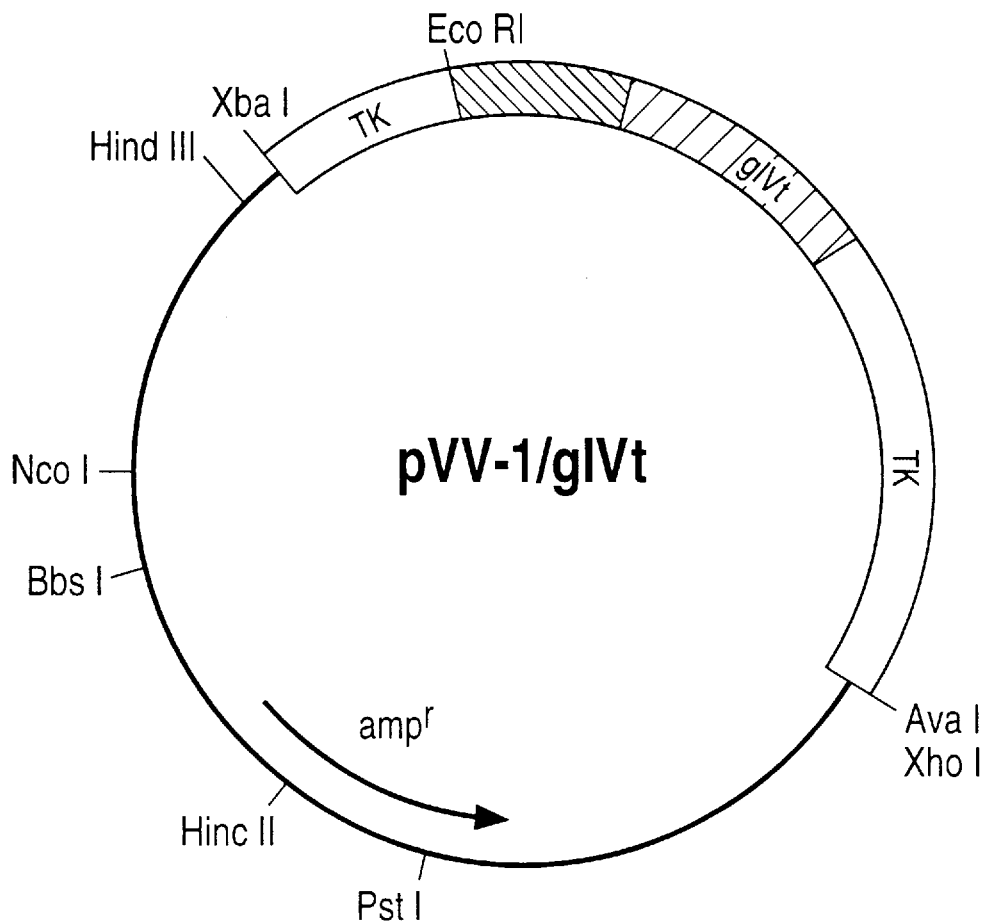
FIG. 14 shows the vaccinia expression vector pVV-1/gIVt which includes a modified BHV-1 gIV gene inserted into the BglII cloning site of pVVSL-1.

The BglII adapted gene for BHV-1 gIV was partially digested with SacII. Gene fragments cut at nucleotide position 1154 were identified and isolated. The SacII site was then converted into a XhoI site using commercially obtained oligonucleotide linkers (Pharmacia). A second synthetic oligonucleotide linker was then inserted at the XhoI site to yield an in-frame stop codon. The resulting modified BHV-1 gIV gene was then cloned into the BglII cloning site of pVVSL-1 to yield the expression vector pVV-1/gIVt (FIG. 14).

II.C.4. Purification of Recombinantly Expressed gIV

BSC-1 cells were cultured in MEM containing 10% fetal bovine serum. Confluent monolayers were infected with the recombinant vaccinia, BHV-1 gIV virus, at a multiplicity of 0.1. 72 hours after infection or at the appearance of total cytopathic effect, the recombinant gIV was harvested.

For full-length gIV, the cells were scraped from the surface of the culture flasks; into the growth media, which was then centrifuged (1000 g for 20 min) and the cell pellet collected. The cells were disrupted with detergent and further processed as previously described.

Truncated gIV was collected by harvesting the media from the culture flasks. Cell debris was removed by centrifugation at 1000 g for 20 min. The clarified media was frozen at −70° C. until processing. After thawing, the media was filtered through a 0.45 micron filter. The detergents, Nonidet P40 and Na Deoxycholate, were then added to the filtrate to final concentrations of 0.1%. The truncated gIV was then purified by affinity chromatography through BHV-1 gIV specific columns, as has been described previously.

III

This example demonstrates the production of non-native BHV-1 subunit antigens in recombinant SV40 and RSV vectors.

III.A. Materials and Methods

III.A.1. Reagents and Media

Restriction enzymes, T4 DNA polymerase, T4 DNA ligase, calf intestine alkaline phosphatase, phosphorylated BglII linker oligonucleotides, deoxynucleotide triphosphates and protein A-Sepharose were purchased from Pharmacia, Dorval, Quebec, Canada and used as recommended by the manufacturer. Other chemicals and reagents for DNA manipulations, transfections and protein analysis were purchased from Sigma Chemicals, St. Louis, Mo., and used according to the standard methods described by Maniatis et al. (1982), supra, and Davis et al. *Basic Methods in Molecular Biology* (1986), except where noted otherwise below. Cell culture media, fetal bovine serum (FBS), G418 and other cell culture reagents were obtained from GIBCO/BRL, Burlington, Ontario, Canada. Antibodies, wheat germ agglutinin, avidin-biotin immunoperoxidase staining kits, and other reagents for enzyme immunoassays were purchased from Dimension Laboratories, Mississauga, Ontario, Canada and used according to the manufacturers' recommendations. Radioisotopically labeled compounds and reagents for fluorography were purchased from Amersham, Oakville, Ontario, Canada.

III.A.2. Plasmid Construction

Figure 17:
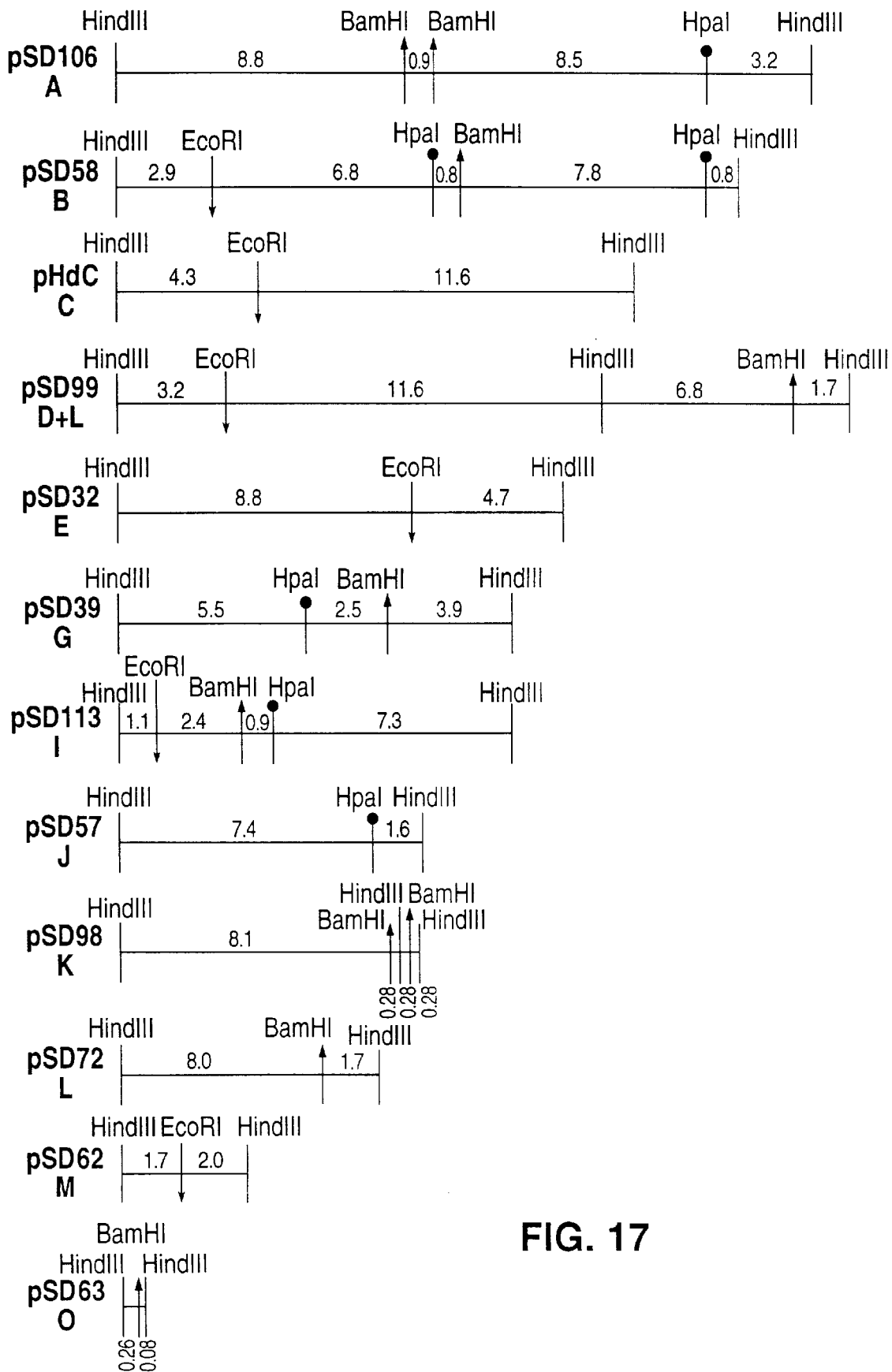
Figure 18:
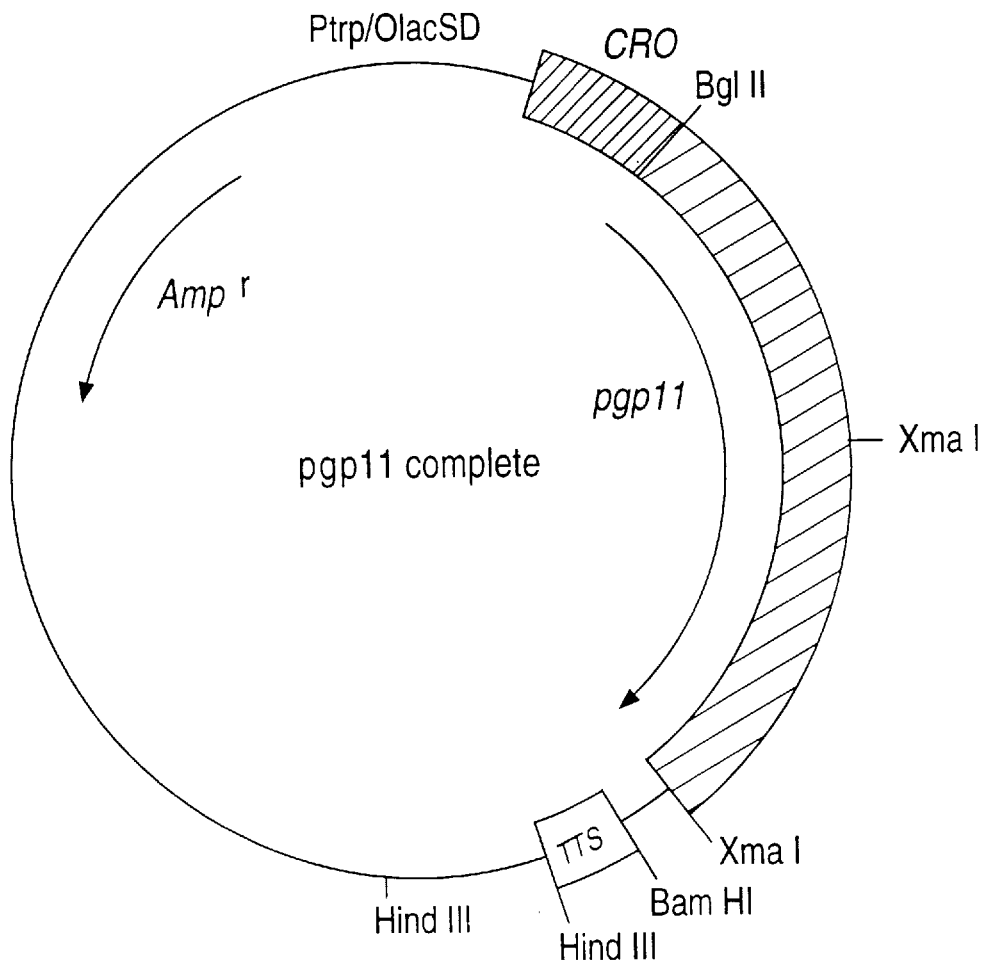

The complete coding sequence of BHV-1 gI was excised from a subclone of pSD106 (Mayfield et al. 1983, supra; the genomic library is shown in FIG. 17) and inserted into the expression vector pRSVcat (Gorman et al. 1982, supra) in place of the cat gene by ligation of the 3.3 kilobase pair (kbp) BglII-BamHI gI gene fragment into the HindIII-HpaI sites of PRSV cat after the latter sites had been converted into a unique BglII cloning site by blunt end repair, BglII linker addition, and BglII digestion (FIG. 15A). The gI gene was similarly subcloned into the expression vector pSV2neo (Southern et al. 1982, supra) in place of the neo gene by ligation of the 3.3 kbp BglII-BamHI gI gene fragment into the HindIII-SmaI sites of pSV2neo after the latter sites had been converted into a unique BglII cloning site as described for pRSVcat (FIG. 15B).

The complete coding sequence of BHV-1 gIII was excised from a subclone of pSD113 (Mayfield et al. (1983), supra) as a 2.4 kbp BamHI-EcoRI fragment treated with T4 DNA polymerase, ligated to BglII linkers, digested with BglII then cloned into pRSVcat and pSV2neo as described for BHV-1 gI.

Plasmid DNA was prepared for transfection by equilibrium banding in CsCl-ethidium bromide gradients and sterilized by ethanol precipitation.

III.A.3. Cells and Virus

Madin-Darby bovine kidney (MDBK) and murine 3T3 cells were cultured in Eagle's minimal essential medium supplemented with 10% FBS. Murine LMTK⁻ and L929 cells were cultured in Dulbecco modified Eagle medium (DMEM) supplemented with 5% FBS. Virus stocks of BHV-1 strain P8-2 were grown in MDBK or Georgia bovine kidney cells as previously described in Example I. Virus stocks of vaccinia virus strain WR were grown in BSC-1 cells as described in Example II.

III.A.4. Transfections

LMTK⁻ cells were transfected with expression plasmid constructions by a modified calcium phosphate precipitation procedure. LMTK⁻ cells at approximately 50% confluence were rinsed and incubated at 37° C. in fresh growth medium for 3 h before transfection. Calcium phosphate precipitates of plasmid DNA were prepared as previously described with pSV2neo DNA incorporated into each precipitate as a co-transfecting selectable marker. Graham et al. (1973) Virology 52:456–467; Wigler et al. (1979) Proc. Natl. Acad. Sci. USA 76:1373–1376. Control precipitates were prepared with pSV2neo or salmon sperm DNA only. Medium was removed from the cells and the DNA precipitates were added and adsorbed for 45 min at room temperature. Growth medium was then added and adsorption continued at 37° C. in a 4% $CO_2$ atmosphere. Chen et al. (1987) Mol. Cell. Biol. 7:2745–2757. After 4 h the medium was removed and the cells were exposed to 20% glycerol shock for 2 min at room temperature then incubated at 37° C. in growth medium supplemented with 8 mM Nabutyrate. Frost et al. (1978) Virology 91:39–50; Gorman et al. (1983) Nucleic Acids Res. 11:7631–7648. After 16–24 h the supplemented medium was removed and replaced by growth medium for 48 h. Cells were then passaged in selective growth medium containing 400 μg of G418 per ml which was replaced every 3 to 5 days. Resistant colonies appeared in 10 to 14 days at a frequency of approximately $10^{-3}$ using this method. The colonies derived from each transfection were pooled and cloned by limiting dilution at least once before screening.

III.A.5. Immunocytochemistry and Enzyme Linked Immunosorbent Assays

G418 resistant LMTK⁻ cell clones were seeded onto glass chamber slides (Miles Laboratories, Rexdale, Ontario, Canada) and 96 well plastic tissue culture plates (Nunclon, Roskilde, DK) which had been precoated with 2 μg of poly-L-lysine hydrobromide per $cm^2$, and grown to confluence. For BHV-1 infected control cells, MDBK or LMTK⁻ cells were similarly seeded onto poly-L-lysine coated slides and plates, grown to 80% confluence and then infected with BHV-1 at a multiplicity of infection of 1. After 1 h adsorption at 37° C., fresh medium containing 2% FBS was added and incubation was continued for a further 12 to 18 h, for MDBK cells, or for a few minutes, for infected LMTK⁻ cells. Transfected LMTK⁻ cell clones and control cells were either fixed and permeabilized with methanol at −20° C. for 15 min and washed in Hank's balanced salt solution (HBSS) or, for surface expression studies, washed in HBSS without fixing. Nonspecific binding sites were blocked by adding heat inactivated normal equine serum diluted 1:75 in HBSS and incubating at room temperature for 1 h. The blocking solution was removed and biotinylated wheat germ agglutinin, or monoclonal antibodies specific for gI and gIII were diluted 1:1,000 in HBSS, and added to the slides and plates, which were incubated at room temperature for 1 h. The slides and plates were then processed with an avidin-biotin enhanced immunoperoxidase assay kit specific for mouse IgG (Vector Laboratories, Burlingame, Calif.) according to the manufacturer's recommendations up to the final substrate development step. For slides, the final substrate was 50 mM Tris hydrochloride, pH 7.5, 0.01% $H_2O_2$, 1.7 mM $NiCl_2$, and 1 mg 3,3'-diaminobenzidine tetrahydrochloride per ml. The substrate reaction was stopped after 5 min incubation at room temperature by rinsing the slides in tap water. For enzyme linked immunosorbent assays (ELISAs) the final substrate was 0.1 M citric acid, pH 4.0, 0.015% $H_2O_2$, and 1 mg ABST (2,2'-amino-di-[3-ethylbenzthiazoline sulfonate(6)] per ml. The ELISA substrate reactions were stopped after 5 to 10 min incubation at room temperature by addition of sodium dodecyl sulfate (SDS) to a final concentration of 5% and the absorbance of each well was read at 405 nm in a microtiter plate reader.

III.A.6. Radioimmunoprecipitation

To radiolabel cellular proteins, clones or transfected LMTK⁻ cells at approximately 80% confluence were incubated in methionine free DMEN supplemented with 2% FBS at 37° C. for 6h. For glycosylation inhibition studies, antibody was included at this point at a final concentration of 2 μg per ml. After 6 h of incubation, [$^{35}$S] methionine was added to a final concentration of 50 uci per ml and the cells were then incubated for an additional 18 h. BHV-1 infected MDBK cells were radiolabeled by a similar method as previously described. van Drunen Littel-van den Hurk et al. (1985) Virology 144:204–215.

Radiolabeled cells were harvested by scraping, washed with HBSS, and resuspended in modified RIPA buffer (50 mM Tris hydrochloride, pH 8.0, 150 mM NaCl, 1% sodium deoxycholate, 1% Nonidet P-40, 0.1% SOS and 1 mM phenylmethylsulfonyl fluoride). After incubation on ice for 15 min, the cell suspensions were sonicated then centrifuged at 75,000 x g for 1 h at 4° C. The supernatants were collected, gI or gIII-specific monoclonal antibody ascites fluid were added to a final dilution of 1:20, SDS was added to a final concentration of 0.2 to 0.5%, and the samples were incubated for 16 to 18 h at 4° C. on a rocking platform. Coated protein A-Sepharose (PAS) beads were prepared by swelling lyophilized PAS beads in modified RIPA buffer at a concentration of 10 mg per ml for 1 h at 4° C. on a rocking platform then adding rabbit IgG anti-mouse IgG to a final concentration of 800 $\mu$g per ml, and incubating for a further 16–18 h. After incubation, unbound rabbit IgG anti-mouse IgG was removed from the coated PAS beads by washing three times with modified RIPA buffer. Approximately 10 mg of coated PAS beads were added to each mixture of radiolabeled cell lysate plus monoclonal antibody and the samples were incubated at 4° C. on a rocking platform. After 3–4 h, the samples were washed 4 times with modified RIPA buffer then resuspended in reducing sample buffer (62 mM Tris hydrochloride, pH 6.8, 2% SDS, 5% 2-mercaptoethanol, 10% glycerol and 0.01% bromophenol blue) and boiled for 4 min. Samples were separated by electrophoresis in 10% SDS-polyacrylamide gels and fluorographed.

III.A.7. AbCC

Transfected murine clones were seeded into 96-well round-bottomed plastic tissue culture plates at a density of $2 \times 10^3$ cells per well and incubated at 37° C. in growth medium containing 1.5 uCi per well of $Na_2{}^{51}CrO_4$ for 24 h. The plates were washed 3 times and gI, or gIII-specific monoclonal antibodies were added at various dilutions in DMEM containing 2% FBS and 1 $\mu$g of actinomycin D per ml. The transformed cells, like all normal nucleated cells, are resistant to complement attack in the absence of metabolic inhibitors such as actinomycin D. After 2 h incubation at 37° C., freshly thawed rabbit complement (Cedar Lane, Hornby, Ontario, Canada), at various dilutions, was added. Control wells for calculation of total releasable radiolabel received 3% Triton X-100 instead of complement. After 90 min incubation at 37° C., 50% of the supernatant fluid from each well was harvested, counted and the specific release was calculated as previously described. Misra et al. (1982), supra.

III.A.8. Cytotoxic T Cell Cytotoxicity (CTCC)

C3H/HeJ ($H-2^k$) or Balb/c ($H-2^d$) mice were immunized intraperitoneally with approximately $10^8$ PFU of BHV-1 at 8 and 11 weeks of age. Three weeks after the second immunization, the spleens were excised and cell suspensions prepared by gentle homogenization. The suspensions were treated with 0.83% ammonium chloride to remove erythrocytes, then washed, counted, viability scored, and seeded into 6-well tissue culture plates at a concentration of approximately $2 \times 10^6$ cells per well in RPMI 1640 medium containing 10% FBS, 25 mM HEPES and $5 \times 10^{-5}$ M 2-mercaptoethanol. The cells were restimulated with $2 \times 10^6$ PFU of BHV-1 per well and incubated at 37° C. in a humidified, 5% $CO_2$ atmosphere for 6 days.

L929 and 3T3 cells to be used as targets were suspended in RPMI medium and infected with BHV-1 or vaccinia virus at a multiplicity of infection of 5 for 1 h at 37° C. Infected targets, uninfected controls, and transfected cells were then labeled with $Na_2{}^{51}CrO_4$ for 1 h at 37° C. The labeled target cells were washed three times with RPMI medium containing 5% FBS, 25 mM HEPES, and $5 \times 10^{-5}$ M 2-mercaptoethanol, then seeded into U-bottom microtiter plates at $10^4$ cells per well.

Restimulated effector cells were washed, counted, viability scored and added to the plates containing radiolabeled targets at various effector to target cell ratios, with quadruplicate wells for each variable. The plates were then incubated for 7 h at 37° C. in a 5% $CO_2$ atmosphere before supernatant fluids were harvested, counted and specific cytotoxicity values calculated as previously described. Lawman et al. (1980) Infec. Immun. 30:451–461.

III.A.9. Immunizations with Transfected Cells and Antibody Titrations

C3H/HeJ mice were immunized intraperitoneally with $10^{6.5}$ transfected cells suspended in 0.5 ml of HBSS, without adjuvant, at 6, 10 and 14 weeks of age. Pooled sera were obtained at 5, 8, 11 and 15 weeks of age from groups of 5 identically immunized mice. BHV-1-specific antibody levels were measured by virus neutralization and ELISA assays as described in Example I.

III.B. Results

III.B.1. Construction of Plasmids (i) gI Constructions. The gene encoding BHV-1 gI was inserted into the eukaryotic expression vector pRSVcat in place of the cat gene such that the start codon of the gI gene was situated 100 base pairs (bp) downstream of the RSV promoter and 70 bp downstream of the transcriptional start site associated with this promoter to give pRSVgI (FIG. 15A). Yamamoto et al. (1980) Cell 22:787–797. These manipulations removed the normal viral promoter upstream of the gI gene and placed the gene under the control of the Rous sarcoma virus enhancer/promoter unit. Approximately 480 bp lay between the stop codon and the SV40 based polyadenylation signals remaining in the expression vector after removal of the cat gene. A polyadenylation signal of BHV-1 origin approximately 30 bp downstream of the gI gene stop codon was retained in this construction, however, polyadenylation signal utilization was not examined for this or any of the plasmid constructions described below. An LMTK$^-$ cell line transfected with pRSVgI was designated RSVgI.

The gI gene was also inserted into the expression vector pSV2neo in place of the neo gene such that the start codon of the gI gene was situated approximately 130 bp downstream of the SV40 early promoter and approximately 100 bp downstream of the transcriptional start site associated with this promoter to give pSV2gI (FIG. 15B). Fiers et al. (1978) Nature (London) 273:113–130. Following the gI gene stop codon were approximately 430 bp of non-coding BHV-1 DNA, 170 bp of non-coding Tn5 DNA, the sequences encoding the SV40 small t antigen intron, and the SV40 polyadenylation signals. Southern et al. (1982) J. Mol. App. Genetics 1:327–341. An LMTK$^-$ cell line transfected with pSV2gI was designated SV2gI.

(ii) GIII Constructions. The gIII gene was inserted into pRSVcat in place of the cat gene such that the gIII start codon was situated approximately 140 bp downstream of the RSV promoter and approximately 110 bp downstream of the transcriptional start site to give pRSVgIII (FIG. 15C). Approximately 850 bp lay between the gIII stop codon and the vector associated SV40 polyadenylation signals. Whether this non-coding region contained polyadenylation signals of BHV-1 origin was not examined. An LMTK$^-$ cell line transfected with pRSVgIII was designated RSVgIII.

To place the gIII gene under the control of the SV40 enhancer/early promoter region, the gIII start codon was positioned approximately 170 bp downstream of the early promoter and approximately 140 bp downstream of the transcriptional start site to give pSV2gIII (FIG. 15D). Following the gIII stop codon were approximately 800 bp of BHV-1 DNA, plus the Tn5 and SV40 sequences noted above for pSV2gI. An LMTK- cell line transfected with pSV2gIII was designated SV2gIII.

III.B.2. Expression of Recombinant gI and gIII

Approximately 120 limit diluted clones from transfections of the four expression constructions described above, plus negative control clones derived from a transfection conducted with pSV2neo alone, were screened for expression of BHV-1 gI or gIII by ELISA and immunocytochemistry assays. The use of unfixed or methanol fixed and permeabilized cells in each assay revealed surface or surface plus intracellular glycoprotein expression, respectively.

ELISAs were used to compare the relative amount of surface and intracellular gI or gIII expression by clones derived from a single transfection, and, by clones derived from transfections with the different expression vectors. For 17 clones positive for gI expression, and 35 clones positive for gIII expression, a similar range and distribution of ELISA readings was obtained with either pRSV- or pSV2- based constructions.

Immunocytochemistry revealed that expression of gI was localized predominantly intracellularly in a perinuclear region which probably corresponds to the Golgi apparatus and/or rough endoplasmic reticulum of these cells as evidenced by the identical localization of wheat germ agglutinin. However, nuclear membrane and cell surface expression of gI were also visible. In addition, clones expressing gI exhibited a high degree of cell fusion, polykaryon formation, nucleus fusion and giant cell formation which was not apparent in clones expressing gIII or negative control clones. Expression of gIII was localized predominantly in the nuclear and plasma membranes although diffuse cytoplasmic staining was also evident. The subcellular distributions of recombinant gI and gIII are similar to those observed for these glycoproteins in BHV-1-infected bovine cells, although the perinuclear accumulation of gI in the transfected murine cells appears to be greater than that observed in infected bovine cells.

III.B.3. Comparison of Recombinant gI and gIII With Native gI and gIII

Radioimmunoprecipitation of gI from BHV-1-infected bovine cells revealed three major protein bands of approximately 130,000 (130K), 75K and 55K molecular weight which correspond, respectively, to the intact uncleaved glycoprotein and the two cleavable fragments which are linked by disulfide bonding in the mature non-denatured molecule. Only the latter two cleavage fragments were precipitated from two clones of murine cells transfected with gI expression plasmids, indicating that proteolytic cleavage of gI occurred to completion in these cells. In addition, the larger of the two fragments produced in the transfected murine cells was slightly lower in MW than the equivalent fragment produced in infected bovine cells. Identical results were obtained with a number of other clones positive for gI expression.

Radioimmunoprecipitation of gIII from BHV-1-infected bovine cells yielded two major bands of approximately 99K and 73K. These correspond, respectively, to the mature glycosylated gIII and its partially glycosylated precursor form. Only the former band was precipitated from clones of murine cells transfected with the gIII expression plasmids, suggesting that the precursor form(s) of gIII are more completely processed to mature molecules in the murine cells. As observed for gI, recombinant gIII had a slightly lower MW compared to the mature form of gIII produced in infected bovine cells. These results were also verified by analysis of a number of other clones positive for gIII expression.

Analysis of the proteins precipitated from cells treated with an N-linked glycosylation inhibitor, antibody, was conducted to compare the N- and O-linked glycosylation patterns of the recombinant and infected cell glycoproteins. Radioimmunoprecipitation with gI-specific antibodies yielded a single band of approximately 105K MW from both infected bovine cells and gI transfected murine cell clones although additional partially glycosylated products of approximately 45–50K MW also accumulated in the transfected cells. The 105K MW band corresponds to the nonglycosylated, uncleaved form of gI which accumulates due to the dependence of gI proteolytic cleavage on N-linked glycosylation and/or associated function(s) which are blocked by antibody. The identical MW of this band in both infected bovine cells and transfected murine cells indicates that no O-linked oligosaccharides are added to gI in either cell type, and suggests that the MW differences described above for untreated cells may be due to differences in N-linked glycosylation.

Radioimmunoprecipitation of gIII from antibody-treated, BHV-1-infected bovine cells yielded two bands of approximately 80K and 57K. These correspond to a glycosylated form of gIII, containing only O-linked oligosaccharides, and its nonglycosylated precursor. Only a 70K band was precipitated from the antibody-treated, gIII-transfected murine cell clones, suggesting that any precursor forms of gIII are rapidly processed in these cells, and that the amount of O-linked oligosaccharides added to gIII is lower compared to that added in infected bovine cells.

The antigenic structure of the recombinant gI and gIII produced in the murine cell clones was analyzed with a panel of gI- and gIII-specific monoclonal antibodies, the majority of which have been mapped to different epitopes on these glycoproteins. Relative antibody re- activity was assessed by ELISA and immunocytochemistry assays on both fixed and unfixed cells, and for selected monoclonal antibodies, by radioimmunoprecipitation and/or flow cytometry. The reactivity pattern of the entire monoclonal antibody panel was identical for the recombinant and viral forms of gI and gIII, including two gI-specific, and four gIII-specific antibodies which do not recognize denatured forms of these glycoproteins. These results suggest that the primary, secondary and/or tertiary structures of the recombinant glycoproteins, in the vicinity of the epitopes recognized by this panel of monoclonal antibodies, is indistinguishable from those of the glycoproteins produced in BHV-1-infected bovine cells.

III.B.4. AbCC and CTCC

The AbCC results indicate that gI and gIII are expressed on the surface of transfected murine cell clones at a level and in a manner which is recognized by complement-fixing gI- and gIII-specific monoclonal antibodies and which thereby renders the cells susceptible to attack by complement. The lower levels of lysis of cells expressing gI is primarily due to the higher spontaneous release of radioactive label from unstable fusing cells and polykaryons.

In CTCC assays using transfected murine cell clones expressing gI or gIII as targets, splenic lymphocytes from mice immunized and restimulated with BHV-1 recognized and lysed histocompatible transfected cells expressing gI and gIII, as well as positive controls infected with BHV-1. A portion of this activity was nonspecific natural killer cell-like cytotoxicity as evidenced by the lysis of vaccinia virus-infected targets and nonhistocompatible targets.

However, the marked restriction of cytotoxicity which occurred when nonhistocompatible target cells were used provided proof of the involvement of cytotoxic, MHC-restricted, T lymphocytes. The levels of lysis for pRSV- versus pSV2-based transfected cells does not correlate with the comparable total expression of the recombinant glycoproteins as measured by radioimmunoprecipitation and ELISA and may, therefore, reflect quantitative and/or qualitative differences in the amount of processed antigen(s) which is produced by the different transfected cell lines and recognized by the cytotoxic effector cells in this assay.

III.B.5. Immunogenicity of Transfected Cells in Mice

Histocompatible mice immunized with transfected cells in the absence of adjuvant produced detectable BHV-1-specific antibody after only one immunization. Both ELISA and virus-neutralizing antibody levels were significantly boosted by secondary but not by tertiary immunization. The induction of comparable antibody levels with cells expressing gI or gIII under the control of different enhancer/promoter units corroborates the data above which suggests that the SV40 and RSV elements are quantitatively equivalent expression units for these glycoproteins in LMTK⁻ cells. The induction of. significant levels of virus-neutralizing antibody supports the reactivity and cytotoxicity data which indicate that the recombinant glycoproteins are antigenically authentic.

IV

This example demonstrates the production of non-native BHV-1 subunit antigens using a Baculovirus system.

IV.A. Materials and Methods

IV.A.1. Cells. Viruses and Antibodies

Madin Darby bovine kidney (MDBK) cells were cultured in Eagle's minimal essential medium (MEM; GIBCO Laboratories, Grand Island, N.Y.) supplemented with 105 fetal bovine serum (GIBCO). S. *frugiperda* (SF9) cells were grown and maintained in TNM-FH medium (GIBCO) containing 10% fetal bovine serum as described by Summers and Smith (Summers, M. D., and Smith, G. E., "A manual of methods for baculovirus vectors and insect cell culture procedures" Texas Agricultural Experiment Station bulletin no. 1555 (1987). Texas Agricultural Experiment Station, College Station, Tex.). Virus stocks of BHV-1 strain P8-2 were grown in MDBK cells as described in Example I. Virus stocks of the baculovirus ACNPV and recombinant viruses were prepared in SF9 cells as described by Summers and Smith (supra,). Monoclonal antibodies specific for gIV were developed and characterized by van Drunen Littel-van den Hurk et al. (1987) Virology 160:465–472; and Hughes et al. (1988) Arch. Virol. 103:47–60. The gIV-spec:ific monoclonal antibody mixture used for identification of recombinant gIV consisted of equivalent amounts of 136 (epitope Ia), 9D6 (epitope Ib), 3E7 (epitope II), 10C2 (epitope IIIa), 4C1 (epitope IIIb), 2C8 (epitope IIIc), 3C1 (epitope IIId), and 3D9S (epitope IV).

IV.A.2. Insertion of BHV-1 Glycoproteins into the AcNPV Transfer Vector

The gIV glycoprotein gene was isolated from a subclone of pSD48 as a 1.3 kb MaeI fragment (Tikoo, S. K. et al. (1990) J. Virol. 64:5132–5142, which was blunt end repaired and inserted into the plasmid pRSV cat (Fitzpatrick, D. R. et al. (1988) J. Virol. 62:4239–4248). The 1.3 kb BglII fragment was then subcloned into the BamHI site of the baculovirus transfer vector pVL941 (Luckow, V. A. and Summers, M. D. (1989) Virology 170:31–39). Plasmid DNA was prepared by alkaline lysis and cesium chloride gradient centrifugation by standard methods. After transformation of *E. coli* JM105, colonies appearing on LB agar containing 100 $\mu$g of ampicillin per ml were inoculated into L broth containing ampicillin and incubated at 37° C. overnight with vigorous shaking. Small scale preparations of plasmid from each colony were prepared, and the presence of the gIV gene was confirmed by digestion with endonucleases AvaI and EcoRV. A single clone was identified containing the gIV gene in the desired orientation and designated pVLgIV. Clone pVLgIV was inoculated into 500 ml. of L broth containing ampicillin; after 24 h at 37° C., the plasmid was prepared by alkaline lysis and further purified by equilibrium centrifugation on CsCl.

A modified BHV-1 gIV gene, as described in Example II.C.3, that produces a truncated form of gIV, was digested with BglII, the fragment isolated and subcloned into the BacHI site of the baculovirus transfer vector pVL941. This construct was named pVLgIVt.

The gI glycoprotein gene contained in plasmid pgB complete, described in Example II.B.1, was digested with BglII and BamHI and inserted into the BamHI site of the baculovirus transfer vector pVL941.

The gIII glycoprotein gene contained in plasmid p113R1 Bgl 3.0, as described in ExampLe II.B.1, was transferred to the BamHI site of baculovirus transfer vector pVL941 as an EcoRI+BamHI subfragment. This construct was designated pVLgIII.

IV.A.3. Transfection and Selection of Recombinant Viruses

After two cycles of ethanol precipitation, purified plasmid was mixed with an equal amount of *A. californica* viral DNA and used to transfect subconfluent monolayers of SF9 cells as outlined by Summers and Smith (supra). After incubation at 28° C. for 5 days, the supernatant was serially diluted and inoculated onto confluent monolayers of SF9 cells. After 1 h, an overlay consisting of TNM-FH medium containing 6% fetal bovine serum and 1.5% low-gelling-temperature agarose was added, and the plates were incubated at 28° C. for 5 days. Recombinant baculoviruses were identified by plaque hybridization essentially as outlined by Summers and Smith (supra). The polyhedrin-negative recombinants were plaque purified three to four times on SF9 cells to remove contaminating wild-type baculoviruses.

IV.A.4. Preparation of Cell Lysates

To analyze expression of recombinant gIV confluent monolayers of SF9 cells on 35 mm petri dishes were infected with individual polyhedrin-negative recombinants at a multiplicity of infection of 5 and incubated for 48 h at 28° C. The cells were scraped into phosphate-buffered saline (PBS), pelleted at 150 x g for 1 min, and suspended in 50 $\mu$l of RIPA buffer (0.02 M Tris hydrochloride [pH 8.0], 0.15 M NaCl, L% sodium deoxycholate, 1% Nonidet P-40, 10 mM EDTA, 10 mM phenylmethylsulfonyl fluoride). The postnuclear supernatant was collected, combined with reducing electrophoresis sample buffer, and boiled for 2 min.

To determine approximate yields of recombinant gIV, SF9 cells in monolayers or suspension cultures were infected with recombinant virus at a multiplicity of infection of 1. The cells were harvested at various times postinfection, washed with PBS, and suspended in RIPA buffer at $10^7$ cells per ml. Samples representing $5\times10^4$ to $2.5\times10^5$ cells were combined with reducing electrophoresis sample buffer and boiled for 2 min. Equivalent samples from uninfected cells and/or cells infected with the parental virus were always included as controls.

IV.A.5. SDS Gel Electrophoresis, Immunoblotting, and Enzyme-Linked Immunosorbent Assay (ELISA)

SDS-polyacrylamide gel electrophoresis was performed in 8.5 or 10% polyacrylamide discontinuous gels as previously described (van Drunen Littel-van den Hurk, S. et al. (1984) Virology 135:466–479). Electrophoresis was carried out under reducing conditions. Protein bands were visualized by staining with Coomassie brilliant blue, and the stained gels were scanned at 595 nm with a Helena Cliniscan II densitometer (Helena Laboratories, Mississauga, Ontario, Canada).

To identify recombinant gIV, produced by baculovirus, an immunoblot assay was performed as previously described (van Drunen Littel-van den Hurk, S. et al. (1984) Virology 135:466–479). Briefly, after electrophoresis cell lysates were electrophoretically transferred to nitrocellulose sheets, then the instructions for use of the Bio-Rad (Mississauga, Ontario, Canada) immunoblot assay kit were followed.

Sandwich assays and indirect ELISAs were used to determine the yield of gIV in recombinant baculovirus-infected SF9 cells. In the sandwich assay, microtiter plates were coated with the immunoglobulin G (IgG) fraction of bovine hyperimmune serum as the captive antibody and then incubated with lysates from recombinant virus-infected and control cells or affinity-purified standard gIV. In the indirect assay, the cell lysates and glycoproteins were directly adsorbed to the microtiter plates. Mixtures of gIV-specific monoclonal antibodies, followed by horseradish peroxidase-conjugated goat anti-mouse IgG (Boehringer-Mannheim, Dorval, Quebec, Canada) were used for detection as previously described (van Drunen Littel-van den Hurk, S. et: al. (1984) Virology 135:466–479). The reaction was visualized using 0.8 mg of 5-aminosalicyclic acid per ml and 0.006% $H_2O$.

IV.A.6. Immunofluorescence and Flow Cytometry

The expression of glycoprotein gIV in recombinant baculovirus-infected SF9 cells was determined at different times postinfection. Briefly, cells were washed in PBS, and cytospin smears were prepared and fixed in methanol. they were incubated for 30 min at 37° C. with a 1:100 dilution of a gIV-specific monoclonal antibody mixture and washed in PBS and double-distilled water. Then the cells were stained with fluorescein isothiocyanate-conjugated rabbit anti-mouse IgG (Boehringer-Mannheim) for 30 min at 37° C. and washed again before being mounted in PBS-glycerol for examination. For surface staining and flow cytometric analysis, cells were suspended in PBS containing 0.2% gelatin and 0.03% $NaN_3$ (PBSG) at $4 \times 10^7$ cells per ml. They were plated in microtiter plates at $2 \times 10^6$ cells per well and incubated with serial dilutions of monoclonal antibody mixtures for 30 min on ice. Subsequently, they were washed in PBSG and then incubated with fluorescein isothiocyanate-conjugated rabbit anti-mouse IgG (Becton and Dickenson, MIssissauga, Ontario, Canada) for 30 min at 4° C. After the cells were washed, they were fixed in 2% formaldehyde and analyzed with an EPICS CS flow cytometer (Coulter Electronics Ltd., Hialeah, Fla.) as described (Campos, M. et al. (1989) Cell. Immunol. 120:259–269). The percentage of positive cells was calculated by using the immuno-program (Coulter Electronics Ltd.; MDAPS system) for the analysis of immunofluorescence histograms.

IV.A.7. Partial and Affinity Purification of Recombinant Proteins

To obtain a standard glycoprotein for the quantitative ELISA, glycoprotein gIV was purified by immunoadsorbant chromatography from recombinant baculovirus-infected SF9 cells as previously described (van Drunen Littel-van den Hurk, S., and Babiuk, L. A. (1985) Virology 144:204–215). PartialLy purified membrane preparations were made from recombinant baculovirus-infected SF9 cells to immunize cattle. Briefly, infected cells were harvested at 48 to 72 h postinfection, when maximal production of recombinant gIV was achieved. the cells were collected by centrifugation, washed with PBS and suspended in MEM containing 10 mM phenylmethylsulfonyl fluoride and 10 mM EDTA at $10^7$ cells per ml. Subsequently, they were disrupted by treatment for 15 s with a polytron homogenizer (Brinkmann Instruments, Rexdale, Ontario, Canada). The insoluble material was collected by centrifugation for 8 min at 1,800 x g and suspended in MEM containing 10 mM phenylmethylsulfonyl fluoride and 10 mM EDTA.

IV.A.8. Immunization of Cattle

Groups of eight animals each were immunized with crude cell lysate, a membrane preparation, or affinity-purified glycoprotein from recombinant baculovirus-infected SF9 cells expressing gIV. All preparations were diluted to a concentration of 100 µg of gIV per dose and mixed with Avridine as previously described (Babiuk, L.A. et al. (1987) Virology 159:57–66) or with Emulsigen PLUS at a ratio of 7:3 (vol/vol), as outlined by the manufacturer (MVP Laboratories, Ralston, Nebr.). Control groups were immunized with affinity-purified authentic gIV, a commercially available killed BHV-1 vaccine, or placebo containing AcNPV-infected SF9 cells. The animals were injected intramuscularly, and they received a booster immunization 21 days later. Blood samples were taken from animals at the times of immunization and 2 weeks after the second immunization for assessment of antibody responses.

IV.A.9. Antibody Responses to Vaccination

The antibody responses to recombinant gIV in the vaccinated animals were determined by ELISA with affinity-purified authentic gIV from BHV-1 infected MDBK cells as the antigen, essentially as previously described (Babiuk, L. A. et al. (1987) Virology 159:57–66); van Drunen Littel-van den Hurk, S. et al. (1984) Virology 135:466–479). Affinity-purified horseradish peroxidase-conjugated rabbit anti-bovine IgG (Zymed, Mississauga, Ontario, Canada) was used at a dilution of 1:3,000 for detection.

The neutralization titers of the bovine sera were determined as previously described (Babiuk, L. A. et al. (1975) Infect. Immun. 12:958–963). The titer was expressed as the reciprocal of the highest dilution of antibody that caused a 50% reduction of plaques relative to the virus control.

The epitope specificities of the antibody responses to recombinant gIV were determined in a competitive antibody binding assay, which is based on the ELISA modified as previously described (van Drunen Littel-van den Hurk, S. et al. (1990) Vaccine 8:368–36); and van Drunen LIttel-van den Hurk, S. et al. (1985) Virology 144:216–227). The percentage of competition was calculated by using the formula [100×(A−B)/A], where A is the absorbance in absence of competitor antibody and B is the absorbance in the presence of competitor monospecific antibody; this is a modification of the formula described by Kimura-Kuroda, J. and Yasui, K., J. Virol. 45:124–132.

IV.B. Results

IV.B.I. Identification of Recombinant gIV Glycoprotein in Infected SF9 Cells

Several baculovirus recombinants containing the gIV gene insert were initially identified and tested for their ability to produce BHV-1 glycoprotein gIV after infection of SF9 cells. All of the glV recombinants produced a polypeptide with an apparent molecular mass of 63 kDa which was absent from uninfected cells and cells infected with the parental baculovirus. To confirm the identify of this glycoprotein, immunoblot analysis was performed. Recombinant baculovirus-infected SF9 cells and BHV-1-infected MDBK cells were harvested at 48 h postinfection, and total proteins were separated and transferred electrophoretically to nitrocellulose. A gIV-specific monoclonal antibody mixture recognized authentic gIV (71 kDa) in BHV-1-infected MDBK cells and a polypeptide with an apparent molecular mass of 63 kDa in recombinant baculovirus-infected SF9 cells. This suggests that the recombinant gIV is equivalent to the 63-kDa partially glycosylated form of authentic gIV (van Drunen Littel-van den Hurk and Babiuk, L. A., *J. Virol.* 59:401–410). In addition to the 63 kDa species, four bands of lower apparent molecular mass were observed in the immunoblot of recombinant gIV. These bands, which were also present in a preparation of pure authentic gIV, may be due to proteolytic cleavage or incomplete processing of the glycoprotein. No reaction was observed between the gIV-specific monoclonal antibodies and SF9 cells infected with the parental baculovirus.

IV.B.2. Cellular Localization of the Recombinant gIV Glycoprotein

To determine the intracellular distribution of the recombinant gIV glycoprotein, indirect and surface immunofluorescence tests were performed on recombinant baculovirus-infected SF9 cells. At 48 h after infection, the gIV glycoprotein was primarily localized in the cytoplasmic membranes of the perinuclear region of the insect cells. Surface fluorescence was observed on unfixed cells, indicating that the recombinant glycoprotein is transported to the extracellular surface of the plasma membrane of the insect cells.

IV.B.3. Kinetics and Levels of Expression of the Recombinant gIV Glycoprotein

To analyze the kinetics and the efficiency of infection with the recombinant baculovirus and expression of the gIV glycoprotein, SF9 cells were grown in suspension cultures and infected with the recombinant baculovirus at a multiplicity of infection of 1. In this experiment, the viability of the cells, percentage of infected cells, and yield of gIV were determined. Flow cytometric analysis showed an increase in percentage of infected cells as well as total protein yield over time. The percentage of infected cells reached peak levels of 80% at 48 h after infection, when the viability of the cells was down to 30%. The viability of the cells was too low for flow cytometric analysis beyond this time point. Analysis by ELISA demonstrated that up to 85 $\mu$g of gIV was produced per $2.5 \times 10^6$ cells. This was confirmed by SDS-polyacrylamide gel electrophoretic analysis of the proteins produced during the first 72 h postinfection. The gel was scanned; polyhedrin made up 36% of the total protein, whereas gIV made up 18%. The total protein concentration of recombinant virus- and AcNPV-infected cells was determined by the Bradford test to be about 500 $\mu$g per $2.5 \times 10^6$ cells. This corresponds to about 180 $\mu$g of polyhedrin and 90 $\mu$g of gIV, demonstrating the feasibility of growing the recombinant baculovirus on a large scale and yet obtaining good yields of the glycoprotein.

IV.B.4. Antigenic Properties of gIV Expressed by the Recombinant Baculovirus

The antigenic properties of recombinant gIV were evaluated by using a gIV-specific panel of monoclonal antibodies. The epitopes recognized by these monoclonal antibodies have been identified and characterized previously (Hughes, G. et al., *Arch. Virol.* 103:47–60). Reactivity of all of these monoclonal antibodies in an ELISA indicated that all of the epitopes identified on the authentic glycoprotein are also present on recombinant gIV, although some of the conformation-dependent epitopes (IIIb, IIIc, IIId [Hughes, G., et al., supra]) were recognized slightly better on authentic gIV than on recombinant gIV. Since it has been shown that these epitopes are not directly carbohydrate dependent (van Drunen Littel-van den Hurk, S. et al. (1990) *J. Gen. Virol.* 71:2053–2063), this suggests that incomplete glycosylation might lead to some conformation changes in the gIV molecule. In contrast, the continuous epitope IV seemed to be more reactive on recombinant gIV.

IV.B.5. Immunogenic Properties of gIV Produced by the Recombinant Baculovirus

Figure 16A:
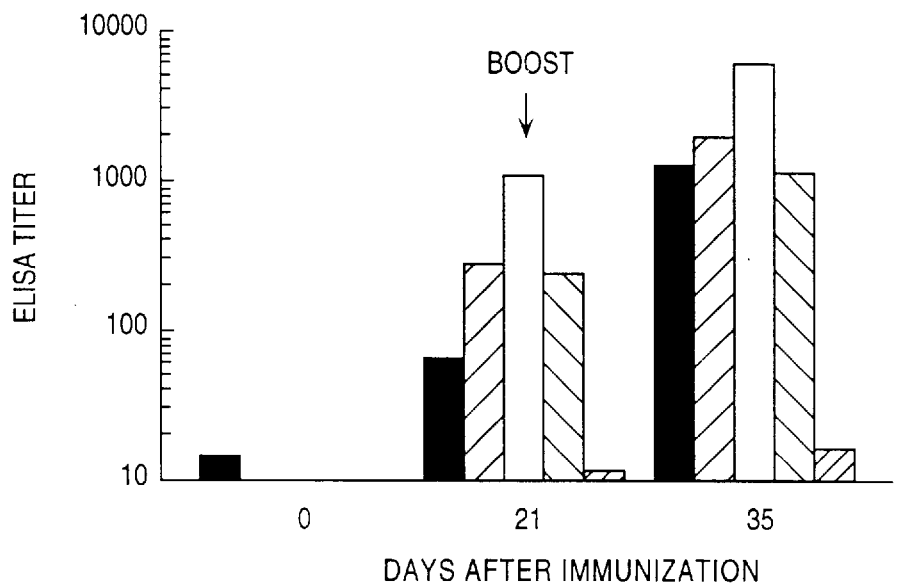
Figure 16B:
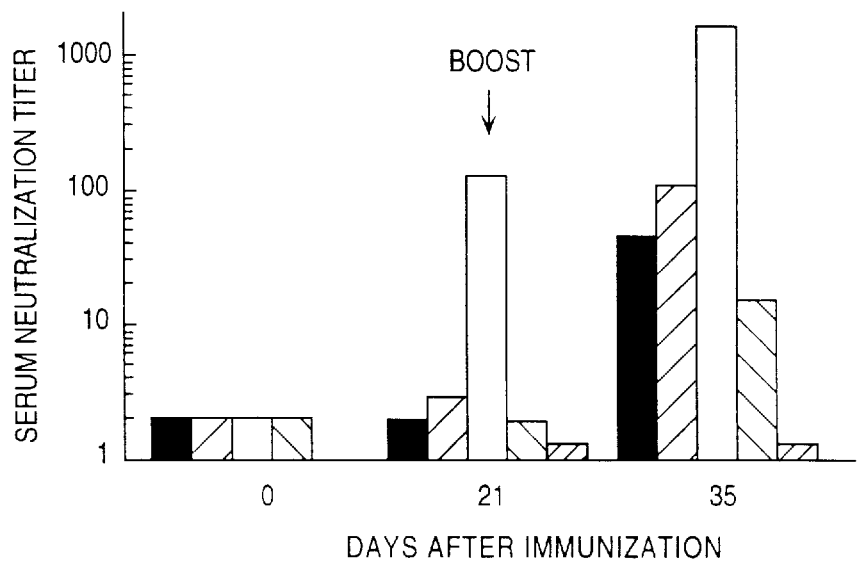

The immunogenicity of recombinant gIV was studied by immunizing cattle with crude, partially purified, or affinity-purified glycoprotein from recombinant baculovirus-infected SF9 cells, as described above. This experiment showed that two immunizations of affinity-purified glycoprotein or partially purified membrane preparation in Emulsigen PLUS elicit antibodies that are reactive with authentic gIV and able to neutralize infectivity of BHV-1 in vitro. The crude cell lysate, however, induced antibodies that were reactive with authentic gIV but that neutralized poorly. Since the partially purified membrane preparation was as immunogenic as the affinity-purified recombinant gIV, whereas the crude cell lysate was not, the membrane preparation was used for further studies. A second experiment was designed to compare the efficacies of two different adjuvants and to compare the immunogenicity of recombinant gIV with that of an experimental vaccine consisting of authentic gIV (Babiuk, L. A. et al. (1987) *Virology* 159:57–66) and a commercially available and widely used killed HBV-1 vaccine (FIG. 16). Two immunizations with 100 $\mu$g of recombinant gIV induced high neutralizing antibody titers, three- to six-fold higher than those induced by the killed virus vaccine. this experiment also showed that Avridine is superior to Emulsigen PLUS, resulting in twofold-higher ELISA and neutralizing antibody titers (FIGS. 16A and 16B). A significant difference was observed between the immune responses induced by authentic and recombinant gIV. Authentic gIV induced 4-fold-higher ELISA titers and 20-fold higher neutralizing antibody titers. this difference may be due to alterations in some of the conformation-dependent neutralizing epitopes on recombinant gIV.

IV.B.6. Epitope Specificity of the Immune Response to the Glycoprotein Vaccines

Figure 16C:
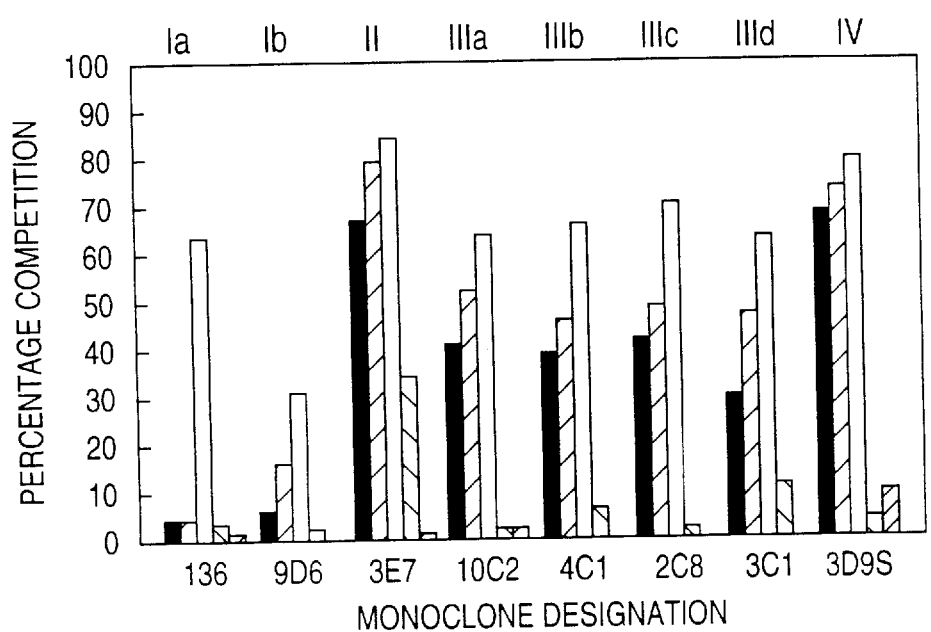

To determine whether the lower neutralizing antibody response to recombinant gIV was due to impaired recognition of one or more of the neutralizing epitopes, the sera from the immunized animals were tested with respect to epitope specificity. All epitopes on gIV were recognized by animals immunized with authentic gIV; blocking varied between 84 and 30% (FIG. 16C). These values are in good agreement with previously reported values between 85 and 50% (van Drunen Littel-van den Hurk, S. et al. (1990) *Vaccine* 8:358–368). However, two of the neutralizing epitopes on gIV, Ia and Ib, were poorly recognized by animals vaccinated with recombinant gIV. This may explain the difference in neutralizing antibody titers. These animals did show a reaction to all of the other epitopes, although the reaction was not as strong as those of animals immunized with authentic gIV. The reactivity of the sera was to a certain extent also dependent upon the choice of adjuvant; Avridine was slightly superior. Calves immunized with killed BHV-1 vaccine only reacted to epitope 3E7.

V

This example demonstrates the production of non-native BHV-1 subunit antigens in *E. coli* vectors.

V.A. Cloning and Expression of the BHV-1 gI Gene in *E. coli*

A BHV-1 genome library of BHV-1 strain Cooper as represented in 12 HindIII fragments cloned in to pBR322, was screened according to the methods of Southern, using probes corresponding to HSV-1 gB and the pseudorabies virus (PRV) gB gene counterpart. A single clone, pSD106, was found to bind to the probes.

In order to specify the actual coding sequences of the BHV-1 gI gene, a detailed restriction map was constructed for pSD106. The application of the techniques of Southern using separate probes specific for the HSV-1 gB amino and carboxy-termini, located the BHV-1 gI gene within a KpnI-SalI sub-fragment of pSD106 (pSD106 KpnI-SalI; FIG. 17).

Figure 19:
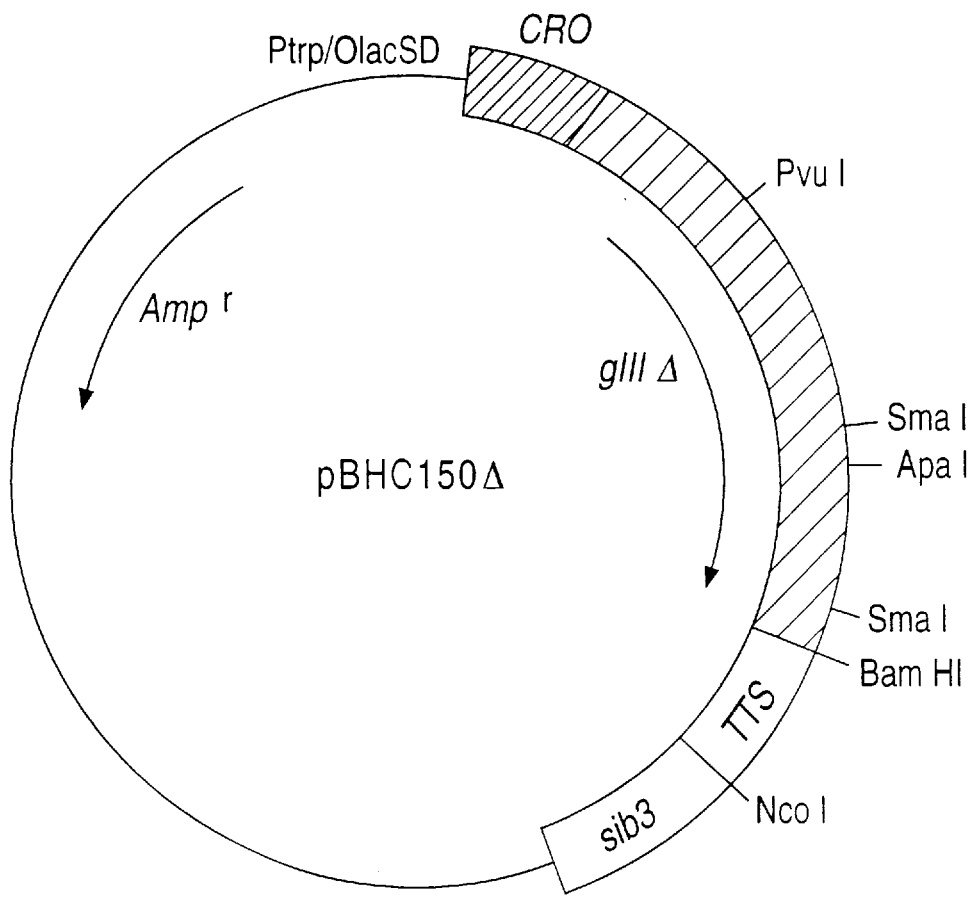

It is not expected that foreign viral proteins produced in E. coli would be folded into a configuration that mimics the protein in the native virus particle. Therefore, the most active immunogen obtained from bacterially expressed genes is likely to be composed of a contiguous stretch of amino acids rather than one which requires the positioning of two or more contiguous sequences of amino acids (i.e., tertiary structure). An additional limitation is that *E. coli* will not process pre gI to gIb+gIc. Thus, it was hypothesized that the optimal formulation of bacterially expressed gI would be composed of gIb and gIc, expressed individually and then utilized either separately or in combination.

To construct a clone expressing the amino terminus of mature gIb+gIc, the pSD106 KpnI-SalI fragment was cut with ApaI and the lengths of the ApaI fragments randomized by treatment with Bal31 exonuclease. Any asymmetric fragment\ends produced by imprecise Bal3l activity were blunted by Klenow fill-in reactions. The ApaI digested plasmid was then cut with XmaI and the population of fragments carrying sequences encoding the amino terminus of gIb were isolated from LMP agarose gels as a 600-520 bp smear. This fragment sub-population was then ligated to the HpaI-XmaI sites of polink 26. Polink 26 was a modified form of pBR328 and contained a synthetic oligonucleotide inserted into the EcoRI and SalI sites. The oligonucleotide contained restriction enzyme sites in the following order: EcoRI, XbaI, BglII, BalI, HpaI, ClaI, HindIII, KpnI, BamHI, SmaI, SphI, SacI, XhoI, SalI.

Inserts from the clone bank of the gIb+gIc amino terminus were isolated by BglII and SmaI digestion of sBHB5' and transferred to the BglII plus SmaI sites of the *E. coli* expression vector pHK414. The resulting clone was named pRed30. To complete the construction of the gp11 gene, SmaG was isolated as a 775 bp XmaI fragment from pSd106 KpnI-SalI and was ligated to the XmaI site of pRed30 to produce pgp11:βgal. This plasmid was transformed into the *E. coli* strain NF1829, produced a gpll:β-galactosidase fusion protein of approximately 175k. An unfused gIb peptide was made by the "gp11 complete" clone. "pgp11 complete" (FIG. 18) was constructed by transferring the 1340 bp BglII-BamHI fragment from pgp11:βgal to the *E. coli* expression plasmid pGH346. The 1340 bp fragment carries the entire gIb coding sequence plus DNA encoding the first eight amino acids of gIc. In NF1829, "pgp11 complete" produces a 60k protein which specifically reacts to BHV-1 gIc polyclonal sera and gIb specific monoclonal antibodies.

V.B. Cloning and Expression of BHV-1 gIII gene in *E. coli*

The BHV-1 genomic library was screened by the techniques of Southern using probes specific for the coding sequence of the HSV-1 gC and the PRV gC homolog (PRV gI). One of the HindIII clones, designated pSD113 (FIG. 17), hybridized to both the probes. A restriction endonuclease map of the pSD113 plasmid was prepared in order to locate the region within the HindIII fragment which specifically encoded the BHV-1 gIII gene. By using a probe specific for the PRV gC gene homolog, the BHV-1 gIII gene was located within an approximately 2500 bp EcoRI-BglII subfragment of pSD113.

An *E. coli* clone expressing the carboxy- terminal two-thirds of the BHV-1 gIII gene was made in the following way. The pSD113 EcoRI—BglI subfragment of pSD113 was digested with XmaI and inserted into the XmaI site of the plasmid pJS413 to form pBHC'. The pSD113 EcoRI-BglII subfragment of pSD113 was digested with PvuI and the PvuI asymmetric ends were treated with Klenow enzyme to blunt them. The PvuI digested plasmid was then cut with SacI, and the 1600 bp PvuI-SacI fragment containing the carboxy-terminus of the gIII was purified from LMP agarose gels. This fragment was ligated to SmaI plus SacI sites of plasmid ptac413 to produce p113Pvu/413. The extraneous sequences 3' to the stop codon were removed by replacing the 900 bp AbaI-SacI fragment from p113Pvu/413 with the 2220 bp AbaI-SacI fragment from BHC3'. The new plasmid "p113 Pvu end" carried 900 bp of BHV-1 gIII gene carboxy-terminus in frame to the reconstituted β-galactosidase gene. The *E. coli* strain NF1829 was transformed with this plasmid.

Upon induction with lactose, these cells produced approximately 5% of the total protein as a gIII related protein. The fusion product was collected as aggregates and solubilized in 10 mMol urea, pH 9.0. The solubilized protein was dialyzed against 10 mMol triethylamine, pH 9.0 to remove urea and then concentrated by Amicon filtration to a final concentration of 2 mgs/ml of BHV-1 protein. The concentrated gIII fusion protein was formulated with Freunds' Complete Adjuvant and injected intramuscularly to rabbits in 1 mg doses. The antisera raised in these rabbits was used to immunoprecipitate BHV-1 infected cell extract and was found to specifically react with the gIII glycoprotein.

In an attempt to express the full-length BHV-1 gIII gene in *E. coli*, the expressor clone "113Pvu end" was extended to include all gIII coding sequences up to the NcoI site ("gIII complete"). This full-length clone failed to produce significant amounts of gIII protein. The simple removal of the signal sequence and/or addition of preferred *E. coli* codons upstream of the gIII sequences failed to improve expression. In order to produce the largest *E. coli* gIII expressor clone possible, and to avoid the apparent problem in expressing the amino terminal gene sequences, a library of gIII clones was generated with randomized amino termini. The *E. coli* plasmid "gIII complete", which does not express significant amounts of gIII protein, was digested with NcoI and then treated with Bal31 for varying lengths of time. NcoI cut at the ATG of the gIII gene and Bal31 treatment removed nucleotides starting from the NcoI cut ends to varying extents. The population of random sized plasmids were treated with Klenow enzyme to blunt asymmetric ends and were then digested with BamHI to excise the BHV-1 gIII insert. The population of NcoI-Bal31-BamHI fragments ranging in size from 1530 bp to 1250 bp were isolated from LMP agarose and ligated to the SmaI-BamHI sites of pJS413. *E. coli* NF1829 was transformed with this ligation mixture and plated to MacKonkey's Agar. Putative expressor clones were picked as red colonies. The positive colonies were then tested for protein production by lactose induction and protein analysis by SDS-PAGE. Three clones were found to express gIII as a β-galactosidase fusion protein. The clones were found to differ in the amount of amino terminal sequence removed by the Bal31 treatment: losing 150, 250, and 350 bp, respectively. The gIII gene inserts were excised by BglII-BamHI digestion of the Bal31 expresser plasmids and then purified from LMP agarose gels. Each gIII carrying fragment was; then ligated into the BglII-BamHI sites of the *E. coli* expressor plasmid GH435. pGH435 carries stop codons in each of the three possible reading frames immediately 3' to the BamHI insertion site. Therefore, expression of any insert at the BglII and BamHI sites would generate a nonfused peptide. The largest Bal31 clone, called pBHC150Δ (FIG. 19), which had a deletion of approximately 150 bp at the amino terminus of gIII, makes a peptide of approximately 53K upon lactose induction. This plasmid is carried in the *E. coli* strain W3110F'Iq.

V.C. Expression of Full-Length Mature BHV-1 gIV in *E. coli*

The BHV-1 genomic library clone pSD98 (FIG. 17) was identified as carrying the bulk of the amino-terminal half of gIV+signal sequence, in addition to several other putative BHV-1 genes. Restriction enzyme mapping of pSD98 mapped the gIV protein sequences plus signal sequence to within a XmaII-XhoI fragment of the plasmid. The pSD98 was digested with XmaI and XhoI, the fragment isolated and inserted into the plasmid polink 26 to produce p98XmaI-XhoI.

Figures 20A, 20B:
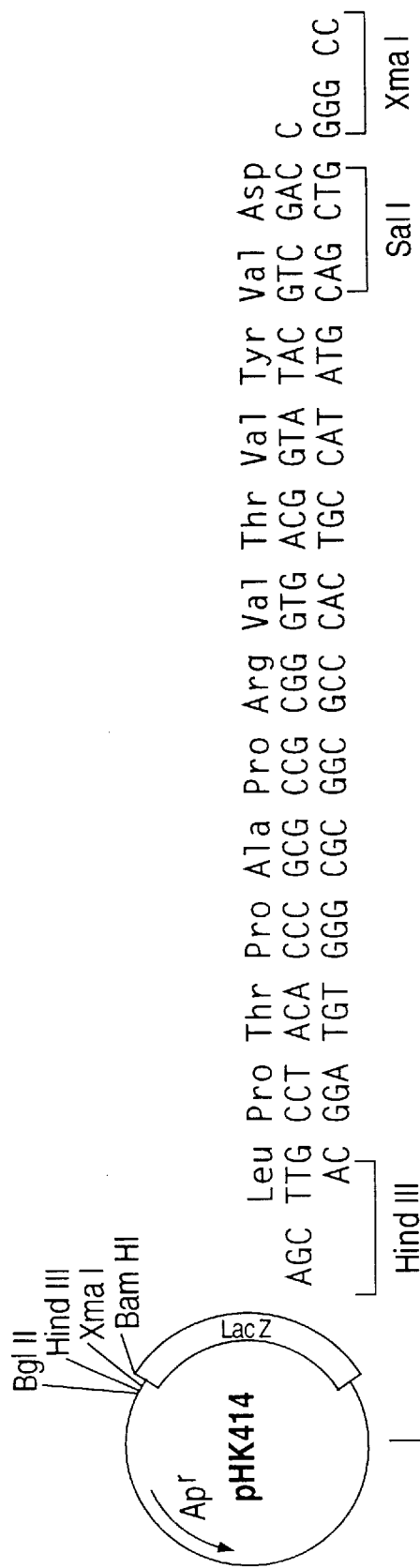
Figure 20B:
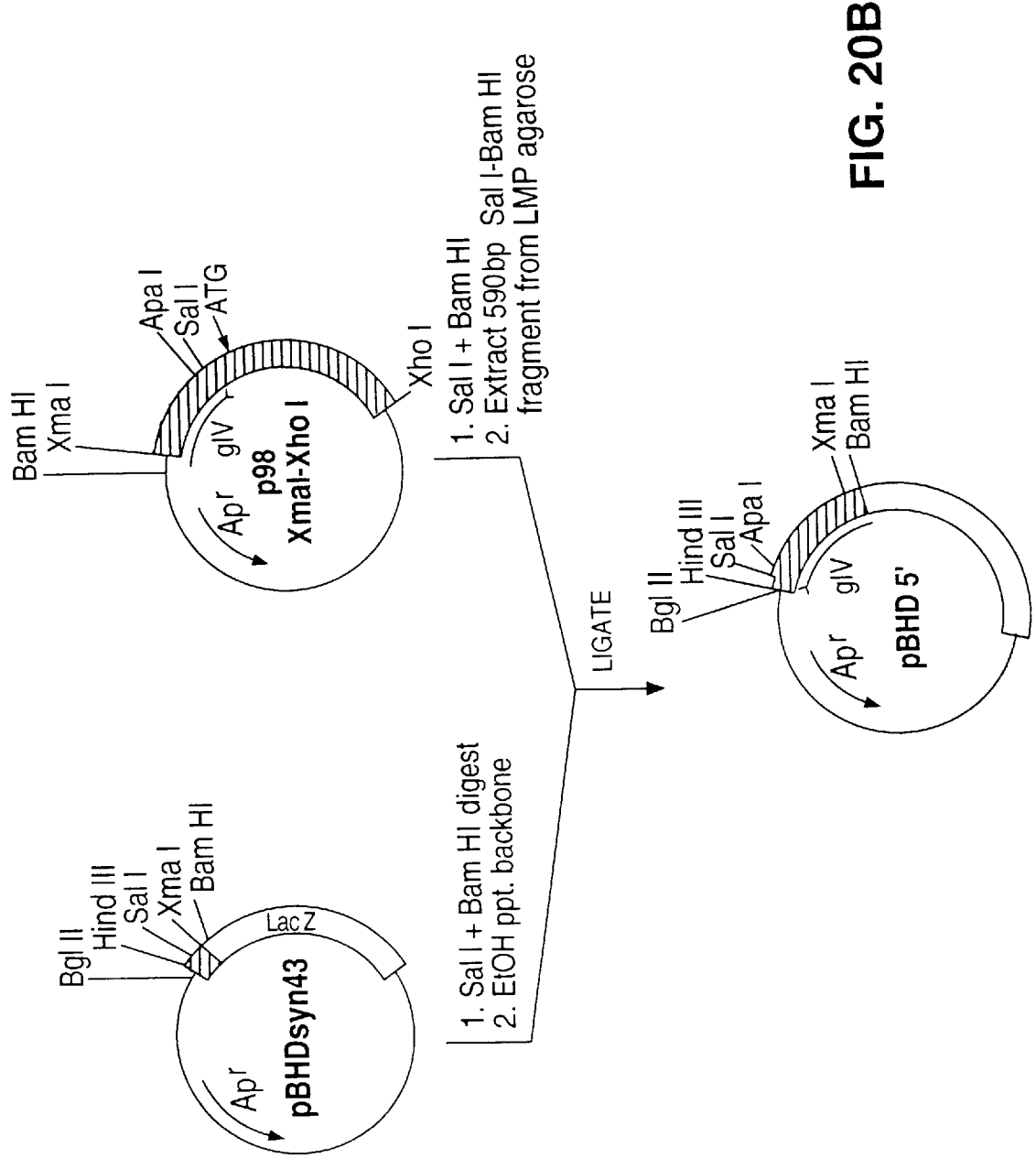
Figure 20C:
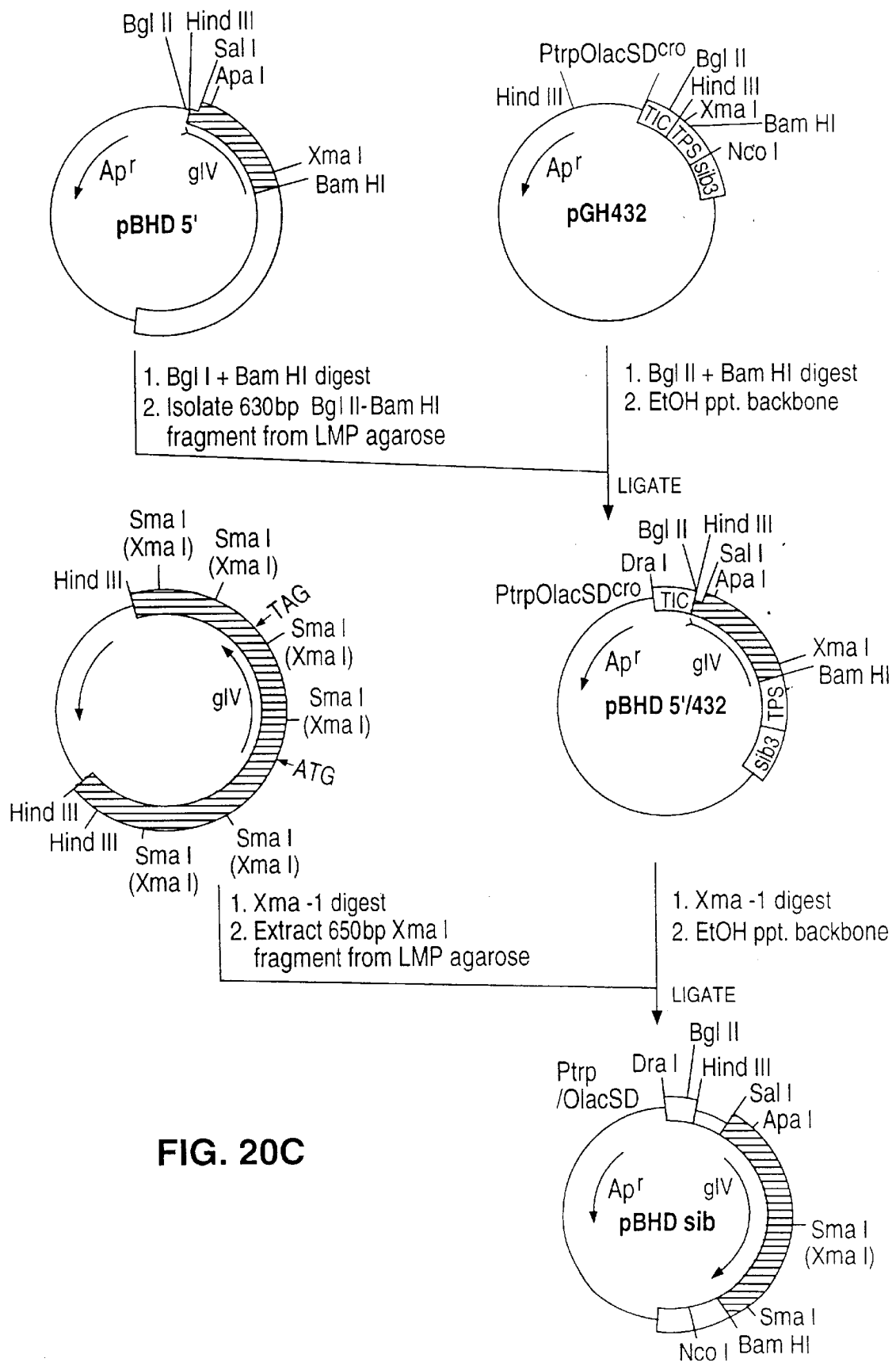

The construction of the gIV gene containing expression vector is depicted in FIG. 20. The signal sequence does not appear in the mature gIV protein and does not contribute to immunogenicity of the glycoprotein. Therefore, the signal sequence was removed by making a synthetic oligonucleotide corresponding to the coding sequence of the first amino acid of the mature BHV-1 gIV gene (i.e., Leu) and extending to the SalI site 88 bp downstream from the start (ATG) of the gene (see FIG. 7). An engineered HindIII asymmetric overhang was added immediately 5' to the Leu codon and a XmaI asymmetric end was added immediately 3' to the SalI site (see FIG. 20). The HindIII and XmaI overhangs permitted ligation of the oligonucleotide into the HindIII plus XmaI sites of the *E. coli* expression vector pHK414. The resultant plasmid was called BHDsyn43 and is carried in the *E. coli* strain MC1066.

The amino-terminus of the gIV clone BHDsyn43 was extended by ligating the 590 bp BamHI-SalI fragment from p98Xma-XhoI to the SalI plus BamHI sites of the BHDsyn43. This ligation produced pBHD5' and carries the first 620 bps of the coding sequence for mature BHV-1 gIV. The pBHD5' was also maintained in the *E. coli* strain MC106.

An *E. coli* clone expressing full length mature BHV-1 gIV was made by first transferring the gIV insert from pBHD5' carried in a 630 bp BglII-BamHI fragment, to the BglII-BamHI sites of the *E. coli* expression plasmid GH432. The carboxy terminal half of the gIV gene was then added by ligating the 640 bp XmaI fragment from pSD98 to the XmaI site in the new construction BHD5'/432. The plasmid pSD98 was part of the original BHV-1 genomic library BHV-1 strain Cooper (FIG. 17). The library takes the form of 12 HindIII clones of the viral genome inserted into the pBR322. Plasmid pSD98 was identified as part of the gIV gene partially by its location in the "S" region of the BHV-1 genome, that corresponds to the location of the gD of other herpesviruses, e.g., HSV-1 and 2, PRV and EHV-1, and reactivity in Southern blots using a probe corresponding to the PRV gIV gene homologue.

Figure 21:
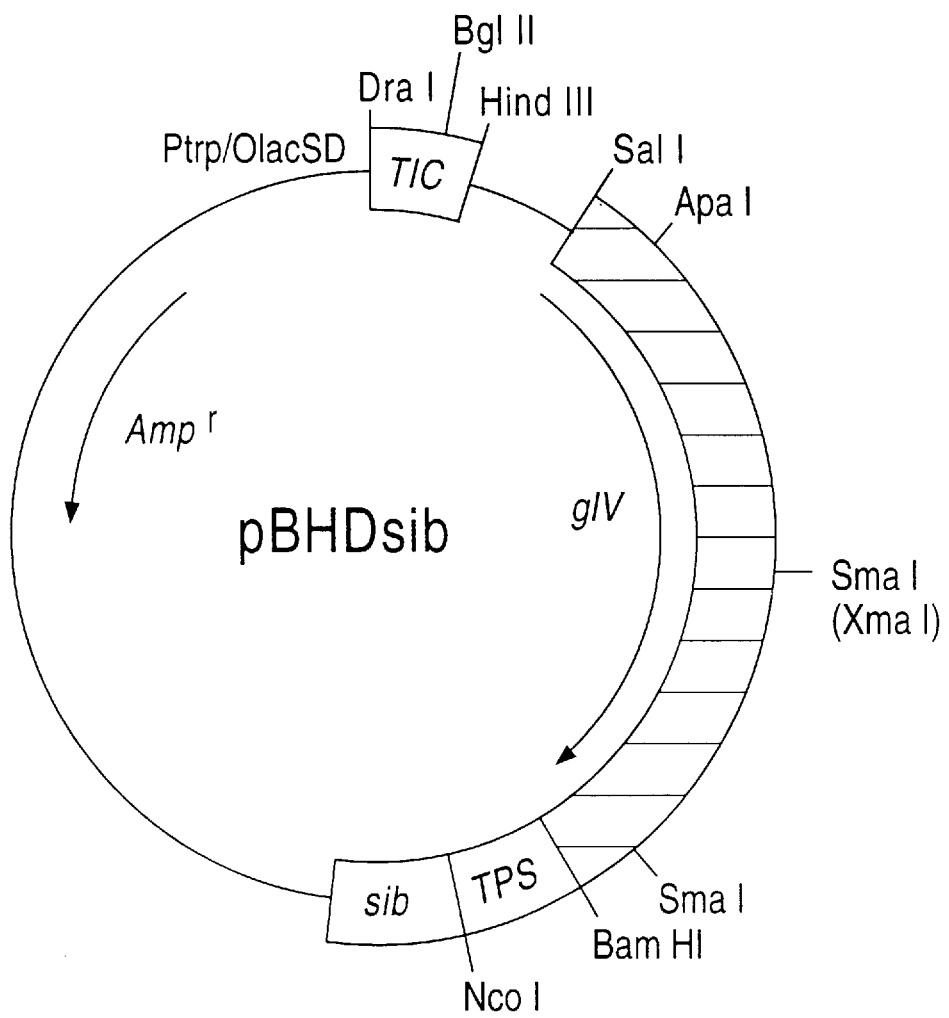

The final BHV-1 gIV *E. coli* expressive plasmid is called pBHDsib (FIG. 21) and was transformed in the *E. coli* strain W31104'Iq. Upon induction with lactose (2% final concentration), pBHDsib made a 58K protein which represented approximately 10% of the total protein produced by the clone. In a western blot assay, the 58K protein reacted specifically with anti-BHV-1 hyperimmune serum and the BHV-1 gIV specific monoclonal antibody 3D9.

An aggregate preparation from pBHDsib was solubilized in 50 mMol β-mercaptoethanol, 0.5% SDS pH 8.0. Doses containing 150 μg of the 58K solubilized protein were prepared in Freunds' Complete Adjuvant and administered to rabbits by intramuscular injection. Sera raised in these animals reacted specifically with a glycoprotein from BHV-1 infected cell extracts indistinguishable from gIV. When assessed for BHV-1 virus neutralizing activity in vitro, the rabbit sera was found to have a plaque reduction titre of 1:128.

V.D. Purification of Recombinant BHV-1 Glycoproteins

*E. coli* W3110 transfected with pBHDsib was cultured in L broth supplemented with ampicillin (50 μg/ml). Late log growth phase cultures were induced with either 2% lactose or 2 mM IPTG. Five hours after induction, the cultures were harvested, the cells pelleted by centrifugation (2000 g for 20 min) and then mechanically disrupted. The aggregates were subsequently dispersed by treatment with 6M GuHCl and then dialyzed to reduce the GuHCl concentration to 2M.

The other BHV-1 glycoproteins expressed in *E. coli* are similarly purified.

VI

The following example illustrates the production of non-native BHV-1 subunit: antigens in recombinant adenovirus vectors.

VI.A. Expression of BHV-1 gIV Using Adenovirus Vectors

In one form, this expression system is based on human adenovirus serotype 5. The E3 region of the virus has been deleted to facilitate the accommodation of large gene inserts into the viral genome. When 293 cells (human kidney cells) are transformed with human adenovirus type 5 DNA, the cell line expresses the viral E1 protein constitutively. As a result, the combination of vectors based on human adenovirus type 5 and 293 cells form an ideal expression system.

Figure 22:
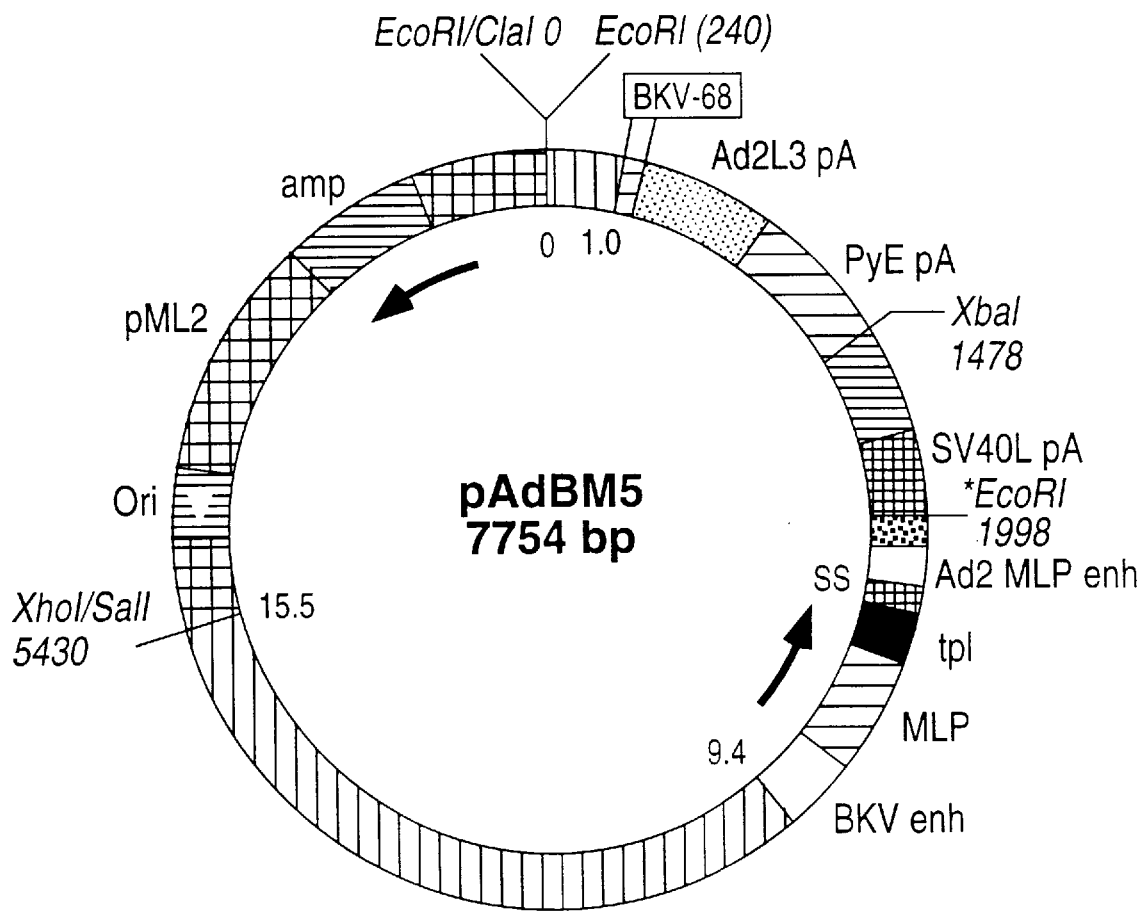

A transfer vector, pAdBM5 (FIG. 22), was developed in order to insert foreign gene sequences into human adenovirus serotype 5. The vector contains the adenovirus major late promoter (Ad2MLP), enhancer sequences, and polyadenylation sequences, flanked by the adenovirus serotype 5 E1 flanking sequences. A unique BamHI site is located downstream of the MLP and is used for the insertion of foreign genes.

Figure 23:
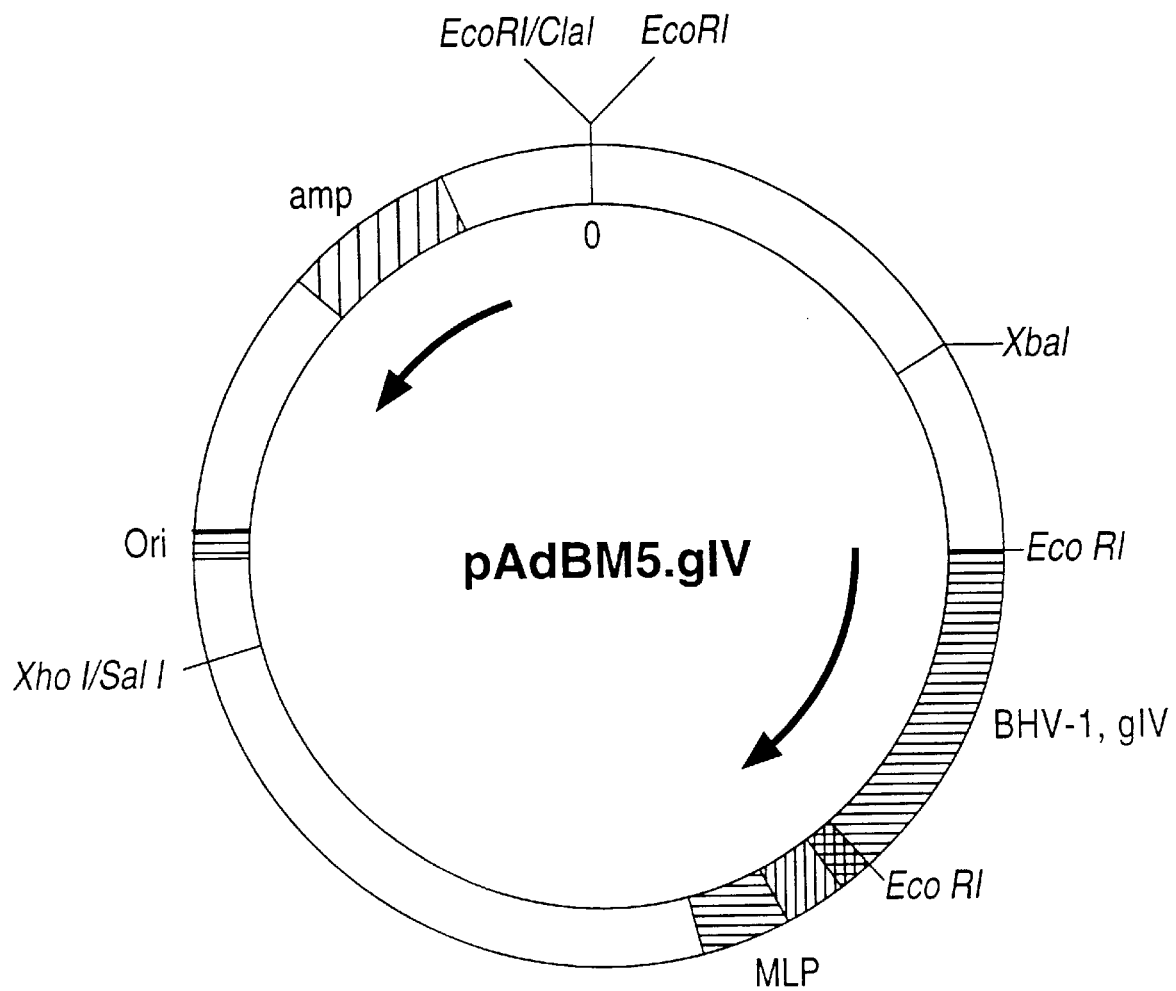

For the expression of either full-length BHV-1 gIV or truncated BHV-1 gIV, the appropriate gene was digested with MaeI and inserted into the dephosphorylated BamHI site of the pAdBM5. FIG. 23 depicts pAdBM5.gIV, the adenovirus vector including the gene encoding for full-length gIV. The plasmid vector DNA was digested with ClaI, mixed with purified human adenovirus serotype 5 DNA and was used to transfect 293 cells using the calcium phosphate technique. The transfected cells were plated out and incubated at 37° C. until a cytopathic effect developed. Supernatant from these cultures was then removed and used to reinfect 293 cells. Once the cytopathic effect had developed, the cellular DNA infected with virus. Recombinant virions expressing BHV-1 gIV were identified, selected and then further purified by plaque assay.

VI.B. Purification of Recombinant Expressed BHV-1 gIv 293 cells were cultured in I4EM containing 10% fetal bovine serum and supplemented with 1X vitamins and minerals. Confluent monolayers were infected with the recombinant adenovirus: BHV-1 gIV virus, at a multiplicity of 0.1. 24 hours after infection or at the appearance of total cytopathic effect, the recombinant gIV was harvested.

For full-length gIV, the cells were scraped from the surface of the culture flasks into the growth media, which was then centrifuged (1000 g for 20 min) and the cell pellet collected. The cells were disrupted with detergent and further processed as previously described.

Truncated gIV was collected by harvesting the media from the culture flasks. Cell debris was removed by centrifugation at 1000 g for 20 min. The clarified media was frozen at −70° C. until processing. The truncated gIV was purified by affinity chromatography through BHV-1 gIV specific columns, as has been described previously.

VII

This example illustrates the efficacy of recombinantly produced BHV-1 subunit antigens.

VII.A. Materials and Methods

VII.A.1. Cells and Viruses

*E. coli* cells were cultured in L Broth. Madin Darby bovine kidney cells (MDBK) cells, BSC-1 cells, and 293 cells were cultured in Eagle's minimal essential medium (MEM; GIBCO laboratories, Grand Island, N.Y., USA), supplemented with 10% fetal bovine serum (FBS; GIBCO). *Spodoptera frugiperda* (SF9) cells were grown and maintained in TNM-FH medium (GIBCO) containing 10% FBS. Strains P8-2 and 108 of BHV-1 were propagated in MDBK cells as described previously (Babiuk et al. (1975) Infect.Immun. 12:958). Virus recovered from nasal swabs was quantified by plaque titration on MDBK cells in microtiter plates with an antibody overlay as previously described (Rouse et al. (1974) J.Immunol. 113:1391). Vaccinia virus (WR strain) and recombinant vaccinia virus were propagated in BSC-1 cells as described in Example II. Human adenovirus type-5 and recombinant adenovirus were grown in 293 cells as described in Example VI. Virus stocks of the baculovirus AcNPV and recombinant virus were prepared in SF9 cells as described by Summers and Smith (Summers et al., "A manual of methods for baculovirus vectors and insect cell culture procedures." Texas Agricultural Experiment Station Research bulletin no. 1987, 1555, Texas Agricultural Experiment Station, College Station, Tex.).

VII.A.2. Recombinant Expression of gIV

BHV-1 gIV was recombinantly expressed in *E. coli*, SF9 cells, adenovirus and vaccinia virus, as explained in the above examples.

VII.A.3. Preparation of Immunoadsorbent Columns

The IgG fraction of the gIV-specific monoclonal antibody 3D9S was prepared from ascites fluid, using a protein A-Sepharose CL-4B (Pharmacia, Montreal, Quebec, Canada) column. The purified IgG was dialyzed thoroughly against 0.1 M HEPES, pH 7.5 and linked to activated Affigel-10 (BioRad Laboratories, Mississauga, Ontario, Canada) at 5 mg protein per ml gel according to the manufacturer's instructions. An immunoadsorbent column was packed for each of four different gIV species.

VII.A.4. Purification of Glycoproteins

Glycoprotein gIV was purified from BHV-1 (strain P8-2) infected MDBK cells, recombinant AcNPV infected SF9 cells, recombinant adenovirus infected 293 cells or recombinant vaccinia virus infected BSC-1 cells. Cell lysates were prepared from the virus infected cells, essentially as described previously (Van Drunen Littel-van den Hurk et al. (1985) Virology 144:204–215). Briefly, the cells were harvested, centrifuged at 1000 rpm and resuspended in 10 mM Tris-hydrochloride, 150 mM NaCl, pH 7.5 containing 1% Nonidet P40 (NP40) and 1% sodium deoxycholate. After the cell lysates had cycled three times through the respective gIV-specific monoclonal antibody columns, the columns were washed with one volume of sample application buffer and two volumes of wash buffer (10 mM Tris-hydrochloride, 500 mM MaCl, 0.1% NP40, pH 7.5). Specifically bound antigen was eluted with 50 mM diethylamine, pH 11.5, immediately neutralized with 1 M Tris-hydrochloride, pH 7, and concentrated on an Amicon YM30 membrane. The columns were re-equilibrated in sample application buffer for reuse or stored in phosphate-buffered saline (PBS), containing 0.02% sodium azide. The protein content was determined with the BioRad protein determination kit. The purity was assessed by polyacrylamide gel electrophoresis alone and in combination with western blotting. Finally, the purified proteins were applied to appropriate cells to test for residual input virus.

VII.A.5. Polyacrylamide Gel Electrophoresis

Sodium dodecyl sulphate (SDS)-polyacrylamide gel electrophoresis (PAGE) was carried out in 10% discontinuous gels under reducing conditions as described previously (Laemmli, U. K. (1970) Nature 227:680–685).

VII.A.6. Immunization

Groups of eight calves each were immunized intramuscularly with 25 ug of purified gIV, produced by BHV-1, baculovirus, adenovirus or vaccinia virus, or 100 ug of gIV produced in *E. coli*. The glycoproteins were combined with the adjuvant Avridine as described previously (Babiuk et al. (1987) Virology 159:57–66). A control group was vaccinated with Avridine only. Twenty-one days later the animals were boosted and then challenged with BHV-1 fourteen days after the booster immunization. Blood samples were taken from the animals at the time of the first immunization, booster immunization, and challenge, as well as ten days after challenge for assessment of antibody responses.

VII.A.7. Experimental Challenge

Fourteen days after the second immunization, animals were transported into an isolation pen and examined clinically. Their weights and rectal temperatures were determined and recorded. Blood samples and nasal swabs were collected to establish baseline values. The calves were then individually exposed to an aerosol of $10^7$ pfu per ml of BHV-1 strain 108, which was generated by a DeVilbis Nebulizer, model 65 (DeVilbis, Barrie, Ontario, Canada). The duration of the treatment was 4 min per calf.

VII.A.8. Clinical Evaluation

The clinical evaluations were performed at the same time each day by two independent investigators who were uninformed about the specific treatments of the individual animals. The parameters evaluated included depression, appetite, fever, conjunctivitis, rhinitis, mouth-breathing and tracheitis. In each case, a score of 0 was assigned to healthy animals. Clinical scores of 1–4 were assigned to sick animals as follows: 4, severe; 3, marked; 2, moderate; 1, mild. Temperatures were taken every day and nasal swabs were collected every other day and processed the same day. Blood samples were collected ten days after challenge.

VII.A.9. Enzyme-linked Immunosorbent Assay (ELISA)

In order to determine the gIV-specific antibody responses of the calves, the ELISA was performed essentially as previously described (Van Drunen Littel-van den Hurk (1984) Virology 135:466). Polystyrene microtiter plates (Immulon 2, Dynatech Laboratories Inc., Alexandria, Va., USA) were coated with 0.05 ug purified gIV per well and incubated with serially diluted bovine sera. Affinity-purified horseradish peroxidase (HRPO)-conjugated rabbit anti-bovine IgG (Kirkegaard & Perry Laboratories, Gaithersburg, Md., USA), at a dilution of 1:5000, was used as the detecting antibody. Antibody isotypes were determined in an indirect ELISA using gIV-coated coated plates and isotype-specific monoclonal antibodies (provided by Dr. K. Nielsen, Agriculture Canada, Animal Diseases Research Institute, Nepean). Affinity-purified HRPO-conjugated goat anti-mouse IgG (Boehringer-Mannheim, Dorval, Quebec, Canada) at a dilution of 1:10,000 was used as the detecting antibody.

VII.A.10. Competitive Antibody Binding Assay (CBA)

The CBA was based on the ELISA modified as previously described (Van Drunen Littel-van den Hurk et al. (1985) Virology 144:216–227). Briefly, gIV coated plates were incubated with serially diluted competitor antibodies from the gIV-immunized calves. After a 1 hour incubation at 37° C., the plates were washed and incubated with HRPO-conjugated monoclonal antibodies specific for eight different epitopes on gIV (Van Drunen Littel-van den Hurk (1984) Virology 135:466; and Hughes et al. (1988) Arch. Virol. 103:47). After a 3 hour incubation at 37° C., the plates were washed again and developed. The percentage competition was calculated using the formula [100×(A−B)/A] where A is absorbance in absence of competitor antibody and B is absorbance in the presence of competitor monospecific antibody.

VII.A.11. Neutralization Test

The neutralization titers of the bovine sera were determined as described previously (Babiuk, L. A. et al. (1975) Infect.Immun. 12:958). The titers were expressed as the reciprocal of the highest dilution of antibody that caused a 50% reduction of plaques relative to the virus control. Neutralization titers were also determined for the nasal swabs of the immunized animals and calculated in the same manner.

VII.B. Results

VII.B.1. Purification of Authentic and Recombinant gIV

Authentic and recombinant gIVs were purified on gIV-specific monoclonal antibody columns. All of the recombinant gIV glycoproteins were produced at higher levels than the authentic gIV from BHV-1 (Table 2).

TABLE 2

| Source of gIV | $^a$Yield1(ug/10$^6$ cells) |
|---|---|
| BHV-1 | 1–2.5 |
| Baculovirus | 15–35 |
| Adenovirus | 3.5–8.5 |
| Vaccinia virus | 2.5–5.5 |
| E. coli | $^b$500–1000 |

$^a$The yields of gIV from mammalian cells were determined with the BioRad protein determination kit.
$^b$The yields of gIV from E. coli are expressed in ug per liter and represent values obtained on bench scale before optimization.

The purity of the glycoprotein preparations was assessed by SDS-PAGE. All of the recombinant forms of gIV bound specifically to the columns. The apparent molecular weights of authentic gIV and gIV from vaccinia virus and adenovirus were identical, indicating that processing and glycosylation of authentic gIV in MDBK cells and recombinant gIV in BSC-1 or 293 cells are very similar. Recombinant gIV from baculovirus, however, had an apparent molecular weight of 63 kDa, which is lower than that of the 71 kDa authentic form. In addition to the 63 kDa species, four bands of lower apparent molecular weight were observed. These bands were consistently seen both in pure and in crude preparations of gIV from baculovirus. Recombinant gIV from E. coli had an apparent molecular weight of 54 kDa, which corresponds to the molecular weight of the unglycosylated form of gIV (Van Drunen Littel-van den Hurk (1986) Virology 59:401–410). As about 50% of the total protein preparation from E. coli consisted of gIV, this recombinant protein was not further purified. The gIV from E. coli was not dimerized at all, whereas the gIV from baculovirus showed a much reduced degree of dimerization as compared to authentic gIV.

VII.B.2. Immune Responses to Authentic and Recombinant gIV

Figure 24A:
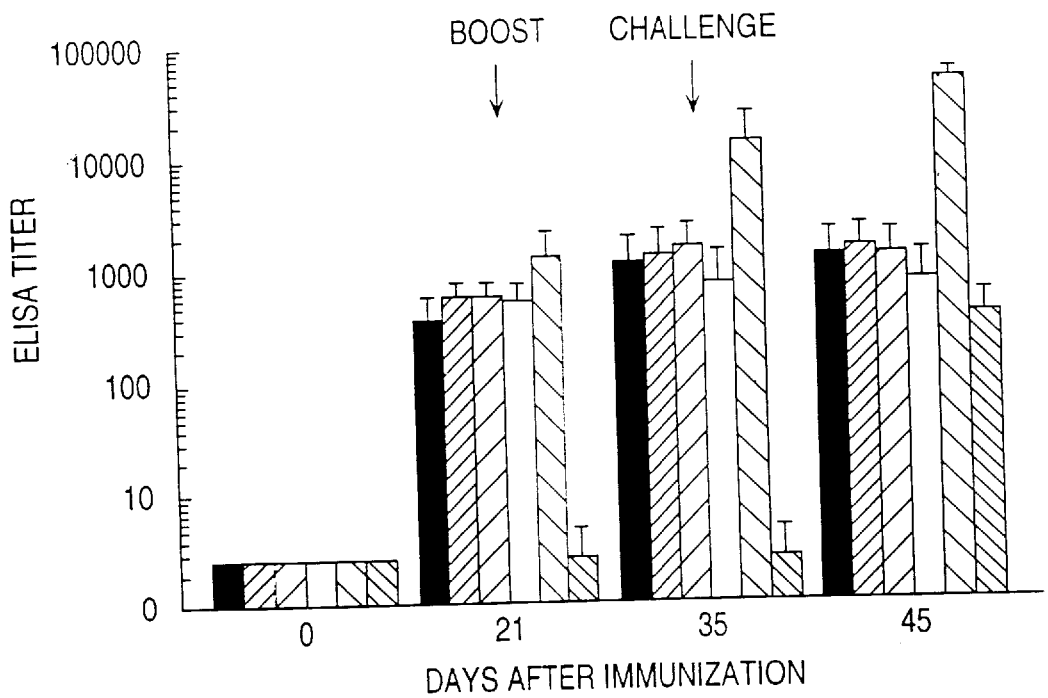

In order to determine whether the different forms of recombinant gIV have the same protective capacity as authentic gIV, they were evaluated in a BHV-1 challenge experiment as described above. The level and the specificity of the total antibody response following immunization was determined in an ELISA using authentic gIV, gI or gIII as the antigens. As shown in FIG. 24A, after one immunization, high levels of gIV-specific antibodies were found in the sera of all immunized animals. The antibody titers increased following the booster immunization. There was no significant difference between the antibody titers induced by gIV from BHV-1, baculovirus, adenovirus or vaccinia virus. However, the antibody titers generated by gIV from E. coli were 5-fold higher after the booster immunization. None of the animals reacted with gI or gIII, showing the specificity of the immune response. In no case did the placebo-vaccinated animals produce any immune response.

Figure 24B:
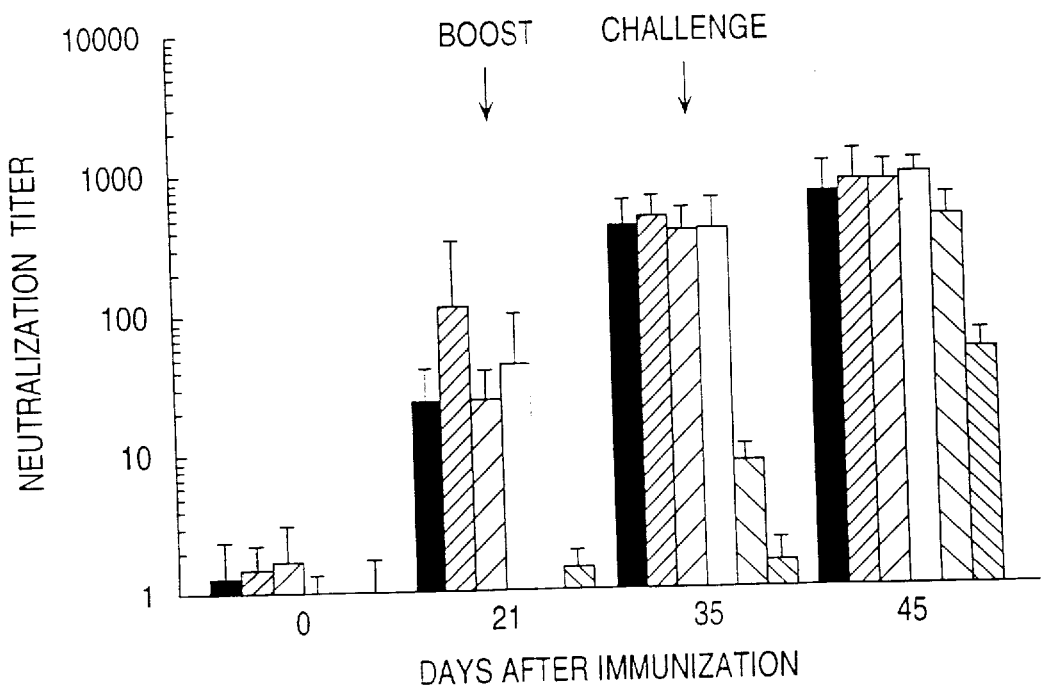

In order to predict the effectiveness of the glycoprotein-specific antibodies to prevent infection, the serum neutralizing antibody titers were determined. FIG. 24B indicates that after one immunization, gIV from BHV-1, baculovirus, adenovirus and vaccinia virus induced reasonably good levels of neutralizing antibodies, which increased to very high levels following the booster immunization. Again, there was essentially no difference between the immune responses to these four forms of gIV. In contrast, there was a significant difference in the neutralizing antibody response to gIV from E. coli. Even after two immunizations, the neutralizing antibody titer induced by this form of gIV was lower than the level induced by one immunization of any of the other forms of gIV.

Figure 25A:
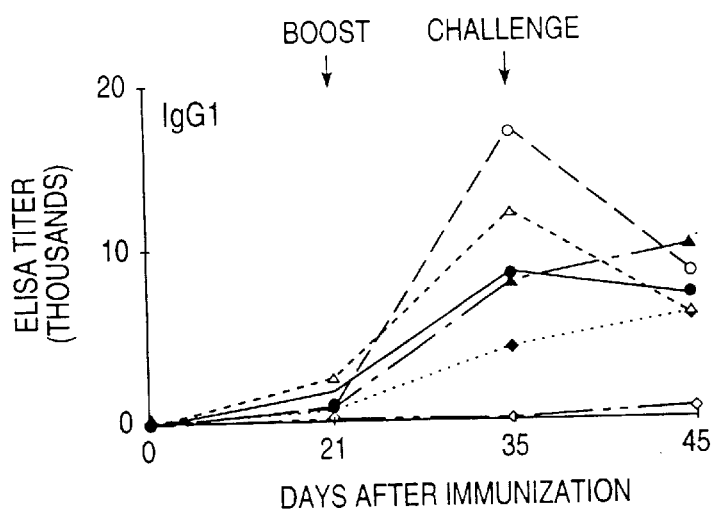
Figure 25B:
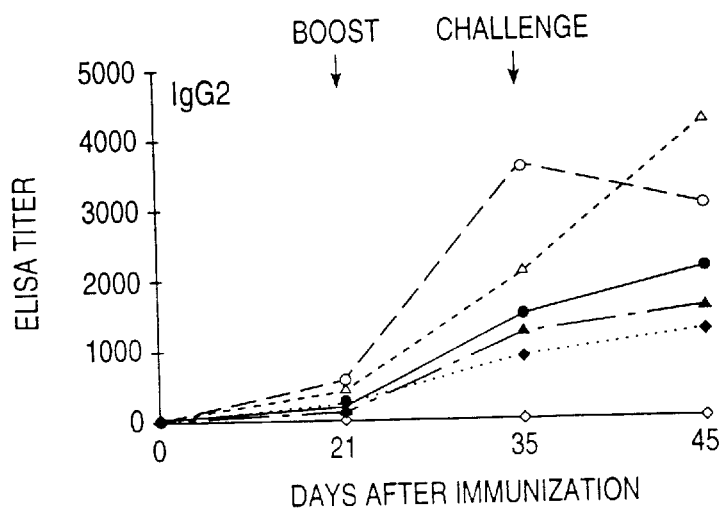
Figure 25C:
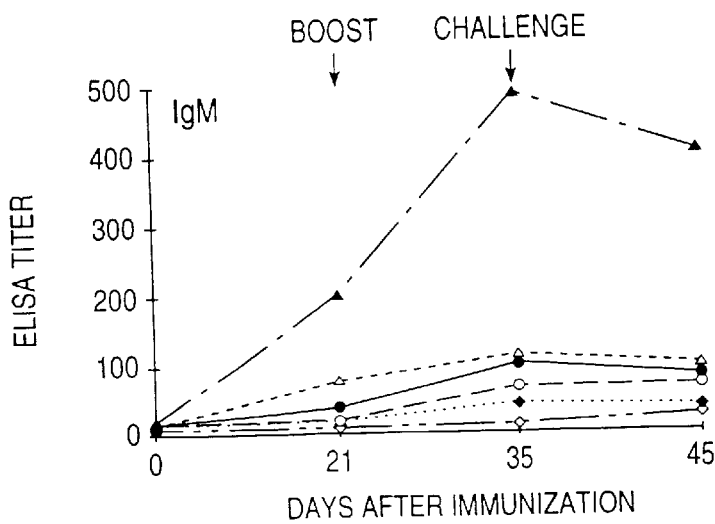

The contribution of antibody isotypes to the immune response was investigated by indirect ELISA (FIG. 25). The IgG1 titers (FIG. 25A) were higher than the IgG2 titers (FIG. 25B) throughout the period before challenge. The IgG1 titers reached peak values after two immunizations and then started to plateau and decrease after challenge. The IgG2 titers were lower initially, but generally continued to increase after challenge. The IgM titers (FIG. 25C) were much lower than the IgG1 or IgG2 titers throughout the duration of the experiment. The antibody isotypes were generally similar between the groups immunized with the different forms of recombinant gIV. However, the IgM levels induced by gIV from E. coli were significantly higher than those induced by the other forms of gIV. The IgG1 response, however, was slower in this group.

Figure 26:
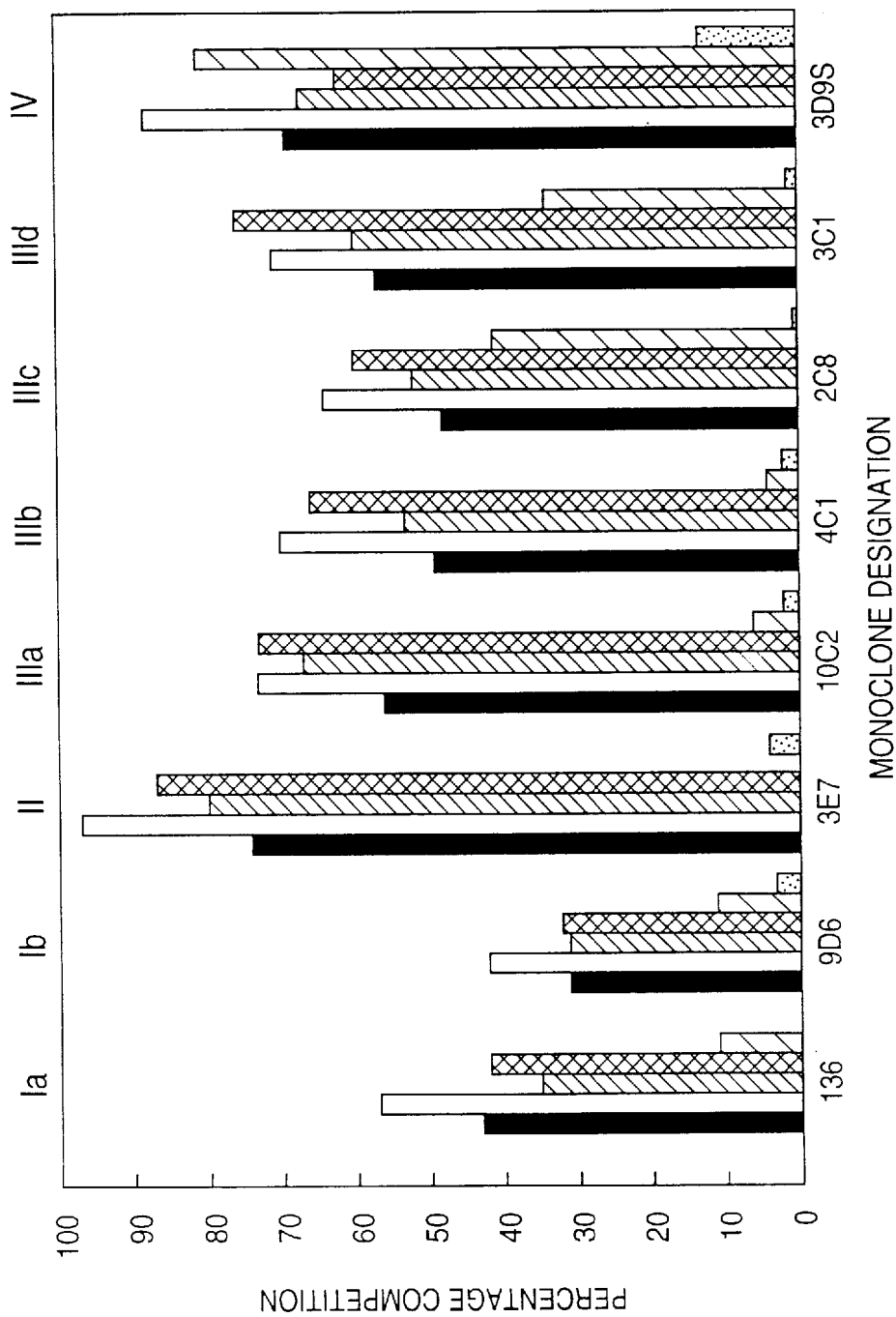

VII.B.3. Epitope Specificity of the Immune Response to Authentic and Recombinant gIV Recombinant gIV from E. coli induced a lower level of neutralizing antibodies to BHV-1 than the other recombinant gIVs, although the total antibody response was equivalent or higher. In order to determine which of the neutralizing epitopes on gIV were recognized, the sera from all immunized animals were tested with respect to epitope specificity. Seven neutralizing epitopes (epitopes Ia, Ib, II, IIIa, IIIb, IIIc, and IIId) and one non-neutralizing epitope (epitope IV) have been mapped on gIV (Hughes et al. (1988) Arch. Virol. 103:47). All epitopes on gIV were recognized by animals immunized with gIV from BHV-1, baculovirus, adenovirus, or vaccinia virus; blocking varied between 30 and 95%, depending on the epitope (FIG. 26). These values correlate well with previously reported values between 30 and 85% (Van Drunen Littel-van den Hurk (1990) Vaccine 8:358–368). However, the neutralizing epitopes on gIV were either not at all (Ia, Ib, II, IIIa, and IIIb), or poorly (IIIc and IIId) recognized by animals immunized with gIV from *E. coli*. The only epitope recognized well by these animals was the non-neutralizing epitope IV. These results indicate that the neutralizing epitopes on gIV, most of which are conformation-dependent (Hughes et al. (1988) Arch. Virol. 103:47), are present on gIV from baculovirus, adenovirus and vaccinia virus, but not on gIV from *E. coli*.

VII.B.4. Protection from Challenge with BHV-1

Figure 27A:
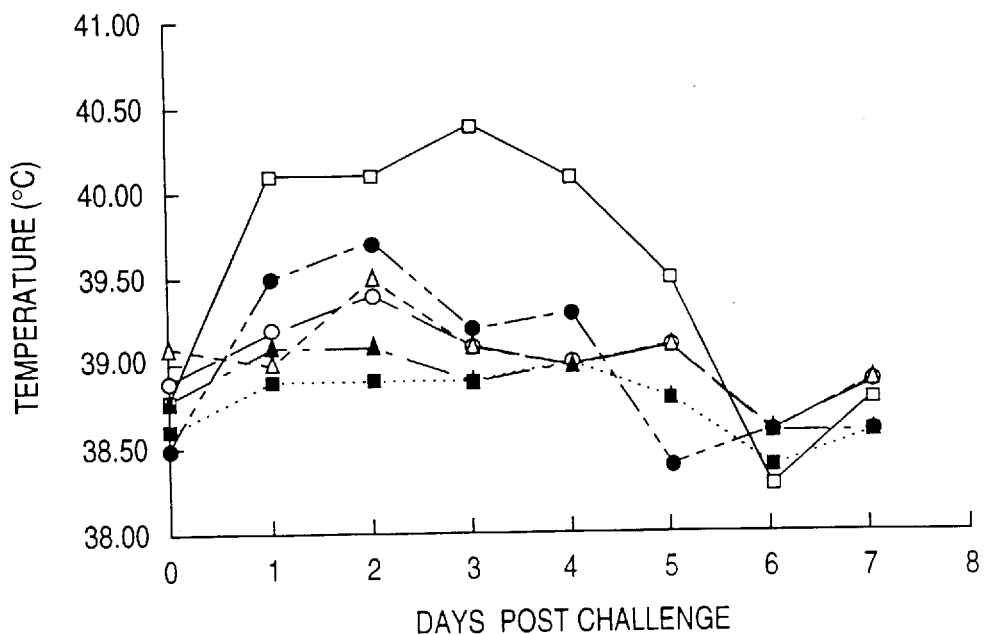
Figure 27B:
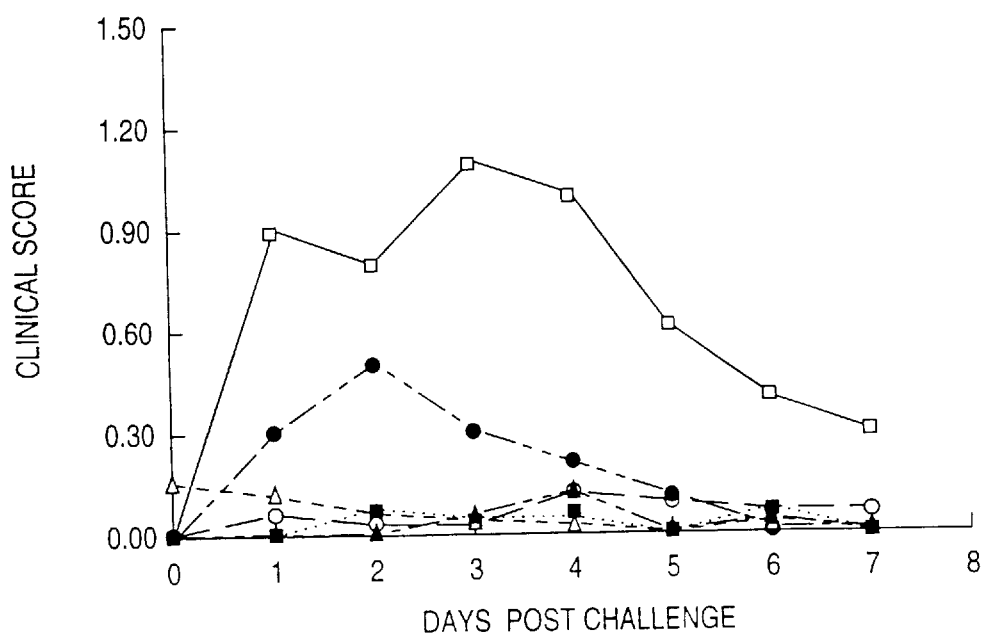

All animals were challenged with an aerosol of BHV-1. Prior to challenge, all animals were healthy and they had a normal rectal temperature. However, within 24 h post infection, the animals in the placebo-immunized group started to exhibit a sharp rise in temperature. The temperatures continued to increase until three days post challenge, whereafter they declined again. There was no significant increase in temperature in the gIV-vaccinated groups, although the animals immunized with gIV from *E. coli* did experience some elevated temperatures during the first two days after infection (FIG. 27A). In addition to the temperature responses the calves were clinically evaluated for signs of respiratory disease. The clinical illness scores correlated well with the temperature responses. The animals in the placebo-immunized group showed signs of clinical illness from day 1 until day 7 post challenge, whereas the groups immunized with gIV from BHV-1, baculovirus, adenovirus or vaccinia virus experienced no illness at all. The group that received gIV from *E. coli* showed mild disease for three days after infection (FIG. 27B). A further non-subjective assessment of morbidity is the extent of weight loss of animals challenged with BHV-1. The weight loss observed in the placebo-immunized group is a reflection of the anorexia as a result of the morbidity due to viral challenge. In contrast to the placebo-immunized group, gIV immunized animals experienced minimal or no weight loss during the 8 days following challenge (FIG. 28).

VII.B.5. Induction of Mucosal Immunity

Figure 29A:
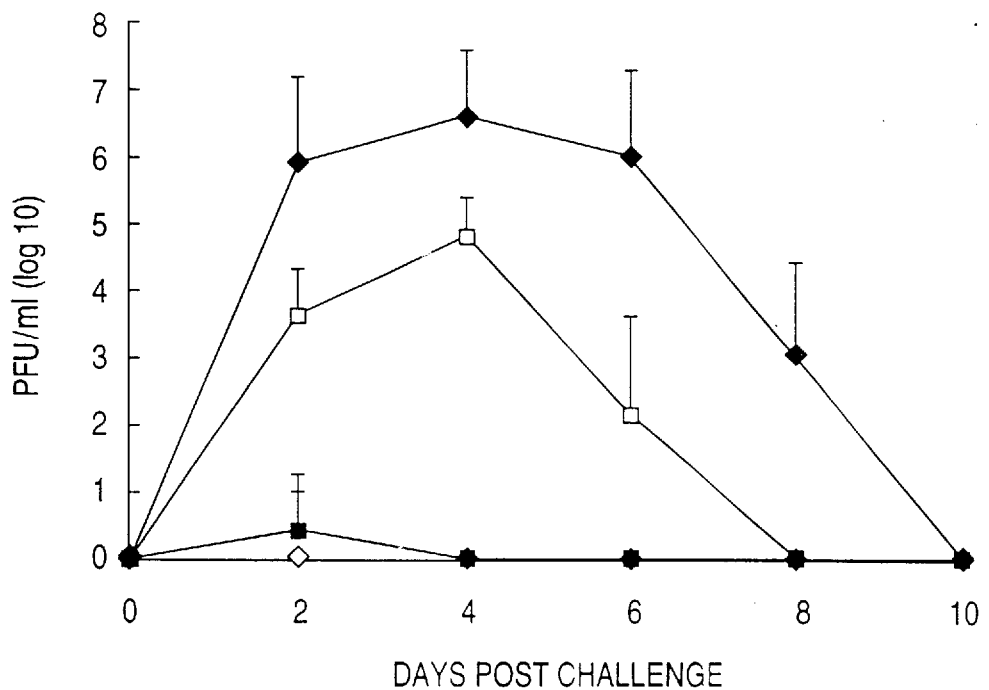
Figure 29B:
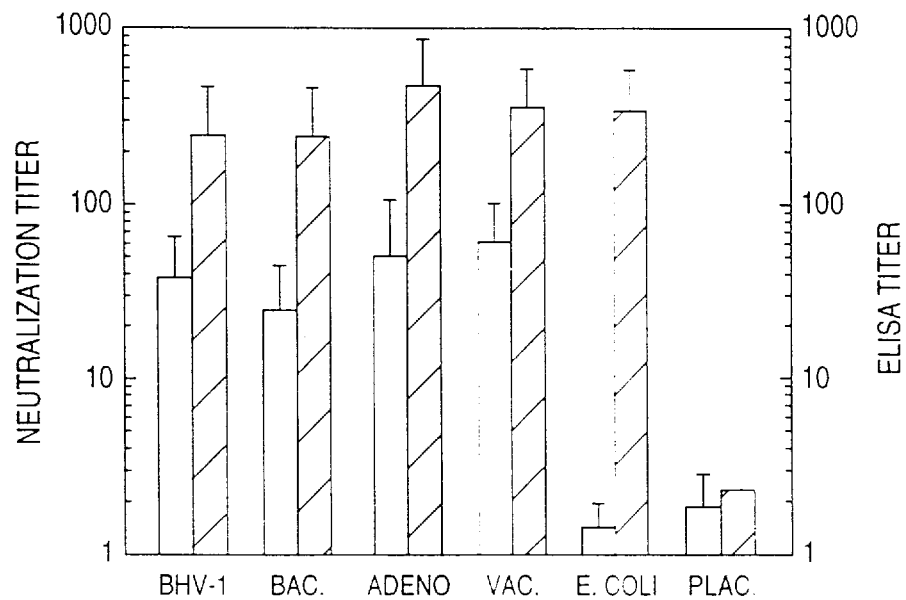

With the exception of the group immunized with gIV from *E. coli*, all animals vaccinated with authentic or recombinant gIV were fully protected from disease, when challenged with BHV-1. To determine whether they were also protected from viral infection, the extent of virus shedding from the nasal passages was assessed. FIG. 29A demonstrates that essentially no virus was recovered from the nasal swabs of animals vaccinated with gIV from BHV-1, baculovirus, adenovirus or vaccinia virus. One animal in each of the groups vaccinated with gIV from baculovirus and adenovirus shed virus for one day. In contrast, all animals immunized with gIV from *E. coli* or placebo shed virus for 7 to 9 days post challenge. These data indicated that intramuscular immunization with a subunit vaccine induced mucosal immunity in the nasal passages, thereby preventing viral infection. In addition, the extent of the mucosal immunity appeared to correlate with the level of the neutralizing antibodies in the serum. To confirm the presence of a mucosal immune response in the nasal passages, the antibody titers in the nasal swabs were determined. On the challenge day, groups vaccinated with gIV from BHV-1, baculovirus, adenovirus, or vaccinia virus had mean neutralizing antibody titers between 25 and 65 (FIG. 29B). The gIV-specific ELISA titers, also shown in FIG. 29B, correlated well with the neutralizing antibody titers. The group immunized with gIV from *E. coli* did not have any neutralizing antibodies in the nasal secretions, although the total gIV-specific antibody levels were as high as in the other groups. No gI-or gIII-specific antibodies were found in the nasal secretions (data not shown). These data correlate well with the serum antibody levels.

VIII

This example illustrates the production of a BHV-1 gI by recombinant baculovirus vectors.

VIII.A. Materials and methods

VIII.A.1. Cells. viruses and antibodies

Madin Darby bovine kidney (MDBK) cells were cultured in Eagle's minimal essential medium (Grand Island Biological Co., Grand Island, N.Y.) supplemented with 10% fetal bovine seruma (FBS) (Gibco). Virus stocks of BHV-1 strain Cooper were grown in MDBK cells as previously described (Babiuk et al., 1975 *Infect. Immun.* 12:958–963). *Spodoptera frugiperda* (Sf9) cells were grown and maintained in TNM-FH medium (GIBCO) containing 10% FBS according to the procedures described by Summers and Smith (1987 Texas Agricultural Experimental Station Bulletin No. 1555, College Station, Tex.). Virus stocks of wild-type AcNPV and recombinant virus were prepared in Sf9 cells as described by Summers and Smith (1987 supra). Monclonal antibodies specific for gI were developed and characterized by van Drunen Littel-van den Hurk et al. (1984 *Virology* 135:466–479). The gI-specific monclonal antibody mixture used for identification of recombinant gI consisted of equivalent amounts of 1B10 (epitope I), 3F3 (epitope II), 1E11 (epitope III), 1F8 (epitope IVa), 5G2 (epitope IVb), 3G11 (epitope IVb), 5G11 (epitope IVc), 6G111 (epitope IVc), 1F10 (epitope V) and 2C5 (epitope V).

VIII.A.2. Insertion of BHV-1 gI DNA into the transfer vector

A cassette of the gI glycoprotein gene has been prepared in plasmid pSV2Neo as previously described (Fitzpatrick et al., (1988), J. Virol., 62:4239–4248. The plasmid was digested with restriction endonuclease BglII and the fragment representing the gI gene was purified by agarose gel electrophoresis and ligated into the BamHI site of baculovirus transfer vector pVL941. After transformation of *E. coli* strain JM105, colonies appearing on L agar containing 100 µg/ml ampicillin were inoculated to L broth containing ampicillin and incubated at 37° C. overnight with vigorous shaking. Small scale preparations of plasmid from each colony were prepared and the presence of the gI gene was confirmed by digestion with endonucleases AvaI and EcoRV. A single clone was identified containing the gI gene in the desired orientation and designated pVlgB. Clone pVlgB was inoculated into 500 ml L broth containing ampicillin and after 24 h at 37° C., plasmid was prepared by alkaline lysis and further purified by equilibrium centriguation on CsCl.

VIII.A.3. Transfection and selection of recombinant viruses

After two cycles of ethanol precipitation, purified plasmid was mixed with an equal amount of *A. californica* viral DNA and used to transfect subconfluent monolayers of Sf9 cells as coutlined by Summers and Smith (1987) supra. Recombinant baculoviruses were identified by plaque hybridization essentially as outlined by Summers and Smith (1987) supra. The polyhedrin-negative recombinants were plaque-purified 3 to 4 times on Sf9 cells to remove contaminating wild-type baculovirus.

VIII.A.4. Preparation of cell lysates

To analyze expression of recombinant gI, confluent monolayers of Sf9 cells on 35 mm petri dishes were infected with individual polyhedrin-negative recombinants at a moi of 5 and incubated for 48 h at 28° C. The cells were scraped into PBS, pelleted at 150 xg for 1 min, and resuspended in 50 μl of RIPA buffer (0.02 M Tris-hydrochloride [pH 8.0], 0.15M NaCl, 1% 10 mM phenylmethylsulfonylfluoride [PMSF]). The postnuclear supernatant was collected and 5 μl was combined with reducing electrophoresis sample buffer and boiled for 2 min for analys,is by SDS-PAGE and immunoblotting. To determine approximate yields of recombinant gI, Sf9 cells in monolayers or suspension cultures were infected with recombinant virus at a moi of 1. The cells were harvested at various times post infection, washed with PBS and resuspended in RIPA buffer at $1 \times 10^7$ cells/ml for analysis by ELISA. Equivalent samples from uninfected cells and/or cells infected with the parental virus were always included as controls.

VIII.A.5 Analysis of carbohydrates

Proteins were digested with endoglycosidase H or glycopeptidase F as described by Ronin et al. (1987), *Biochemistry*, 26:5848–5853. Infected cells were collected by centrifugation and $2 \times 10^5$ cells were resuspended in 10 μl of appropriate enzyme incubation buffer. Digestion with glycopeptidase F (Boehringer-Mannheim, Laval, Quebec, Canada) was performed in 50 mM Trishydrochloride (pH 8.6), 25 mM EDTA, 1% Triton X100, 1% 2-mercaptoethanol, 0.2% SDS and 1.5 U of enzyme. Digestion with endo H (Boehringer-Mannheim) was performed in 0.1 M sodium acetate (pH 5), 0.15 M sodium chloride, 1% Triton X100, 1% 2-mercaptoethanol, 0.2% SDS, and 1.5 mU of enzyme. The cells were incubated for 18 h at 37° C. Proteins were precipitated by adding 1 ml of ice-cold acetone and centrifugation. They were subjected to SDS-PAGE followed by immunoblot analysis. Tunicamycin was added to recombinant AcNPV-infected Sf9 cells or BHV-1 infected MDDBK cells at the time of infection from a stock solution of 1 mg/ml in ethanol. Sf9 cells were harvested at 48 h post infection and MDBK cells were harvested at 24 h post infection.

VIII.A.6 SDS-PAGE, Immunoblot and ELISA

Sodium dodecylsulfate-polyacrylamide gel electrophoresis (SDS-PAGE) was performed in 8.5% or 10% polyacrylamide discontinuous gels as previously described (van Drunen Littel-van den Hurk et al., 1984), supra. Electrophoresis was carried out under reducing conditions. Protein bands were visualized by staining with coomassie brilliant blue. In order to identify recombinant gI, produced by baculovirus, an immunoblot assay was performed as previously described in (van Drunen Littel-van den Hurk et al., 1984), supra. Briefly, after electrophoresis, cell lysates were electrophoretically transferred to nitrocellulose sheets. Subsequently, the instructions for use of the Bio-Rad (Missisauga, Ontario) immunoblot assay kit were followed. One gI-positive recombinant baculovirus, named Bac-gI, was amplified by growth on Sf9 cells. The supernatants from this infection were stored at 4° C. and used in all subsequent experiments.

Sandwich and indirect ELISA's were used to determine the yields of glycoprotein gI in recombinant baculovirus-infected Sf9 cells. In the sandwich assay, microtiter plates were coated with the IgG fraction of bovine hyperimmune serum as the capture antibody and then incubated with lysates from recombinant virus-infected and control cells, or affinity-purified standard gI. In the indirect assay, the cell lysates and glycoproteins were directly adsorbed to the microtiter plates. Mixtures of gI-specific monoclonal antibodies, followed by horseradish peroxidase (HRPO)-conjugated goat anti-mouse IgG (Boehringer-Mannheim) were used for detection as previously described (van Durnen Littel-van den Hurk et al., 1984) supra). The reaction was visualized using 0.8 mg/ml of 5-aminosalicylic acid and. 0.006% $H_2O_2$ as described.

VIII.A.7. Immunofluorescence and flow cytrometry

The expression of glycoprotein gI in recombinant baculovirus-infected Sf9 cells was determined at 24, 48 and 72 h post infection. Briefly, cells were washed in PBS and cytospin smears were prepared and fixed in methanol. They were incubated for 30 min at 37° C. with a 1:100 dilution of a gI-specific monoclonal antibody mixture and washed in PBS and dd$H_2O$. They were stained with fluorescein isothiocyanate-conjugated (FITC) rabbit anti-mouse IgG (Boehringer-Mannheim) for 30 min at 37° C. and washed again before being mounted in PBS-glycerol for examination. For surface staining and flow-cytometric analysis, cells were suspended in PBS containing 0.2% gelatin and 0.03% $NaN_3$ (PBSG) at $4 \times 10^7$ cells/ml. They were plated in microtiter plates at $2 \times 10^6$ cells per well and incubated with serial dilutions of monoclonal antibody mixtures for 30 min on ice. Subsequently, they were washed in PBSG and then incubated with FITC rabbit anti-mouse IgG for 30 min at 4° C. After washing, the cells were fixed in 2% formaldehyde and analyzed with an EPICS CS (Coulter Electronics Ltd.) flow cytometer as described elsewhere (Campos et al. (1989), *Cell. Immunol.*, 120:259–269. The percentage of positive cells was calculated using the immuno-program (Coulter Electronics Ltd., MDAPS system) for the analysis of immunofluorescence histograms.

VIII.A.8. Cell fusion assay

Monolayers of Sf9 cells in 24-well tissue culture plates were infected with recombinant virus at a moi of 5–10 PFU per cell. At 36 h post infection, the medium was replaced with TNM-FH medium, adjusted to a pH ranging from 5.0 to 6.5 Syncytia formation was monitored under a phase contrast microscope (Zeiss Model IM35; magnification 200x). Monospecific and monoclonal antibodies were added at a dilution of 1:100 at the time of pH shift.

VIII.A.9. Immunization of cattle

Glycoprotein gI was purified by immunoadsorbant chromatography from Bac-gI infected Sf9 cells or BHV-1 infected MDBK cells as described in detail previously (van Drunen-Littel van den Hurk and Babiuk (1985), *Virology*, 144:204–215. Groups of eight animals each were immunized with 10 μg of affinity-purified recombinant or authentic gI in Emulsigen™ PLUS at a ratio of 7:3 (vol/vol) as outlined by the manufacturer (MVP Laboratories, Ralston, Nebr.). The animals were injected intramuscularly and they received a booster immunization 28 days later. They were bled at the times of immunization and two weeks after the second immunization for assessment of antibody responses. The antibody response to gI in the vaccinated animals was assayed in an immunoblot assay with purified BHV-1 as the antigen, as described previously (van Drunen Littel-van den Hurk et al. (1990), *Vaccine*, 8:353–368.

VIII.B Results 9p VIII.B.1 Production of recombinant gI glycoprotein in Sf9 cells Recombinants containing the gI gene inserts were tested for their ability to produce BHV-1 glycoprotein I after infection of Sf9 cells. All of the gI recombinants directed the synthesis of a polypeptide with an apparent molecular weight of 116 kDa, which was visible on a coomassie brilliant blue stained gel at 48 h post infection. This protein was missing in uninfected cells and cells infected with the parental baculovirus. In order to confirm the identify of this glycoprotein, immunoblot analyses were performed on Bac-gI infected Sf9 cells and BHV-1 infected MDBK cells. A gI-specific monoclonal antibody mixture that recognized the 130k, 74k and 55k components of authentic gI in BHV-1 infected MDBK cells, reacted with three polypeptides; with apparent molecular weights of 116 kDa, 63 kDa, and 52 kDa in Bac-gI infected Sf9 cells. This indicates that terminal glycosylation of gI has not occurred in the recombinant virus-infected Sf9 cells. Recombinant gI was cleaved in infected Sf9 cells, but not with the same efficiency as authentic gI. No reaction was observed between the gI-specific monoclonal antibodies and Sf9 cells infected with the parental baculovirus.

VIII.B.2. Processing of gI in mammalian and insect cells

To further analyze the observed difference in molecular weight of the recombinant and authentic gI, Bac-gI infected Sf9 cells and BHV-1 infected MDBK cells were treated with tunicamycin, an inhibitor of N-linked glycosylation. In these cells only one polypeptide with an apparent molecular weight of 105k was observed, which corresponds to the previously identified polypeptide backbone of authentic gI (van Drunen Littel-van den Hurk and Babiuk, (1986) *J. Virol.*, 59; 401–410. This experiment proved that the reduced molecular weight of gI expressed in insect cells was due to incomplete glycosylation. To compare the type of carbohydrate attached to recombinant and authentic gIV, both glycoproteins were subjected to digestion with endo H or endo F. Digestion with endo H resulted in a slight decrease in apparent molecular weight of authentic: gIa and gIc, but had no effect on gIb, which confirms previous studies (van Drunen Littel-van den Hurk et al., (1986) supra. The greater portion of recombinant gIa and gIc was sensitive to endo H, showing the presence of high-mannose type oligosaccharides. However, the recombinant gIb was not sensitive to endo H, indicating that these oligosaccharides are trimmed. All of the recombinant and authentic forms of gI were endo F sensitive, showing precursor molecules with similar apparent molecular weights in BHV-1 and Bac-gI infected cells.

Authentic and recombinant gI are both cleaved during processing to the mature polypeptide. However, the cleavage process is incomplete in mammalian cells and even less efficient in insect cells. It has been proposed that Arg-Arg-Ala-Arg-Arg sequence (amino acids 501–505 of SEQ ID NO:2), which occurs in the region of non-similarity with HSV-1, may be the processing site for PRV gII (Robbins et al., (1987) *J. Virol.*, 61:2691–2701 and BHV-1 gI (Whitbeck et al., (1988) *J. Virol.*, 62:3319–3327. To confirm the position of the cleavage site of authentic as well as recombinant gI, we sequenced the N-terminus of the gIc glycoprotein from infected MDBK and Sf9 cells. This analysis confirmed that the first 12 N-terminal amino acids of authentic and recombinant gIc correspond to positions 506–517 (FIG. 30). Since recombinant gI was cleaved at the same site as authentic gI, the reduced cleavage efficiency is probably due to the presence of relatively low amounts of enzyme in baculovirus-infected cells, as compared to the large amounts of gI produced in these cells. N-terminal sequencing of the gIb glycoprotein demonstrated that the signal is cleaved in MDBK and Sf9 cells and that the amino terminal residue of authentic as well as recombinant gI is Arg-68.

VIII.B.3 Kinetics and level of expression of the recombinant gI glycoprotein

Figure 31A:
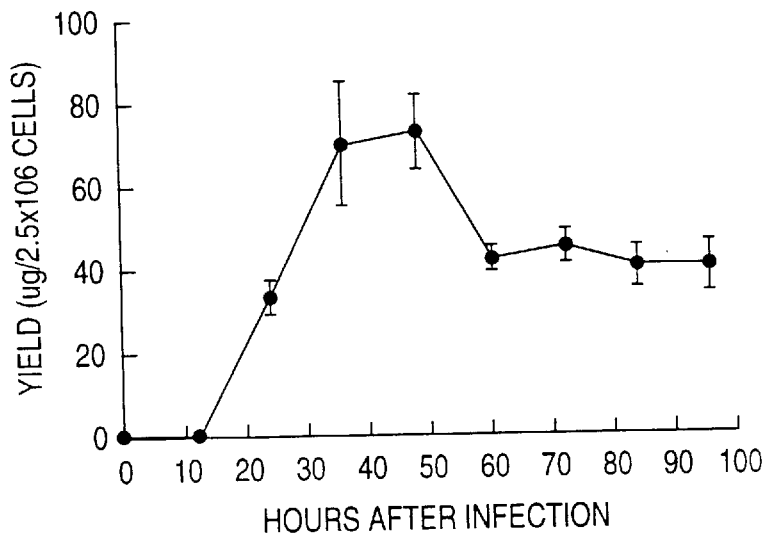
Figure 31B:
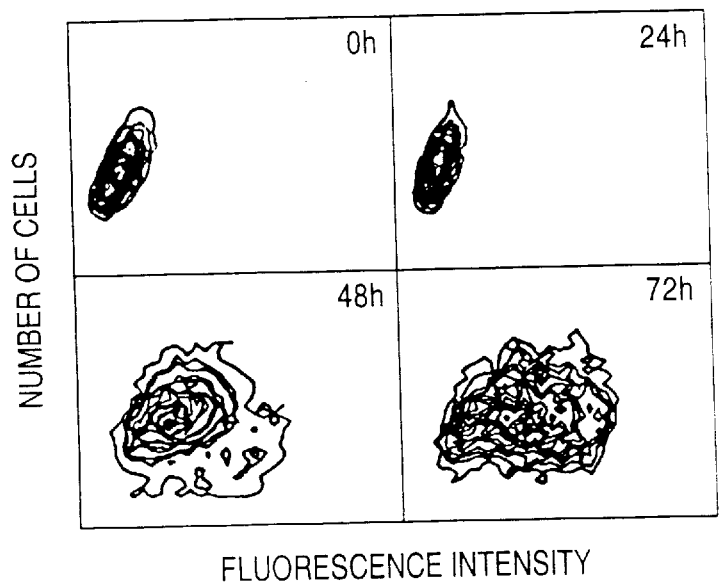
Figure 31C:
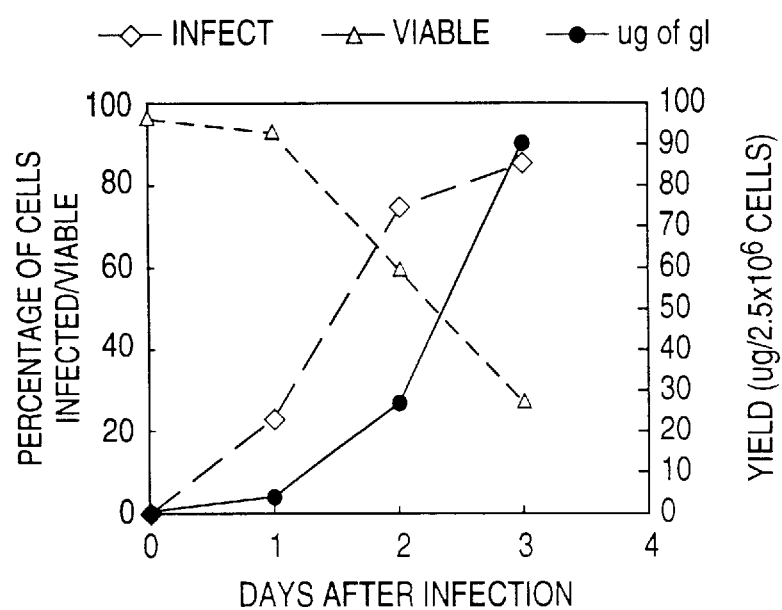

The amount of gI synthesized in recombinant baculovirus-infected Sf9 cells was quantitated by ELISA, standardized with affinity-purified recombinant gI. Sf9 cells grown as monolayers in 35 mm petridishes were infected with Bac-gI at a moi of 5, and aliquots of $1 \times 10^6$ cells were harvested at various times post infection. Cell lysates were prepared and the level of expression of recombinant gI was tested in the ELISA (FIG. 31A). Immunoreactive gI could be detected as early as 24 h after infection and maximal expression was observed between 36 and 48 h, whereafter a slight decrease in measurable glycoprotein occurred. This decline presumably reflected cell lysis and subsequent degradation of the glycoprotein. This analysis showed that, at maximal levels of expression, 30 μg of gI were produced per $10^6$ cells. In order to analyze the possibility to produce recombinant gI at a larger scale, SF9 cells were grown in suspension cultures and infected with the recombinant baculovirus at a moi of 1. In addition to yield by ELISA, the viability of the cells and percentage of infected cells were determined. Flow cytometric analysis showed an increase in percentage of infected cells (y-axis) as well as total protein yield (x-axis) over time (FIG. 31B). FIG. 31C shows that the percentage of infected cells increased gradually, reaching peak levels of 85% at 72 h after infection, when the viability of the cells was down to 25%. The viability of the cells was too low for flow cytometric analysis beyond this time point. Analysis by ELISA demonstrated that up to 35 μg of gI were produced per $10^6$ cells. This demonstrated the feasibility of growing the recombinant baculovirus on a larger scale and yet obtain good yields of the glycoprotein.

VIII.B.4 Intracellular localization of recombinant gI in SF9 cells

The intracellular distribution of the recombinant gI glycoprotein was examined by an indirect immunofluorescence assay. At 48 h post infection, recombinant gI was primarily localized in the perinuclear membranes of the infected Sf9 cells. To determine whether the recombinant gI was present on the surface of infected cells, immunofluorescence analysis was carried out on unfixed cells. Localization of gI was demonstrated by bright fluorescence on the surface. Wild-type AcNPV-infected control cells did not show any fluorescence with the gI-specific monoclonal antibody panel (not shown).

VIII.B.5. Fusogenic properties of recombinant gI in insect cells

It has been shown previously that one of the functional characteristics of gI is its ability to induce cell fusion in absence of other viral proteins (Fitzpatrick et al., (1988) supra; (1990) *J. Gen. Virol.*, 71:1215–1219. To determine whether this functional property was retained in the recombinant protein, Sf9 cells were infected with Bac-gI. Fusion of the insect cells was not evident under standard culture conditions, but after a shift to pH 5.4, fusion was apparent in Bac-gI infected Sf9 cells within two hours. The syncytia formation observed in these cells continued to increase over 8 h of observation. Inclusion of gI-specific rabbit serum or a mixture of gI-specific monoclonal antibodies completely inhibited fusion by gI as set forth in Table 3.

TABLE 3

Inhibition of fusion activity mediated by gI expressed in baculovirus

| Treatment[a] | Fusion activity (%)[b] |
|---|---|
| TNM-FH, pH 5.4 | 80 |
| Trypsin | 80 |
| Normal Rabs | 80 |
| gI-specific Rabs | 0 |
| Control Mabs | 80 |
| gI-specific Mabs mixture | 0 |
| 1B10 mab (I) | 5 |
| 3F3 Mab (II) | 80 |
| 1E11 Mab (III) | 80 |
| 1F8 Mab (IVa) | 80 |
| 5G2 Mab (IVb) | 10 |

TABLE 3-continued

Inhibition of fusion activity mediated by gI
expressed in baculovirus

| Treatment[a] | Fusion activity (%)[b] |
|---|---|
| 5G11 Mab (IVc) | 60 |
| 1F10 Mab (V) | 80 |

[a]Cell fusion was induced at 36 h post infection by replacing the cell culture medium with TNM-FH pH 5.4. At the time of pH shift a final dilution of 1:100 of Rabs (rabbit serum) or Mabs (monoclonal antibodies) was added to the medium. Treatment with 20 μg trypsin was carried out for 10 min, just before pH shift at 36 h.
[b]The cells were counted 8 h after the pH shift. The percentage of fused cells was calculated on a total of 400 cells and rounded to the nearest decimal.

When individual monoclonal antibodies were included in the media, fusion was almost completely inhibited by the monoclonal antibodies 1B10 (epitope I) and 5G2 (epitope IVb) and partially inhibited by 5G11 (epitope IVc). Inclusion of trypsin at the time of pH shift did not affect the fusion activity.

VIII.B.6. Antigenic and immunogenic properties of gI expressed in Sf9 cells

The antigenic properties of recombinant gI were evaluated using a panel of gI-specific monoclonal antibodies. The epitopes recognized by these monoclonal antibodies have been identified and characterized previously (van Drunen Littel-van den Hurk et al. (1985) supra; Fitzpatrick et al. (1990) Virology, 176:145–157. Reactivity of all of these monoclonal antibodies in an ELISA (Table 4) indicated that all of the epitopes identified on the authentic glycoprotein were also present on the recombinant gI glycoprotein.

TABLE 4

| Monoclone Designation[a] | Epitope Specificity[b] | Neutralizing Activity[c] | ELISA Titer[d] BHV-1 gI | ELISA Titer[d] AcNPV gI |
|---|---|---|---|---|
| 1B10 | I | – | 100 | 6400 |
| 3F3 | II | +/– | 6400 | 25600 |
| 1E11 | III | ++ | 1600 | 6400 |
| 1F8 | Iva | + | 25600 | 6400 |
| 5G2 | Ivb | + | 6400 | 6400 |
| 3G11 | Ivb | + | 1600 | 1600 |
| 5G11 | Ivc | + | 1600 | 100 |
| 6G11 | Ivc | ++ | 400 | 100 |
| 1F10 | V | +/– | 1600 | 1600 |
| 2C5 | V | +/– | 6400 | 6400 |

[a]Monoclonal antibodies developed by van Drunen Littel et al. (1984)
[b]gI epitopes assigned by competitive binding assays (van Drunen Littel-van den Hurk al., 1985).
[c]Neutralizing titers were determined for ascites fluids in the presence of guinea pig serum as a source of complement. –; titer < 4; +/–, titer < 100; +, titer > 100; ++; titer > 10,000. (Van Drunen Littel-van den Hurk et al., (1985) supra.
[d]Antigen titer was expressed as the reciprocal of the highest dilution of infected cells giving a reading of at least 0.05 OD (492 nm). A 1:100 dilution corresponds to 2 × 10⁴ cells.

The reaction between the monoclonal antibodies and two carbohydrate-dependent epitopes (IVa and IVc; van Drunen Littel-van den Hurk et al. (1990) J. Gen. Virol., 71:2053–2063 was weaker on recombinant gI than on authentic gI, which is in agreement with lack of terminal glycosylation of gI in Sf9 cells. Epitopes I, II and III, however, appeared to be more reactive on recombinant gI than on its authentic counterpart.

To study the immunogenicity of recombinant gI, cattle were immunized with 10 μg of affinity-purified glycoprotein from recombinant baculovirus-infected SF9 cells. Two immunizations of recombinant gI in Emulsigen elicited antibodies that were reactive with gI from BHV-1 in an immunoblot assay.

IX

Use of recombinant BHV-1 proteins for diagnostic purposes.

IX.A.

The recombinant BHV-1 gI, gIII or gIV may be used as antigens in standard immunological assays, for example ELISA tests, to indicate the presence of antibodies to BHV-1. In this manner, the immunological status of an animal may be assessed with respect to present infection or predisposition to BHV-1.

The recombinant gI, gIII or gIV proteins were diluted in sodium carbonate buffer pH 9.6 and used to coat the wells of an ELISA plate at concentrations ranging from 0.1 to 1 $\mu$g of protein/well. After incubating for a minimum of 1 hour, the plates were washed and dilutions of animal sera added to the plate in a serial fashion. The processing of the ELISA proceeded as described in example XI.

IX.B.

The developed ELISA plate indicated that animals infected by BHV-1 had detectable levels of antisera specific for gI, gIII or gIV and any one of these recombinant BHV-1 proteins would be suitable for use in the diagnosis of BHV-1 infection.

X

Construction of Recombinant AcMNPV Expressing Secreted BHV-1 gIV.

X.A.

Standard protocols, described in “A Manual of Methods for Baculovirus Vectors and Insect Cell Culture Procedures” by Summers and Smith were used to generate the above recombinant. We used the gene replacement vector, pAcYM1 (see *Ann. Rev. Microbiol.* 42:177), to direct the insertion of the modified gIV gene (see below) into the polyhedron gene locus of AcMNPV. Therefore, gIV gene expression was directed by the polyhedron gene promoter and the recombinant virus displayed a polyhedron negative phenotype.

The following procedures were used to generate the insertion plasmid required to produce a baculovirus capable of secreting gIV from infected cells. The entire gIV gene coding sequence is contained within a single 1303 bp Mae I fragment (see gIV gene sequence+restriction endonuclease map, FIG. 34(*b*)). A Mae I site exists approx. 45 bp upstream of the gene’s initiation codon and approx. 10 bp downstream of the stop codon. This Mae I subfragment was isolated from the BHV-1 HindIII K fragment and treated with T4 DNA polymerase to blunt the ends. The modified fragment was then inserted into the Bgl II site (also treated with T4 DNA polymerase) of a cloning vector. This procedure regenerated the Bgl II cloning sites, such that the gIV gene’s coding sequence was now flanked by unique Bgl II sites. In order to make a construct that will permit gIV glycoprotein secretion, the Bgl II modified plasmid was first partially digested with Sac II and a TAB linker (TCGAGC) was added to create a unique Xho I site at the C-terminal Sac II site (located at 1115 bp in the accompanying gIV gene sequence). The C-terminal Sac II site is located at the very 5' terminus of the sequence which encodes the gIV transmembrane sequence. The new plasmid was then digested with Xho I, blunt-end repaired with T4 DNA polymerase followed by insertion of a triphasic translation stop codon linker (CTAGCTAGCTAG (SEQ ID NO:7)) which causes premature translation termination at the 5' terminus of the gIV gene's anchor sequence. The modified gIV gene construct was excised by Bgl II digestion and then inserted into the Bam HI cloning site of pAcYM1. Proper orientation of the gIV gene was established by mapping asymmetric restriction endonuclease sites within the insert relative to unique restriction endonuclease sites in the pAcYMI backbone. This final construct was used to co-transfect Sf9 cells along with purified wild-type genomic ACMNPV DNA by the prescribed procedures of Smith and Summers.

X.B.

Individual polyhedron negative plaques were isolated (see plaque purification procedures), amplified by growth on Sf9 cells and tested for expression of secreted gIV by Western analysis of serum-free growth media (Ex-Cell 400, JR Scientific) collected from virus infected cells (moi 1.0) 48 h post infection. Our analyses demonstrated that approximately 70% of the total gIV produced by this virus was secreted into the media.

XI

XI.A. Methods

XI.A.1. Cells and viruses

Madin-Darby bovine kidney (MDBK) cells, BSC-1 cells and human thymidine kinase negative (TK$^-$) 143 -cells were grown as monolayers in Eagle's minimum essential medium (MEM) (GIBCO/BRL, Mississauga, Ontario, Canada), supplemented with 5% fetal bovine serum (FBS) (GIGCO/BRL, Mississauga, Ontario, Canada). LMTK$^-$ cells were grown in Dulbecco's minimum essential medium (DMEM) (GIBCO/BRL, Mississauga, Ontario, Canada) supplemented with 5% FBS. The P8-2 strain of BHV-1 was propagated in MDBK cells and quantitated as described in Rouse et al. (1974) *J. Immunol.*, 113:1391–1398). Wild type (WR strain) and recombinant VVs were propagated in BSC-1 cells and LMTK$^-$ cells (Mackett et al. (1984) *J. Gen. Virol.*, 49:857–864).

XI.A.2. Construction of recombinant plasmids

Restriction endonucleases, and other DNA modifying enzymes were purchased from Pharmacia (Dorval, Quebec, Canada) and New England Biolabs (Mississauga, Ontario, Canada), and were used as directed by the manufacturer.

Construction of the RSV1.3 and RSV1.3X plasmid: The full-length gIV gene was excised from plasmid pRSDneo-gIV (Tikoo et al. (1990) *J. Virol.*, 64:5132–5142) as a 1.3 kilobase (kb) BglII fragment and inserted into BglII digested pRSV-0 (Fitzpatrick et al. (1988) *J. Virol.*, 62:4239–4248) creating the pRSV1.3 plasmid. This plasmid was partially digested with SacII and a TAB linker (PTCGAGC) was added (Barany, F., (1985) *Proc. Natl. Acad. Sci.* USA 82:4202–4206) to create a unique XhoI site at the C-terminal SacII site. This plasmid was called pRSV1.3X. All subsequent deletions and truncations were constructed beginning with either of these two plasmids.

a) Plasmid pSTgIV: The gIV gene was subcloned from plasmid pRSDneogIV (Tikoo et al. (1990) supra) as a 1.3 kb BglII fragment, treated with T4 DNA polymerase and ligated to SmaI digested pGS20 (Mackett et al. (1984) supra).

b) Plasmid pSTgIVd1: Plasmid pRSV1.3X was digested with XhoI, blunt-end repaired with T4 DNA polymerase, followed by insertion of a triphasic stop codon NheI Linder (pCTAGCTAGCTAG (SEQ ID NO:7)). The DNA was then digested with NheI and religated. The truncated gIV gene was inserted into the SmaI site of pGS20 as a blunt-end repaired BglII fragment.

c) Plasmids pSTgIVd2 and pSTgIVd5: Plasmid pRSV1.3 was partially digested with NarI and a triphasic stop codon HpaI linker (pd[TTAAGTTAACTTAA](SEQ ID NO:8)) was inserted after treating the NarI digested plasmid with T4 DNA polymerase. The DNA was finally digested with HpaI and religated. The insertion of the linker at one of the two NarI sites in the gIV gene was confirmed by restriction endonuclease mapping. These two truncations were cloned separately into the SmaI site of pGS20 as a blunt end repaired BglII fragment, creating plasmid pSTgIVd2 (HpaI linker insertion at 3' NarI site) and plasmid pSTgIVd5 (HpaI linker insertion at 5' NarI site).

d) Plasmid pSTgIVd3: Plasmid pRSV1.3 was partially digested with SalI, blunt-erd repaired with T4 DNA polymerase followed by ligation with a triphasic stop codon NheI linker (pCTAGCTAGCTAG (SEQ ID NO:7)). The DNA was digested with NheI and religated. The truncated gene was inserted into the SmaI site of pGS20 as a blunt-end repaired BglII fragment.

e) Plasmid pSTgIVd4: Plasmid pRSV1.3 was digested with SmaI, the large fragment purified and then ligated with a triphasic stop codon NheI linker (pCTAGCTAGCTAG (SEQ ID NO:7)). The DNA was digested with NheI and religated. The truncated gene was inserted into the SmaI site of pGS20 as a blunt-end repaired BglII fragment.

f) Plasmid pSTgIVd6: Plasmid pRSV1.3X was digested to completion with DraIII and XhoI. The large fragment was purified, blunt-end repaired with T4 DNA polymerase and ligated. The partial gene deletion was inserted into the SmaI site of pGS20 as a blunt-end repaired BglII fragment.

g) Plasmid pSTgIVd7: Plasmid pRSV1.3 was digested to completion with SalI and the large fragment was purified and religated. The partial gene deletion was inserted into the SmaI site of pGS10 as a blunt-end repaired BglII fragment.

h) Plasmid pSTgIVd8: Plasmid pRSV1.3X was digested with XhoI and treated with mung bean nuclease to create blunt ends. Then DNA was partially digested with XmaI, treated with Klenow enzyme and the large fragment was then purified and religated. The partial gene deletion was inserted into the SmaI site of pGS20 as a blunt-end repaired BglII fragment.

i) Plasmid pSTgIVd9: Plasmid pRSV1.3 was partially digested with SalI followed by complete digestion with XhoI. The large fragment was purified, blunt-end repaired and then religated. The partial gene deletion was inserted into the SmaI site of pGS20 as a blunt-end repaired BglI fragment.

XI.A.3. Isolation of recombinant vaccinia viruses

The desired recombinant VVs were made by homologous recombination as previously described (Mackett et al. (1985) "DNA Cloning: A Practical Approach," pp. 191–211, Ed. by D. M. Clover, Oxford: IRL press). A newly confluent monolayer (75 cm$^2$) of BSC-1 cells was infected with wild-type VV (WR strain) at a multiplicity of infection of 0.05 PFU/cell. At 4 hrs post infection the cells were collected by mild trypsinization, washed three times with Hepes buffer (pH 7.1) and adjusted to a concentration of 1-2×10$^6$ cells/ml in Hepes buffer (pH 7.1). Approximately 10 μg of cesium chloride gradient purified linearized plasmid DNA was mixed with 750 μl of the infected cell suspension and placed on ice in an electroportion cuvette for 10 min before and immediately after electroporation at 200 volts and 500 μFD using a Bio-Rad Gene Pulser. The cells were then diluted in MEM containing 10% FBS and incubated at 37° C. After 2–3 days, to permit virus replication, transfected cells and supernatants were collected, frozen and thawed twice and sonicated for 20 sec to release virus. Putative recombinants were selected by plating the sonicated supernatants on TK$^-$ 143 cells and overlaying with 1% agarose in growth medium containing 5-bromo-2'- deoxyuridine (25 μg/ml). After 3 days, the TK⁻ plaques were visualized by staining the monolayer with neutral red, picked individually and grown on BSC-1 cells to amplify virus. Recombinant VV were selected by screening the TK⁻ plaques for gIV expression by immunocytochemistry before replaquing and making viral stocks in LMTK⁻ cells.

XI.A.4. Polyclonal and monoclonal antibody gIV specific monoclonal antibody (MAb) production and characterization, in particular their reactivity with native or denatured gIV, neutralizing activity, and grouping based on competition binding assays have been described (Hughes et al. (1988) *Arch. Virol.*, 103:47–60 and van Drunen Littel-van den Hurk et al. (1990) *J. Gen. Virol.*, 71:2053–2063). Before use, MAb ascites fluids were clarified and filtered. Monospecific polyclonal gIV specific antisera produced in rabbits have been described (Hughes et al. (1988) supra).

XI.A.5. Protein expression

For immunoprecipitation, LNTK⁻ cells were infected at a multiplicity of infection (MOI) of 5. At 10 hrs post infection, the cells were washed and incubated in cysteine-methionine free DMEM for 90 min before labeling with [$^{35}$S] cysteine-methionine (100 μCi/ml). After 4–8 hrs of labeling, the cells and/or medium was harvested. In pulse-chase experiments, cells were labelled at 10 hrs post infection with 150 μCi of [$^{35}$S] methionine-cysteine for 15 min. Depending on the specific experiment, either the cells were harvested immediately or the label was removed and cells were incubated for different time periods in DMEM containing an excess of cold methionine (chase). Proteins were immunoprecipitated from the medium or from the infected cells, lysed with modified RIPA buffer and analyzed by SDS-PAGE as previously described (van Drunen Littel-van den Hurk (1990) supra).

XI.A.6. Enzyme treatments

Immunoprecipitated proteins were eluted in 20 μl of 0.5% SDS by boiling for 3 min. The eluted proteins were digested with 20 mU of endo H in 0.125M sodium citrate pH 5.5, 0.1M 2-mercaptoethanol, 0.5mM phenylmethylsulphonyl fluoride and 0.1% SDS. For analysis by SDS-PAGE, the digested proteins were precipitated with ice-cold acetone, resuspended in electrophoresis sample buffer and boiled for 3 min before analysis (van Drunen Littel-van den Hurk (1990) supra).

XI.A.7. Immunoperoxidase staining

LMTK⁻ cells grown in 4 well Lab-Tek chamber slides were infected with the appropriate recombinant VV at an MOI of 5. After 16 hrs of incubation the cells were fixed with 3% paraformaldehyde for 15 minutes at 4° C. (surface staining) and stained by immunoperoxidase staining procedure as previously described (Fitzpatrick et al. (1988) supra).

RESULTS

XI.B.

To examine the structure and function of different domains of gIV, the complete open reading frame and the mutated forms (internal deletions or truncations) of gIV gene (FIG. 34a) were cloned into the VV expression vector pGS20 (FIG. 34b) to generate recombinant VVs designated here as STgIV expressing wild-type gIV, and STgIVd1 to STgIVd9 expressing mutant proteins d1 to d9 respectively.

XI.B.1. Characterization of proteins made by recombinant VVS

To examine the product of the wild type gIV gene, LMTK- cells were infected with recombinant VV STgIV and metabolically labelled with [$^{35}$S] cysteine-methionine. For comparison with authentic gIV, MDBK cells were infected with BHV-1 and labelled similarly with [$^{35}$S] cysteine-methionine. The radiolabelled proteins were immunoprecipitated with rabbit anti-gIV antiserum and analyzed by SDS-PAGE under reducing conditions.

Radioimmunoprecipitation of recombinant pSTgIV VV infected cells revealed a major protein band of approximately 71 kDa molecular weight which comigrated with the authentic gIV protein produced in BHV-1 infected cells. No similar band was observed in uninfected cells or cells infected with wild-type VV. This suggests that recombinant gIV produced in LMTK- cells was post-translationally modified in a manner similar to authentic gIV. The proteins produced by the recombinants carrying deleted or truncated forms of gIV were also analyzed by SDS-PAGE under reducing conditions. The mutant forms of gIV protein d1–d9 were detected as single bands at approximately the expected molecular weights, except d7 which migrated more slowly than expected. This aberrant mobility of d7 protein appears to be due to the addition of O-linked oligosaccharides (Tikoo et al. unpublished data).

XI.B.2. Antigenic structure of gIV proteins

To examine the antigenic properties of wild type gIV, radiolabelled protein was immunoprecipitated from VV STgIV infected cell lysates with gIV specific MAbs (Hughes et al. (1988) supra and van Drunen Littel-van Den Hurk et al. (1984) *Virology*, 135:466–479) and analyzed by SDS-PAGE under reducing conditions. In addition to the recognition of the recombinant gIV by MAbs directed against continuous epitopes Ib (MAb 9D6), IV (MAb 3D9S) and IIIa (MAb 10C2), the protein was also recognized by MAbs directed against discontinuous epitopes Ib (MAb 136), II (MAb 3E7), IIIc (MAb 2C8), IIId (MAb 3C1) and IIIb (MAb 4C1). This suggests that the antigenic structure of gIV produced in VV StgIV infected cells is similar to gIV produced by BHV-1 infected cells.

In order to locate the antigenic sites on the gIV glycoprotein, the mutated proteins were similarly immunoprecipitated from recombinant infected cell lysates with individual MAbs and analyzed by SDS-PAGE under reducing conditions. The results are as follows:

a) A truncated form of gIV (AAs 1–355), expressed by recombinant VV STgIVd1, which lacks 62 amino acids at the carboxy terminus including the transmembrane anchor sequence, reacted with all of the gIV specific MAbs recognizing both continuous and discontinuous epitopes.

b) A truncated form of gIV (AAs 1–320), expressed by recombinant VV STgIVd2, which lacks 97 amino acids at the carboxy terminus, reacted with all of the MAbs, except 3D9S (which recognized a continuous epitope) and 136 (which recognized a discontinuous epitope). The reactivity of MAbs 2C8 and 4C1 to this protein was also reduced.

c) A truncated form of gIV (AAs 1–244), expressed by recombinant VV StgIVd3, which lacks 173 amino acids at the carboxy terminus reacted with only MAb 9D6, which recognize a continuous epitope.

d) A truncated form of gIV (AAs 1–216), expressed by recombinant VV STgIVd4, which lacks 201 amino acids at the carboxy terminus, also reacted only with MAb 9D6.

e) A truncated form of gIV (AAS 1–164), expressed by recombinant VV STgIVd5, which lacks 253 amino acids at the carboxy-terminus, did not react with any of the MAb.

f) A deleted form of gIV expressed by recombinant VV STgIV6, which lacks 265 AAs from residue 90 to 354 in the extracellular domain of gIV, also did not react with any of the MAbs.

g) A deleted form of gIV expressed by recombinant VV STgIVd7, which lacks 2:L3 residues from AAs 32–244 in the extracellular region of gIV, reacted only with MAb 3D9S which recognize a continuous epitope.

h) A deleted form of gIV expressed by recombinant pSTgIVd8, which lacks 139 AAs from residue 218–355 in the extracellular region of gIV, reacted only with MAb 9D6.

i) A deleted from of gIV expressed by recombinant VV STgIVd9, which lacks 112 residues from AAs 245–355 in the extracellular region of gIV reacted only with MAb 9D6.

These observations suggest that binding sites for MAb 9D6 and 3D9 lie between amino acid 164–216 and amino acid 320–355, respectively. In addition amino acids 244–320 are important for the formation of discontinuous epitopes recognized by MAbs 2C8 and 4C1, whereas amino acids 320–355 are critical for the formation of discontinuous epitope recognized by MAb 136.

XI.B.3. Secretion of truncated gIV proteins.

In order to determine whether truncated forms of gIV were efficiently secreted into the medium, LMTK⁻ cells infected with recombinant VVs were labeled with [$^{35}$S] cysteine-methionine for 4–8 hrs beginning 10 hrs after infection. Cell culture supernatants were immunoprecipitated with rabbit anti-gIV polyclonal antiserum. Proteins expressed by recombinant VV STgIVd1 and VV STgIVd2 were detected in the medium where as proteins truncated at or upstream of amino acid 244 (VV STgIVd3 to VV STgIVd5) were never detected in the medium. This suggests that amino acid 244–320 are required for efficient secretion of the truncated gIV molecules and confirmed our previous observation concerning the location of transmembrane anchor domain between amino acids 361 to 389 (Tikoo et al. (1990) supra).

XI.C.1.

A number of strategies have been used to locate the antigenic sites of a viral glycoprotein. Since the induction of protective humoral immune response is dependent on the conformation of gIV, the approach of expressing deleted and truncated forms; of gIV in mammalian cells by recombinant vaccinia viruses has allowed the mapping of the binding sites of different MAbs in gIV and study the effect of these mutations on the native structure of the glycoprotein (FIG. 35). A similar approach has been used to localize the functional domains of HSV-1 glycoprotein D (Cohen et al. (1988) *J. Virol.* 62:1932–1940).

To confirm the validity of this approach, insertion of the full-length gIV gene into vaccinia virus showed that gIV expressed by recombinant VV STgIV had an antigenic profile indistinguishable from authentic gIV synthesized after viral infection (Hughes et al. (1988) and van Drunen Littel-van den Hurk et al. (1986) supra). These results confirm and extend the observations previously reported for recombinant gIV expressed in transfected bovine cells (Tikoo et al. (1990) supra).

Previously, four antigenic domains of gIV were identified using a panel of MAbs (Hughes et al. (1988) and van Drunen Littel-van den Hurk et al. (1986) supra). Domain I consists of two epitopes; epitope Ia is a continuous epitope recognized by MAb 9D6 and epitope Ib is a discontinuous epitope recognized by MAb 136. The present results indicate that epitope Ia is located between residue 164–216 and a portion of epitope Ib is located between residue 320–355. The second portion of epitope Ib is located upstream of residue 245, perhaps upstream of residue 216 but downstream of residue 31. This assumption is based on the fact that recombinant VV STgIVd7 which expresses a mutant protein devoid of residues 32–244 is not recognized by MAb 136. In addition, competitive bidding experiments indicate that either these two epitopes share common amino acids or that they lie in close proximity to one another (Hughes et al. (1988) supra).

Domain II of gIV is represented by a discontinuous epitope which is recognized by MAB 3E7. This epitope is located upstream of residue 320 and at least a portion of the epitope is located upstream of residue 245. This is based on two observations. First, if the binding site is composed entirely of residues between 245–320, the protein expressed by recombinant VV STgIVd7 should be recognized by MAB 3E7. Second, the epitope is destroyed by the addition of reducing agents, and all of the cysteine residues that could possibly contribute to disulphide binding are located between residue 74 to 214.

Domain III is represented by four epitopes, three of which have been shown to be discontinuous (Hughes et al. (1988) supra). Analysis of the mutant proteins expressed by recombinant VV STgIVd2, VV STgIVd7 and VV STgIVd9 indicate that the binding site for MAb 10C2, which recognizes the continuous epitope IIIa, lies in close proximity to amino acids 244 and 245. The epitopes IIIB, IIIC and IIId recognized by conformation dependent MAbs 4C1, 2C8 and 3C1 respectively, are located between amino acid 19 to 320.

Domain IV is represented by a continuous epitope recognized by a non-neutralizing MAb 3D9S. This epitope was mapped between residues 320–355.

Formation of discontinuous epitopes depends on certain tertiary structures of gIV which in part involve disulphide bonds. The observation that the MAbs recognizing discontinuous epitopes (destroyed by reducing agent) react with residues 1–355 suggests that this polypeptide maintains its normal disulphide bonding pattern. Six of the seven gIV cysteine residues located within residues 75 to 213 probably play a role in the structure of these discontinuous epitopes. Interestingly, these six cysteine residues are readily aligned in all gIV homologs thus far identified (Tikoo et al. (1990) supra). All six cysteines are involved in intramolecular disulphide bond formation in HSV-1 gD (Wilcox et al. (1988) *J. Virol.* 62:1941–1947) and are suggested to be important for the structure and function of the protein (Long et al. (1990) *J. Virol.* 64:5542–5552). The cysteine at residue 376 is within the transmembrane domain of gIV and is not involved in the formation of these epitopes, indicating that this cysteine is not involved in intramolecular disulphide bonding in gIV required for attaining the proper tertiary structure. A similar observation has been made previously for the HSV-1 gD glycoprotein (Wilcox et al. (1988) supra).

Earlier studies have shown the presence of both N-linked and O-linked oligosaccharides in gIV (van Drunen Littel-van den Hurk et al. (1986) supra). In BHV-1 infected cells, N-linked oligosaccharides are processed from high mannose oligosaccharides present on precursor gIV (pgIV) to complex oligosaccharides; of mature gIV which is transported to the surface of the infected cell and also incorporated into the virion envelope (Marshall et al. (1986) *J. Virol.* 57:745–753 and van Drunen Littel-van den Hurk (1986) supra). At 24 hrs postinfection, most of the protein is found in the mature form. Essentially similar transport and processing kinetics were observed for recombinant gIV produced by VV STgIV indicating that VV is an acceptable vector for expressing BHV-1 glycoproteins.

Processing and transport of a viral glycoprotein through the exocytic pathway is dependent on its conformational and structural signals, which may include the location of N-linked glycosylation sites, position of cysteine residues forming disulphide bonds that promote the juxtaposition of residues on the molecule, and amino acid residues required for membrane insertion, anchoring, local folding of monomers and formation of oligomers (Guan et al. (1985) *Cell* 42:489–496; Kreis et al. (1986) *Cell* 46:929–937; Rose et al. (1988) *Ann. Rev. Cell Biol.* 4:257–288 and Wilcox et al. (1988) supra). Alterations of any of these signals may affect processing, and/or transport of a glycoprotein. The results of this study indicate that the extent of processing of the genetically engineered gIV mutant proteins correlated with the transport of the proteins to the cell surface/media. However, a loss in the ability to form discontinuous epitopes was not associated with the loss of transport of the mutant protein to the cell surface/media. All mutant proteins containing amino acids 245–320 (d1, d2, d7) were processed from precursor to product, contained endo H resistance oligosaccharides and were located on the surface of the cell or secreted into the medium when the transmembrane anchor sequence was also been deleted. These results suggest that these proteins retained signals necessary for the proper folding, processing and consequently transport of the protein to the cell surface. In contrast, all mutants lacking amino acids 245–320 (d3, d4, d5, d6, d8, d9) failed to be processed from precursor to product form and were not transported to the cell surface or secreted in the medium. In addition, virtually all of the oligosaccharides were of the high-mannose form indicating that these mutant proteins are retained in the endoplasmic reticulum. It is in this organellese that membrane-bound and secretory proteins acquire high-mannose oligosaccharides, fold and in many cases oligomerize (Rose et al. (1988) supra). Both misfolded and unassembled subunits are retained in the endoplasmic reticulum and prevented from further transport by interactions with resident cellular proteins (Rose et al. (1988) supra). The altered processing and transport of the mutants lacking amino acid 245–320 could be due to misfolding of the proteins, however, we could not detect protein aggregation (data not shown), as has been observed with the other misfolded proteins (Wilcox et al. (1988) supra). Alternatively, a block in transport could be due to the absence of required signals residing in residues 245–320. Preliminary studies indicate that the O-linked oligosaccharides are attached to serine/threonine located in this region (Tikoo et al. unpublished data). It is possible that the absence of either amino acid sequence or protein modifications present in this region may be responsible for the observed effects.

XII

XII.A. Animal trials were conducted with full-length gIV (gIVA) and truncated gIV (TgIVA) and results analyzed as described previously in XI above.

XII.B. Results

Figure 32:
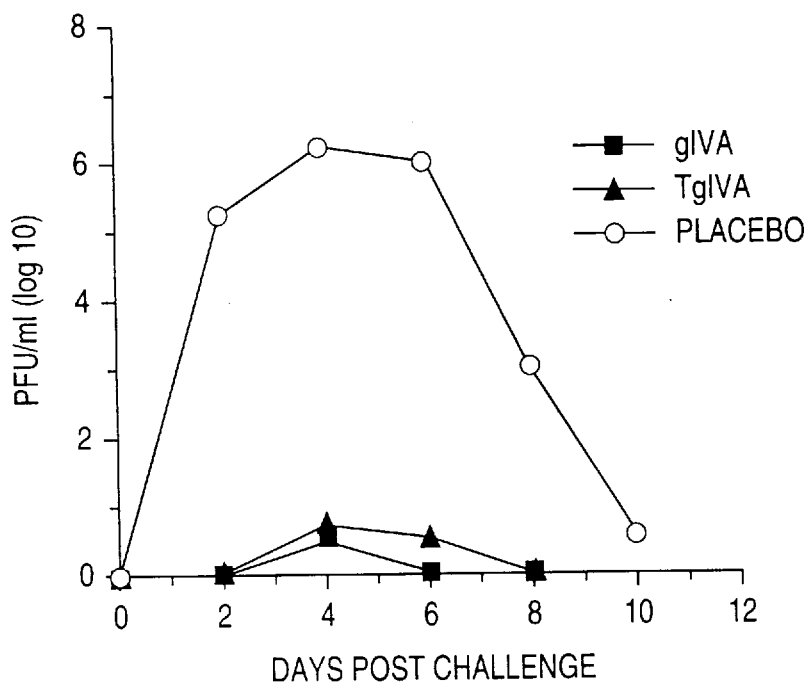
Figure 33:
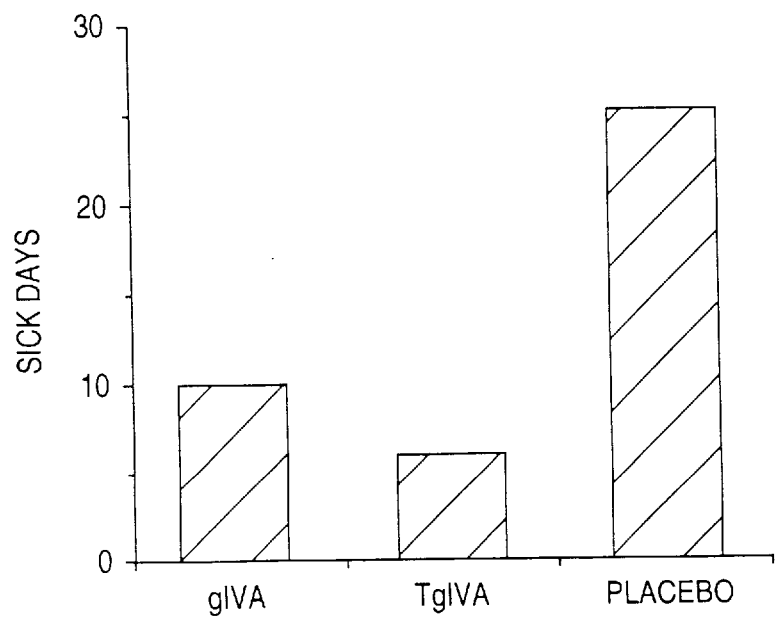

Analysis of the serum samples obtained from the vaccinated animals showed that both the full-length gIV (gIV) and the truncated gIV (TgIV), prepared as in XI above, produced strong immune responses as measured by ELISA and plaque reduction assays as set forth in Table 5 below. Significantly nasal secretions also contain neutralizing antibody, as set forth in Table 6 below. Clinical examination indicated that gIV and TgIV significantly reduced virus shedding and sick-days. The placebo animals in every case succumbed to BHV-1 infection as indicated by conventional virus-shedding (FIG. 32) and prolonged sickness (FIG. 33).

TABLE 5

| ELISA Assay | | | | | | | |
|---|---|---|---|---|---|---|---|
| | | | | | αgIV ELISA Titer | | |
| Group | No. | Dose | Adjuvant | No. An. | 21 Days | 35 Days | 45 Days |
| Placebo | 1 | — | Avridine | 6 | 8 | 5 | 19 |
| gIV | 2 | 25 μg | Avridine | 8 | 24 | 1,076 | $4.5 \times 10^5$ |
| TgIV | 3 | 25 μg | Avridine | 8 | 28 | 380 | $4.9 \times 10^4$ |

TABLE 6

| | | | | | Neutralization Titers | | | |
|---|---|---|---|---|---|---|---|---|
| Group | No. | Dose | Adjuvant | No. An. | 21 Days | 35 Days | 45 Days | 55 Days |
| Placebo | 1 | — | Avridine | 6 | <2 | 2.4 | <2 | 1.4 |
| gIV | 2 | 25 μg | Avridine | 8 | 2.4 | 18 | 977 | 22 |
| TgIV | 3 | 25 μg | Avridine | 8 | 2.1 | 9 | 335 | 8 |

XIII

XIII.A. BHV-1 DNA Immunization Section

XIII.A.1 Reagent Preparation

Plasmid DNA was produced by cultivating *E. coli*, strain Hb101, transformed with pRSO, Fitzpatrick, D. R. et al. (1988) *Journal of Virology,* 62, 4239–4248, and pRSgIV, Tikoo, S. K. et al. (1990) *Journal of Virology,* 64, 5132–5142. Plasmid DNA was extracted and purified on CaCl gradients followed by dialysis against distilled water and ethanol precipitation. Purified plasmid was solubilized in 0.85% saline.

XIII.1.2. Vaccination

Plasmid DNA was presented by intramuscular injection of four sites in the hind quarters of hereford calves. Volume of the injections was 2 ml with plasmid at a concentration of 62.5 μg/ml. Venous blood was drawn on regular intervals the presence of BHV-1 gIV-specific IgG antibody was determined by ELISA, western blots and neutralization assays.

XIII.B. Results

A gIV gene-specific immune response has been demonstrated by Western blots and IgG ELISA titres of 3200 have been attained. Plaque-reduction assays indicate serum neutralizing titres as high as 48 (a titre of 16 correlates highly with protection from disease).

DEPOSIT OF BIOLOGICAL MATERIALS

The following materials have been deposited or will be deposited with the American Type Culture Collection (ATCC), 12301 Parklawn Drive, Rockville, Md. 20852, U.S.A. during the pendancy of this application as necesary. These deposits will be maintained under the terms of the Budapest Treaty on the deposit of microorganisms. The nucleotide sequences of the deposited materials are incorporated by reference herein, as well as the sequences of polypeptides encoded thereby. In the event of any discrepancy between a sequence expressly disclosed herein and a deposited sequence, the deposited sequence is controlling. The deposit of the sequence is not the grant of a license to make, use or sell any of the deposited materials.

| Material | Accession Number | Deposit Date |
|---|---|---|
| 1E11-1F6 | HB 9774 | July 22, 1988 |
| 1D6-G11 | HB 9775 | July 22, 1988 |
| 1G6-2D9 | HB 9776 | July 22, 1988 |
| VAC-I | VR 2223 | July 22, 1988 |
| VAC-III | VR 2224 | July 22, 1988 |
| RSV-gI | CRL 9780 | July 22, 1988 |
| RSV-gIII | CRL 9779 | July 22, 1988 |
| SV2gI | CRL 9778 | July 22, 1988 |
| SV2gIII | CRL 9777 | July 22, 1988 |
| pVSL-1 | | |
| pVV-1/gI | | |
| pVV-1/gIII | | |
| pVV-1/gIV | | |
| pVV-1/gIVt | | |
| pVLgI | | |
| pVLgIII | | |
| pVLgIV | | |

-continued

| Material | Accession Number | Deposit Date |
|---|---|---|
| pVLgIVT | | |
| pAdBM5.gIV | | |
| pAdBM5.gIVt | | |
| pgp11 complete | | |
| pBHC150Δ | | |
| pBHDsib | | |
| pVLgB | | |

While the present invention has been illustrated above by certain specific embodiments, it is not intended that the specific examples should limit the scope of the invention as described in the appended claims.

---

We claim:

1. A vaccine composition to prevent or ameliorate the symptoms of disease comprising an isolated nucleotide sequence encoding a polypeptide containing at least one protective determinant of a BHV-1 polypeptide, operably linked to one or more control sequences such that said isolated nucleotide sequence is expressed in a host cell, the polypeptide being selected from the group consisting of gI, wherein said isolated nucleotide sequence comprises the contiguous nucleotide sequence depicted in FIG. 5; gIII, wherein said isolated nucleotide sequence comprises the contiguous nucleotide sequence depicted in FIG. 6; and gIV, wherein said isolated nucleotide sequence comprises the contiguous nucleotide sequence depicted in FIG. 7.

2. A method of treating or preventing BHV-1 infection in a bovine host comprising administering to said bovine host a therapeutically effective amount of a vaccine composition according to claim 1.

3. The vaccine composition of claim 1, wherein the nucleotide sequence is the contiguous nucleotide sequence depicted in FIG. 5.

4. The vaccine composition of claim 1, wherein the nucleotide sequence is the contiguous nucleotide sequence depicted in FIG. 6.

5. The vaccine composition of claim 1, wherein the nucleotide sequence is the contiguous nucleotide sequence depicted in FIG. 7.

6. A vaccine composition to prevent or ameliorate the symptoms of disease comprising an isolated nucleotide sequence encoding a polypeptide containing at least one protective determinant of a recombinant BHV-1 glycoprotein, operably linked to one or more control sequences such that said isolated nucleotide sequence is expressed in a host cell, said recombinant BHV-1 glycoprotein selected from the group consisting of BHV-1 gI having an unglycosylated molecular weight of about 105 kDa and encoded by the nucleotide sequence as depicted in FIG. 5; gIII glycoprotein having a molecular weight of about 91 kDa and encoded by the nucleotide sequence as depicted in FIG. 6; and a gIV glycoprotein having a molecular weight of about 71 kDa and encoded by the nucleotide sequence as depicted in FIG. 7.

7. The vaccine composition of claim 6 wherein the BHV-1 glycoprotein is BHV-1 gI glycoprotein having an unglycosylated molecular weight of about 105 kDa and encoded by the nucleotide sequence as depicted in FIG. 5.

8. The vaccine composition of claim 6 wherein the BHV-1 glycoprotein is BHV-1 gIII glycoprotein having a molecular weight of about 91 kDa and encoded by the nucleotide sequence as depicted in FIG. 6.

9. The vaccine composition of claim 6 wherein the BHV-1 glycoprotein is BHV-1 gIV glycoprotein having a molecular weight of about 71 kDa and encoded by the nucleotide sequence as depicted in FIG. 7.

10. A method of treating or preventing BHV-1 infection in a bovine host comprising administering to said bovine host a therapeutically effective amount of a vaccine composition according to claim 6.

11. A vaccine composition to prevent or ameliorate the symptoms of disease comprising an isolated nucleotide sequence encoding a polypeptide containing at least one protective determinant of a truncated BHV-1 gIV polypeptide operably linked to one or more control sequences such that said isolated nucleotide sequence is expressed in a host cell, wherein said polypeptide consists of residues 1–355 as depicted in FIG. 5.

12. A method of treating or preventing BHV-1 infection in a bovine host comprising administering to said bovine host a therapeutically effective amount of a vaccine composition according to claim 11.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 3382 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 432..3230

(xi) SEQUENCE DESCRIPTION: SEQ ID NO:1:

```
GTCGACCCGG  CAACGTGGCC  CGCGTTGACG  CACCAGTTCT  TCGACCTAGT  TAACGGGCCG         60

CTCTTTGACG  GCAGCGCGCA  CAACTTCGCG  CAGCCGCCAA  ACACCGCGCT  GTACTTTAGC        120

GTGGAAAACG  TGGGCCTGCT  CCCGCACCTC  AAGGAGGAGC  TGGCCGCGTT  TATGCTGGCG        180

GCCGCGGGGG  GCGGGTGGGC  GGTAAGCGAC  TTCCAGCAGT  TTTTTTGCTT  CGCATCCGCG        240

CGGGCGCGGG  GCGTCACCGC  CGCGCAGCGG  CTCGCCTGGC  AATATATCCG  CGAGCTCGTT        300

CTGGCCCGCG  CCGTCTTTGC  GTCCGTCTTC  CACTGCGGAC  GCGTCCGCT   GCTGCGTGCG        360

GACCGAACGG  CGCCGGGCCC  GGACGGGCGG  CAGTCGTGTC  CCAGCGGCGT  CTACCTGACC        420

TACGAGGAGT  C  ATG  GCC  GCT  CGC  GGC  GGT  GCT  GAA  CGC  GCC  GCG  GGC  GCC       470
              Met  Ala  Ala  Arg  Gly  Gly  Ala  Glu  Arg  Ala  Ala  Gly  Ala
               1                 5                          10

GGA  GAC  GGT  CGG  CGA  GGA  CAG  CGT  CGT  CAT  CTA  CGA  CCG  GGA  CGT  GTT       518
Gly  Asp  Gly  Arg  Arg  Gly  Gln  Arg  Arg  His  Leu  Arg  Pro  Gly  Arg  Val
      15                      20                          25

CTC  GCT  GCT  CTA  CGC  GGT  CCT  GCA  GCG  CCT  GGC  GCC  GGG  GCG  CGC         566
Leu  Ala  Ala  Leu  Arg  Gly  Pro  Ala  Ala  Pro  Gly  Ala  Gly  Gly  Ala  Arg
 30                     35                          40                      45

GCC  GCG  CAT  GCC  GCT  GCC  CTG  CTA  TGG  GCG  ACG  TGG  GCC  CTG  CTG  CTG       614
Ala  Ala  His  Ala  Ala  Ala  Leu  Leu  Trp  Ala  Thr  Trp  Ala  Leu  Leu  Leu
                    50                          55                      60

GCG  GCG  CCC  GCC  GCG  GGG  CGA  CCG  GCG  ACA  ACG  CCC  CCG  GCG  CCC  CCG       662
Ala  Ala  Pro  Ala  Ala  Gly  Arg  Pro  Ala  Thr  Thr  Pro  Pro  Ala  Pro  Pro
```

|     |     |     |     |     | 65  |     |     |     |     | 70  |     |     |     |     | 75  |     |     |      |
|-----|-----|-----|-----|-----|-----|-----|-----|-----|-----|-----|-----|-----|-----|-----|-----|-----|-----|------|
| CCC | GAA | GAG | GCC | GCG | AGC | CCG | GCG | CCC | CCC | GCG | AGC | CCC | AGC | CCC | CCC |     |     | 710  |
| Pro | Glu | Glu | Ala | Ala | Ser | Pro | Ala | Pro | Pro | Ala | Ser | Pro | Ser | Pro | Pro |     |     |      |
|     |     | 80  |     |     |     |     | 85  |     |     |     |     | 90  |     |     |     |     |     |      |
| GGC | CCC | GAC | GGC | GAC | GAC | GCC | GCC | AGC | CCC | GAC | AAC | AGC | ACA | GAC | GTG |     |     | 758  |
| Gly | Pro | Asp | Gly | Asp | Asp | Ala | Ala | Ser | Pro | Asp | Asn | Ser | Thr | Asp | Val |     |     |      |
|     | 95  |     |     |     |     |     | 100 |     |     |     |     | 105 |     |     |     |     |     |      |
| CGC | GCC | GCG | CTC | CGG | CTC | GCG | CAG | GCG | GCC | GGG | GAA | AAC | TCG | CGC | TTC |     |     | 806  |
| Arg | Ala | Ala | Leu | Arg | Leu | Ala | Gln | Ala | Ala | Gly | Glu | Asn | Ser | Arg | Phe |     |     |      |
| 110 |     |     |     |     | 115 |     |     |     |     | 120 |     |     |     |     | 125 |     |     |      |
| TTC | GTG | TGC | CCG | CCG | CCC | TCG | GGC | GCC | ACG | GTG | GTC | CGG | CTC | GCG | CCC |     |     | 854  |
| Phe | Val | Cys | Pro | Pro | Pro | Ser | Gly | Ala | Thr | Val | Val | Arg | Leu | Ala | Pro |     |     |      |
|     |     |     |     | 130 |     |     |     |     | 135 |     |     |     |     | 140 |     |     |     |      |
| GCG | CGG | CCG | TGC | CCT | GAG | TAC | GGG | CTC | GGG | CGG | AAC | TAC | ACG | GAG | GGC |     |     | 902  |
| Ala | Arg | Pro | Cys | Pro | Glu | Tyr | Gly | Leu | Gly | Arg | Asn | Tyr | Thr | Glu | Gly |     |     |      |
|     |     |     | 145 |     |     |     |     | 150 |     |     |     |     | 155 |     |     |     |     |      |
| ATC | GGC | GTC | ATT | TAC | AAG | GAG | AAC | ATC | GCG | CCG | TAC | ACG | TTC | AAG | GCC |     |     | 950  |
| Ile | Gly | Val | Ile | Tyr | Lys | Glu | Asn | Ile | Ala | Pro | Tyr | Thr | Phe | Lys | Ala |     |     |      |
|     |     | 160 |     |     |     |     | 165 |     |     |     |     | 170 |     |     |     |     |     |      |
| TAC | ATT | TAC | TAC | AAA | AAC | GTG | ATC | GTG | ACC | ACG | ACT | TGG | GCG | GGC | AGC |     |     | 998  |
| Tyr | Ile | Tyr | Tyr | Lys | Asn | Val | Ile | Val | Thr | Thr | Thr | Trp | Ala | Gly | Ser |     |     |      |
| 175 |     |     |     |     | 180 |     |     |     |     | 185 |     |     |     |     |     |     |     |      |
| ACG | TAC | GCG | GCC | ATT | ACA | AAC | CAG | TAC | ACG | GAC | CGC | GTG | CCC | GTG | GGC |     |     | 1046 |
| Thr | Tyr | Ala | Ala | Ile | Thr | Asn | Gln | Tyr | Thr | Asp | Arg | Val | Pro | Val | Gly |     |     |      |
| 190 |     |     |     |     | 195 |     |     |     |     | 200 |     |     |     |     | 205 |     |     |      |
| ATG | GGC | GAG | ATC | ACG | GAC | CTG | GTG | GAC | AAG | AAG | TGG | CGC | TGC | CTT | TCG |     |     | 1094 |
| Met | Gly | Glu | Ile | Thr | Asp | Leu | Val | Asp | Lys | Lys | Trp | Arg | Cys | Leu | Ser |     |     |      |
|     |     |     |     | 210 |     |     |     |     | 215 |     |     |     |     | 220 |     |     |     |      |
| AAA | GCC | GAG | TAC | CTG | CGC | AGC | GGG | CGC | AAG | GTG | GTG | GCC | TTT | GAC | CGC |     |     | 1142 |
| Lys | Ala | Glu | Tyr | Leu | Arg | Ser | Gly | Arg | Lys | Val | Val | Ala | Phe | Asp | Arg |     |     |      |
|     |     |     | 225 |     |     |     |     | 230 |     |     |     |     | 235 |     |     |     |     |      |
| GAC | GAC | GAC | CCC | TGG | GAG | GCG | CCG | CTG | AAG | CCT | GCG | CGG | CTG | AGC | GCG |     |     | 1190 |
| Asp | Asp | Asp | Pro | Trp | Glu | Ala | Pro | Leu | Lys | Pro | Ala | Arg | Leu | Ser | Ala |     |     |      |
|     |     | 240 |     |     |     |     | 245 |     |     |     |     | 250 |     |     |     |     |     |      |
| CCC | GGG | GTG | CGG | GGC | TGG | CAC | ACG | ACG | GAC | GAT | GTG | TAC | ACG | GCG | CTG |     |     | 1238 |
| Pro | Gly | Val | Arg | Gly | Trp | His | Thr | Thr | Asp | Asp | Val | Tyr | Thr | Ala | Leu |     |     |      |
|     | 255 |     |     |     |     | 260 |     |     |     |     | 265 |     |     |     |     |     |     |      |
| GGC | TCG | GCG | GGG | CTC | TAC | CGC | ACG | GGC | ACC | TCT | GTG | AAC | TGC | ATC | GTG |     |     | 1286 |
| Gly | Ser | Ala | Gly | Leu | Tyr | Arg | Thr | Gly | Thr | Ser | Val | Asn | Cys | Ile | Val |     |     |      |
| 270 |     |     |     |     | 275 |     |     |     |     | 280 |     |     |     |     | 285 |     |     |      |
| GAA | GAA | GTG | GAG | GCG | CGC | TCG | GTG | TAC | CCG | TAC | GAC | TCG | TTC | GCG | CTC |     |     | 1334 |
| Glu | Glu | Val | Glu | Ala | Arg | Ser | Val | Tyr | Pro | Tyr | Asp | Ser | Phe | Ala | Leu |     |     |      |
|     |     |     |     | 290 |     |     |     |     | 295 |     |     |     |     | 300 |     |     |     |      |
| TCG | ACC | GGG | GAC | ATT | ATC | TAC | ATG | TCG | CCC | TTT | TAC | GGG | CTG | CGC | GAG |     |     | 1382 |
| Ser | Thr | Gly | Asp | Ile | Ile | Tyr | Met | Ser | Pro | Phe | Tyr | Gly | Leu | Arg | Glu |     |     |      |
|     |     |     | 305 |     |     |     |     | 310 |     |     |     |     | 315 |     |     |     |     |      |
| GGC | GCG | CAC | CGC | GAG | CAC | ACC | AGC | TAC | TCG | CCG | GAG | CGC | TTC | CAG | CAG |     |     | 1430 |
| Gly | Ala | His | Arg | Glu | His | Thr | Ser | Tyr | Ser | Pro | Glu | Arg | Phe | Gln | Gln |     |     |      |
|     |     | 320 |     |     |     |     | 325 |     |     |     |     | 330 |     |     |     |     |     |      |
| ATC | GAG | GGC | TAC | TAC | AAG | CGC | GAC | ATG | GCC | ACG | GGC | CGG | CGC | CTC | AAG |     |     | 1478 |
| Ile | Glu | Gly | Tyr | Tyr | Lys | Arg | Asp | Met | Ala | Thr | Gly | Arg | Arg | Leu | Lys |     |     |      |
|     |     | 335 |     |     |     |     | 340 |     |     |     |     | 345 |     |     |     |     |     |      |
| GAG | CCG | GTC | TCG | CGG | AAC | TTT | TTG | CGT | ACA | CAG | CAC | GTG | ACG | GTA | GCC |     |     | 1526 |
| Glu | Pro | Val | Ser | Arg | Asn | Phe | Leu | Arg | Thr | Gln | His | Val | Thr | Val | Ala |     |     |      |
| 350 |     |     |     |     | 355 |     |     |     |     | 360 |     |     |     |     | 365 |     |     |      |
| TGG | GAC | TGG | GTG | CCC | AAG | CGC | AAA | AAC | GTG | TGC | TCG | CTG | GCC | AAG | TGG |     |     | 1574 |
| Trp | Asp | Trp | Val | Pro | Lys | Arg | Lys | Asn | Val | Cys | Ser | Leu | Ala | Lys | Trp |     |     |      |
|     |     |     |     | 370 |     |     |     |     | 375 |     |     |     |     | 380 |     |     |     |      |
| CGC | GAG | GCG | GAC | GAA | ATG | CTG | CGA | GAC | GAG | AGC | CGC | GGG | ACC | TTC | CGC |     |     | 1622 |
| Arg | Glu | Ala | Asp | Glu | Met | Leu | Arg | Asp | Glu | Ser | Arg | Gly | Thr | Phe | Arg |     |     |      |

-continued

```
                    385                            390                            395
TTC  ACG  GCC  CGC  TCG  CTC  TCG  GCG  ACC  TTT  GTG  AGC  GAC  AGC  CAC  ACC    1670
Phe  Thr  Ala  Arg  Ser  Leu  Ser  Ala  Thr  Phe  Val  Ser  Asp  Ser  His  Thr
          400                      405                      410

TTC  GCG  TTG  CAG  AAT  GTG  CCG  CTG  AGC  GAC  TGC  GTG  ATC  GAA  GAG  GCC    1718
Phe  Ala  Leu  Gln  Asn  Val  Pro  Leu  Ser  Asp  Cys  Val  Ile  Glu  Glu  Ala
          415                      420                      425

GAG  GCC  GCG  GTC  GAG  CGC  GTC  TAC  CGC  GAG  CGC  TAC  AAC  GGC  ACG  CAC    1766
Glu  Ala  Ala  Val  Glu  Arg  Val  Tyr  Arg  Glu  Arg  Tyr  Asn  Gly  Thr  His
430            435                      440                            445

GTG  CTG  TCG  GGC  AGC  TTG  GAG  ACG  TAC  CTG  GCG  CGC  GGC  GGC  TTT  GTC    1814
Val  Leu  Ser  Gly  Ser  Leu  Glu  Thr  Tyr  Leu  Ala  Arg  Gly  Gly  Phe  Val
                    450                      455                      460

GTG  GCC  TTC  CGG  CCG  ATG  CTC  AGC  AAC  GAG  CTG  GCC  AAG  CTG  TAC  CTG    1862
Val  Ala  Phe  Arg  Pro  Met  Leu  Ser  Asn  Glu  Leu  Ala  Lys  Leu  Tyr  Leu
               465                      470                      475

CAG  GAG  CTG  GCG  CGC  TCG  AAC  GGC  ACG  CTC  GAG  GGG  CTG  TTC  GCC  GCC    1910
Gln  Glu  Leu  Ala  Arg  Ser  Asn  Gly  Thr  Leu  Glu  Gly  Leu  Phe  Ala  Ala
          480                      485                      490

GCG  GCG  CCC  AAG  CCG  GGC  CCG  CGG  CGC  GCG  CGC  CGC  GCC  GCG  CCG  TCT    1958
Ala  Ala  Pro  Lys  Pro  Gly  Pro  Arg  Arg  Ala  Arg  Arg  Ala  Ala  Pro  Ser
          495                      500                      505

GCG  CCC  GGC  GGC  CCG  GGC  GCG  GCC  AAC  GGG  CCC  GCC  GGC  GAC  GGC  GAC    2006
Ala  Pro  Gly  Gly  Pro  Gly  Ala  Ala  Asn  Gly  Pro  Ala  Gly  Asp  Gly  Asp
510                      515                      520                      525

GCC  GGC  GGG  CGG  GTG  ACT  ACC  GTG  AGC  TCG  GCC  GAG  TTT  GCG  GCG  CTG    2054
Ala  Gly  Gly  Arg  Val  Thr  Thr  Val  Ser  Ser  Ala  Glu  Phe  Ala  Ala  Leu
                    530                      535                      540

CAG  TTC  ACC  TAC  GAC  CAC  ATC  CAG  GAC  CAC  GTG  AAC  ACC  ATG  TTC  AGC    2102
Gln  Phe  Thr  Tyr  Asp  His  Ile  Gln  Asp  His  Val  Asn  Thr  Met  Phe  Ser
               545                      550                      555

CGC  CTG  GCC  ACG  TCC  TGG  TGC  CTG  CTG  CAG  AAC  AAG  GAG  CGC  GCC  CTG    2150
Arg  Leu  Ala  Thr  Ser  Trp  Cys  Leu  Leu  Gln  Asn  Lys  Glu  Arg  Ala  Leu
          560                      565                      570

TGG  GCC  GAG  GCG  GCT  AAG  CTC  AAC  CCC  AGC  GCG  GCG  GCC  AGC  GCT  GCG    2198
Trp  Ala  Glu  Ala  Ala  Lys  Leu  Asn  Pro  Ser  Ala  Ala  Ala  Ser  Ala  Ala
575                      580                      585

CTG  GAC  CGC  CGC  GCC  GCC  GCG  CGC  ATG  TTG  GGG  GAC  GCC  ATG  GCC  GTG    2246
Leu  Asp  Arg  Arg  Ala  Ala  Ala  Arg  Met  Leu  Gly  Asp  Ala  Met  Ala  Val
590                      595                      600                      605

ACG  TAC  TGC  CAC  GAG  CTG  GGC  GAG  GGG  CGC  GTG  TTC  ATC  GAG  AAC  TCG    2294
Thr  Tyr  Cys  His  Glu  Leu  Gly  Glu  Gly  Arg  Val  Phe  Ile  Glu  Asn  Ser
                    610                      615                      620

ATG  CGC  GCG  CCC  GGC  GGC  GTT  TGC  TAC  AGC  CGC  CCG  CCG  GTC  TCC  TTT    2342
Met  Arg  Ala  Pro  Gly  Gly  Val  Cys  Tyr  Ser  Arg  Pro  Pro  Val  Ser  Phe
               625                      630                      635

GCC  TTC  GGC  AAC  GAG  AGC  GAG  CCG  GTG  GAG  GGC  CAG  CTC  GGC  GAG  GAC    2390
Ala  Phe  Gly  Asn  Glu  Ser  Glu  Pro  Val  Glu  Gly  Gln  Leu  Gly  Glu  Asp
          640                      645                      650

AAC  GAG  CTG  CTG  CCG  GGC  CGC  GAG  CTC  GTG  GAG  CCC  TGC  ACC  GCC  AAC    2438
Asn  Glu  Leu  Leu  Pro  Gly  Arg  Glu  Leu  Val  Glu  Pro  Cys  Thr  Ala  Asn
          655                      660                      665

CAC  AAG  CGC  TAC  TTC  CGC  TTT  GGC  GCG  GAC  TAC  GTG  TAC  TAC  GAG  AAC    2486
His  Lys  Arg  Tyr  Phe  Arg  Phe  Gly  Ala  Asp  Tyr  Val  Tyr  Tyr  Glu  Asn
670                      675                      680                      685

TAC  GCG  TAC  GTG  CGG  CGG  GTC  CCG  CTC  GCG  GAG  CTG  GAG  GTG  ATC  AGC    2534
Tyr  Ala  Tyr  Val  Arg  Arg  Val  Pro  Leu  Ala  Glu  Leu  Glu  Val  Ile  Ser
                    690                      695                      700

ACC  TTT  GTG  GAC  CTA  AAC  CTC  ACG  GTT  CTG  GAG  GAC  CGC  GAG  TTC  TTG    2582
Thr  Phe  Val  Asp  Leu  Asn  Leu  Thr  Val  Leu  Glu  Asp  Arg  Glu  Phe  Leu
```

```
            705                         710                           715
CCG  CTA  GAA  GTG  TAC  ACG  CGC  GCC  GAG  CTC  GCC  GAC  ACG  GGT  CTG  CTC     2630
Pro  Leu  Glu  Val  Tyr  Thr  Arg  Ala  Glu  Leu  Ala  Asp  Thr  Gly  Leu  Leu
          720                      725                730

GAC  TAC  AGC  GAG  ATA  CAG  CGC  CGC  AAC  CAG  CTG  CAC  GAG  CTC  CGG  TTC     2678
Asp  Tyr  Ser  Glu  Ile  Gln  Arg  Arg  Asn  Gln  Leu  His  Glu  Leu  Arg  Phe
     735                      740                     745

TAC  GAC  ATT  GAC  CGC  GTG  GTC  AAG  ACG  GAC  GGC  AAT  ATG  GCC  ATC  ATG     2726
Tyr  Asp  Ile  Asp  Arg  Val  Val  Lys  Thr  Asp  Gly  Asn  Met  Ala  Ile  Met
750                           755                760                           765

CGA  GGG  CTC  GCC  AAC  TTC  TTT  CAG  GGC  CTG  GGC  GCC  GTC  GGG  CAG  GCG     2774
Arg  Gly  Leu  Ala  Asn  Phe  Phe  Gln  Gly  Leu  Gly  Ala  Val  Gly  Gln  Ala
                    770                     775                     780

GTG  GGC  ACG  GTG  GTG  CTG  GGC  GCC  GCG  GGT  GCC  GCG  CTC  TCG  ACC  GTG     2822
Val  Gly  Thr  Val  Val  Leu  Gly  Ala  Ala  Gly  Ala  Ala  Leu  Ser  Thr  Val
               785                     790                     795

TCG  GGC  ATC  GCC  TCG  TTT  ATT  GCG  AAC  CCG  TTC  GGC  GCG  CTG  GCC  ACG     2870
Ser  Gly  Ile  Ala  Ser  Phe  Ile  Ala  Asn  Pro  Phe  Gly  Ala  Leu  Ala  Thr
          800                     805                     810

GGG  CTG  CTG  GTG  CTC  GCC  GGG  CTG  GTG  GCC  GCT  TTC  CTG  GCG  TAC  CGG     2918
Gly  Leu  Leu  Val  Leu  Ala  Gly  Leu  Val  Ala  Ala  Phe  Leu  Ala  Tyr  Arg
     815                     820                     825

TAC  ATT  TCC  CGC  CTC  CGC  AGC  AAC  CCC  ATG  AAG  GCG  CTG  TAC  CCG  ATC     2966
Tyr  Ile  Ser  Arg  Leu  Arg  Ser  Asn  Pro  Met  Lys  Ala  Leu  Tyr  Pro  Ile
830                      835                     840                          845

ACC  ACG  CGC  GCG  CTC  AAG  GAC  GAC  GCC  CGG  GGC  GCA  ACC  GCC  CCG  GGC     3014
Thr  Thr  Arg  Ala  Leu  Lys  Asp  Asp  Ala  Arg  Gly  Ala  Thr  Ala  Pro  Gly
                         850                     855                     860

GAG  GAA  GAG  GAG  GAG  TTT  GAC  GCG  GCC  AAA  CTG  GAG  CAG  GCC  CGC  GAG     3062
Glu  Glu  Glu  Glu  Glu  Phe  Asp  Ala  Ala  Lys  Leu  Glu  Gln  Ala  Arg  Glu
               865                     870                     875

ATG  ATC  AAG  TAT  ATG  TCG  CTC  GTG  TCA  GCG  GTC  GAG  CGG  CAA  GAG  CAC     3110
Met  Ile  Lys  Tyr  Met  Ser  Leu  Val  Ser  Ala  Val  Glu  Arg  Gln  Glu  His
          880                     885                     890

AAG  GCG  AAA  AAG  AGC  AAC  AAG  GGC  GGC  CCG  CTG  CTG  GCG  ACC  CGG  CTG     3158
Lys  Ala  Lys  Lys  Ser  Asn  Lys  Gly  Gly  Pro  Leu  Leu  Ala  Thr  Arg  Leu
          895                     900                     905

ACG  CAG  CTC  GCG  CTT  CGG  CGG  CGA  GCG  CCG  CCG  GAG  TAC  CAG  CAG  CTT     3206
Thr  Gln  Leu  Ala  Leu  Arg  Arg  Arg  Ala  Pro  Pro  Glu  Tyr  Gln  Gln  Leu
910                     915                     920                          925

CCG  ATG  GCC  GAC  GTC  GGG  GGG  GCA  TGAGGCCTAT  GTATGGGCAG  TTCGGGTGCC     3260
Pro  Met  Ala  Asp  Val  Gly  Gly  Ala
                         930

AATAATAAAT  TTTGCGCGAA  TCTTATTTAA  GTGCACACCG  TGTTATTTGC  GGCTGTTTGT     3320

TTTTCCTGGA  GGCGGGACGC  TGCGCGCGAG  CTCGGCCGGA  TTAGGGTTCG  GCGCCACCCG     3380

GG                                                                            3382
```

( 2 ) INFORMATION FOR SEQ ID NO:2:

( i ) SEQUENCE CHARACTERISTICS:
        ( A ) LENGTH: 933 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ala  Ala  Arg  Gly  Gly  Ala  Glu  Arg  Ala  Ala  Gly  Ala  Gly  Asp  Gly
  1                 5                    10                       15

Arg  Arg  Gly  Gln  Arg  Arg  His  Leu  Arg  Pro  Gly  Arg  Val  Leu  Ala  Ala
```

-continued

|  |  |  | 20 |  |  |  | 25 |  |  |  | 30 |  |  |
|--|--|--|--|--|--|--|--|--|--|--|--|--|--|

Leu Arg Gly Pro Ala Ala Pro Gly Ala Gly Gly Ala Arg Ala Ala His
        35              40              45

Ala Ala Ala Leu Leu Trp Ala Thr Trp Ala Leu Leu Leu Ala Ala Pro
        50              55              60

Ala Ala Gly Arg Pro Ala Thr Thr Pro Pro Ala Pro Pro Pro Glu Glu
65              70              75              80

Ala Ala Ser Pro Ala Pro Pro Ala Ser Pro Ser Pro Pro Gly Pro Asp
                85              90                      95

Gly Asp Asp Ala Ala Ser Pro Asp Asn Ser Thr Asp Val Arg Ala Ala
            100             105             110

Leu Arg Leu Ala Gln Ala Ala Gly Glu Asn Ser Arg Phe Phe Val Cys
            115             120             125

Pro Pro Pro Ser Gly Ala Thr Val Val Arg Leu Ala Pro Ala Arg Pro
    130             135             140

Cys Pro Glu Tyr Gly Leu Gly Arg Asn Tyr Thr Glu Gly Ile Gly Val
145             150             155             160

Ile Tyr Lys Glu Asn Ile Ala Pro Tyr Thr Phe Lys Ala Tyr Ile Tyr
                165             170             175

Tyr Lys Asn Val Ile Val Thr Thr Trp Ala Gly Ser Thr Tyr Ala
            180             185             190

Ala Ile Thr Asn Gln Tyr Thr Asp Arg Val Pro Val Gly Met Gly Glu
        195             200             205

Ile Thr Asp Leu Val Asp Lys Lys Trp Arg Cys Leu Ser Lys Ala Glu
    210             215             220

Tyr Leu Arg Ser Gly Arg Lys Val Val Ala Phe Asp Arg Asp Asp
225             230             235             240

Pro Trp Glu Ala Pro Leu Lys Pro Ala Arg Leu Ser Ala Pro Gly Val
            245             250             255

Arg Gly Trp His Thr Thr Asp Asp Val Tyr Thr Ala Leu Gly Ser Ala
            260             265             270

Gly Leu Tyr Arg Thr Gly Thr Ser Val Asn Cys Ile Val Glu Glu Val
        275             280             285

Glu Ala Arg Ser Val Tyr Pro Tyr Asp Ser Phe Ala Leu Ser Thr Gly
290             295             300

Asp Ile Ile Tyr Met Ser Pro Phe Tyr Gly Leu Arg Glu Gly Ala His
305             310             315             320

Arg Glu His Thr Ser Tyr Ser Pro Glu Arg Phe Gln Gln Ile Glu Gly
            325             330             335

Tyr Tyr Lys Arg Asp Met Ala Thr Gly Arg Arg Leu Lys Glu Pro Val
            340             345             350

Ser Arg Asn Phe Leu Arg Thr Gln His Val Thr Val Ala Trp Asp Trp
            355             360             365

Val Pro Lys Arg Lys Asn Val Cys Ser Leu Ala Lys Trp Arg Glu Ala
    370             375             380

Asp Glu Met Leu Arg Asp Glu Ser Arg Gly Thr Phe Arg Phe Thr Ala
385             390             395             400

Arg Ser Leu Ser Ala Thr Phe Val Ser Asp Ser His Thr Phe Ala Leu
            405             410             415

Gln Asn Val Pro Leu Ser Asp Cys Val Ile Glu Glu Ala Glu Ala Ala
            420             425             430

Val Glu Arg Val Tyr Arg Glu Arg Tyr Asn Gly Thr His Val Leu Ser
            435             440             445

```
Gly  Ser  Leu  Glu  Thr  Tyr  Leu  Ala  Arg  Gly  Gly  Phe  Val  Val  Ala  Phe
     450                 455                      460

Arg  Pro  Met  Leu  Ser  Asn  Glu  Leu  Ala  Lys  Leu  Tyr  Leu  Gln  Glu  Leu
465                      470                 475                           480

Ala  Arg  Ser  Asn  Thr  Leu  Glu  Gly  Leu  Phe  Ala  Ala  Ala  Ala  Pro
               485                      490                           495

Lys  Pro  Gly  Pro  Arg  Arg  Ala  Arg  Arg  Ala  Ala  Pro  Ser  Ala  Pro  Gly
               500                      505                      510

Gly  Pro  Gly  Ala  Ala  Asn  Gly  Pro  Ala  Gly  Asp  Gly  Asp  Ala  Gly  Gly
               515                 520                      525

Arg  Val  Thr  Thr  Val  Ser  Ser  Ala  Glu  Phe  Ala  Ala  Leu  Gln  Phe  Thr
          530                 535                      540

Tyr  Asp  His  Ile  Gln  Asp  His  Val  Asn  Thr  Met  Phe  Ser  Arg  Leu  Ala
545                      550                      555                           560

Thr  Ser  Trp  Cys  Leu  Leu  Gln  Asn  Lys  Glu  Arg  Ala  Leu  Trp  Ala  Glu
                    565                 570                      575

Ala  Ala  Lys  Leu  Asn  Pro  Ser  Ala  Ala  Ser  Ala  Ala  Leu  Asp  Arg
               580                      585                      590

Arg  Ala  Ala  Ala  Arg  Met  Leu  Gly  Asp  Ala  Met  Ala  Val  Thr  Tyr  Cys
          595                      600                      605

His  Glu  Leu  Gly  Glu  Gly  Arg  Val  Phe  Ile  Glu  Asn  Ser  Met  Arg  Ala
     610                      615                      620

Pro  Gly  Gly  Val  Cys  Tyr  Ser  Arg  Pro  Val  Ser  Phe  Ala  Phe  Gly
625                      630                      635                      640

Asn  Glu  Ser  Glu  Pro  Val  Gly  Gln  Leu  Gly  Glu  Asp  Asn  Glu  Leu
               645                      650                           655

Leu  Pro  Gly  Arg  Glu  Leu  Val  Glu  Pro  Cys  Thr  Ala  Asn  His  Lys  Arg
               660                      665                      670

Tyr  Phe  Arg  Phe  Gly  Ala  Asp  Tyr  Val  Tyr  Glu  Asn  Tyr  Ala  Tyr
          675                      680                      685

Val  Arg  Arg  Val  Pro  Leu  Ala  Glu  Leu  Glu  Val  Ile  Ser  Thr  Phe  Val
     690                      695                      700

Asp  Leu  Asn  Leu  Thr  Val  Leu  Glu  Asp  Arg  Glu  Phe  Leu  Pro  Leu  Glu
705                      710                 715                           720

Val  Tyr  Thr  Arg  Ala  Glu  Leu  Ala  Asp  Thr  Gly  Leu  Leu  Asp  Tyr  Ser
               725                      730                      735

Glu  Ile  Gln  Arg  Arg  Asn  Gln  Leu  His  Glu  Leu  Arg  Phe  Tyr  Asp  Ile
               740                      745                      750

Asp  Arg  Val  Val  Lys  Thr  Asp  Gly  Asn  Met  Ala  Ile  Met  Arg  Gly  Leu
          755                      760                      765

Ala  Asn  Phe  Phe  Gln  Gly  Leu  Gly  Ala  Val  Gly  Gln  Ala  Val  Gly  Thr
     770                      775                      780

Val  Val  Leu  Gly  Ala  Ala  Gly  Ala  Ala  Leu  Ser  Thr  Val  Ser  Gly  Ile
785                      790                      795                      800

Ala  Ser  Phe  Ile  Ala  Asn  Pro  Phe  Gly  Ala  Leu  Ala  Thr  Gly  Leu  Leu
               805                      810                      815

Val  Leu  Ala  Gly  Leu  Val  Ala  Ala  Phe  Leu  Ala  Tyr  Arg  Tyr  Ile  Ser
               820                      825                      830

Arg  Leu  Arg  Ser  Asn  Pro  Met  Lys  Ala  Leu  Tyr  Pro  Ile  Thr  Thr  Arg
               835                      840                      845

Ala  Leu  Lys  Asp  Asp  Ala  Arg  Gly  Ala  Thr  Ala  Pro  Gly  Glu  Glu  Glu
     850                      855                      860

Glu  Glu  Phe  Asp  Ala  Ala  Lys  Leu  Glu  Gln  Ala  Arg  Glu  Met  Ile  Lys
865                      870                      875                      880
```

| | | | | | | | | | | | | | | | |
|---|---|---|---|---|---|---|---|---|---|---|---|---|---|---|---|
| Tyr | Met | Ser | Leu | Val | Ser | Ala | Val | Glu | Arg | Gln | Glu | His | Lys | Ala | Lys |
| | | | | 885 | | | | | 890 | | | | | 895 | |
| Lys | Ser | Asn | Lys | Gly | Gly | Pro | Leu | Leu | Ala | Thr | Arg | Leu | Thr | Gln | Leu |
| | | | 900 | | | | | 905 | | | | | 910 | | |
| Ala | Leu | Arg | Arg | Arg | Ala | Pro | Pro | Glu | Tyr | Gln | Gln | Leu | Pro | Met | Ala |
| | | 915 | | | | | 920 | | | | | 925 | | | |
| Asp | Val | Gly | Gly | Ala | | | | | | | | | | | |
| | | 930 | | | | | | | | | | | | | |

( 2 ) INFORMATION FOR SEQ ID NO:3:

( i ) SEQUENCE CHARACTERISTICS:
        ( A ) LENGTH: 1829 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 160..1722

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| CGCGCCTGCA | GCCGCGCGTG | TGCTCAATCC | CGGACCACGA | AAGCACAAAA | CGGACGCCCT | | | | | | | | | | | 60 |
| TAAAAATGTA | GCCCGCGCCG | CGGTCGCGGC | CATCTTGGAT | CCACCCGCGC | GCACGACCGC | | | | | | | | | | | 120 |
| CGAGAGACCG | CCAGCCCGAG | ACCTCGCCGC | GCGTCCGCC | ATG | GGC | CCG | CTG | GGG | | | | | | | | 174 |
| | | | | | Met | Gly | Pro | Leu | Gly | | | | | | | |
| | | | | | | | | | 935 | | | | | | | |
| CGA | GCG | TGG | CTG | ATC | GCA | GCT | ATT | TTC | GCC | TGG | GCG | CTC | CTG | TCT | GCC | 222 |
| Arg | Ala | Trp | Leu | Ile | Ala | Ala | Ile | Phe | Ala | Trp | Ala | Leu | Leu | Ser | Ala | |
| | | | | 940 | | | | 945 | | | | | 950 | | | |
| CGG | CGG | GGG | CTC | GCC | GAG | GAG | GCG | GAA | GCC | TCG | CCC | TCG | CCT | CCG | CCC | 270 |
| Arg | Arg | Gly | Leu | Ala | Glu | Glu | Ala | Glu | Ala | Ser | Pro | Ser | Pro | Pro | Pro | |
| 955 | | | | | 960 | | | | 965 | | | | | 970 | | |
| TCC | CCG | TGC | CCA | ACC | GAG | ACG | GAA | AGC | TCC | GCT | GGG | ACC | ACC | GGC | GCA | 318 |
| Ser | Pro | Cys | Pro | Thr | Glu | Thr | Glu | Ser | Ser | Ala | Gly | Thr | Thr | Gly | Ala | |
| | | | | 975 | | | | 980 | | | | | 985 | | | |
| ACG | CCC | CCC | ACG | CCC | AAC | AGC | CCC | GAC | GCT | ACG | CCA | GAG | GAC | AGC | ACG | 366 |
| Thr | Pro | Pro | Thr | Pro | Asn | Ser | Pro | Asp | Ala | Thr | Pro | Glu | Asp | Ser | Thr | |
| | | | 990 | | | | 995 | | | | | 1000 | | | | |
| CCC | GGT | GCT | ACT | ACG | CCC | GTG | GGG | ACG | CCG | GAG | CCG | CCG | TCC | GTG | TCC | 414 |
| Pro | Gly | Ala | Thr | Thr | Pro | Val | Gly | Thr | Pro | Glu | Pro | Pro | Ser | Val | Ser | |
| | | | 1005 | | | | 1010 | | | | | 1015 | | | | |
| GAG | CAC | GAC | CCG | CCC | GTT | ACC | AAC | AGC | ACG | CCG | CCG | CCC | GCC | CCG | CCC | 462 |
| Glu | His | Asp | Pro | Pro | Val | Thr | Asn | Ser | Thr | Pro | Pro | Pro | Ala | Pro | Pro | |
| | | 1020 | | | | 1025 | | | | | 1030 | | | | | |
| GAG | GAC | GGG | CGA | CCC | GGC | GGC | GCT | GGC | AAC | GCG | AGC | CGC | GAT | GGG | CGA | 510 |
| Glu | Asp | Gly | Arg | Pro | Gly | Gly | Ala | Gly | Asn | Ala | Ser | Arg | Asp | Gly | Arg | |
| 1035 | | | | 1040 | | | | 1045 | | | | | 1050 | | | |
| CCT | AGC | GGC | GGG | GGG | CGG | CCT | CGC | CCC | CCG | CGG | CCG | AGC | AAA | GCC | CCG | 558 |
| Pro | Ser | Gly | Gly | Gly | Arg | Pro | Arg | Pro | Pro | Arg | Pro | Ser | Lys | Ala | Pro | |
| | | | | 1055 | | | | 1060 | | | | | 1065 | | | |
| CCG | AAG | GAG | CGC | AAG | TGG | ATG | CTC | TGC | GAG | CGC | GAG | GCC | GTG | GCC | GCC | 606 |
| Pro | Lys | Glu | Arg | Lys | Trp | Met | Leu | Cys | Glu | Arg | Glu | Ala | Val | Ala | Ala | |
| | | | 1070 | | | | 1075 | | | | | 1080 | | | | |
| TCG | TAC | GCC | GAG | CCG | CTG | TAC | GTG | CAC | TGC | GGC | GTG | GCC | GAC | AAC | GCC | 654 |
| Ser | Tyr | Ala | Glu | Pro | Leu | Tyr | Val | His | Cys | Gly | Val | Ala | Asp | Asn | Ala | |
| | | | 1085 | | | | 1090 | | | | | 1095 | | | | |
| ACT | GGC | GGT | GCG | CGC | CTG | GAG | CTC | TGG | TTT | CAG | CGC | GTG | GGC | AGG | TTC | 702 |
| Thr | Gly | Gly | Ala | Arg | Leu | Glu | Leu | Trp | Phe | Gln | Arg | Val | Gly | Arg | Phe | |

```
                1100                         1105                         1110
CGC  TCC  ACG  CGC  GGC  GAC  GAC  GAG  GCC  GTG  CGC  AAC  CCC  TTT  CCG  CGG    750
Arg  Ser  Thr  Arg  Gly  Asp  Asp  Glu  Ala  Val  Arg  Asn  Pro  Phe  Pro  Arg
1115                     1120                    1125                    1130

GCC  CCG  CCC  GTG  CTG  CTG  TTC  GTA  GCC  CAG  AAC  GGC  TCG  ATC  GCG  TAC    798
Ala  Pro  Pro  Val  Leu  Leu  Phe  Val  Ala  Gln  Asn  Gly  Ser  Ile  Ala  Tyr
                         1135                    1140                    1145

CGT  AGC  GCG  GAG  CTG  GGC  GAC  AAC  TAT  ATT  TTC  CCT  TCG  CCC  GCC  GAC    846
Arg  Ser  Ala  Glu  Leu  Gly  Asp  Asn  Tyr  Ile  Phe  Pro  Ser  Pro  Ala  Asp
                    1150                    1155                    1160

CCC  CGC  AAC  TTG  CCC  CTG  ACC  GTG  CGC  TCC  CTG  ACG  GCC  GCC  ACC  GAG    894
Pro  Arg  Asn  Leu  Pro  Leu  Thr  Val  Arg  Ser  Leu  Thr  Ala  Ala  Thr  Glu
               1165                    1170                    1175

GGC  GTG  TAC  ACT  TGG  CGC  CGC  GAC  ATG  GGC  ACC  AAG  TCA  CAG  CGC  AAG    942
Gly  Val  Tyr  Thr  Trp  Arg  Arg  Asp  Met  Gly  Thr  Lys  Ser  Gln  Arg  Lys
          1180                    1185                    1190

GTC  GTG  ACC  GTC  ACG  ACG  CAC  CGC  GCG  CCC  GCT  GTT  TCC  GTC  GAA  CCC    990
Val  Val  Thr  Val  Thr  Thr  His  Arg  Ala  Pro  Ala  Val  Ser  Val  Glu  Pro
1195                    1200                    1205                    1210

CAG  CCA  GCG  CTA  GAA  GGC  GCC  GGC  TAC  GCG  GCC  GTG  TGC  CGC  GCC  GCC   1038
Gln  Pro  Ala  Leu  Glu  Gly  Ala  Gly  Tyr  Ala  Ala  Val  Cys  Arg  Ala  Ala
                         1215                    1220                    1225

GAG  TAC  TAC  CCG  CCG  CGC  TCC  ACG  CGC  CTG  CAC  TGG  TTC  CGC  AAC  GGC   1086
Glu  Tyr  Tyr  Pro  Pro  Arg  Ser  Thr  Arg  Leu  His  Trp  Phe  Arg  Asn  Gly
                    1230                    1235                    1240

TAC  CCC  GTG  GAG  GCT  CGG  CAC  GCG  CGC  GAC  GTC  TTT  ACG  GTC  GAC  GAC   1134
Tyr  Pro  Val  Glu  Ala  Arg  His  Ala  Arg  Asp  Val  Phe  Thr  Val  Asp  Asp
               1245                    1250                    1255

TCC  GGG  CTC  TTT  TCG  CGC  ACG  TCC  GTC  CTT  ACG  CTC  GAG  GAC  GCG  ACG   1182
Ser  Gly  Leu  Phe  Ser  Arg  Thr  Ser  Val  Leu  Thr  Leu  Glu  Asp  Ala  Thr
          1260                    1265                    1270

CCA  ACC  GCC  CAC  CCG  CCC  AAC  CTG  CGC  TGC  GAC  GTC  TCC  TGG  TTC  CAG   1230
Pro  Thr  Ala  His  Pro  Pro  Asn  Leu  Arg  Cys  Asp  Val  Ser  Trp  Phe  Gln
1275                    1280                    1285                    1290

AGC  GCT  AAC  ATG  GAG  CGC  CGC  TTT  TAC  GCG  GCT  GGC  ACG  CCG  GCC  GTT   1278
Ser  Ala  Asn  Met  Glu  Arg  Arg  Phe  Tyr  Ala  Ala  Gly  Thr  Pro  Ala  Val
                         1295                    1300                    1305

TAC  CGC  CCG  CCC  GAG  CTG  CGC  GTG  TAC  TTC  GAG  GGC  GGC  GAG  GCC  GTC   1326
Tyr  Arg  Pro  Pro  Glu  Leu  Arg  Val  Tyr  Phe  Glu  Gly  Gly  Glu  Ala  Val
                    1310                    1315                    1320

TGC  GAG  GCG  CGC  TGC  GTC  CCC  GAG  GGG  CGC  GTC  TCC  CTG  CGC  TGG  ACG   1374
Cys  Glu  Ala  Arg  Cys  Val  Pro  Glu  Gly  Arg  Val  Ser  Leu  Arg  Trp  Thr
               1325                    1330                    1335

GTG  CGC  GAC  GGC  ATC  GCC  CCG  TCG  CGC  ACT  GAG  CAG  ACC  GGC  GTC  TGC   1422
Val  Arg  Asp  Gly  Ile  Ala  Pro  Ser  Arg  Thr  Glu  Gln  Thr  Gly  Val  Cys
          1340                    1345                    1350

GCC  GAG  CGG  CCC  GGG  CTG  GTA  AAC  CTG  CGC  GGC  GTG  CGC  CTG  CTT  TCT   1470
Ala  Glu  Arg  Pro  Gly  Leu  Val  Asn  Leu  Arg  Gly  Val  Arg  Leu  Leu  Ser
1355                    1360                    1365                    1370

ACA  ACC  GAC  GGG  CCC  GTC  GAC  TAC  ACC  TGC  ACC  GCC  ACT  GGC  TAC  CCG   1518
Thr  Thr  Asp  Gly  Pro  Val  Asp  Tyr  Thr  Cys  Thr  Ala  Thr  Gly  Tyr  Pro
                         1375                    1380                    1385

GCA  CCG  CTG  CCC  GAG  TTC  TCC  GCG  ACC  GCC  ACG  TAC  GAC  GCC  TCG  CCC   1566
Ala  Pro  Leu  Pro  Glu  Phe  Ser  Ala  Thr  Ala  Thr  Tyr  Asp  Ala  Ser  Pro
                    1390                    1395                    1400

GGC  CTA  ATC  GGA  AGC  CCC  GTC  CTC  GTC  AGC  GTC  GTG  GCC  GTC  GCC  TGC   1614
Gly  Leu  Ile  Gly  Ser  Pro  Val  Leu  Val  Ser  Val  Val  Ala  Val  Ala  Cys
               1405                    1410                    1415

GGT  CTC  GGC  GCC  GTG  GGG  CTC  CTG  CTG  GTG  GCG  GCC  TCG  TGC  CTG  CGG   1662
Gly  Leu  Gly  Ala  Val  Gly  Leu  Leu  Leu  Val  Ala  Ala  Ser  Cys  Leu  Arg
```

|  |  |  |  | 1420 |  |  |  |  | 1425 |  |  |  |  | 1430 |  |  |
|---|---|---|---|---|---|---|---|---|---|---|---|---|---|---|---|---|
| CGC | AAG | GCC | CGG | GTA | ATC | CAA | CCC | GGT | CTT | ACT | CGC | GCT | CGC | GCC | CTC | 1710 |
| Arg | Lys | Ala | Arg | Val | Ile | Gln | Pro | Gly | Leu | Thr | Arg | Ala | Arg | Ala | Leu |  |
| 1435 |  |  |  | 1440 |  |  |  |  | 1445 |  |  |  |  | 1450 |  |  |

| GGC | TCC | GCG | CCC | TAGACGACCG | GCACGGCCTG | GAGGCGCTGG | CGGCTGCCGG | 1762 |
|---|---|---|---|---|---|---|---|---|
| Gly | Ser | Ala | Pro |  |  |  |  |  |

| TGCCGCTCAC | ACCGCGCGCC | ACAACCGCGA | CGTGTGGCGG | CGCTTTTCCC | GCGTCTGCGA | 1822 |
|---|---|---|---|---|---|---|

| GGCCGGC | 1829 |
|---|---|

(2) INFORMATION FOR SEQ ID NO:4:

(i) SEQUENCE CHARACTERISTICS:
        (A) LENGTH: 521 amino acids
        (B) TYPE: amino acid
        (D) TOPOLOGY: linear (ii) MOLECULE TYPE: protein (xi) SEQUENCE DESCRIPTION: SEQ ID NO:4:

| Met | Gly | Pro | Leu | Gly | Arg | Ala | Trp | Leu | Ile | Ala | Ala | Ile | Phe | Ala | Trp |
|---|---|---|---|---|---|---|---|---|---|---|---|---|---|---|---|
| 1 |  |  |  | 5 |  |  |  |  | 10 |  |  |  |  | 15 |  |
| Ala | Leu | Leu | Ser | Ala | Arg | Arg | Gly | Leu | Ala | Glu | Glu | Ala | Glu | Ala | Ser |
|  |  |  | 20 |  |  |  |  | 25 |  |  |  |  | 30 |  |  |
| Pro | Ser | Pro | Pro | Ser | Pro | Cys | Pro | Thr | Glu | Thr | Glu | Ser | Ser | Ala |  |
|  |  | 35 |  |  |  | 40 |  |  |  |  | 45 |  |  |  |  |
| Gly | Thr | Thr | Gly | Ala | Thr | Pro | Pro | Thr | Pro | Asn | Ser | Pro | Asp | Ala | Thr |
|  | 50 |  |  |  |  | 55 |  |  |  |  | 60 |  |  |  |  |
| Pro | Glu | Asp | Ser | Thr | Pro | Gly | Ala | Thr | Thr | Pro | Val | Gly | Thr | Pro | Glu |
| 65 |  |  |  |  | 70 |  |  |  |  | 75 |  |  |  |  | 80 |
| Pro | Pro | Ser | Val | Ser | Glu | His | Asp | Pro | Pro | Val | Thr | Asn | Ser | Thr | Pro |
|  |  |  |  | 85 |  |  |  |  | 90 |  |  |  |  | 95 |  |
| Pro | Pro | Ala | Pro | Pro | Glu | Asp | Gly | Arg | Pro | Gly | Gly | Ala | Gly | Asn | Ala |
|  |  |  | 100 |  |  |  |  | 105 |  |  |  |  | 110 |  |  |
| Ser | Arg | Asp | Gly | Arg | Pro | Ser | Gly | Gly | Gly | Arg | Pro | Arg | Pro | Pro | Arg |
|  |  | 115 |  |  |  |  | 120 |  |  |  |  | 125 |  |  |  |
| Pro | Ser | Lys | Ala | Pro | Pro | Lys | Glu | Arg | Lys | Trp | Met | Leu | Cys | Glu | Arg |
|  | 130 |  |  |  |  | 135 |  |  |  |  | 140 |  |  |  |  |
| Glu | Ala | Val | Ala | Ala | Ser | Tyr | Ala | Glu | Pro | Leu | Tyr | Val | His | Cys | Gly |
| 145 |  |  |  |  | 150 |  |  |  |  | 155 |  |  |  |  | 160 |
| Val | Ala | Asp | Asn | Ala | Thr | Gly | Gly | Ala | Arg | Leu | Glu | Leu | Trp | Phe | Gln |
|  |  |  |  | 165 |  |  |  |  | 170 |  |  |  |  | 175 |  |
| Arg | Val | Gly | Arg | Phe | Arg | Ser | Thr | Arg | Gly | Asp | Asp | Glu | Ala | Val | Arg |
|  |  |  | 180 |  |  |  |  | 185 |  |  |  |  | 190 |  |  |
| Asn | Pro | Phe | Pro | Arg | Ala | Pro | Pro | Val | Leu | Leu | Phe | Val | Ala | Gln | Asn |
|  |  | 195 |  |  |  |  | 200 |  |  |  |  | 205 |  |  |  |
| Gly | Ser | Ile | Ala | Tyr | Arg | Ser | Ala | Glu | Leu | Gly | Asp | Asn | Tyr | Ile | Phe |
|  | 210 |  |  |  |  | 215 |  |  |  |  | 220 |  |  |  |  |
| Pro | Ser | Pro | Ala | Asp | Pro | Arg | Asn | Leu | Pro | Leu | Thr | Val | Arg | Ser | Leu |
| 225 |  |  |  |  | 230 |  |  |  |  | 235 |  |  |  |  | 240 |
| Thr | Ala | Ala | Thr | Glu | Gly | Val | Tyr | Thr | Trp | Arg | Arg | Asp | Met | Gly | Thr |
|  |  |  |  | 245 |  |  |  |  | 250 |  |  |  |  | 255 |  |
| Lys | Ser | Gln | Arg | Lys | Val | Val | Thr | Val | Thr | Thr | His | Arg | Ala | Pro | Ala |
|  |  |  | 260 |  |  |  |  | 265 |  |  |  |  | 270 |  |  |
| Val | Ser | Val | Glu | Pro | Gln | Pro | Ala | Leu | Glu | Gly | Ala | Gly | Tyr | Ala | Ala |
|  |  | 275 |  |  |  |  | 280 |  |  |  |  | 285 |  |  |  |
| Val | Cys | Arg | Ala | Ala | Glu | Tyr | Tyr | Pro | Pro | Arg | Ser | Thr | Arg | Leu | His |

|     |     |     |     |     | 290 |     |     |     | 295 |     |     |     |     | 300 |     |
| --- | --- | --- | --- | --- | --- | --- | --- | --- | --- | --- | --- | --- | --- | --- | --- |
| Trp 305 | Phe | Arg | Asn | Gly | Tyr 310 | Pro | Val | Glu | Ala | Arg 315 | His | Ala | Arg | Asp | Val 320 |
| Phe | Thr | Val | Asp | Asp 325 | Ser | Gly | Leu | Phe | Ser 330 | Arg | Thr | Ser | Val | Leu 335 | Thr |
| Leu | Glu | Asp | Ala 340 | Thr | Pro | Thr | Ala | His 345 | Pro | Pro | Asn | Leu | Arg 350 | Cys | Asp |
| Val | Ser | Trp 355 | Phe | Gln | Ser | Ala | Asn 360 | Met | Glu | Arg | Arg | Phe 365 | Tyr | Ala | Ala |
| Gly | Thr 370 | Pro | Ala | Val | Tyr | Arg 375 | Pro | Pro | Glu | Leu | Arg 380 | Val | Tyr | Phe | Glu |
| Gly 385 | Gly | Glu | Ala | Val | Cys 390 | Glu | Ala | Arg | Cys | Val 395 | Pro | Glu | Gly | Arg | Val 400 |
| Ser | Leu | Arg | Trp | Thr 405 | Val | Arg | Asp | Gly | Ile 410 | Ala | Pro | Ser | Arg | Thr 415 | Glu |
| Gln | Thr | Gly | Val 420 | Cys | Ala | Glu | Arg | Pro 425 | Gly | Leu | Val | Asn | Leu 430 | Arg | Gly |
| Val | Arg | Leu 435 | Leu | Ser | Thr | Thr | Asp 440 | Gly | Pro | Val | Asp | Tyr 445 | Thr | Cys | Thr |
| Ala | Thr 450 | Gly | Tyr | Pro | Ala | Pro 455 | Leu | Pro | Glu | Phe | Ser 460 | Ala | Thr | Ala | Thr |
| Tyr 465 | Asp | Ala | Ser | Pro | Gly 470 | Leu | Ile | Gly | Ser | Pro 475 | Val | Leu | Val | Ser | Val 480 |
| Val | Ala | Val | Ala | Cys 485 | Gly | Leu | Gly | Ala | Val 490 | Gly | Leu | Leu | Leu | Val 495 | Ala |
| Ala | Ser | Cys | Leu 500 | Arg | Arg | Lys | Ala | Arg 505 | Val | Ile | Gln | Pro | Gly 510 | Leu | Thr |
| Arg | Ala | Arg 515 | Ala | Leu | Gly | Ser | Ala 520 | Pro |     |     |     |     |     |     |     |

( 2 ) INFORMATION FOR SEQ ID NO:5:

( i ) SEQUENCE CHARACTERISTICS:
        ( A ) LENGTH: 1405 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 85..1335

( x i ) SEQUENCE DESCRIPTION: SEQ ID NO:5:

| GGGCCGCAGC | CCCGGCTGGG | TATATATCCC | CGACGGGCGA | CTAGAGATAC | ACTCGCCCCG | 60 |
| --- | --- | --- | --- | --- | --- | --- |

| CGCGGCTGCT | GCGAGCGGGC | GAAC | ATG | CAA | GGG | CCG | ACA | TTG | GCC | GTG | CTG | 111 |
| --- | --- | --- | --- | --- | --- | --- | --- | --- | --- | --- | --- | --- |
|            |            |      | Met | Gln | Gly | Pro | Thr | Leu | Ala | Val | Leu |     |
|            |            |      |     |     |     | 525 |     |     |     |     | 530 |     |

| GGC | GCG | CTG | CTC | GCC | GTT | GCG | GTG | AGC | TTG | CCT | ACA | CCC | GCG | CCG | CGG | 159 |
| --- | --- | --- | --- | --- | --- | --- | --- | --- | --- | --- | --- | --- | --- | --- | --- | --- |
| Gly | Ala | Leu | Leu | Ala | Val | Ala | Val | Ser | Leu | Pro | Thr | Pro | Ala | Pro | Arg |     |
|     |     |     |     | 535 |     |     |     |     | 540 |     |     |     |     | 545 |     |     |

| GTG | ACG | GTA | TAC | GTC | GAC | CCG | CCG | GCG | TAC | CCG | ATG | CCG | CGA | TAC | AAC | 207 |
| --- | --- | --- | --- | --- | --- | --- | --- | --- | --- | --- | --- | --- | --- | --- | --- | --- |
| Val | Thr | Val | Tyr | Val | Asp | Pro | Pro | Ala | Tyr | Pro | Met | Pro | Arg | Tyr | Asn |     |
|     |     |     | 550 |     |     |     |     | 555 |     |     |     |     | 560 |     |     |     |

| TAC | ACT | GAA | CGC | TGG | CAC | ACT | ACC | GGG | CCC | ATA | CCG | TCG | CCC | TTC | GCA | 255 |
| --- | --- | --- | --- | --- | --- | --- | --- | --- | --- | --- | --- | --- | --- | --- | --- | --- |
| Tyr | Thr | Glu | Arg | Trp | His | Thr | Thr | Gly | Pro | Ile | Pro | Ser | Pro | Phe | Ala |     |
|     |     |     | 565 |     |     |     | 570 |     |     |     |     | 575 |     |     |     |     |

| GAC | GGC | CGC | GAG | CAG | CCC | GTC | GAG | GTG | CGC | TAC | GCG | ACG | AGC | GCG | GCG | 303 |
| --- | --- | --- | --- | --- | --- | --- | --- | --- | --- | --- | --- | --- | --- | --- | --- | --- |

|     |     |     |     |     |     |     |     |     |     |     |     |     |     |     |     |
|-----|-----|-----|-----|-----|-----|-----|-----|-----|-----|-----|-----|-----|-----|-----|-----|
| Asp | Gly | Arg | Glu | Gln | Pro | Val | Glu | Val | Arg | Tyr | Ala | Thr | Ser | Ala | Ala |
|     | 580 |     |     |     | 585 |     |     |     |     | 590 |     |     |     |     |     |

| GCG | TGC | GAC | ATG | CTG | GCG | CTG | ATC | GCA | GAC | CCG | CAG | GTG | GGG | CGC | ACG | 351 |
|-----|-----|-----|-----|-----|-----|-----|-----|-----|-----|-----|-----|-----|-----|-----|-----|-----|
| Ala | Cys | Asp | Met | Leu | Ala | Leu | Ile | Ala | Asp | Pro | Gln | Val | Gly | Arg | Thr |     |
| 595 |     |     |     | 600 |     |     |     |     | 605 |     |     |     |     | 610 |     |     |

| CTG | TGG | GAA | GCG | GTA | CGC | CGG | CAC | GCG | CGC | GCG | TAC | AAC | GCC | ACG | GTC | 399 |
| Leu | Trp | Glu | Ala | Val | Arg | Arg | His | Ala | Arg | Ala | Tyr | Asn | Ala | Thr | Val |     |
|     |     |     |     | 615 |     |     |     |     | 620 |     |     |     |     | 625 |     |     |

| ATA | TGG | TAC | AAG | ATC | GAG | AGC | GGG | TGC | GCC | CGG | CCG | CTG | TAC | TAC | ATG | 447 |
| Ile | Trp | Tyr | Lys | Ile | Glu | Ser | Gly | Cys | Ala | Arg | Pro | Leu | Tyr | Tyr | Met |     |
|     |     |     |     | 630 |     |     |     |     | 635 |     |     |     |     | 640 |     |     |

| GAG | TAC | ACC | GAG | TGC | GAG | CCC | AGG | AAG | CAC | TTT | GGG | TAC | TGC | CGC | TAC | 495 |
| Glu | Tyr | Thr | Glu | Cys | Glu | Pro | Arg | Lys | His | Phe | Gly | Tyr | Cys | Arg | Tyr |     |
|     |     |     | 645 |     |     |     |     | 650 |     |     |     |     | 655 |     |     |     |

| CGC | ACA | CCC | CCG | TTT | TGG | GAC | AGC | TTC | CTG | GCG | GGC | TTC | GCC | TAC | CCC | 543 |
| Arg | Thr | Pro | Pro | Phe | Trp | Asp | Ser | Phe | Leu | Ala | Gly | Phe | Ala | Tyr | Pro |     |
|     |     | 660 |     |     |     |     | 665 |     |     |     |     | 670 |     |     |     |     |

| ACG | GAC | GAC | GAG | CTG | GGA | CTG | ATT | ATG | GCG | GCG | CCC | GCG | CGG | CTC | GTC | 591 |
| Thr | Asp | Asp | Glu | Leu | Gly | Leu | Ile | Met | Ala | Ala | Pro | Ala | Arg | Leu | Val |     |
| 675 |     |     |     |     | 680 |     |     |     |     | 685 |     |     |     |     | 690 |     |

| GAG | GGC | CAG | TAC | CGA | CGC | GCG | CTG | TAC | ATC | GAC | GGC | ACG | GTC | GCC | TAT | 639 |
| Glu | Gly | Gln | Tyr | Arg | Arg | Ala | Leu | Tyr | Ile | Asp | Gly | Thr | Val | Ala | Tyr |     |
|     |     |     |     | 695 |     |     |     |     | 700 |     |     |     |     | 705 |     |     |

| ACA | GAT | TTC | ATG | GTT | TCG | CTG | CCG | GCC | GGG | GAC | TGC | TGG | TTC | TCG | AAA | 687 |
| Thr | Asp | Phe | Met | Val | Ser | Leu | Pro | Ala | Gly | Asp | Cys | Trp | Phe | Ser | Lys |     |
|     |     |     | 710 |     |     |     |     | 715 |     |     |     |     | 720 |     |     |     |

| CTC | GGC | GCG | GCT | CGC | GGG | TAC | ACC | TTT | GGC | GCG | TGC | TTC | CCG | GCC | CGG | 735 |
| Leu | Gly | Ala | Ala | Arg | Gly | Tyr | Thr | Phe | Gly | Ala | Cys | Phe | Pro | Ala | Arg |     |
|     |     | 725 |     |     |     |     | 730 |     |     |     |     | 735 |     |     |     |     |

| GAT | TAC | GAG | CAA | AAG | AAG | GTT | CTG | CGC | CTG | ACG | TAT | CTC | ACG | CAG | TAC | 783 |
| Asp | Tyr | Glu | Gln | Lys | Lys | Val | Leu | Arg | Leu | Thr | Tyr | Leu | Thr | Gln | Tyr |     |
| 740 |     |     |     |     | 745 |     |     |     |     | 750 |     |     |     |     |     |     |

| TAC | CCG | CAG | GAG | GCA | CAC | AAG | GCC | ATA | GTC | GAC | TAC | TGG | TTC | ATG | CGC | 831 |
| Tyr | Pro | Gln | Glu | Ala | His | Lys | Ala | Ile | Val | Asp | Tyr | Trp | Phe | Met | Arg |     |
| 755 |     |     |     |     | 760 |     |     |     |     | 765 |     |     |     |     | 770 |     |

| CAC | GGG | GGC | GTC | GTT | CCG | CCG | TAT | TTT | GAG | GAG | TCG | AAG | GGC | TAC | GAG | 879 |
| His | Gly | Gly | Val | Val | Pro | Pro | Tyr | Phe | Glu | Glu | Ser | Lys | Gly | Tyr | Glu |     |
|     |     |     |     | 775 |     |     |     |     | 780 |     |     |     |     | 785 |     |     |

| CCG | CCG | CCT | GCC | GCC | GAT | GGG | GGT | TCC | CCC | GCG | CCA | CCC | GGC | GAC | GAC | 927 |
| Pro | Pro | Pro | Ala | Ala | Asp | Gly | Gly | Ser | Pro | Ala | Pro | Pro | Gly | Asp | Asp |     |
|     |     |     | 790 |     |     |     |     | 795 |     |     |     |     | 800 |     |     |     |

| GAG | GCC | CGC | GAG | GAT | GAA | GGG | GAG | ACC | GAG | GAC | GGG | GCA | GCC | GGG | CGG | 975 |
| Glu | Ala | Arg | Glu | Asp | Glu | Gly | Glu | Thr | Glu | Asp | Gly | Ala | Ala | Gly | Arg |     |
|     |     | 805 |     |     |     |     | 810 |     |     |     |     | 815 |     |     |     |     |

| GAG | GGC | AAC | GGC | GGC | CCC | CCA | GGA | CCC | GAA | GGC | GAC | GGC | GAG | AGT | CAG | 1023 |
| Glu | Gly | Asn | Gly | Gly | Pro | Pro | Gly | Pro | Glu | Gly | Asp | Gly | Glu | Ser | Gln |      |
|     |     | 820 |     |     |     |     | 825 |     |     |     |     | 830 |     |     |     |      |

| ACC | CCC | GAA | GCC | AAC | GGA | GGC | GCC | GAG | GGC | GAG | CCG | AAA | CCC | GGC | CCC | 1071 |
| Thr | Pro | Glu | Ala | Asn | Gly | Gly | Ala | Glu | Gly | Glu | Pro | Lys | Pro | Gly | Pro |      |
| 835 |     |     |     |     | 840 |     |     |     |     | 845 |     |     |     |     | 850 |      |

| AGC | CCC | GAC | GCC | GAC | CGC | CCC | GAA | GGC | TGG | CCG | AGC | CTC | GAA | GCC | ATC | 1119 |
| Ser | Pro | Asp | Ala | Asp | Arg | Pro | Glu | Gly | Trp | Pro | Ser | Leu | Glu | Ala | Ile |      |
|     |     |     |     | 855 |     |     |     |     | 860 |     |     |     |     | 865 |     |      |

| ACG | CAC | CCC | CCG | CCC | GCC | CCC | GCT | ACG | CCC | GCG | GCC | CCC | GAC | GCC | GTG | 1167 |
| Thr | His | Pro | Pro | Pro | Ala | Pro | Ala | Thr | Pro | Ala | Ala | Pro | Asp | Ala | Val |      |
|     |     |     | 870 |     |     |     |     | 875 |     |     |     |     | 880 |     |     |      |

| CCG | GTC | AGC | GTC | GGG | ATC | GGC | ATT | GCG | GCT | GCG | GCG | ATC | GCG | TGC | GTG | 1215 |
| Pro | Val | Ser | Val | Gly | Ile | Gly | Ile | Ala | Ala | Ala | Ala | Ile | Ala | Cys | Val |      |
|     |     | 885 |     |     |     |     | 890 |     |     |     |     | 895 |     |     |     |      |

| GCC | GCC | GCC | GCC | GCC | GGC | GCG | TAC | TTC | GTC | TAT | ACG | CGC | CGG | CGC | GGT | 1263 |

```
Ala  Ala  Ala  Ala  Ala  Gly  Ala  Tyr  Phe  Val  Tyr  Thr  Arg  Arg  Arg  Gly
     900                 905                      910

GCG  GGT  CCG  CTG  CCC  AGA  AAG  CCA  AAA  AAG  CTG  CCG  GCC  TTT  GGC  AAC        1311
Ala  Gly  Pro  Leu  Pro  Arg  Lys  Pro  Lys  Lys  Leu  Pro  Ala  Phe  Gly  Asn
915                      920                      925                      930

GTC  AAC  TAC  AGC  GCG  CTG  CCC  GGG  TGAGCGGCCT  AGGCCCTCCC  CCGACCGCCC           1365
Val  Asn  Tyr  Ser  Ala  Leu  Pro  Gly
                    935

CCTTTGCTCC  TAGCCCCGGC  TCCTGCCGAG  CCGCGCGGGG                                        1405
```

( 2 ) INFORMATION FOR SEQ ID NO:6:

( i ) SEQUENCE CHARACTERISTICS:
        ( A ) LENGTH: 417 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Gln  Gly  Pro  Thr  Leu  Ala  Val  Leu  Gly  Ala  Leu  Leu  Ala  Val  Ala
  1                 5                     10                      15

Val  Ser  Leu  Pro  Thr  Pro  Ala  Pro  Arg  Val  Thr  Val  Tyr  Val  Asp  Pro
               20                      25                      30

Pro  Ala  Tyr  Pro  Met  Pro  Arg  Tyr  Asn  Tyr  Thr  Glu  Arg  Trp  His  Thr
               35                      40                      45

Thr  Gly  Pro  Ile  Pro  Ser  Pro  Phe  Ala  Asp  Gly  Arg  Glu  Gln  Pro  Val
      50                     55                      60

Glu  Val  Arg  Tyr  Ala  Thr  Ser  Ala  Ala  Ala  Cys  Asp  Met  Leu  Ala  Leu
 65                      70                      75                       80

Ile  Ala  Asp  Pro  Gln  Val  Gly  Arg  Thr  Leu  Trp  Glu  Ala  Val  Arg  Arg
                    85                      90                      95

His  Ala  Arg  Ala  Tyr  Asn  Ala  Thr  Val  Ile  Trp  Tyr  Lys  Ile  Glu  Ser
                100                      105                     110

Gly  Cys  Ala  Arg  Pro  Leu  Tyr  Tyr  Met  Glu  Tyr  Thr  Glu  Cys  Glu  Pro
               115                      120                     125

Arg  Lys  His  Phe  Gly  Tyr  Cys  Arg  Tyr  Arg  Thr  Pro  Pro  Phe  Trp  Asp
     130                      135                     140

Ser  Phe  Leu  Ala  Gly  Phe  Ala  Tyr  Pro  Thr  Asp  Asp  Glu  Leu  Gly  Leu
145                           150                     155                     160

Ile  Met  Ala  Ala  Pro  Ala  Arg  Leu  Val  Glu  Gly  Gln  Tyr  Arg  Arg  Ala
                    165                     170                     175

Leu  Tyr  Ile  Asp  Gly  Thr  Val  Ala  Tyr  Thr  Asp  Phe  Met  Val  Ser  Leu
               180                      185                     190

Pro  Ala  Gly  Asp  Cys  Trp  Phe  Ser  Lys  Leu  Gly  Ala  Ala  Arg  Gly  Tyr
               195                      200                     205

Thr  Phe  Gly  Ala  Cys  Phe  Pro  Ala  Arg  Asp  Tyr  Glu  Gln  Lys  Lys  Val
     210                      215                     220

Leu  Arg  Leu  Thr  Tyr  Leu  Thr  Gln  Tyr  Tyr  Pro  Gln  Glu  Ala  His  Lys
225                           230                     235                     240

Ala  Ile  Val  Asp  Tyr  Trp  Phe  Met  Arg  His  Gly  Val  Val  Pro  Pro
                    245                     250                     255

Tyr  Phe  Glu  Glu  Ser  Lys  Gly  Tyr  Glu  Pro  Pro  Ala  Ala  Asp  Gly
               260                      265                     270

Gly  Ser  Pro  Ala  Pro  Pro  Gly  Asp  Asp  Glu  Ala  Arg  Glu  Asp  Glu  Gly
               275                      280                     285

Glu  Thr  Glu  Asp  Gly  Ala  Ala  Gly  Arg  Glu  Gly  Asn  Gly  Gly  Pro  Pro
```

-continued

```
                      290                           295                           300
Gly  Pro  Glu  Gly  Asp  Gly  Glu  Ser  Gln  Thr  Pro  Glu  Ala  Asn  Gly  Gly
305                      310                      315                           320

Ala  Glu  Gly  Glu  Pro  Lys  Pro  Gly  Pro  Ser  Pro  Asp  Ala  Asp  Arg  Pro
                    325                      330                     335

Glu  Gly  Trp  Pro  Ser  Leu  Glu  Ala  Ile  Thr  His  Pro  Pro  Pro  Ala  Pro
               340                    345                          350

Ala  Thr  Pro  Ala  Ala  Pro  Asp  Ala  Val  Pro  Val  Ser  Val  Gly  Ile  Gly
          355                    360                     365

Ile  Ala  Ala  Ala  Ala  Ile  Ala  Cys  Val  Ala  Ala  Ala  Ala  Ala  Gly  Ala
     370                    375                    380

Tyr  Phe  Val  Tyr  Thr  Arg  Arg  Arg  Gly  Ala  Gly  Pro  Leu  Pro  Arg  Lys
385                      390                     395                          400

Pro  Lys  Lys  Leu  Pro  Ala  Phe  Gly  Asn  Val  Asn  Tyr  Ser  Ala  Leu  Pro
                    405                    410                     415

Gly
```

( 2 ) INFORMATION FOR SEQ ID NO:7:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CTAGCTAGCT AG        12

( 2 ) INFORMATION FOR SEQ ID NO:8:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TTAAGTTAAC TTAA        14